United States Patent
Chikuma et al.

(10) Patent No.: US 11,332,527 B2
(45) Date of Patent: May 17, 2022

(54) ANTI AQP3 MONOCLONAL ANTIBODY SPECIFICALLY BINDING TO EXTRACELLULAR DOMAIN OF AQUAPORIN 3 (AQP3) AND USE THEREOF

(71) Applicant: Keio University, Tokyo (JP)

(72) Inventors: Mariko Chikuma, Shinjuku (JP); Masato Yasui, Kamakura (JP)

(73) Assignee: Keio University, Tokyo (JP)

(*) Notice: Subject to any disclaimer, the term of this patent is extended or adjusted under 35 U.S.C. 154(b) by 0 days.

(21) Appl. No.: 16/754,576

(22) PCT Filed: Oct. 12, 2018

(86) PCT No.: PCT/JP2018/038220
§ 371 (c)(1),
(2) Date: Apr. 8, 2020

(87) PCT Pub. No.: WO2019/074124
PCT Pub. Date: Apr. 18, 2019

(65) Prior Publication Data
US 2021/0130455 A1    May 6, 2021

(30) Foreign Application Priority Data
Oct. 12, 2017  (JP) .............................. JP2017-198895

(51) Int. Cl.
*C07K 16/28* (2006.01)
*A61K 47/68* (2017.01)

(52) U.S. Cl.
CPC .......... *C07K 16/28* (2013.01); *A61K 47/6801* (2017.08); *C07K 2317/24* (2013.01); *C07K 2317/55* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| 2009/0005296 A1* | 1/2009 | Jahn ................... | A61K 38/1709 514/1.2 |
| 2015/0196663 A1* | 7/2015 | Shusta ................. | A61K 9/0085 424/178.1 |
| 2015/0266947 A1* | 9/2015 | Sierks ................ | G01N 33/6896 424/135.1 |
| 2017/0355756 A1* | 12/2017 | Julien .................... | C12N 15/86 |

FOREIGN PATENT DOCUMENTS

| WO | WO 2008068048 | * 6/2008 |
| WO | 2020/213710 A1 | 10/2020 |

OTHER PUBLICATIONS

Chen "Enhancement and destruction of antibody function by somatic mutation: unequal occurrence is controlled by V gene combinatorial associations" EMBO 14(12):2784-2794 (Year: 1995).*
Kussie "A Single Engineered Amino Acid Substitution Changes Antibody Fine Specificity" J immunol 152(1):146-52 (Year: 1994).*
Therapeutic "Antibody Structure-Function Relationships" Therapeutic antibody engineering, woodhead publishing, excerpt only accessed from sciencedirect.com on Apr. 21, 2021 (Year: 2012).*
Vemulapalli "Overexpression of Protective Antigen as a Novel Approach To Enhance Vaccine Efficacy of *Brucella abortus* Strain RB51"Infection and Immunity, Jun. 2000,68(6) p. 3286-3289 (Year: 2009).*
Uniprot "A9Y006" accessed from uniprot.org on Apr. 23, 2021 (Year: 2008).*
International Search Report and Written Opinion dated Dec. 11, 2018 in connection with PCT/JP2018/038220.
Hara-Chikuma et al., 2008, "Roles of Aquaporin-3 in the Epidermis," Journal of Investigative Dermatology 128(9):2145-2151.
Ishibashi et al., 1994, "Molecular Cloning and expression of a member of the aquaporin family with permeability to glycerol and urea in addition to water expressed at the basolateral membrane of kidney collecting duct cells," Proc. Natl. Acad. Sci. 91:6269-6273.
Liu et al., 2007, "Expression of aquaporin 3 (AQP3) in normal and neoplastic lung tissues," Human Pathology 38:171-178.
Satooka et a!., 2016, "Aquaporin-3 Controls Breast Cancer Cell Migration by Regulating Hydrogen Peroxide Transport and Its Downstream Cell Signaling," Molecular and Cellular Biology 36(7):1206-1218.
Tamma et al., 2011, "Integrin Signaling Modulates AQP2 Trafficking via Arg-Gly-Asp (RGD) Motif," Cellular Physiology and Biochemistry 27:739-748.
Hara-Chikuma et al., 2015, "Aquaporin-3-mediated hydrogen peroxide transport is required for NF-kB signalling in keratinocytes and development of psoriasis" Nature Communications 6:7454.
Hara-Chikuma et al., 2016, "Involvement of aquaporin-3 in epidermal growth factor receptor signaling via hydrogen peroxide transport in cancer cells" Biochemical and Biophysical Research Communications 471(4):603-609.
Hara-Chikuma et al., 2020, "Inhibition of aquaporin-3 in macrophages by a monoclonal antibody as potential therapy for liver injury" Nature Communications 11(1):5666.

(Continued)

*Primary Examiner* — Adam Weidner
(74) *Attorney, Agent, or Firm* — Biospark Intellectual Property Law

(57) ABSTRACT

A subject of the present invention is to provide an anti AQP3 antibody specifically recognizing the extracellular domain of aquaporin 3 (AQP3), which is one type of a water channel protein. By selecting a monoclonal antibody which specifically binds to an oligopeptide included in loop C as one of the extracellular domains of AQP3, an anti AQP3 antibody that is desired in the present invention is provided. An anti AQP3 monoclonal antibody of the present invention can directly bind, from the outside of a cell, to AQP3 present in a cell membrane. Furthermore, as an anti AQP3 monoclonal antibody of the present invention can have an inhibitory activity, the function of permeating a low molecular weight molecule or the like, which is carried by AQP3, can be suppressed.

28 Claims, 20 Drawing Sheets
Specification includes a Sequence Listing.

(56) References Cited

OTHER PUBLICATIONS

International Search Report and Written Opinion dated Jul. 30, 2020 in connection with PCT/JP2020/016856.
"AQP3 (H-30): SC-20811," retrieved from https://datasheets.scbt.com/sc-20811.pdf by the EPO on Dec. 5, 2019.
Soler et al., 2017, "Overexpression of AQP3 and AQP10 in the skin exacerbates psoriasiform acanthosis" Experimental Dermatology, 26(10):949-951.
Matsuzaki et al., 1999, "Water Channel Protein AQP3 Is Present in Epithelia Exposed to the Environment of Possible Water Loss" Journal of Histochemistry and Cytochemistry, 47(1):1275-1286.
Vieceli Dalia Sega et al., 2014, "Specific aquaporins facilitate Nox-produced hydrogen peroxide transport through plasma membrane in leukaemia cells" Biochimica et Biophysica Acta. Molecular Cell Research, 1843(4):806-814.
Yang et al., 2015, "Aquaporin 3 is regulated by estrogen in the chicken oviduct and is involved in progression of epithelial cell-derived ovarian carcinomas" Domestic Animal Endocrinology, 55(23):97-106.
Li et al., 2006, "Expression of aquaporin-1 in SMMC-7221 liver carcinoma cells promotes cell migration" Chinese Science Bulletin, 51(21):2466-2471.

\* cited by examiner

[Fig. 1]
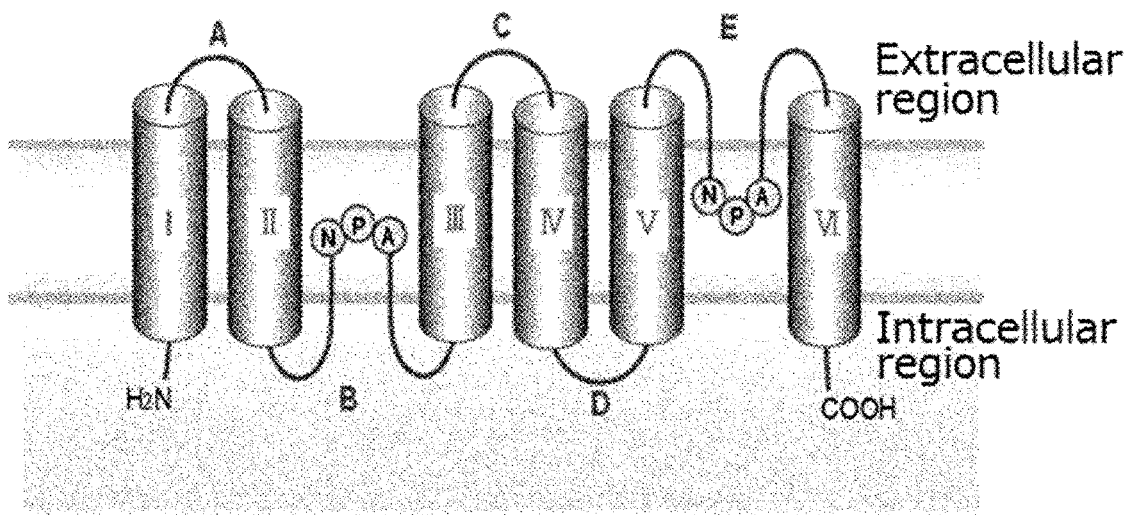
[Fig. 2]
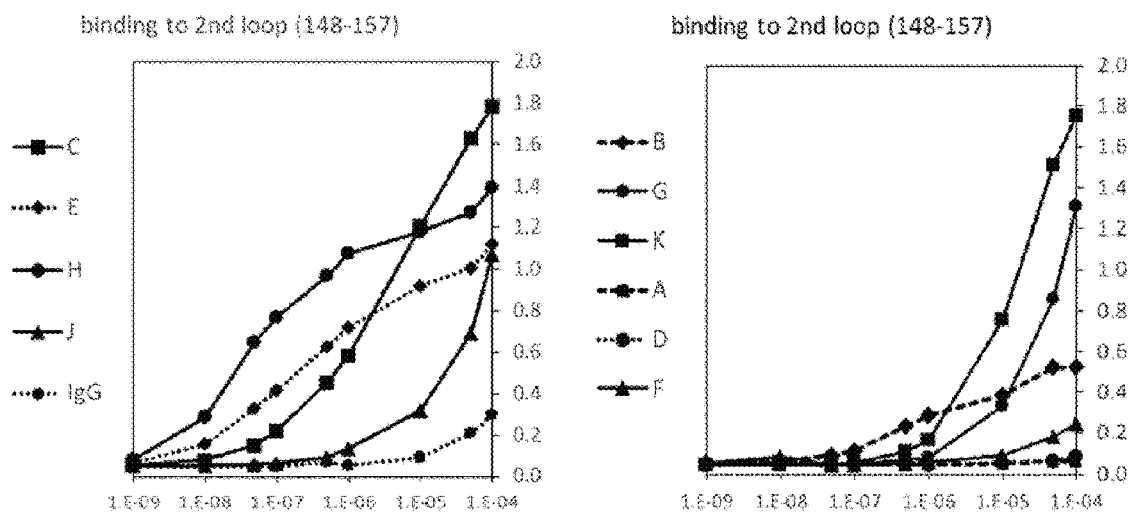
[Fig. 3]
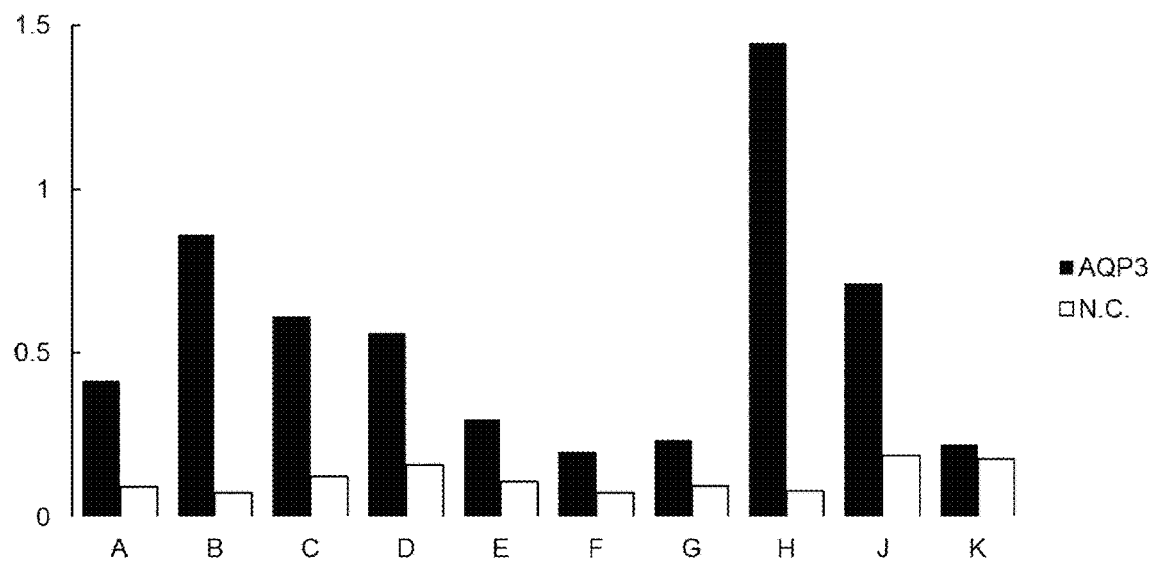

[Fig. 4]
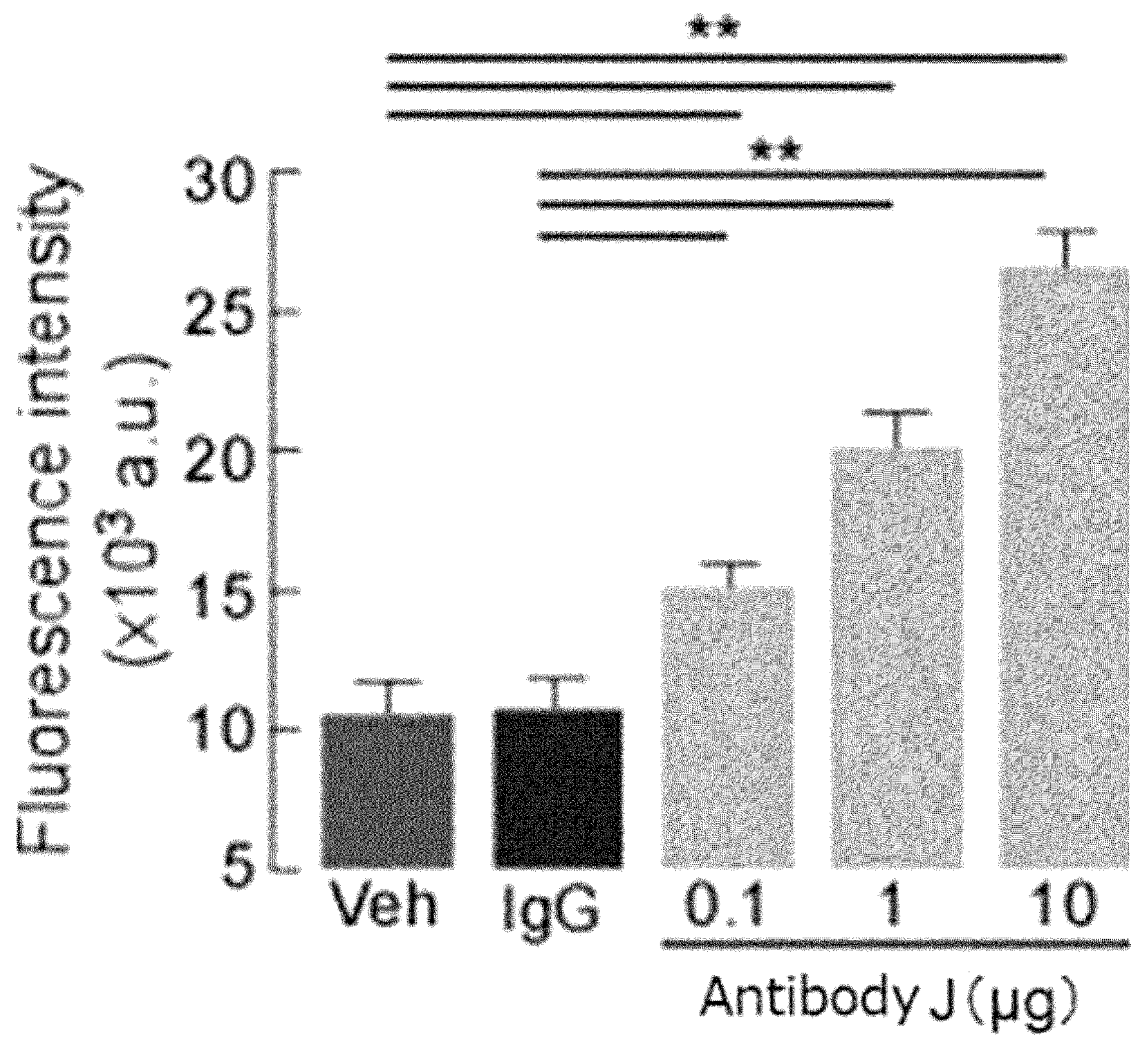

[Fig. 5A]
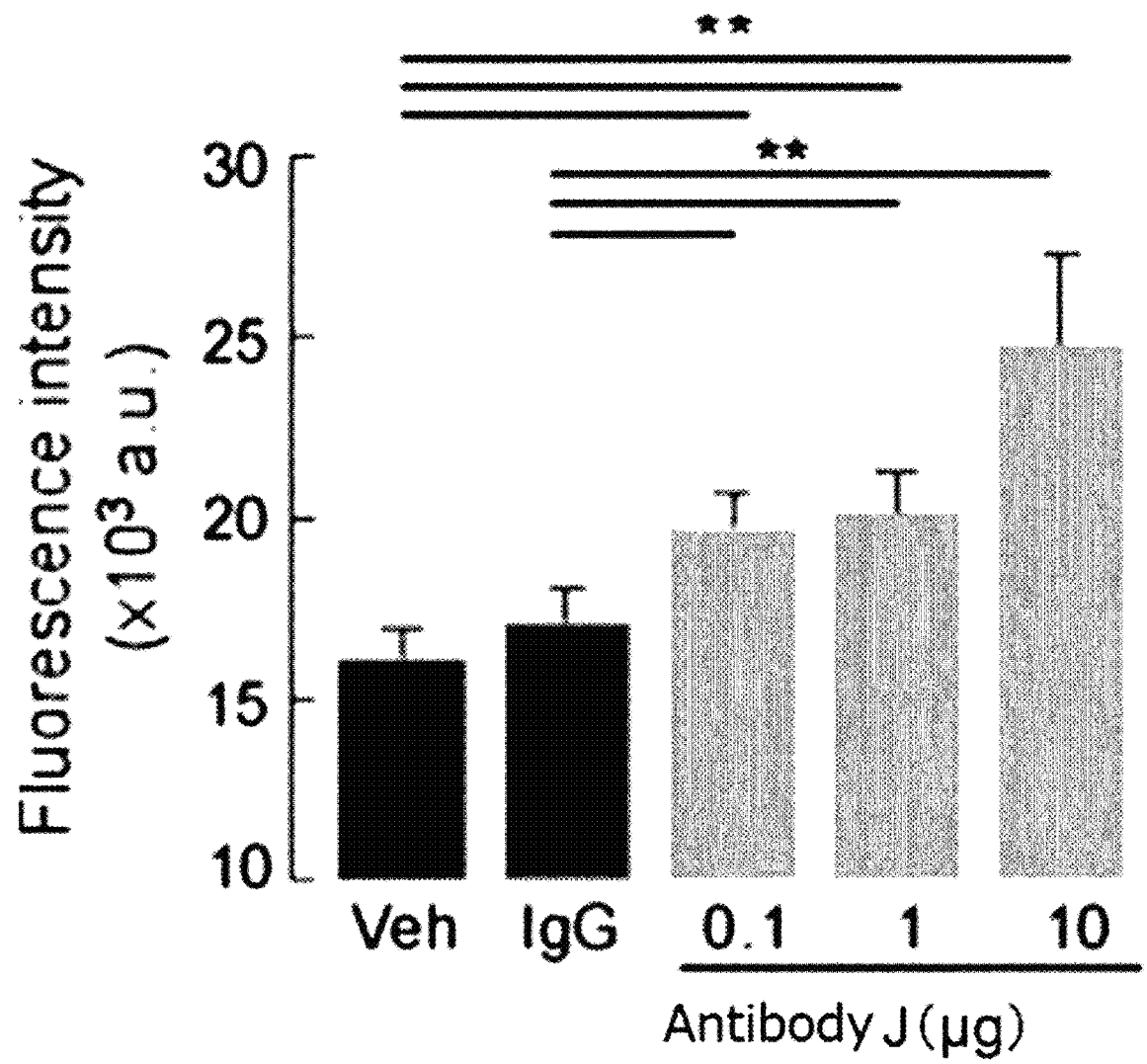

[Fig. 5B]
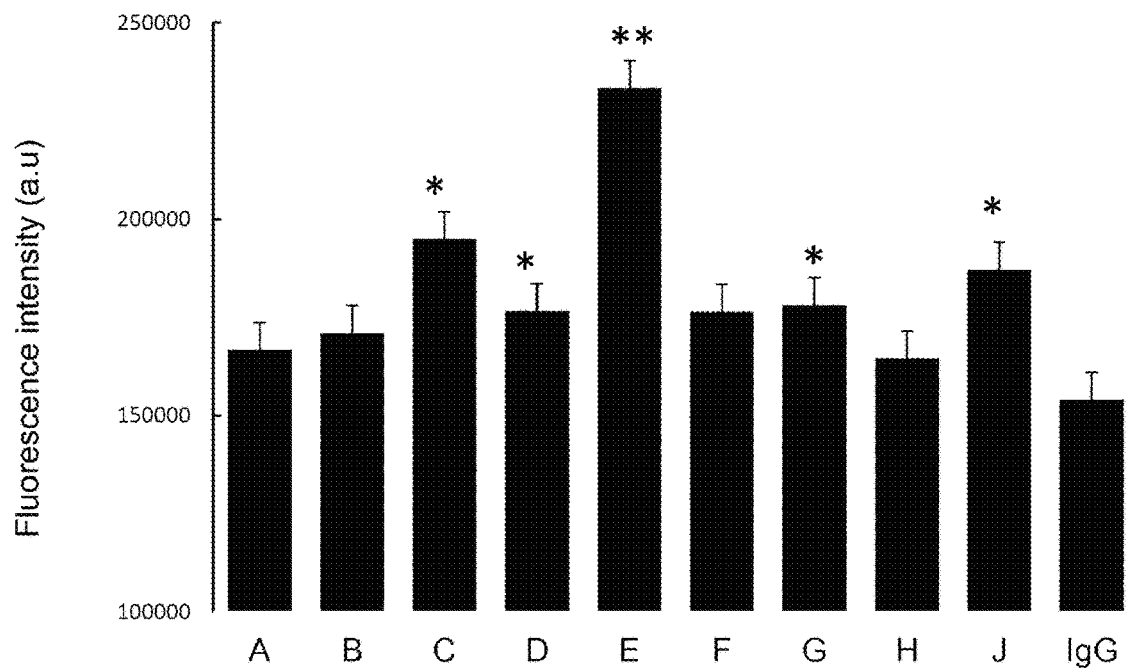
*; p<0.05, **; p<0.01
[Fig. 5C]
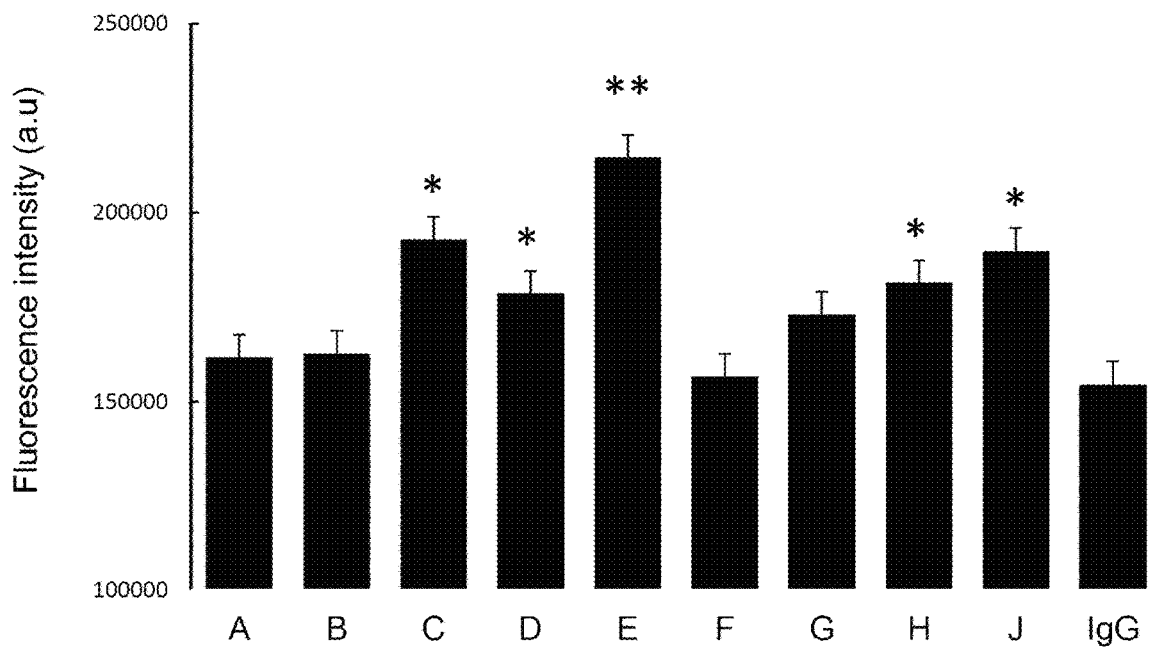
*; p<0.05, **; p<0.01

[Fig. 6A]
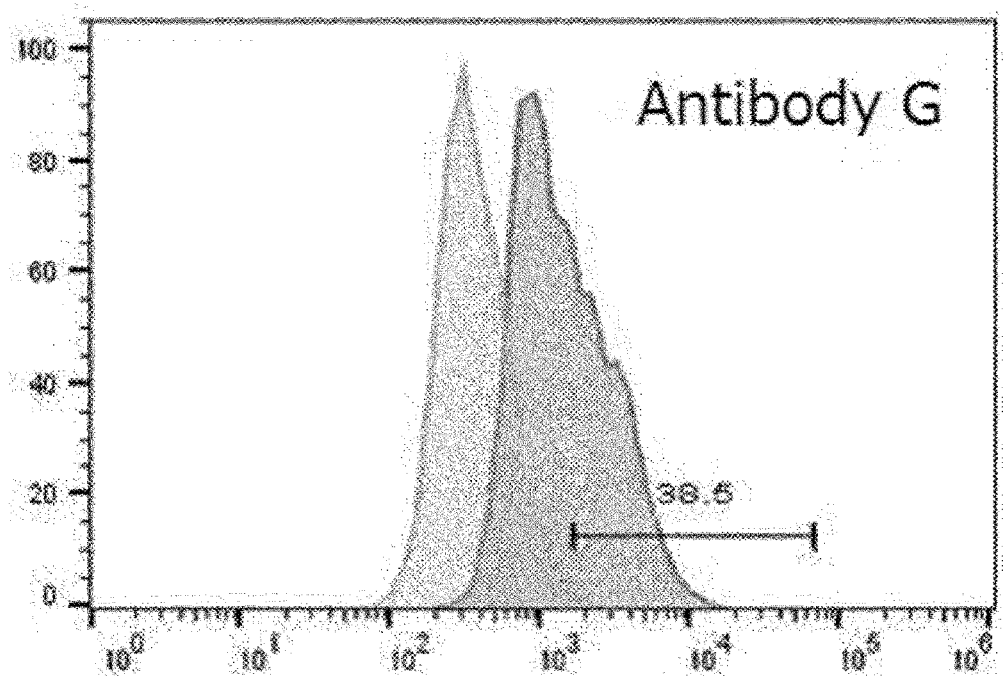
[Fig. 6B]
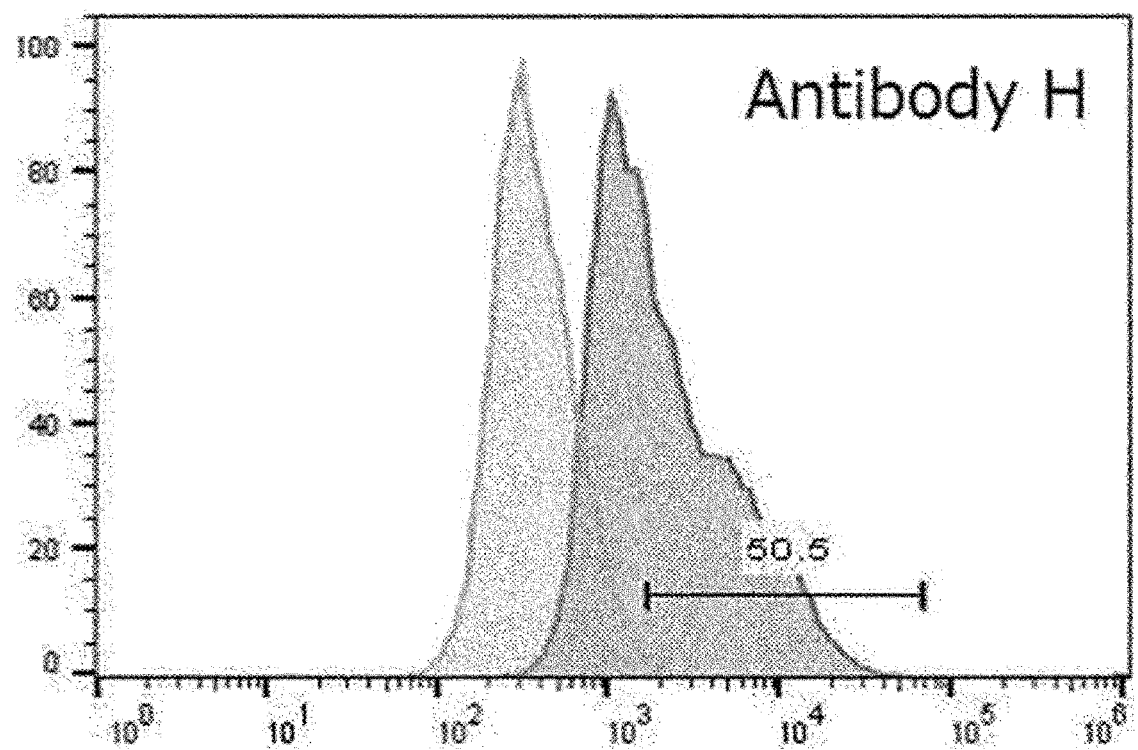

[Fig. 6C]
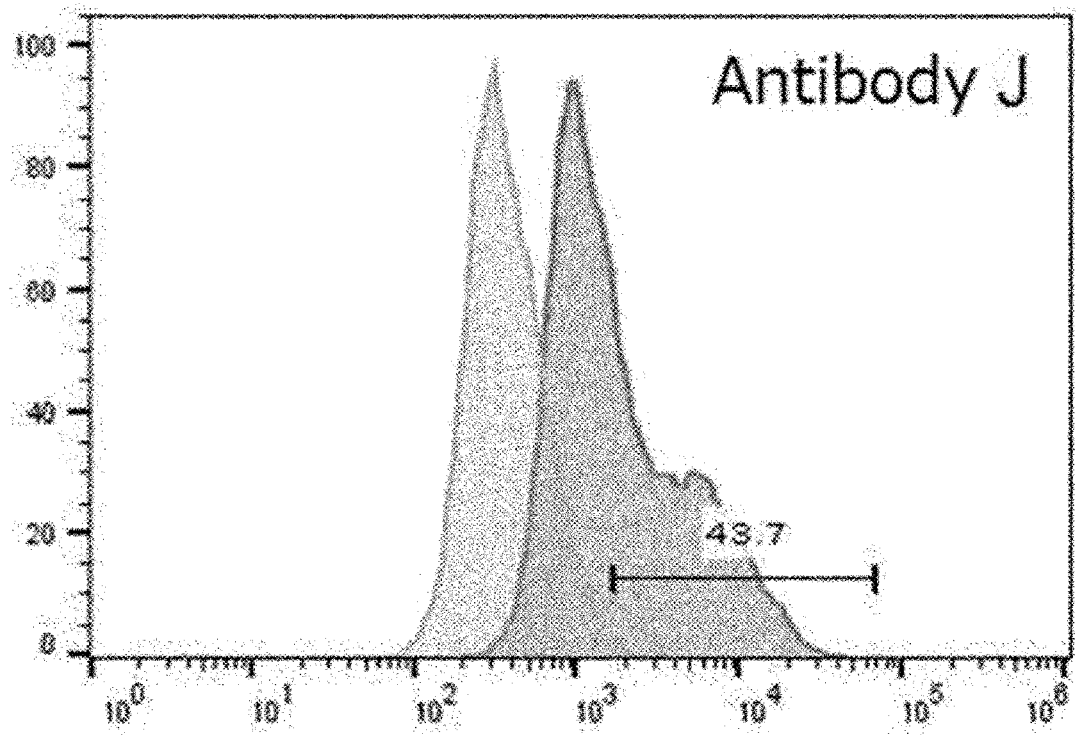
[Fig. 6D]
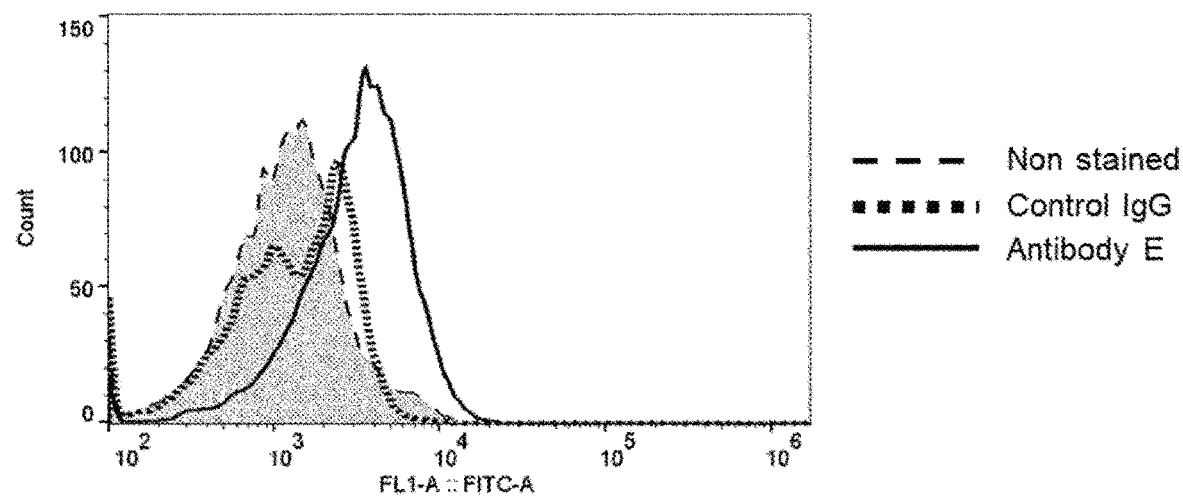

[Fig. 6E]
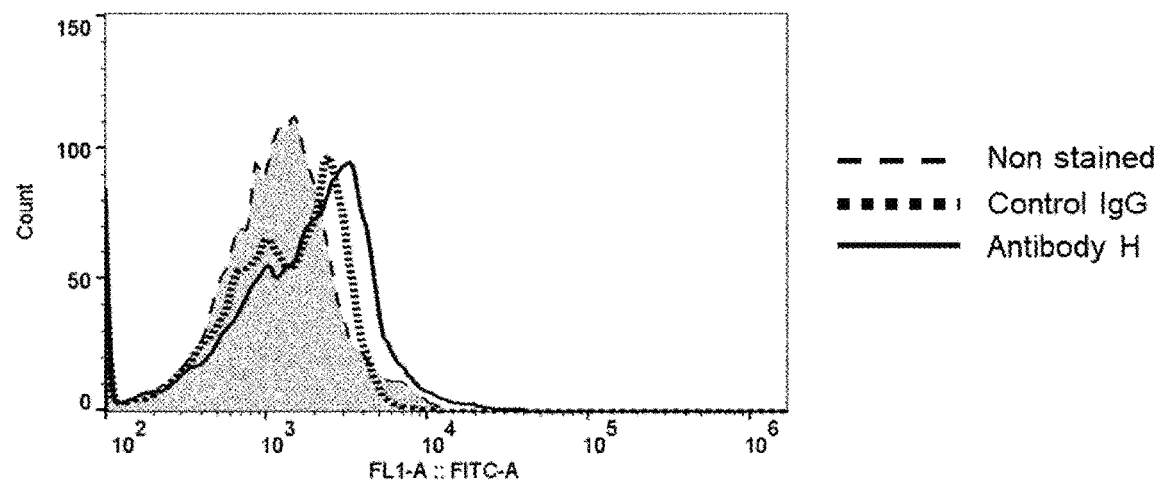
[Fig. 6F]
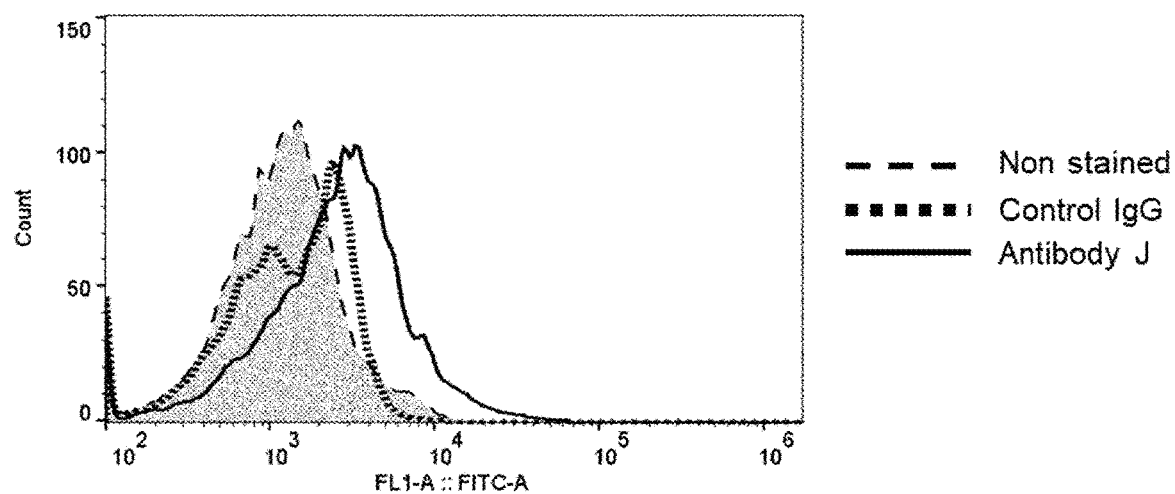
[Fig. 6G]
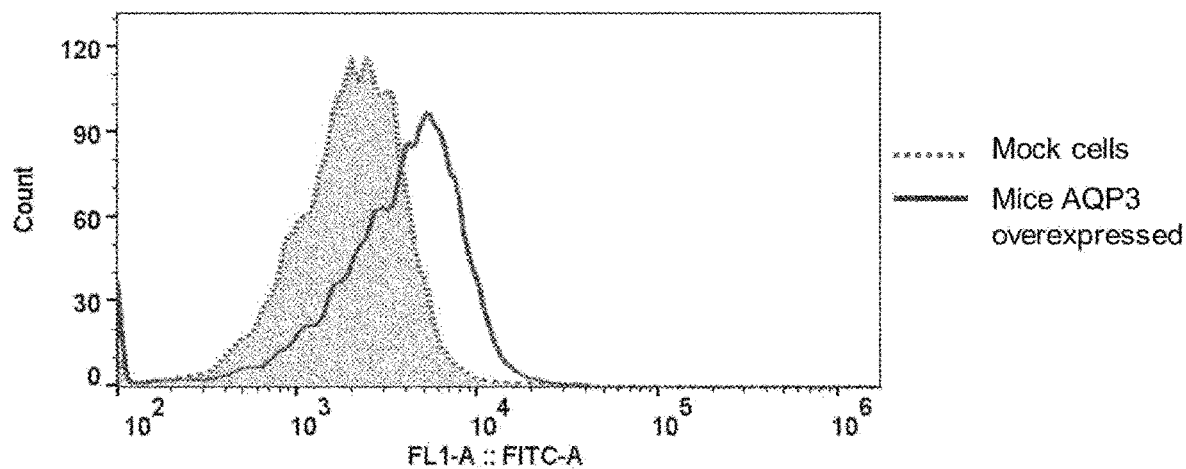

[Fig. 6H]
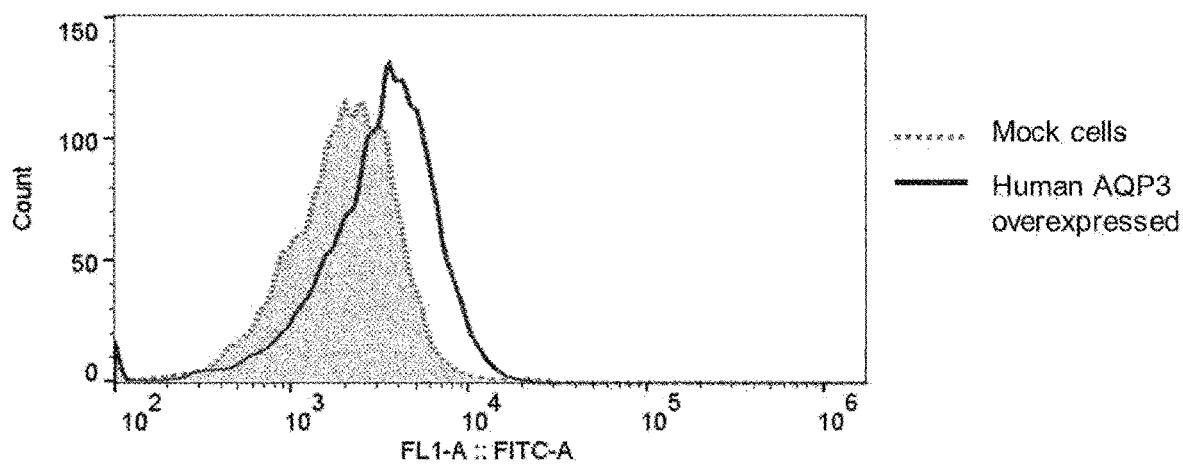
[Fig. 7A]
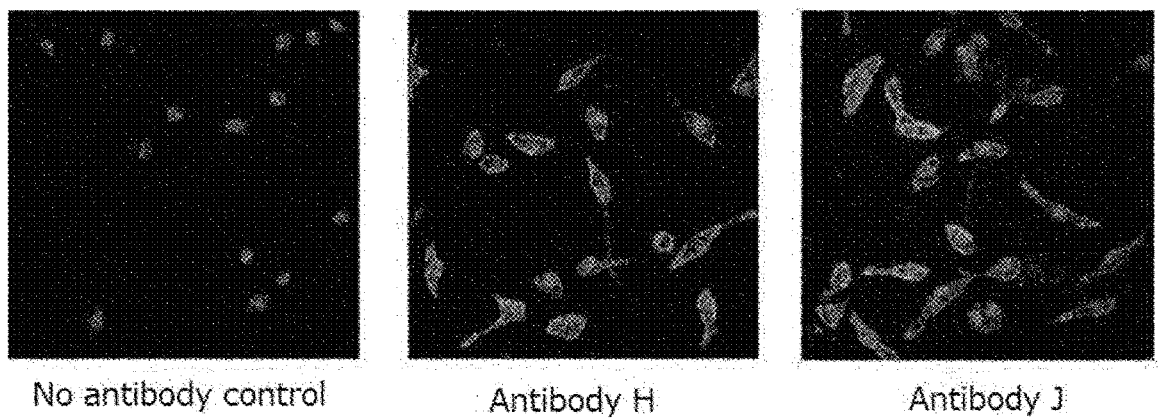

[Fig. 7B]
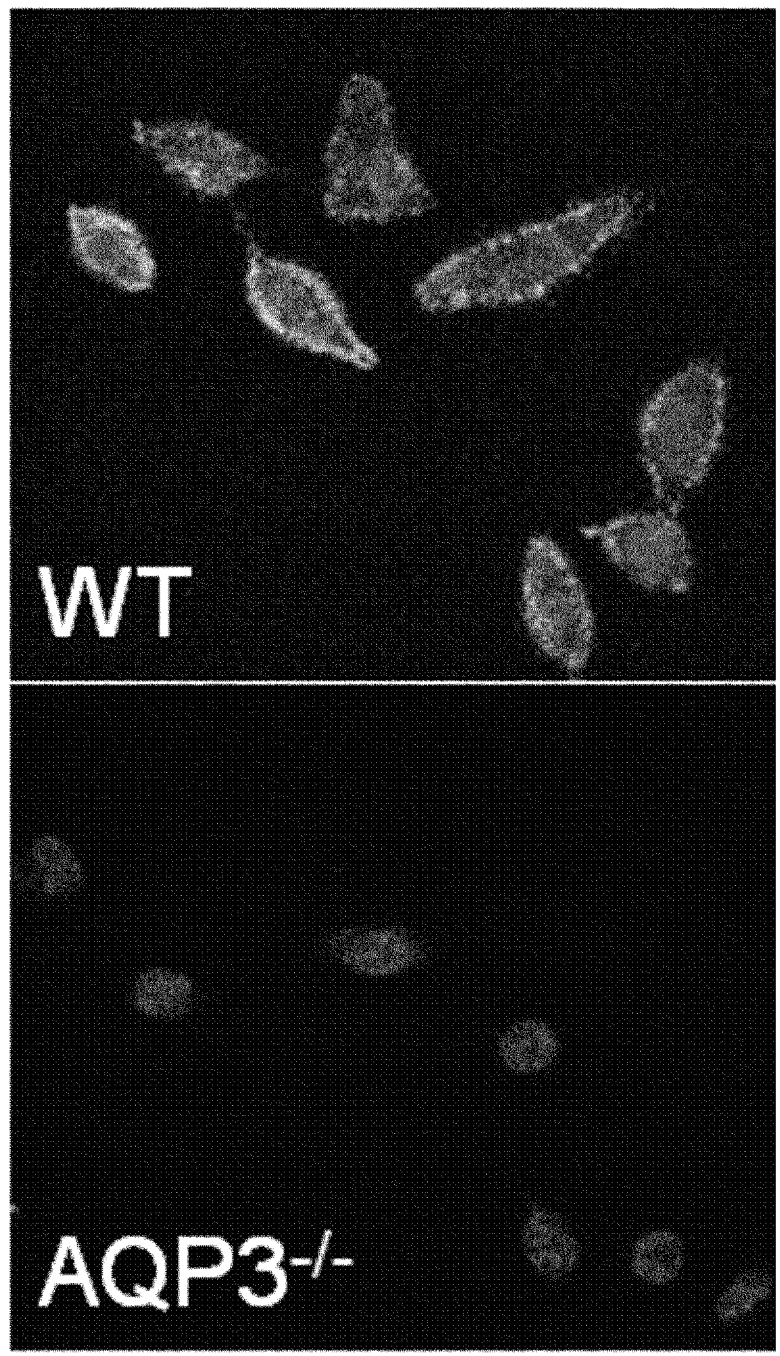

[Fig. 8A]
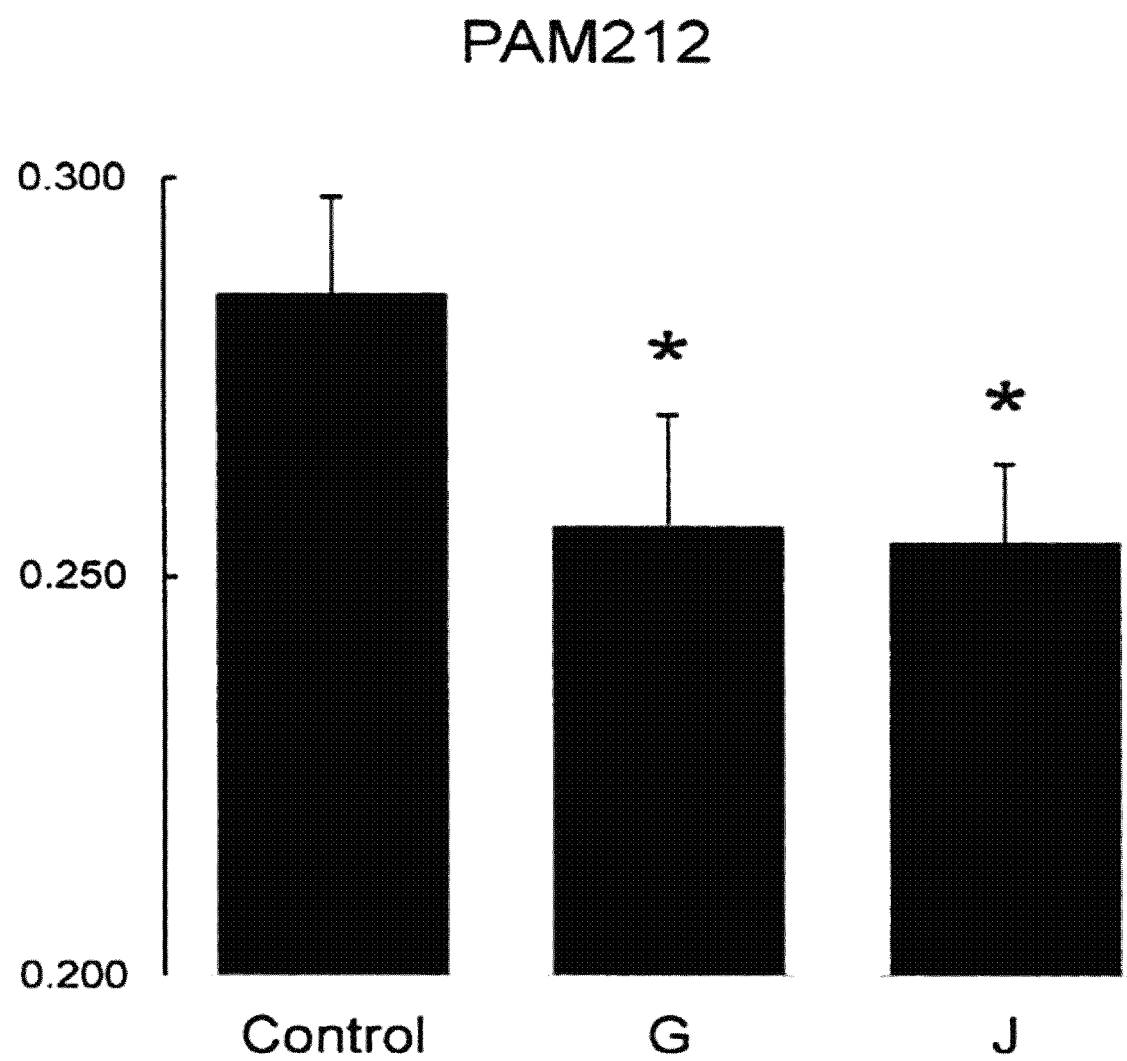

[Fig. 8B]
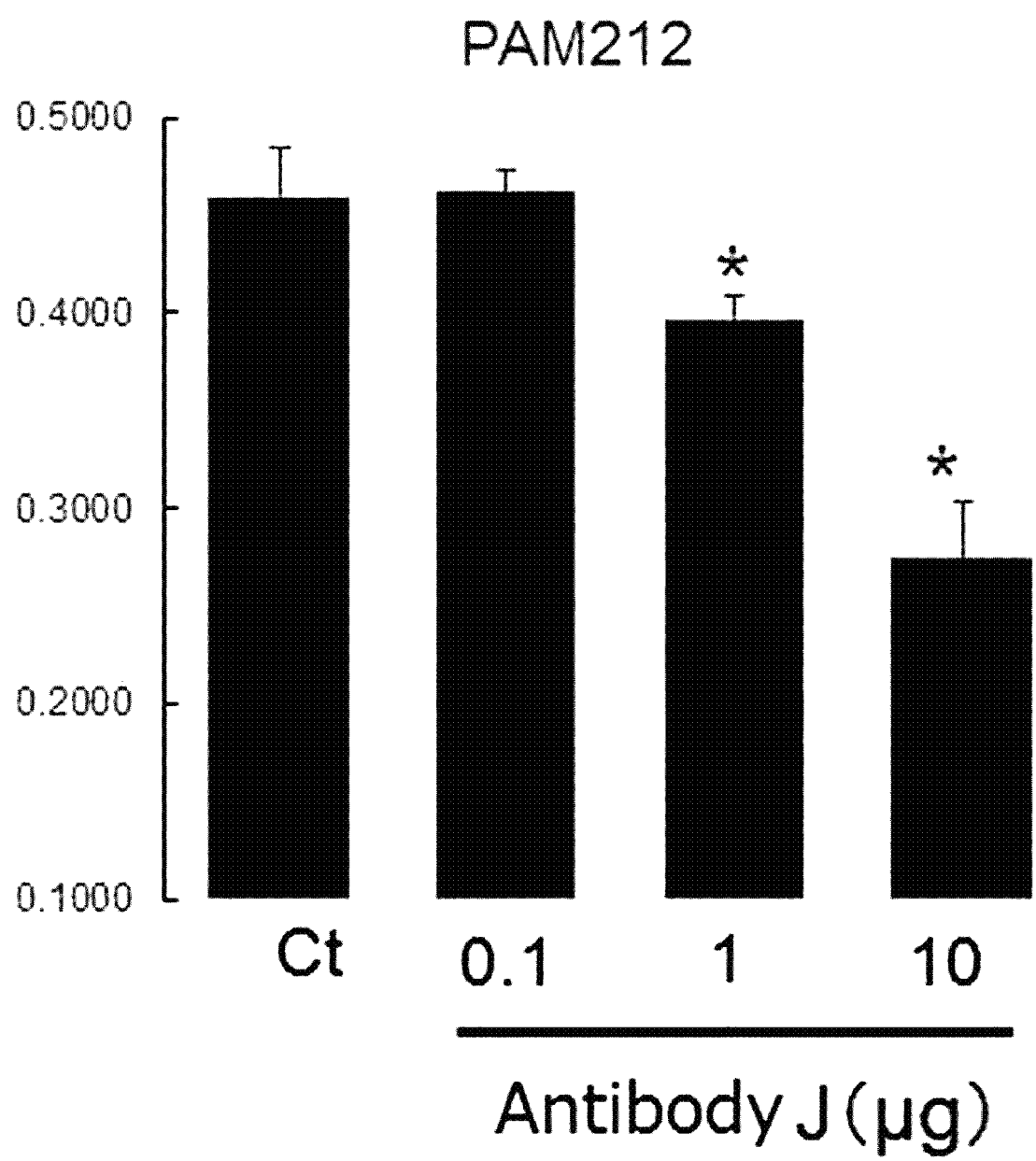

[Fig. 8C]
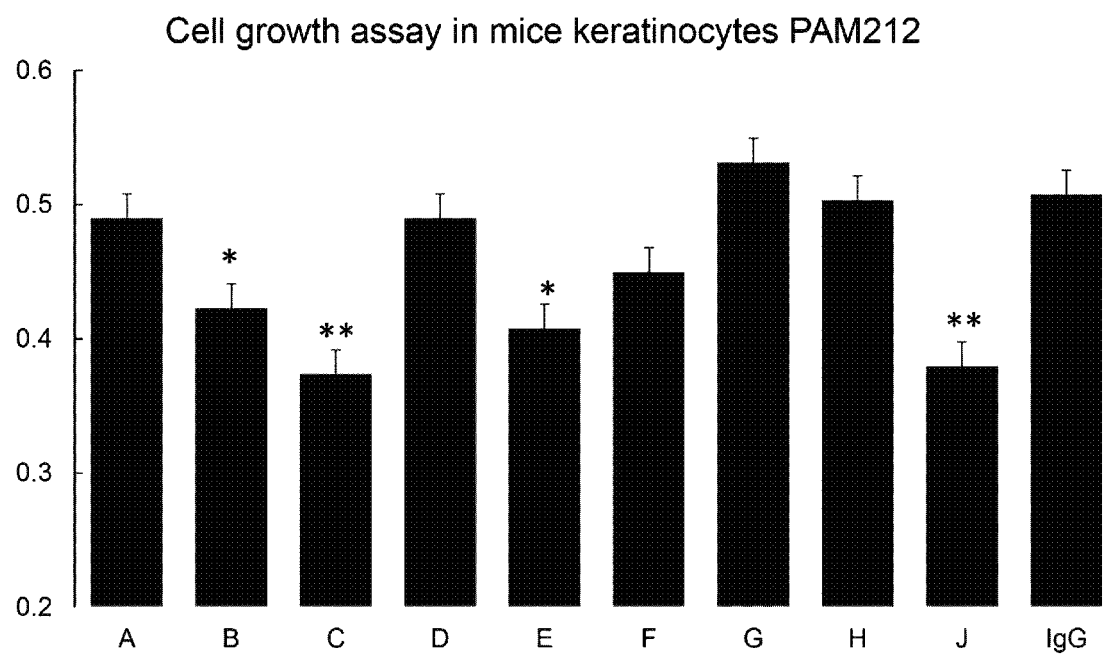

[Fig. 9]
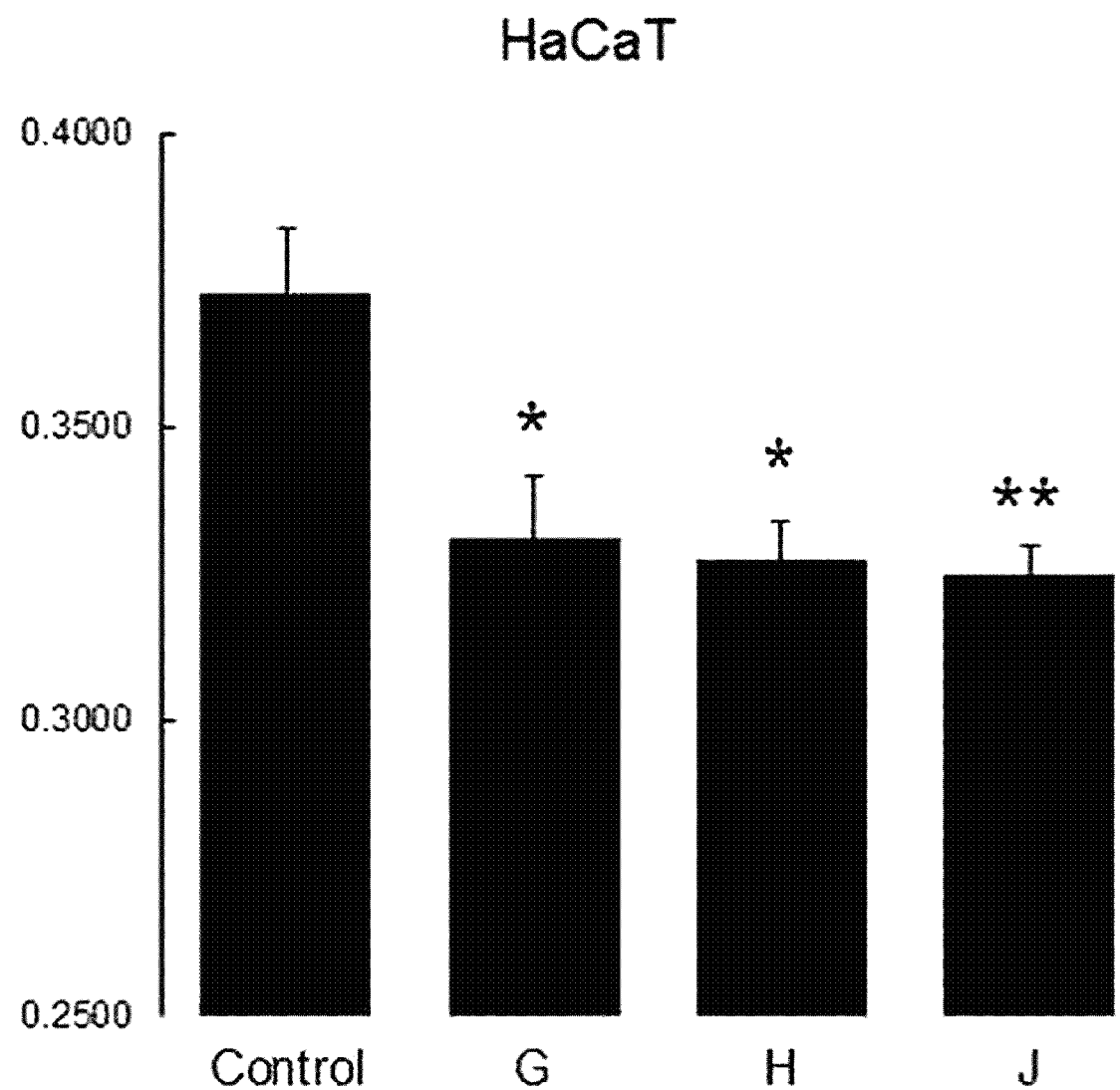

[Fig. 10]
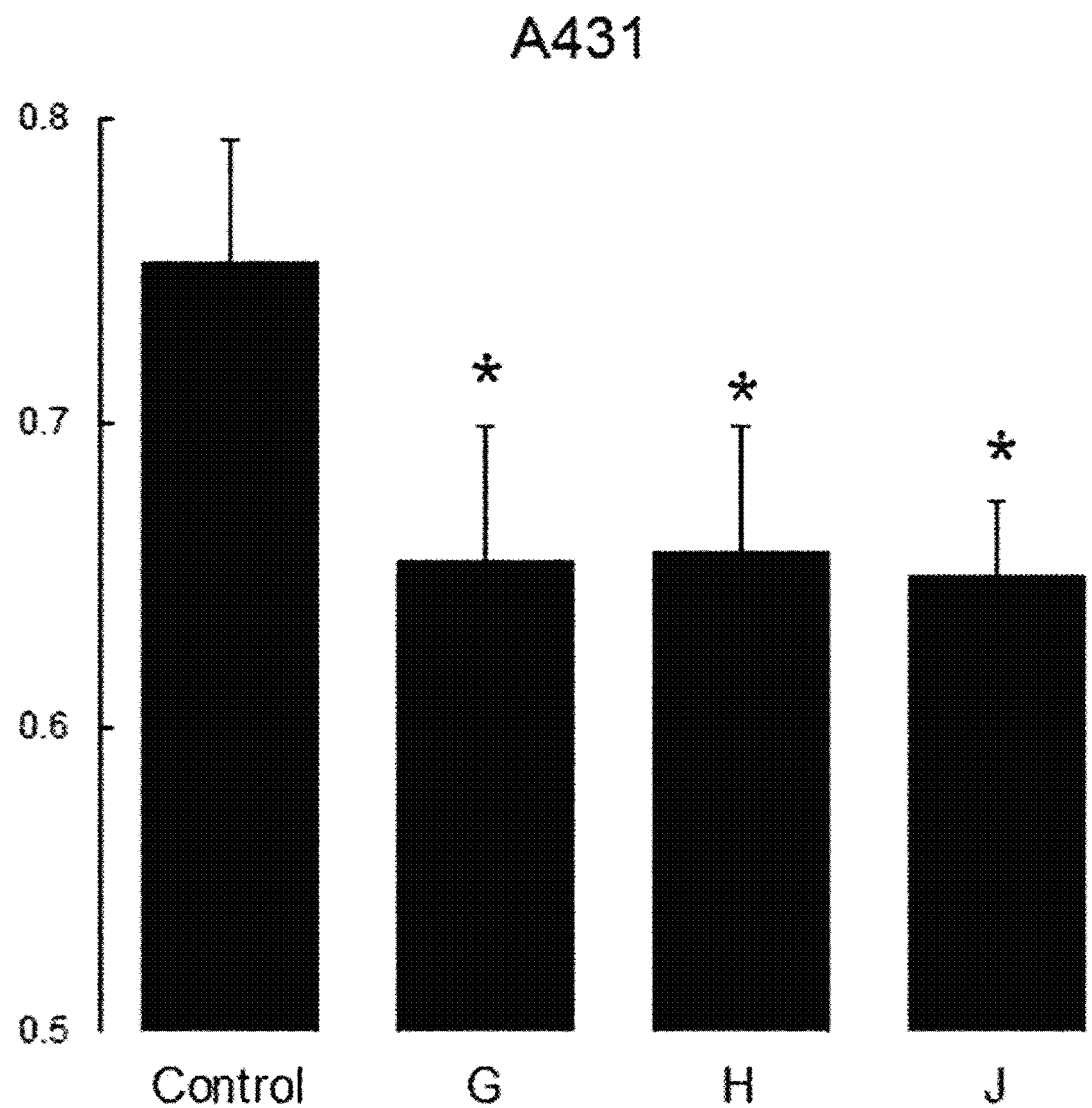

[Fig. 11]
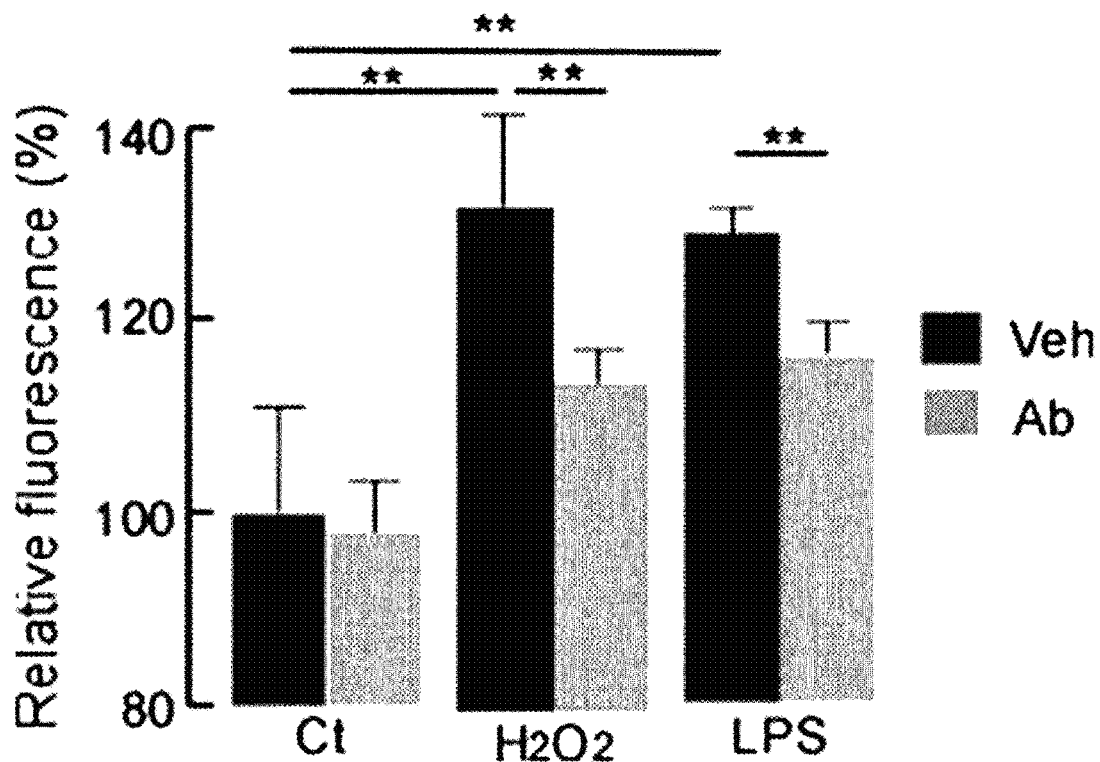
[Fig. 12]
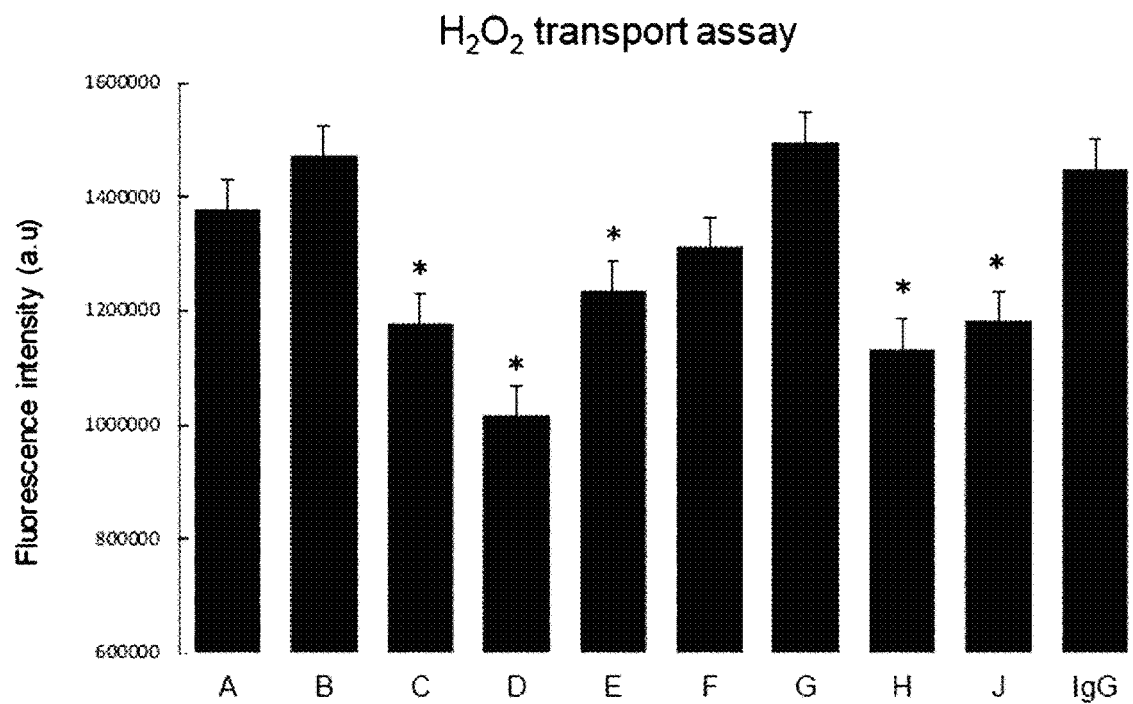
*; p<0.05, v.s. IgG

[Fig. 13]
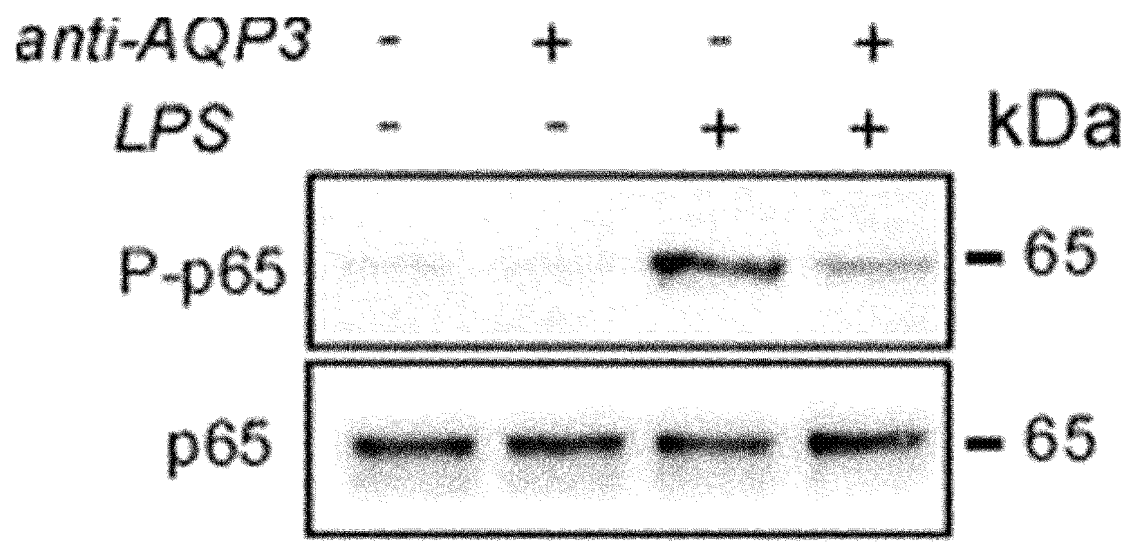

[Fig. 14A]
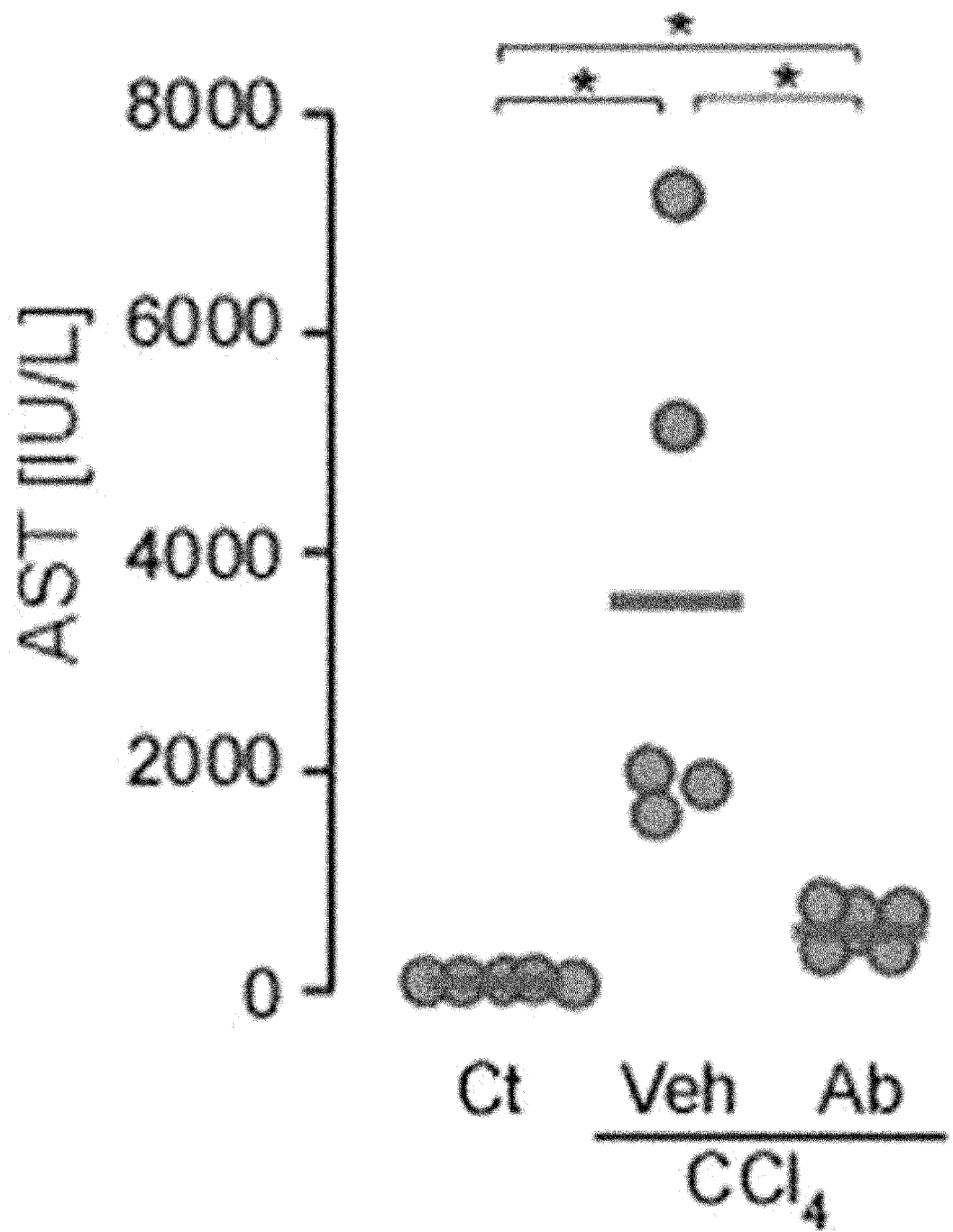

[Fig. 14B]
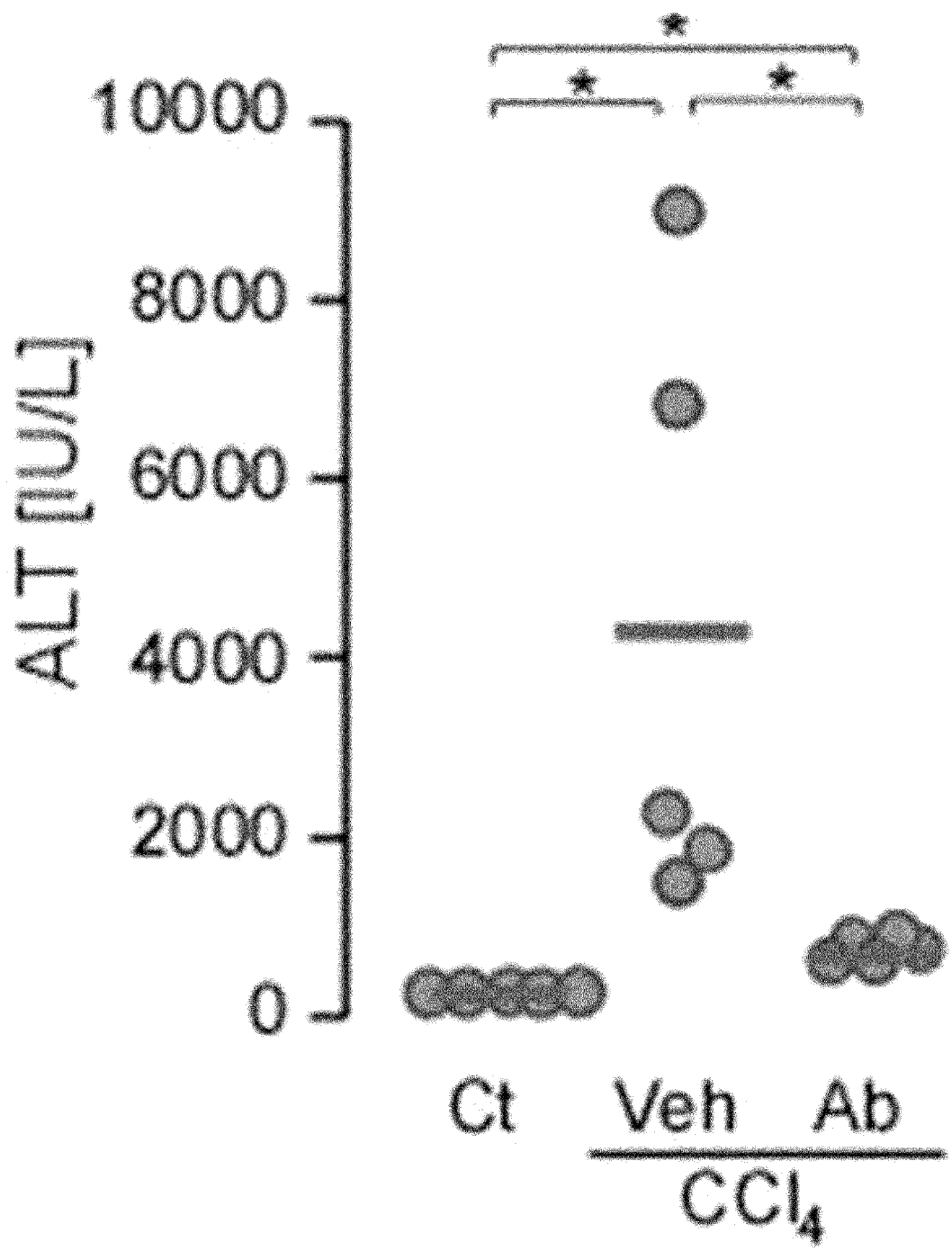

[Fig. 15A]
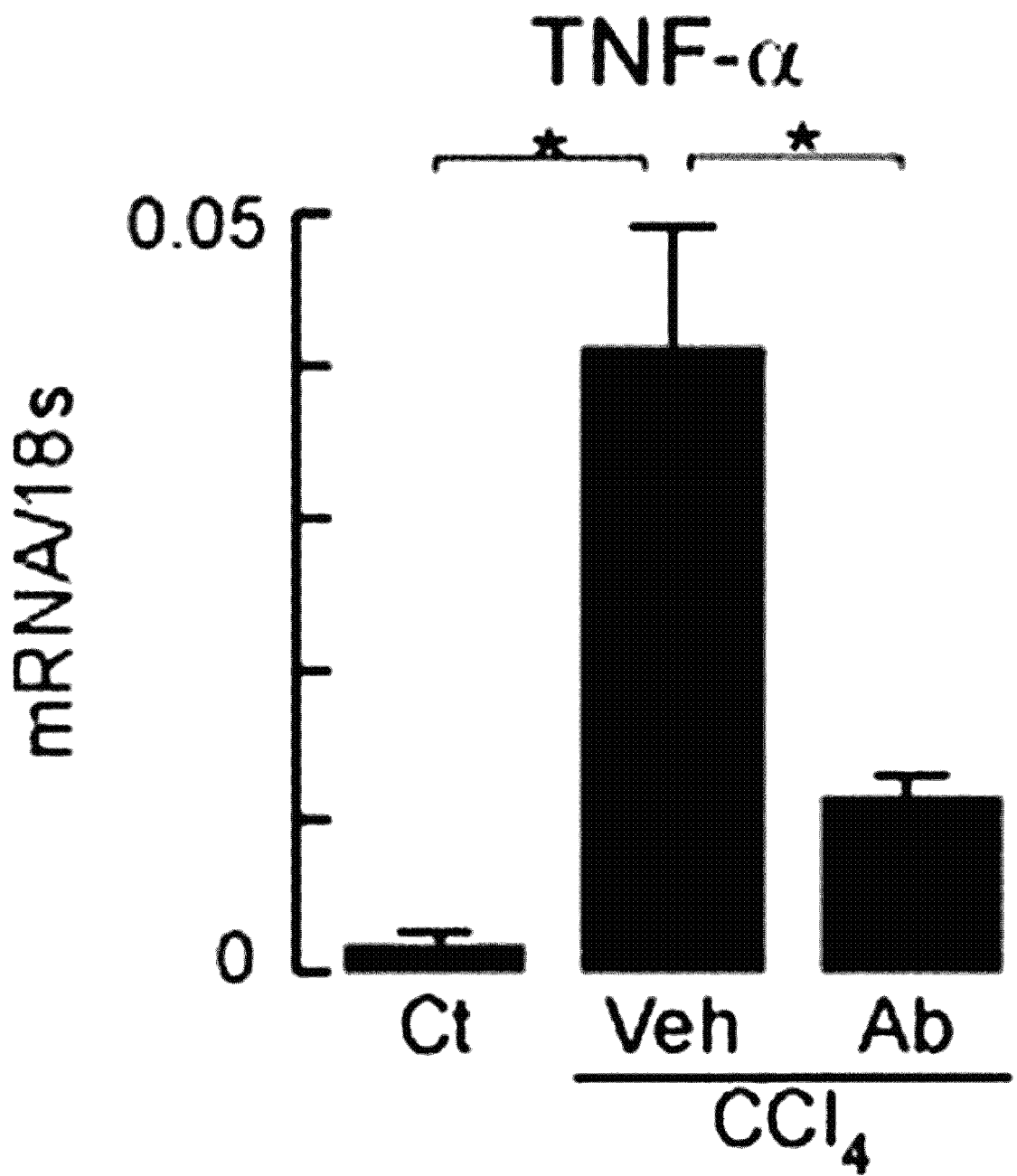

[Fig. 15B]
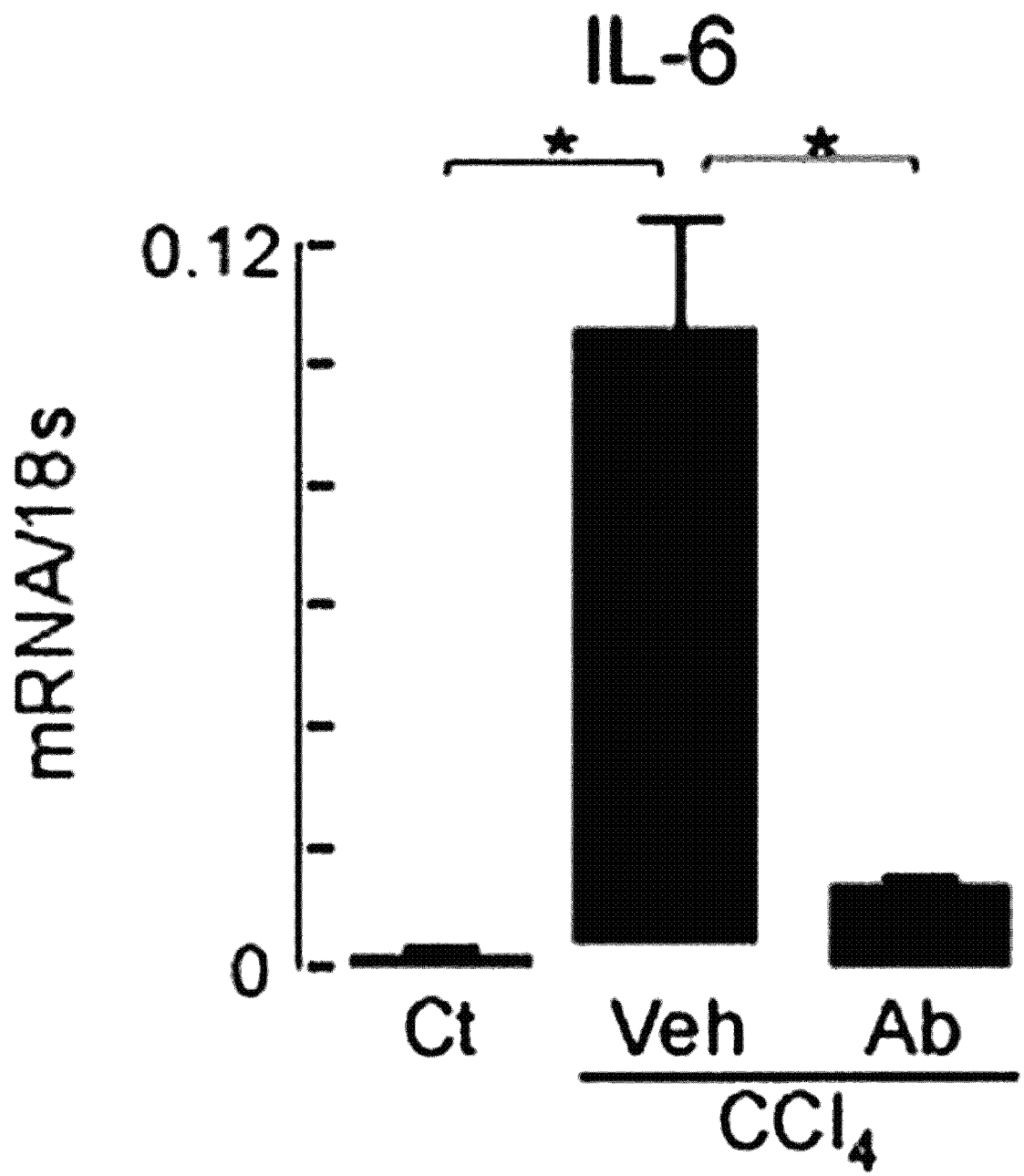

ANTI AQP3 MONOCLONAL ANTIBODY SPECIFICALLY BINDING TO EXTRACELLULAR DOMAIN OF AQUAPORIN 3 (AQP3) AND USE THEREOF

SEQUENCE LISTING

The instant application contains a Sequence Listing which has been submitted electronically in ASCII format and is hereby incorporated by reference in its entirety. Said ASCII copy, created on Jun. 16, 2020, is named AQR-001US_Sequence_Listing.txt and is 205,201 bytes in size.

TECHNICAL FIELD

The present invention relates to an anti AQP3 antibody specifically recognizing the extracellular domain of aquaporin 3 (AQP3), which is one kind of water channel protein. The present invention further relates to a composition containing an anti AQP3 antibody of the present invention, and a reagent for detecting AQP3, a reagent for identifying and separating AQP3-expressing cells, and a reagent for measuring AQP3, which each contain an anti AQP3 antibody of the present invention. The present invention further relates to an anti AQP3 monoclonal antibody (an inhibitory anti AQP3 mAb) which specifically binds to the extracellular domain of AQP3 and has an inhibitory activity against the channel function or the like of AQP3. The present invention further relates to a composition containing an inhibitory anti AQP3 mAb of the present invention, an AQP3 inhibitor containing an inhibitory anti AQP3 mAb of the present invention, and a pharmaceutical composition containing an inhibitory anti AQP3 mAb of the present invention. The present invention further relates to a method for detecting AQP3 by using an anti AQP3 antibody or reagent for detecting AQP3 of the present invention, a method for separating and purifying AQP3-expressing cells by using an anti AQP3 antibody or reagent for identifying and separating AQP3 of the present invention, and a method for measuring AQP3 by using an anti AQP3 antibody or reagent for detecting AQP3 of the present invention. The present invention further relates to a method for inhibiting the function (channel function or the like) of AQP3 by using an inhibitory anti AQP3 mAb, a composition containing an inhibitory anti AQP3 mAb, or AQP3 inhibitor of the present invention, and a method for inhibiting the transport of a low molecular weight material (water, glycerol, hydrogen peroxide, or the like) across a biological membrane by using an inhibitory anti AQP3 mAb, a composition containing an inhibitory anti AQP3 mAb, or AQP3 inhibitor of the present invention. The present invention still further relates to a method for preventing/treating disorders associated with AQP3 by using an inhibitory anti AQP3 mAb, a composition containing an inhibitory anti AQP3 mAb, or a pharmaceutical composition containing an inhibitory anti AQP3 mAb of the present invention.

BACKGROUND ART

A biological membrane has low permeability to water molecules as it is composed of a lipid bilayer. Due to this reason, when it is desired to transport (permeate) water molecules rapidly and also in a large amount across a biological membrane, a water channel comprised of a membrane protein is necessary. Aquaporin (AQP) as a water channel is a membrane protein which has fine holes (pores) which allow pass-through of water molecules only, and it was discovered from red blood cell membranes by Peter Agre's group in 1992. Since then, aquaporin has been discovered in various bacteria, animals, and plants, and is known to be a water channel that is commonly present in a biological system. It is also confirmed that a number of AQP molecular types (isoforms) are present even in one biological species. For example, 13 kinds of aquaporin molecular types, from AQP0 to AQP12, are confirmed in a human. In addition, functional differentiation among molecular types is recognized like molecular types allowing selective pass-through of water molecules (AQP1 and the like) and molecular types allowing pass-through of a low molecular weight material such as water molecule, glycerin, or hydrogen peroxide (AQP3 and the like). It is clearly shown that the 13 kinds of AQP molecular types exhibit various expression patterns in many organs, and, in an organ like a kidney in which water transport frequently occurs, expression of plural molecular types of aquaporin in one organ is recognized.

It has become gradually evident that an abnormal expression and/or function of aquaporin is related to certain disorders. For example, it is known that deficiency of AQP0 can result in congenital cataract. It is known that the reduced expression/function of AQP2 is related to diabetes insipidus, and, on the other hand, it is suggested that hyperactivity of AQP2 is related to edema, high blood pressure, and congestive heart failure, associated with pregnancy. In the case of neuromyelitis optica as a demyelinating disorder, it is known that anti AQP4 autoantibodies are involved with an occurrence of pathological conditions. It is also reported that there is a relation between a mutation in AQP5 and palmoplantar keratoderma (Non Patent Literature 1).

Aquaporin is a membrane protein which traverses the cell membrane six times, and has six transmembrane domains and five loops connecting the transmembrane domains (loop A to loop E). Among the AQP polypeptides in AQP present in a cell membrane, each of the N-terminal regions, loop B, loop D, and C-terminal region is present at the cytoplasmic side, while each of loop A, loop C, and loop E is present at the extracellular side (FIG. 1). This six-transmembrane structure is commonly found in all AQP molecular types.

Although one molecule of aquaporin has one passage route, aquaporin is present as a multimer (homotetramer) in a biological membrane. In addition, aquaporin is responsible for the function of passive transport of low molecular weight molecules like water molecules, glycerol, hydrogen peroxide, carbon dioxide, ammonia, and urea through a passage route.

Although various analyses have been made with regard to the expression characteristics or function of each molecular type of aquaporin, sufficient elucidation is yet to be made. As one reason of not having sufficient elucidation, non-availability of an anti-aquaporin antibody with a sufficient property of identifying each molecular type can be mentioned. At the present moment, there are several reports regarding the obtainment of an anti AQP antibody, and there is also an anti AQP antibody which is commercially supplied. However, most of those antibodies are polyclonal antibodies, and they have the intracellular domain of AQP as an epitope. With a polyclonal antibody, there are many cases in which the specific identifying property is not sufficient, and there is also limitation in that detection or measurement cannot be made with high precision. Furthermore, with a polyclonal antibody, it is practically impossible to carry out the isolation and purification of AQP-expressing cells. Because most of the anti AQP antibodies of a related art are an antibody which recognizes an epitope present inside a cell, there is also limitation in terms of carrying out an immunohistological analysis or an analysis using living cells.

Although the reason of having very limited example of obtaining an antibody which specifically recognizes the extracellular domain of aquaporin remains unclear, a membrane protein like aquaporin is difficult to be handled as an immunogen, and obtaining an antibody which specifically recognizes a membrane protein is not easy in general. It is also considered that, as the sequence conservation is relatively high among biospecies, it is difficult to produce a desired specific antibody when an animal of different species is immunized by using the aquaporin protein or a fragment thereof as an immunogen.

Like other molecular types of AQP, aquaporin 3 (AQP3) is a water channel protein which is localized in a biological membrane and formed of six transmembrane regions (transmembrane regions I to VI) each consisting of an a helix and five loops connecting them (loop A to loop E), and it has a structure in which both the N-terminal region and the C-terminal region are present at the cytoplasmic side. The a helix which traverses the biological membrane forms fine holes (pores) which allow pass-through of a water molecule or other low molecular weight components (glycerol and hydrogen peroxide).

It is known that AQP3 is expressed in various cells including epithelial cells, immune cells, and cancer cells. As one of the cells in which AQP3 is expressed in a large amount, keratinocyte is known. In skin, AQP3 is considered to play an important role in physiological moisturization of skin and recovery of skin wounds as it promotes transport of water and glycerol (Patent Literature 1). Meanwhile, for a skin disorder accompanying abnormal keratinocyte proliferation like psoriasis, actinic keratosis, ichthyosis, and seborrheic dermatitis, therapy based on suppression of AQP3 production by having, as a target, AQP3 as a factor for regulating cell proliferation of keratinocyte is suggested (Patent Literature 2). Involvement with skin cancerization is also reported. A mechanism in which each AQP3 exhibits its physiological activity based on glycerol transporting activity for moisturization, oncogenesis, and recovery of barrier function in skin or based on water molecule transporting activity for recovery of wounded skin is suggested (Non Patent Literature 2).

As for the relationship between AQP3 and cancer, many cases have been reported without being limited to skin cancer. Increased expression level of each AQP3 is confirmed in tissues of colorectal cancer, cervical cancer, liver cancer, lung cancer, esophageal cancer, kidney cancer, stomach cancer, tongue cancer, and the like. It is furthermore suggested that, in those cancers, the AQP3 function is related to progress level, prognosis, tumor angiogenesis, infiltration, metastasis of cancer, and energy metabolism of cancer tissues, and the like. Due to such reasons, although (lowering the expression level of) AQP3 has been suggested as a therapeutic target for those cancers, favorable results have not yet been obtained from an actual trial (Non Patent Literature 1, Non Patent Literature 3, and Non Patent Literature 4). The large intestine is known as one of other main tissues in which AQP3 is expressed, and there is a report indicating the relationship between the expression level and physiological state of AQP3 in intestinal epithelium. According to the report, it is evident that the expression level of AQP3 in large intestine is lowered by several laxatives. Severe constipation caused by morphine is associated with the increased expression level of AQP3 in large intestine (Non Patent Literature 5).

For the analysis of AQP3, a compound suppressing the channel's activity of permeating water molecules or glycerol is reported as an AQP3 inhibitor (Non Patent Literatures 6 and 7). Without being limited to the AQP3 inhibitor, most AQP inhibitors are metal compounds which contain a metal like mercury, copper, or gold. Being a metal compound means that there is a high possibility of exhibiting cytotoxicity. Due to such reasons, although certain usefulness is recognized for this AQP inhibitor, it is limited in terms of the application both in functional analysis using cultured cells and a test in which administration to a test animal is made. Furthermore, molecular type specificity for AQP of the AQP inhibitor as a metal compound is generally not high. For example, there is a report indicating a problem that it causes not only the inhibition on AQP3 but also functional inhibition of other AQP molecular types like AQP1 and AQP4. As such, the administration to a human as a clinical application of the AQP3 inhibitor is not pragmatically feasible.

As another approach of the AQP3 functional analysis, a case in which AQP3 deficient cells or AQP3 knock-down cells are used has been reported (Non Patent Literature 8). It is found that the cell proliferation property or cell migration is reduced and the response caused by inflammation (inflammatory response) is reduced in AQP3 deficient or knock-down cells. It is also reported that, when a treatment causing an inflammatory disorder like atopic dermatitis, psoriasis, asthma or the like is carried out for an AQP3 knock-out mouse, an occurrence of those inflammatory disorders is suppressed compared to a control in which a wild type mouse is used. It is also reported that, in a transplant experiment from cancer cells derived from human to a mouse, cancer malignancy can be suppressed according to knock-down of the expression of AQP3. For the knock-down, an example of using SiRNA, shRNA, and miRNA is reported. However, all of those studies are just at a basic stage, and development of a clinically applicable agent for regulating AQP3 expression is not achieved yet.

For having a progress in the analysis of AQP3, detecting at high precision the expression site or expression level of AQP3 is one of the necessary means. AQP3-specific detection is widely carried out based on detection of accumulation level of AQP3 mRNA by using a specific probe or primer. However, according to an analysis at nucleic acid level, it is impossible to know that AQP3 is actually present at which distribution in which amount. Meanwhile, because an anti AQP3 antibody is established and several antibodies are commercially available, expression analysis of AQP3 can be also made. However, all of the commercially available anti AQP3 antibodies are a polyclonal antibody, and they are not enough for the high-precision analysis. Furthermore, because all of the commercially available anti AQP3 antibodies are an antibody which has, as an epitope, the intracellular domain present at N-terminal part or C-terminal part of the AQP3, it is difficult to have detection of AQP3 by an experiment using living cells. Furthermore, being a polyclonal antibody, they are practically impossible to be used for selecting AQP3-expressing cells using an antibody. Under the circumstances, a monoclonal antibody for AQP3, in particular, a monoclonal antibody specifically recognizing the extracellular domain of AQP3, is strongly desired.

CITATION LIST

Patent Literature

PTL 1: JP 2011-32191 A
PTL 2: WO 2014/013727 A

Non Patent Literature

NPL 1: Verkman et al., Nat. Rev. Drug Discov. (2014) vol. 13, pp. 259-277
NPL 2: Hara-Chikuma et al., J. Invest. Dermatol. (2008) vol. 128, pp. 2145-2151
NPL 3: Papadopoulos and Saadoun, Biochem. Biochim. Acta (2015) vol. 1848, pp. 2576-2583
NPL 4: Wang et al., J. Transl. Med. (2015) vol. 13: 96
NPL 5: Ikarashi et al., Int. J. Mol. Sci. (2016) vol. 17, 1172
NPL 6: Zelenina et al., J. Biol. Chem. (2004) vol. 279, pp. 51939-51943
NPL 7: Martins et al., PLoS ONE (2012) 7(5): e37435
NPL 8: Hara-Chikuma et al., Biochem. Biophys. Res. Commun. (2016) vol. 471, pp. 603-609

SUMMARY OF INVENTION

Technical Problem

An object of the present invention is to provide an anti AQP3 antibody specifically recognizing the extracellular domain of aquaporin 3 (AQP3), which is a kind of water channel protein.

Solution to Problem

In order to provide an anti AQP3 antibody specifically recognizing the extracellular domain of AQP3, the inventors of the present invention performed intensive studies on the structure of AQP3, in particular, the structure of loop A, loop C, and loop E which constitute the extracellular domain, and found that, according to immunization of a host animal by using a fragment (oligopeptide) constituting a part of loop C (extracellular second loop) as an immunogen, together with AQP3-overexpressing cells, a desired antibody specifically recognizing AQP3 can be obtained, plural anti AQP3 monoclonal antibodies (anti AQP3 mAbs) derived from plural hybridoma clones can be obtained, the anti AQP3 mAb specifically binds to an AQP3 polypeptide and the aforementioned fragment, and the anti AQP3 mAb has an activity of specifically inhibiting the AQP3-based channel function, proliferation activity of AQP3-expressing cells, and/or migration activity of AQP3-expressing cells. Based on those findings, the inventors completed the present invention.

According to the present invention, an anti AQP3 antibody specifically recognizing the extracellular domain of AQP3 is provided. Furthermore, a composition containing an anti AQP3 antibody of the present invention, a reagent for detecting AQP3, a reagent for identifying and separating AQP3-expressing cells, and a reagent for measuring AQP3, which each contain an anti AQP3 antibody of the present invention, are provided. Furthermore, a kit including any of those reagents is provided. Furthermore, an anti AQP3 monoclonal antibody (inhibitory anti AQP3 mAb) which specifically binds to the extracellular domain of AQP3 and has an inhibitory activity for the channel function or the like of AQP3 is provided. Furthermore, a composition containing an inhibitory anti AQP3 mAb of the present invention, an AQP3 inhibitor containing an inhibitory anti AQP3 mAb of the present invention, and a pharmaceutical composition containing an inhibitory anti AQP3 mAb of the present invention are provided. Furthermore, an antibody drug conjugate (ADC) comprising an anti AQP3 antibody of the present invention and a cytotoxic agent, and pharmaceutical compositions comprising an ADC are provided. Furthermore, a method for detecting AQP3 by using an anti AQP3 antibody or reagent for detecting AQP3 of the present invention, a method for separating and purifying AQP3-expressing cells by using an anti AQP3 antibody or reagent for identifying and separating AQP3 of the present invention, and a method for measuring AQP3 by using an anti AQP3 antibody or reagent for detecting AQP3 of the present invention are provided. Furthermore, a method for inhibiting a function (channel function or the like) of AQP3 by using an inhibitory anti AQP3 mAb, composition containing an inhibitory anti AQP3 mAb, or AQP3 inhibitor of the present invention, and a method for inhibiting the transport of a low molecular weight material (water, glycerol, hydrogen peroxide, or the like) across a biological membrane by using an inhibitory anti AQP3 mAb, a composition containing the inhibitory anti AQP3 mAb, or AQP3 inhibitor of the present invention are provided. Still furthermore, a method for preventing/treating disorders associated with AQP3 by using an inhibitory anti AQP3 mAb, a composition containing the inhibitory anti AQP3 mAb, or pharmaceutical composition containing an inhibitory anti AQP3 mAb of the present invention is provided.

In one aspect, the present invention provides an anti AQP3 antibody or a functional fragment thereof that specifically binds to an oligopeptide whose amino acid sequence consists of ATYPSGHLDM (SEQ ID NO:1).

In another aspect, the present invention provides an anti AQP3 antibody or a functional fragment thereof comprising a heavy chain complementarity determining region 1 (HCDR1), a heavy chain complementarity determining region 2 (HCRD2), a heavy chain complementarity determining region 3 (HCDR3), a light chain complementarity determining region 1 (LCDR1), a light chain complementarity determining region 2 (LCDR2), and a light chain complementarity determining region 3 (LCDR3) comprising amino acid sequences selected from the sequences set forth in Tables 1A-5E. The CDR sequences in Tables 1A-5E are derived from the amino acid sequences of antibodies A, B, C, D, E, F, G, H, J, and K, described in the Examples. The framework sequences for anti AQP3 antibodies or functional fragments thereof having CDR sequences set forth in Tables 1A-5E can be, for example, murine framework sequences or human framework sequences.

The CDR sequences set forth in Tables 1A-1J include CDR sequences defined by the IMGT, Kabat, and Chothia numbering systems. See, Lefranc et al., 2003, Dev Comparat Immunol 27:55-77 (IMGT numbering system), Kabat et al., 1991, Sequences of Proteins of Immunological Interest, 5th Ed. Public Health Service, National Institutes of Health, Bethesda, Md. (Kabat numbering system), and Al-Lazikani et al., 1997, J. Mol. Biol 273:927-948 (Chothia numbering system). The tables also include sequences that are the common regions of overlap for the IMGT, Kabat, and Chothia CDRs ("IMGT, Kabat, and Chothia common sequences") and sequences that are the combined regions of overlap for the IMGT, Kabat, and Chothia CDRs ("IMGT, Kabat, and Chothia combined overlap sequences").

Sequences in Tables 2A-5E are consensus sequences derived from the CDR sequences set forth in Tables 1A-1J. Specifically, the sequences in Tables 2A-2E are derived from the CDRs for antibodies A, D, E, and G ("Group I"); the sequences in Tables 3A-3F are derived from the CDRs for antibodies B and H ("Group II"); the sequences in Tables 4A-4E are derived from the CDRs for antibodies C and F ("Group III"); and the sequences in Tables 5A-5E are derived from the CDRs for antibodies J and K ("Group IV").

TABLE 1A

| Description | Sequence | SEQ ID NO: |
|---|---|---|
| Antibody A Sequences | | |
| HCDR1 amino acid sequence (IMGT definition) | GYTFTDYE | 28 |
| HCDR2 amino acid sequence (IMGT definition) | VDPETGGT | 29 |
| HCDR3 amino acid sequence (IMGT definition) | ARHGGSFYAMDY | 30 |
| LCDR1 amino acid sequence (IMGT definition) | QDVSTA | 31 |
| LCDR2 amino acid sequence (IMGT definition) | WAS | 32 |
| LCDR3 amino acid sequence (IMGT definition) | QQHYSTPPT | 33 |
| HCDR1 amino acid sequence (Kabat definition) | DYEMH | 34 |
| HCDR2 amino acid sequence (Kabat definition) | GVDPETGGTGYNQKFRG | 35 |
| HCDR3 amino acid sequence (Kabat definition) | HGGSFYAMDY | 36 |
| LCDR1 amino acid sequence (Kabat definition) | KASQDVSTAVA | 37 |
| LCDR2 amino acid sequence (Kabat definition) | WASTRHT | 38 |
| LCDR3 amino acid sequence (Kabat definition) | QQHYSTPPT | 39 |
| HCDR1 amino acid sequence (Chothia definition) | GYTHTDY | 40 |
| HCDR2 amino acid sequence (Chothia definition) | DPETGG | 41 |
| HCDR3 amino acid sequence (Chothia definition) | HGGSFYAMDY | 42 |
| LCDR1 amino acid sequence (Chothia definition) | SQDVSTA | 43 |
| LCDR2 amino acid sequence (Chothia definition) | WAS | 44 |
| LCDR3 amino acid sequence (Chothia definition) | HYSTPPT | 45 |
| HCDR1 amino acid sequence (IMGT, Kabat, and Chothia common sequences) | DY | 46 |
| HCDR2 amino acid sequence (IMGT, Kabat, and Chothia common sequences) | DPETGG | 47 |
| HCDR3 amino acid sequence (IMGT, Kabat, and Chothia common sequences definition) | HGGSFYAMDY | 48 |
| LCDR1 amino acid sequence (IMGT, Kabat, and Chothi a common sequences) | QDVSTA | 49 |
| LCDR2 amino acid sequence (IMGT, Kabat, and Chothia common sequences) | WAS | 50 |
| LCDR3 amino acid sequence (IMGT, Kabat, and Chothia common sequences) | HYSTPPT | 51 |

TABLE 1A-continued

Antibody A Sequences

| Description | Sequence | SEQ ID NO: |
|---|---|---|
| HCDR1 amino acid sequence (IMGT, Kabat, and Chothia combined overlap sequences) | GYTFTDVEMH | 52 |
| HCDR2 amino acid sequence (IMGT, Kabat, and Chothia combined overlap sequences) | GVDPETGGTGYNQKFRG | 53 |
| HCDR3 amino acid sequence (IMGT, Kabat, and Chothia combined overlap sequences) | ARHGGSFYAMDY | 54 |
| LCDR1 amino acid sequence (IMGT, Kabat, and Chothia combined overlap sequences) | KASQOVSTAVA | 55 |
| LCDR2 amino acid sequence (IMGT, Kabat, and Chothia combined overlap sequences) | WASTRHT | 56 |
| LCDR3 amino acid sequence (IMGT, Kabat, and Chothia combined overlap sequences) | QQHYSTPPT | 57 |
| VH amino acid sequence (predicted mature) | QVQLQQPGAELVRPGASVTLSCKASGYTFTDYEMHWVKQTPVHGLEWIGGVDPETGGTGYNQKFRGKAILTADKSSTAYMELRSLTSEDSAVYYCARHGGGFYAMDYWGQGTSVTSS | 309 |
| VL amino acid sequence (predicted mature) | QVQLQQPGAELVRPGASVTLSCKASGYTFTDYEMHWVKQTRVHGLEWIGGVDPETGGTGYMQKFRGKAILTADKSSTAYMELRSLTSEDSAVYYCARHGGSFYAMDYWGQGTSVTSS | 310 |

TABLE 1B

Antibody B Sequences

| Description | Sequence | SEQ ID NO: |
|---|---|---|
| HCDR1 amino acid sequence (IMGT definition) | GFTFSSYG | 58 |
| HCDR2 amino acid sequence (IMGT definition) | ISRGSIYT | 59 |
| HCDR3 amino acid sequence (IMGT definition) | ARLSLYDYDGARYTMDY | 60 |
| LCDR1 amino acid sequence (IMGT definition) | QDVGTA | 61 |
| LCDR2 amino acid sequence (IMGT definition) | WAS | 62 |
| LCDR3 amino acid sequence (IMGT definition) | QQYSSYHT | 63 |
| HCDR1 amine acid sequence (Kabat definition) | SYGMS | 64 |
| HCDR2 amino acid sequence (Kabat definition) | TISRGSIYTYYPDSVKG | 65 |
| HCDR3 amino acid sequence (Kabat definition) | LSLYDYDGARYTMDY | 66 |

TABLE 1B-continued

Antibody B Sequences

| Description | Sequence | SEQ ID NO: |
|---|---|---|
| LCDR1 amino acid sequence (Kabat definition) | KASQDVGTAVA | 67 |
| LCDR2 amino acid sequence (Kabat definition) | WASTRHT | 68 |
| LCDR3 amino acid sequence (Kabat definition) | QQYSSYHT | 69 |
| HCDR1 amino acid sequence (Chothia definition) | GFTFSSY | 70 |
| HCDR2 amino acid sequence (Chothia definition) | SRGSIY | 71 |
| HCDR3 amino acid secuence (Chothia (definition) | LSLYDYDGARYTMDY | 72 |
| LCDR1 amino acid sequence (Chothia definition) | SQDVGTA | 73 |
| LCDR2 amino acid sequence (Chothia definition) | WAS | 74 |
| LCDR3 amino acid sequence (Chothia definition) | YSSYHT | 75 |
| HCDR1 amino acid sequence (IMGT, Kabat, and Chothia common sequences) | SY | 76 |
| HCDR2 amino acid sequence (IMGT, Kabat, and Chothia common sequences) | SRGSIY | 77 |
| HCDR3 amino acid sequence (IMGT, Kabat, and Chothia common sequences definition) | LSLYDYDGARYTMDY | 78 |
| LCDR1 amino acid sequence (IMGT, Kabat, and Chothia cornmon sequences) | QDVGTA | 79 |
| LCDR2 amino acid sequence (IMGT, Kabat, and Chothia common sequences) | WAS | 80 |
| LCDR3 amino acid sequence (IMGT, Kabat, and Chothia common sequences) | YSSYHT | 81 |
| HCDR1 amino acid sequence (IMGT, Kabat, and Chothia combined overlap sequences) | GFTFSSYGMS | 82 |
| HCDR2 amino acid sequence (IMGT, Kabat, and Chothia combined overlap sequences) | TISRGSIYTYYPDSVKG | 83 |
| HCDR3 amino acid sequence (IMGT, Kabat, and Chothia combined overlap sequences) | ARLSLYDYDGARYTMDY | 84 |
| LCDR1 amino acid sequence (IMGT, Kabat, and Chothia combined overlap sequences) | KASQDVGTAVA | 85 |
| LCDR2 amino acid sequence (IMGT, Kabat, and Chothis combined overlap sequences) | WASTRHT | 86 |
| LCDR3 amino acid sequence (IMGT, Kabat, and Chothia combined overlap sequences) | QQYSSYHT | 87 |
| VH amino acid sequence (predicted mature) | EVQLVESGGDLVKPGGSLKL SCAASGFTFSSYGMSWVRQT PDKRLEWVATISRGSIYTYY PDSVKGRFTISRDNAKNTLY | 311 |

TABLE 1B-continued

Antibody B Sequences

| Description | Sequence | SEQ ID NO: |
|---|---|---|
| | LQMSSLKSEDTAMYYCARLS LYDYDGARYTMDYWGQGTSV TVSS | |
| VL amino acid sequence (predicted mature) | DIVMTQSPKFMSTSVGDRVS ITCKASQDVGTAVAWYQQKP GQSPKLLIYWASTRHTGVPD RFTGSGSGTDFTLTISNVQS EDLADYFCQQYSSYHTFGAG TKLELK | 312 |

TABLE 1C

Antibody C Sequences

| Description | Sequence | SEQ ID NO: |
|---|---|---|
| HCDR1 amino acid sequence (IMGT definition) | GYNFKSYG | 88 |
| HCDR2 amino acid sequence (IMGT definition) | IYPGSGNT | 89 |
| HCDR3 amino acid sequence (IMGT definition) | ARTYGYDSFPWFAY | 90 |
| LCDR1 amino acid sequence (IMGT definition) | KSLLHSNGNTY | 91 |
| LCDR2 amino acid sequence (IMGT definition) | RVS | 92 |
| LCDR3 amino acid sequence (IMGT definition) | MQHLEYPFT | 93 |
| HCDR1 amino acid sequence (Kabat definition) | SYGIS | 94 |
| HCDR2 amino acid sequence (Kabat definition) | EIYPGSGNTYYNEKLKG | 95 |
| HCDR3 amino acid sequence (Kabat definition) | TYGYDSFPWFAY | 96 |
| LCDR1 amino acid sequence (Kabat definition) | RSSKSLLHSNGNTYLY | 97 |
| LCDR2 amino acid sequence (Kabat definition) | RVSNLAS | 98 |
| LCDR3 amino acid sequence (Kabat definition) | MQHLEYPFT | 99 |
| HCDR1 amino acid sequence (Chothia definition) | GYNFKSY | 100 |
| HCDR2 amino acid sequence (Chothia definition) | YPGSGN | 101 |
| HCDR3 amino acid sequence (Chothia definition) | TYGYDSFPWFAY | 102 |
| LCDR1 amino acid sequence (Chothia definition) | SKSLLHSNGNTY | 103 |
| LCDR2 amino acid sequence (Chothia definition) | RVS | 104 |
| LCDR3 amino acid sequence (Chothia definition) | HLEYPFT | 105 |

TABLE 1C-continued

Antibody C Sequences

| Description | Sequence | SEQ ID NO: |
|---|---|---|
| HCDR1 amino acid sequence (IMGT, Kabat, and Chothia common sequences) | SY | 106 |
| HCDR2 amino acid sequence (IMGT, Kabat, and Chothia common sequences) | YPGSGN | 107 |
| HCDR3 amino acid sequence (IMGT, Kabat, and Chothia common sequences definition) | TYGYDSFPWFAY | 108 |
| LCDR1 amino acid sequence (IMGT, Kabat, and Chothia common sequences) | KSLLHSNGNTY | 109 |
| LCDR2 amino acid sequence (IMGT, Kabat, and Chothia common sequences) | WAS | 110 |
| LCDR3 amino acid sequence (IMGT, Kabat, and Chothia common sequences) | HLEYPFT | 469 |
| HCDR1 amino acid sequence (IMGT, Kabat, and Chothia combined overlap sequences) | GYNFKSYGIS | 111 |
| HCDR2 amino acid sequence (IMGT, Kabat, and Chothia combined overlap sequences) | EIYPGSGNTYYNEKLKG | 112 |
| HCDR3 amino acid sequence (IMGT, Kabat, and Chothia combined overlap sequences) | ARTYGYDSFPWFAY | 113 |
| LCDR1 amino acid sequence (IMGT, Kabat, and Chothia combined overlap sequences) | RSSKSLLHSNGNTYLY | 114 |
| LCDR2 amino acid sequence (IMGT, Kabat, and Chothia combined overlap sequences) | RVSNLAS | 115 |
| LCDR3 amino acid sequence (IMGT, Kabat, and Chothia combined overlap sequences) | MQHLEYPFT | 116 |
| VH amino acid sequence (predicted mature) | QVQLKQSGAELARPGASVKLSCKASGYNFKSYGISWVKQRTGQGLEWIGEIYPGSGNTYYNEKLKGKATLTADKSSSTAYMELRSLTSEDSAVYFCARTYGYDSFPWFAYWGQGTLVTVSS | 313 |
| VL amino acid sequence (predicted mature) | DIVMTQAAPSVPVTPGESVSISCRSSKSLLHSNGNTYLYWFLQRPGQSPQLLIYRVSNLASGVPDRFSGSGSGTAFTLRISRVEAEDEGVYYCMQKLEYPFTFGAGTKLEIK | 314 |

TABLE 1D

Antibody D Sequences

| Description | Sequence | SEQ ID NO: |
|---|---|---|
| HCDR1 amino acid sequence (IMGT definition) | GYTFTDYE | 117 |

TABLE 1D-continued

Antibody D Sequences

| Description | Sequence | SEQ ID NO: |
|---|---|---|
| HCDR2 amino acid sequence (IMGT definition) | IDPETGGT | 118 |
| HCDR3 amino acid sequence (IMGT definition) | TRHGSYAMDY | 119 |
| LCDR1 amino acid sequence (IMGT definition) | QDVSTA | 120 |
| LCDR2 amino acid sequence (IMGT definition) | WAS | 121 |
| LCDR3 amino acid sequence (IMGT definition) | QQHYSTPPT | 122 |
| HCDR1 amino acid sequence (Kabat definition) | DYEMH | 123 |
| HCDR2 amino acid sequence (Kabat definition) | GIDPETGGTGYNQKFKG | 124 |
| HCDR3 amino acid sequence (Kabat definition) | HGSYAMDY | 125 |
| LCDR1 amino acid sequence (Kabat definition) | KASQDVSTAVA | 126 |
| LCDR2 amino acid sequence (Kabat definition) | WASTRHT | 127 |
| LCDR3 amino acid sequence (Kabat definition) | QQHYSTPPT | 123 |
| HCDR1 amino acid sequence (Chothia definition) | GYTFTDY | 129 |
| HCDR2 amino acid sequence (Chothia definition) | DPETGG | 130 |
| HCDR3 amino acid sequence (Chothia definition) | HGSYAMDY | 131 |
| LCDR1 amino acid sequence (Chothia definition) | SQDVSTA | 132 |
| LCDR2 amino acid sequence (Chothia definition) | WAS | 133 |
| LCDR3 amino acid sequence (Chothia definition) | HYSTPPT | 134 |
| HCDR1 amino acid sequetice (IMGT, Kabat, and Chothia common sequences) | DY | 135 |
| HCDR2 amino acid sequence (IMGT, Kabat, and Chothia common sequences) | DPETGG | 136 |
| HCDR3 amino acid sequence (IMGT, Kabat, and Chothia common sequences definition) | HGSYAMDY | 137 |
| LCDR1 amino acid sequence (IMGT, Kabat, and Chothia common sequences) | QDVSTA | 133 |
| LCDR2 amino acid sequence (IMGT, Kabat, and Chothia common sequences) | WAS | 139 |
| LCDR3 amino acid sequence (IMGT, Kabat, and Chothia common sequences) | HYSTPPT | 140 |
| BCDR1 amino acid sequence (IMGT, Kabat, and Chothia combined overlap sequences) | GYTFTDYEMH | 141 |

TABLE 1D-continued

Antibody D Sequences

| Description | Sequence | SEQ ID NO: |
|---|---|---|
| HCDR2 amino acid sequence (IMGT, Kabat, and Chothia combined overlap sequences) | GIDPETGGTGYNQKFKG | 142 |
| HCDR3 amino acid sequence (IMGT, Kabat, and Chothia combined overlap sequences) | TRHGSYAMDY | 143 |
| LCDR1 amino acid sequence (IMGT, Kabat, and Chothia combined overlap sequences) | KASQDVSTAVA | 144 |
| LCDR2 amino acid sequence (IMGT, Kabat, and Chothia combined overlap sequences) | WASTRHT | 145 |
| LCDR3 amino acid sequence (IMGT, Kabat, and Chothia combined overlap sequences) | QQHYSTPPT | 146 |
| VH amino acid sequence (predicted mature) | EVQLQQSGAELVRPGASVTL SCKASGYTFTDYEMHWVQQT PVHGLEWIGGIDPETGGTGY NQKFKGKAILTADKSSSTAY MELRSLTSEDSAVYFCTRHG SYAMDYWGQGTSVTVSS | 315 |
| VL amino acid sequence (predicted mature) | DIVMTQSPKFMSTSVGDRVS ITCKASQDVSTAVAWYQQKP GQSPKLLIYWASTRHTGVPD RFTGSGSGTDYTLTISSVQA EDLALYYCQQHYSTPPTFGG GTRLEIK | 316 |

TABLE 1E

Antibody E Sequences

| Description | Sequence | SEQ ID NO: |
|---|---|---|
| HCDR1 amine acid sequence (IMGT definition) | GYTFTDYE | 147 |
| HCDR2 amino acid sequence (IMGT definition) | IDPESGGT | 148 |
| HCDR3 amino acid sequence (IMGT definition) | TRSGYYGSPLLDY | 149 |
| LCDR1 amino acid sequence (IMGT definition) | SSVSSSY | 150 |
| LCDR2 amino acid sequence (IMGT definition) | STS | 151 |
| LCDR3 amino acid sequence (IMGT definition) | HQYHRSPRT | 152 |
| HCDR1 amino acid sequence (Kabat definition) | DYEMH | 153 |
| HCDR2 amino acid sequence (Kabat definition) | GIDPESGGTGYNQKFKG | 154 |
| HCDR3 amino acid sequence (Kabat definition) | SGYYGSPLLDY | 155 |
| LCDR1 amino acid sequence (Kabat definition) | TASSSVSSSYLH | 156 |

TABLE 1E-continued

Antibody E Sequences

| Description | Sequence | SEQ ID NO: |
|---|---|---|
| LCDR2 amino acid sequence (Kabat definition) | STSNLAS | 157 |
| LCDR3 amino acid sequence (Kabat definition) | HQYHRSPPT | 158 |
| HCDR1 amino acid sequence (Chothia definition) | GYTFTDY | 159 |
| HCDR2 amino acid sequence (Chothia definition) | DPSSGG | 160 |
| HCDR3 amino acid sequence (Chothia definition) | SGYYGSPLLDY | 161 |
| LCDR1 amino acid sequence (Chothia definition) | SSSVSSSY | 162 |
| LCDR2 amino acid sequence (Chothia definition) | STS | 163 |
| LCDR3 amino acid sequence (Chothia definition) | YHRSPPT | 164 |
| HCDR1 amino acid sequence (IMGT, Kabat, and Chothia common sequences) | DY | 165 |
| HCDR2 amino acid sequence (IMGT, Kabat, and Chothia common sequences) | DPESGG | 166 |
| HCDR3 amino acid sequence (IMGT, Kabat, and Chothia common sequences definition) | SGYYGSPLLDY | 167 |
| LCDR1 amino acid sequence (IMGT, Kabat, and Chothia common sequences) | SSSVSSSY | 168 |
| LCDR2 amino acid sequence (IMGT, Kabat, and Chothia common sequences) | STS | 169 |
| LCDR3 amino acid sequence (IMGT, Kabat, and Chothia cerumen sequences) | YHRSPPT | 170 |
| HCDR1 amino acid sequence (IMGT, Kabat, and Chothia combined overlap sequences) | GYTFTDYEMH | 171 |
| HCDR2 amino acid sequence (IMGT, Kabat, and Chothia combined overlap sequences) | GIDPESGGTGYNQKFKG | 172 |
| HCDR3 amino acid sequence (IMGT, Kabat, and Chothia combined overlap sequences) | TRSGYYGSPLLDY | 173 |
| LCDR1 amino acid sequence (IMGT, Kabat, and Chothia combined overlap sequences) | TASSSVSSSYLH | 174 |
| LCDR2 amino acid sequence (IMGT, Kabat, and Chothia combined overlap sequences) | STSNLAS | 175 |
| LCDR3 amino acid sequence (IMGT, Kabat, and Chothia combined overlap sequences) | HQYHRSPPT | 176 |
| VH amino acid sequence (predicted mature) | EVKLLESGAELVRPGASVTLSCKASGYTFTDYEMHWVKQTPVHGLEWIGGIDPESGGTGYNQKFKGKAILTADKSSSTAYMELRSLTSEDSAVYFCTRSGYYGSPLLDYWGQGTTLTVSS | 317 |

TABLE 1E-continued

Antibody E Sequences

| Description | Sequence | SEQ ID NO: |
|---|---|---|
| VL amino acid sequence (predicted mature) | QIVLSQSPAIMSASLGERVT MTCTASSSVSSSYLHWYQQK PGSSPKLWIYSTSNLASGVP ARFSGSGSGTSYSLTISSME AEDAATYYCHQYHRSPPTFG AGTKLEIK | 318 |

TABLE 1F

Antibody F Sequences

| Description | Sequence | SEQ ID NO: |
|---|---|---|
| HCDR1 amino acid sequence (IMGT definition) | GYTFTDYY | 10 |
| HCDR2 amino acid sequence (IMGT definition) | IFPGSGST | 11 |
| HCDR3 amino acid sequence (IMGT definition) | ADYGSSYRYFDV | 12 |
| LCDR1 amino acid sequence (IMGT definition) | SSVSY | 13 |
| LCDR2 amino acid sequence (IMGT definition) | ATS | 14 |
| LCDR3 amino acid sequence (IMGT definition) | QQWSSNPLT | 15 |
| HCDR1 amino acid sequence (Kabat definition) | DYYIN | 207 |
| HCDR2 amino acid sequence (Kabat definition) | WIFPGSGSTYYNEKFKG | 208 |
| HCDR3 amino acid sequence (Kabat definition) | YGSSYRYFDV | 209 |
| LCDR1 amino acid sequence (Kabat definition) | RASSSVSYMH | 210 |
| LCDR2 amino acid sequence (Kabat definition) | ATSYLAS | 211 |
| LCDR3 amino acid sequence (Kabat definition) | QQWSSNPLT | 212 |
| HCDR1 amino acid sequence (Chothia definition) | GYTFTDY | 213 |
| HCDR2 amino acid sequence (Chothia definition) | FPGSGS | 214 |
| HCDR3 amino acid sequence (Chothia definition) | YGSSYRYFDV | 215 |
| LCDR1 amino acid sequence (Chothia definition) | SSSVSY | 216 |
| LCDR2 amino acid sequence (Chothia definition) | ATS | 217 |
| LCDR3 amino acid sequence (Chothia definition) | WSSNPLT | 218 |
| HCDR1 amino acid sequence (IMGT, Kabat, and Chothia common sequences) | DY | 219 |

TABLE 1F-continued

Antibody F Sequences

| Description | Sequence | SEQ ID NO: |
|---|---|---|
| HCDR2 amino acid sequence (IMGT, Kabat, and Chothia common sequences) | FPGSGS | 220 |
| HCDR3 amino acid sequence (IMGT, Kabat, and Chothia common sequences definition) | YGSSYRYFDV | 221 |
| LCDR1 amino acid sequence (IMGT, Kabat, and Chothia common sequences) | SSVSY | 222 |
| LCDR2 amino acid sequence (IMGT, Kabat, and Chothia common sequences) | ATS | 223 |
| LCDR3 amino acid sequence (IMGT, Kabat, and Chothia common sequences) | WSSNPLT | 224 |
| HCDR1 amino acid sequence (IMGT, Kabat, and Chothia combined overlap sequences) | GYTFTDYYIN | 225 |
| HCDR2 amino acid sequence (IMGT, Kabat, and Chothia combined overlap sequences) | WIFPGSGSTYYNERFKG | 226 |
| HCDR3 amino acid sequence (IMGT, Kabat, and Chothia combined overlap sequences) | ADYGSSYRYFDV | 227 |
| LCDR1 amino acid sequence (IMGT, Kabat, and Chothia combined overlap sequences) | RASSSVSYMH | 228 |
| LCDR2 amino acid sequence (IMGT, Kabat, and Chothia combined overlap sequences) | ATSYLAS | 229 |
| LCDR3 amino acid sequence (IMGT, Kabat, and Chothia combined overlap sequences) | QQWSSNPLT | 230 |
| VH amino acid sequence (predicted mature) | QVQLRESGPELVRPGASVRISCKASGYTFTDYYINWVKQRPGQGLEWIGWIFPGSGSTYYNERFRGRATLTVDRSSSTAYMLLSSLTSEDSAVYFCADYGSSYRYFDVWGAGTTVTVSS | 321 |
| VL amino acid sequence (predicted mature) | DIVMTQSPAILSASPGEKVTMTCRASSSVSYMHWYQQKPGSSPKPWIYATSYLASGVPARFSGSGSGTSYSLTIGRVEAEDAATYYCQQWSSNPLTFGAGTKLELK | 322 |

TABLE 1G

Antibody G Sequences

| Description | Sequence | SEQ ID NO: |
|---|---|---|
| HCDR1 amino acid sequence (IMGT definition) | GYTFTDYE | 177 |
| HCDR2 amino acid sequence (IMGT definition) | IDPETGGT | 178 |
| HCDR3 amino acid sequence (IMGT definition) | TRWGAITSFVALRGFAY | 179 |
| LCDR1 amino acid sequence (IMGT definition) | QSLLNSGNQKNY | 180 |

TABLE 1G-continued

Antibody G Sequences

| Description | Sequence | SEQ ID NO: |
| --- | --- | --- |
| LCDR2 amino acid sequence (IMGT definition) | GAS | 181 |
| LCDR3 amino acid sequence (IMGT definition) | QNDHSYPPT | 182 |
| HCDR1 amino acid sequence (Kabat definition) | DYEMH | 183 |
| HCDR2 amino acid sequence (Kabat definition) | GIDPETGGTAYNQKFKG | 184 |
| HCDR3 amino acid sequence (Kabat definition) | WGAITSFVALRGFAY | 185 |
| LCDR1 amino acid sequence (Kabat definition) | KSSQSLLNSGNQKNYLA | 186 |
| LCDR2 amino acid sequence (Kabat definition) | GASTRES | 187 |
| LCDR3 amino acid sequence (Kabat definition) | QNDHSYPPT | 188 |
| HCDR1 amino acid sequence (Chothia definition) | GYTFTDY | 189 |
| HCDR2 amino acid sequence (Chothia definition) | DPETGG | 190 |
| HCDR3 amino acid sequence (Chothia definition) | WGAITSFVALRGFAY | 191 |
| LCDR1 amino acid sequence (Chothia definition) | SQSLLNSGNQKNY | 192 |
| LCDR2 amino acid sequence (Chothia definition) | GAS | 193 |
| LCDR3 amino acid sequence (Chothia definition) | DHSYPPT | 194 |
| HCDR1 amino acid sequence (IMGT, Kabat, and Chothia common sequences) | DY | 195 |
| HCDR2 amino acid sequence (IMGT, Kabat, and Chothia common sequences) | DPETGG | 196 |
| HCDR3 amino acid sequence (IMGT, Kabat, and Chothia common sequences definition) | WGAITSFVALRGFAY | 197 |
| LCDR1 amino acid sequence (IMGT, Kabat, and Chothia common sequences) | QSLLNSGNQKNY | 198 |
| LCDR2 amino acid sequence (IMGT, Kabat, and Chothia common sequences) | GAS | 199 |
| LCDR3 amino acid sequence (IMGT, Kabat, and Chothia common sequences) | DHSYPPT | 200 |
| HCDR1 amino acid sequence (IMGT, Kabat, and Chothia combined overlap sequences) | GYTFTDYEMH | 201 |
| HCDR2 amino acid sequence (IMGT, Kabat, and Chothia combined overlap sequences) | GIDPETGGTAYNQKFKG | 202 |
| HCDR3 amino acid sequence (IMGT, Kabat, and Chothia combined overlap sequences) | TRWGAITSFVALRGFAY | 203 |

TABLE 1G-continued

Antibody G Sequences

| Description | Sequence | SEQ ID NO: |
|---|---|---|
| LCDR1 amino acid sequence (IMGT, Kabat, and Chothia combined overlap sequences) | KSSQSLLNSGNQKNYLA | 204 |
| LCDR2 amino acid sequence (IMGT, Kabat, and Chothia combined overlap sequences) | GASTRES | 205 |
| LCDR3 amino acid sequence (IMGT, Kabat, and Chothia combined overlap sequences) | QNDHSYPPT | 206 |
| VH amino acid sequence (predicted mature) | QVQLKQSGAELVRPGASVTL SCKASGYTFTDYEMHWVKQT PVHGLEWIGGIDPETGGTAY NQKFKGKAILTADKSSSTAY MELRSLTSEDSAVYYCTRWG AITSFVALRGFAYWGQTLV TVSS | 319 |
| VL amino acid sequence (predicted mature) | DIQMTQSPSSLSVSAGEKVT MSCKSSQSLLNSGNQKNYLA WYQQKPGQPPKLLIYGASTR ESGVPDRFTGSGSGTDFTLT ISSVQAEDLAVYYCQNDHSY PPTFGAGTKLELK | 320 |

TABLE 1H

Antibody H Sequences

| Description | Sequence | SEQ ID NO: |
|---|---|---|
| HCDR1 amino acid sequence (IMGT definition) | GFTFSSYG | 16 |
| HCDR2 amino acid sequence (IMGT definition) | ISRRSIYT | 17 |
| HCDR3 amino acid sequence (IMGT definition) | ARLSLYDYDGARYTMDY | 18 |
| LCDR1 amino acid sequence (IMGT definition) | QDVGTA | 19 |
| LCDR2 amino acid sequence (IMGT definition) | WAS | 20 |
| LCDR3 amino acid sequence (IMGT definition) | QQYSSYHT | 21 |
| HCDR1 amino acid sequence (Kabat definition) | SYGMS | 231 |
| HCDR2 amino acid sequence (Kabat definition) | TISRRSIYTYYPDSVQG | 232 |
| HCDR3 amino acid sequence (Kabat definition) | LSLYDYDGARYTMDY | 233 |
| LCDR1 amino acid sequence (Kabat definition) | KASQDVGTAVA | 234 |
| LCDR2 amino acid sequence (Kabat definition) | WASTRHT | 235 |
| LCDR3 amino acid sequence (Kabat definition) | QQYSSYHT | 236 |
| HCDR1 amino acid sequence (Chothia definition) | GFTFSSY | 237 |

TABLE 1H-continued

Antibody H Sequences

| Description | Sequence | SEQ ID NO: |
|---|---|---|
| HCDR2 amino acid sequence (Chothia definition) | SRRSIY | 238 |
| HCDR3 amino acid sequence (Chothia definition) | LSLYDYDGARYTMDY | 239 |
| LCDR1 amino acid sequence (Chothia definition) | SQDVGTA | 240 |
| LCDR2 amino acid sequence (Chothia definition) | WAS | 241 |
| LCDR3 amino acid sequence (Chothia definition) | YSSYHT | 242 |
| HCDR1 amino acid sequence (IMGT, Kabat, and Chothia common sequences) | SY | 243 |
| HCDR2 amino acid sequence (IMGT, Kabat, and Chothia common sequences) | SRRSIY | 244 |
| HCDR3 amino acid sequence (IMGT, Kabat, and Chothia common sequences definition) | LSLYDYDGARYTMDY | 245 |
| LCDR1 amino acid sequence (IMGT, Kabat, and Chothia common sequences) | QDVGTA | 246 |
| LCDR2 amino acid sequence (IMGT, Kabat, and Chothia common sequences) | WAS | 247 |
| LCDR3 amino acid sequence (IMGT, Kabat, and Chothia common sequences) | YSSYHT | 248 |
| HCDR1 amino acid sequence (IMGT, Kabat, and Chothia combined overlap sequences) | GFTFSSYGMS | 249 |
| HCDR2 amino acid sequence (IMGT, Kabat, and Chothia combined overlap sequences) | TISRRSIYTYYPDSVQG | 250 |
| HCDR3 amino acid sequence (IMGT, Kabat, and Chothia combined overlap sequences) | ARLSLYDYDGARYTMDY | 251 |
| LCDR1 amino acid sequence (IMGT, Kabat, and Chothia combined overlap sequences) | KASQDVGTAVA | 252 |
| LCDR2 amino acid sequence (IMGT, Kabat, and Chothia combined overlap sequences) | WASTRHT | 253 |
| LCDR3 amino acid sequence (IMGT, Kabat, and Chothia combined overlap sequences) | QQYSSYHT | 254 |
| VH amino acid sequence (predicted mature) | EVKLVESGGDLVKPGGSLKLSCAASGFTFSSYGMSWVRQTPDKRLEWVATISRRSIYTYYPDSVQGRFTISRDNAKNTLYLQMSSLKSEDTAMYYCARLSLYDYDGARYTMDYWGQGTSVTVSS | 323 |
| VL amino acid sequence (predicted mature) | DIKMTQSPKFMSTSVGDRVSITCKASQDVGTAVAWYQQKPGQSPKLLIYWASTRHTGVPDRFTGSGSGTDFTLTISNVQSEDLADYFCQQYSSYHTFGAGTKLEIK | 324 |

TABLE 1I

Antibody J Sequences

| Description | Sequence | SEQ ID NO: |
| --- | --- | --- |
| HCDR1 amino acid sequence (IMGT definition) | GYTFTSYW | 22 |
| HCDR2 amino acid sequence (IMGT definition) | INPSNGGT | 23 |
| HCDR3 amino acid sequence (IMGT definition) | ARGGIYYGNYDYYAMDY | 24 |
| LCDR1 amino acid sequence (IMGT definition) | KSLLHSNGNTY | 25 |
| LCDR2 amino acid sequence (IMGT definition) | RVS | 26 |
| LCDR3 amino acid sequence (IMGT definition) | MQHLEYPFT | 27 |
| HCDR1 amino acid sequence (Kabat definition) | SYWMH | 255 |
| HCDR2 amino acid sequence (Kabat definition) | NINPSNGGTNYNEKFKS | 256 |
| HCDR3 amino acid sequence (Kabat definition) | GGIYYGNYDYYAMDY | 257 |
| LCDR1 amino acid sequence (Kabat definition) | RSSKSLLHSNGNTYLY | 258 |
| LCDR2 amino acid sequence (Kabat definition) | RVSNLAS | 259 |
| LCDR3 amino acid sequence (Kabat definition) | MQHLEYPFT | 260 |
| HCDR1 amino acid sequence (Chothia definition) | GYTFTSY | 261 |
| HCDR2 amino acid sequence (Chothia definition) | NPSNGG | 262 |
| HCDR3 amino acid sequence (Chothia definition) | GGIYYGNYDYYAMDY | 263 |
| LCDR1 amino acid sequence (Chothia definition) | SKSLLHSNGNTY | 264 |
| LCDR2 amino acid sequence (Chothia definition) | RVS | 265 |
| LCDR3 amino acid sequence (Chothia definition) | HLEYPFT | 266 |
| HCDR1 amino acid sequence (IMGT, Kabat, and Chothia common sequences) | SY | 267 |
| HCDR2 amino acid sequence (IMGT, Kabat, and Chothia common sequences) | NPSNGG | 268 |
| HCDR3 amino acid sequence (IMGT, Kabat, and Chothia common sequences definition) | GGIYYGNYDYYAMDY | 269 |
| LCDR1 amino acid sequence (IMGT, Kabat, and Chothia common sequences) | KSLLHSNGNTY | 270 |
| LCDR2 amino acid sequence (IMGT, Kabat, and Chothia common sequences) | RVS | 271 |
| LCDR3 amino acid sequence (IMGT, Kabat, and Chothia common sequences) | HLEYPFT | 272 |

TABLE 1I-continued

Antibody J Sequences

| Description | Sequence | SEQ ID NO: |
|---|---|---|
| HCDR1 amino acid sequence (IMGT, Kabat, and Chothia combined overlap sequences) | GYTFTSYWMH | 273 |
| HCDR2 amino acid sequence (IMGT, Kabat, and Chothia combined overlap sequences) | NINPSNGGTNYNEKFKS | 274 |
| HCDR3 amino acid sequence (IMGT, Kabat, and Chothia combined overlap sequences) | ARGGIYYGNYDYYAMDY | 275 |
| LCDR1 amino acid sequence (IMGT, Kabat, and Chothia combined overlap sequences) | RSSKSLLHSNGNTYLY | 276 |
| LCDR2 amino acid sequence (IMGT, Kabat, and Chothia combined overlap sequences) | RVSNLAS | 277 |
| LCDR3 amino acid sequence (IMGT, Kabat, and Chothia combined overlap sequences) | MQHLEYPFT | 278 |
| VH amino acid sequence (predicted mature) | QVHLQQSGTELVKPGASVKLSCEASGYTFTSYWMHWVKQRPGQGLEWIGNINPSNGGTNYNEKFKSKATLTVDKSSSTAYMQLSSLTSEDSAVYYCARGGIYYGNYDYYAMDYWGQGTSVTVSS | 325 |
| VL amino acid sequence (predicted mature) | DIVMTQAAPSVPVTPGESVSISCRSSKSLLHSNGNTYLYWFLQRPGQSPQLLIYRVSNLASGVPDRFSGSGSGTAFTLRISRVEAEDVGVYYCMQHLEYPFTFGGGTKLEIK | 326 |

TABLE 1J

Antibody K Sequences

| Description | Sequence | SEQ ID NO: |
|---|---|---|
| HCDR1 amino acid sequence (IMGT definition) | GYAFTNYL | 279 |
| HCDR2 amino acid sequence (IMGT definition) | INPGSGGT | 280 |
| HCDR3 amino acid sequence (IMGT definition) | ARWGFYYAMDY | 281 |
| LCDR1 amino acid sequence (IMGT definition) | QEISGY | 282 |
| LCDR2 amino acid sequence (IMGT definition) | AAS | 283 |
| LCDR3 amino acid sequence (IMGT definition) | LQYASYPLT | 284 |
| HCDR1 amino acid sequence (Kabat definition) | NYLIE | 285 |
| HCDR2 amino acid sequence (Kabat definition) | VINPGSGGTNYNEKFKG | 286 |
| HCDR3 amino acid sequence (Kabat definition) | WGFYYAMDY | 287 |

TABLE 1J-continued

Antibody K Sequences

| Description | Sequence | SEQ ID NO: |
|---|---|---|
| LCDR1 amino acid sequence (Kabat definition) | RASQEISGYLS | 288 |
| LCDR2 amino acid sequence (Kabat definition) | AASTLDS | 289 |
| LCDR3 amino acid sequence (Kabat definition) | LQYASYPLT | 290 |
| HCDR1 amino acid sequence (Chothia definition) | GYAFTNY | 291 |
| HCDR2 amino acid sequence (Chothia definition) | INPGSGG | 292 |
| HCDR3 amino acid sequence (Chothia definition) | WGFYYAMDY | 293 |
| LCDR1 amino acid sequence (Chothia definition) | SQEISGY | 294 |
| LCDR2 amino acid sequence (Chothia definition) | AAS | 295 |
| LCDR3 amino acid sequence (Chothia definition) | YASYPLT | 296 |
| HCDR1 amino acid sequence (IMGT, Kabat, and Chothia common sequences) | NY | 297 |
| HCDR2 amino acid sequence (IMGT, Kabat, and Chothia common sequences) | INPGSGG | 298 |
| HCDR3 amino acid sequence (IMGT, Kabat, and Chothia common sequences definition) | WGFYYAMDY | 299 |
| LCDR1 amino acid sequence (IMGT, Rabat, and Chothia common sequences) | QEISGY | 300 |
| LCDR2 amino acid sequence (IMGT, Rabat, and Chothia common sequences) | AAS | 301 |
| LCDR3 amino acid sequence (IMGT, Rabat, and Chothia common sequences) | YASYPLT | 302 |
| HCDR1 amino acid sequence (IMGT, Rabat, and Chothia combined overlap sequences) | GYAFTNYLIE | 303 |
| HCDR2 amino acid sequence (IMGT, Rabat, and Chothia combined overlap sequences) | VINPGSGGTNYNERFKG | 304 |
| HCDR3 amino acid sequence (IMGT, Rabat, and Chothia combined overlap sequences) | ARWGFYYAMDY | 305 |
| LCDR1 amino acid sequence (IMGT, Rabat, and Chothia combined overlap sequences) | RASQEISGYLS | 306 |
| LCDR2 amino acid sequence (IMGT, Rabat, and Chothia combined overlap sequences) | AASTLDS | 307 |
| LCDR3 amino acid sequence (IMGT, Rabat, and Chothia combined overlap sequences) | LQYASYPLT | 308 |
| VH amino acid sequence (predicted mature) | QVQLRQSGAELVRPGTSVRV SCKASGYAFTNYLIEWVKQR PGQGLEWIGVINPGSGGTNY NEKFKGRATLTADRSSSTAY | 327 |

TABLE 1J-continued

Antibody K Sequences

| Description | Sequence | SEQ ID NO: |
|---|---|---|
| VL amino acid sequence (predicted mature) | MQLSSLTSEDSAVYFCARWG FYYAMDYWGQGTSVTVSS DIVMTQSPSSLSASLGERVS LTCRASQEISGYLSWLQQKP DGTIRRLIYAASTLDSGVPR RFSGSRSGSDYSLTISSLES EDFADYYCLQYASYPLTFGA GTLEIK | 328 |

15

TABLE 2A

Group I CDR Consensus sequences-IMGT definition based

| Description | Sequence | SEQ ID NO: |
|---|---|---|
| HCDR1 amino acid sequence (IMGT definition) | GYTFTDYE | 329 |
| HCDR2 amino acid sequence (IMGT definition) | $X_1$DPE$X_2$GGT $X_1$ = V or I; $X_2$ = T or S | 330 |
| HCDR3 amino acid sequence (IMGT definition) | Y | 331 |
| LCDR1 amino acid sequence (IMGT definition) | S | 332 |
| LCDR2 amino acid sequence (IMGT definition) | $X_1X_2$S $X_1$ = W, S, or G; $X_2$ = A or T | 333 |
| LCDR3 amino acid sequence (IMGT definition) | $X_1X_2X_3X_4X_5X_6$PPT $X_1$ = Q or H; $X_2$ = Q or N; $X_3$ = H, Y, or D; $X_4$ = Y or H; $X_5$ = S or R; $X_6$ = T, S, or Y | 334 |

TABLE 2B

Group I CDR Consensus sequences-Kabat definition based

| Description | Sequence | SEQ ID NO: |
|---|---|---|
| HCDR1 amino acid sequence (Kabat definition) | DYEMH | 335 |
| HCDR2 amino acid sequence (Kabat definition) | G$X_1$DPE$X_2$GGT$X_3$YNQKF$X_4$G $X_1$ = V or I; $X_2$ = T or S; $X_3$ = G or A; $X_4$ = R or K | 336 |
| HCDR3 amino acid sequence (Kabat definition) | Y | 337 |
| LCDR1 amino acid sequence (Kabat definition) | S | 338 |
| LCDR2 amino acid sequence (Kabat definition) | $X_1X_2$S$X_3X_4X_5X_6$ $X_1$ = W, S, or G; $X_2$ = A or T; $X_3$ = T or N; $X_4$ = R or L; $X_5$ = H, A, or E; $X_6$ = T or S | 339 |

TABLE 2B-continued

Group I CDR Consensus sequences-Kabat definition based

| Description | Sequence | SEQ ID NO: |
|---|---|---|
| LCDR3 amino acid sequence (Kabat definition) | $X_1X_2X_3X_4X_5X_6$PPT<br>$X_1$ = Q or H; $X_2$ = Q or N; $X_3$ = H, Y, or D; $X_4$ = Y or H; $X_5$ = S or R; $X_6$ = T, S, or Y | 340 |

TABLE 2C

Group I CDR Consensus sequences-Chothia definition based

| Description | Sequence | SEQ ID NO: |
|---|---|---|
| HCDR1 amino acid sequence (Chothia definition) | GYTFTDY | 341 |
| HCDR2 amino acid sequence (Chothia definition) | DPEX$_1$GG<br>$X_1$ = T or S | 342 |
| HCDR3 amino acid sequence (Chothia definition) | Y | 343 |
| LCDR1 amino acid sequence (Chothia definition) | S$X_1X_2X_3X_4X_5X_6$<br>$X_1$ = Q or S; $X_2$ = D or S; $X_3$ = V or L; $X_4$ = S or L; $X_5$ = T, S, or N; $X_6$ = A or S | 344 |
| LCDR2 amino acid sequence (Chothia definition) | $X_1X_2$S<br>$X_1$ = W, S, or G; $X_2$ = A or T | 345 |
| LCDR3 amino acid sequence (Chothia definition) | $X_1X_2X_3X_4$PPT<br>$X_1$ = H, Y, or D; $X_2$ = Y or H; $X_3$ = S or R; $X_4$ = T, S, or Y | 346 |

TABLE 2D

Group I CDR Consensus sequences-combined overlap

| Description | Sequence | SEQ ID NO: |
|---|---|---|
| HCDR1 amino acid sequence (combined overlap) | GYTFTDYEMH | 347 |
| HCDR2 amino acid sequence (combined overlap) | G$X_1$DPE$X_2$GGT$X_3$YNQKF$X_4$G<br>$X_1$ = V or I; $X_2$ = T or S; $X_3$ = G or A; $X_4$ = R or K | 348 |
| HCDR3 amino acid sequence (combined overlap) | Y | 349 |
| LCDR1 amino acid sequence (combined overlap) | $X_1X_2$S$X_3X_4X_5X_6X_7X_8X_9X_{10}$<br>$X_1$ = K or T; $X_2$ = A or S; $X_3$ = Q or S; $X_4$ = D or S; $X_5$ = V or L; $X_6$ = S or L; $X_7$ = T, S, or N; $X_8$ = A or S; $X_9$ = V, Y, or G; $X_{10}$ = A, L, or N | 350 |

TABLE 2D-continued

Group I CDR Consensus sequences-combined overlap

| Description | Sequence | SEQ ID NO: |
|---|---|---|
| LCDR2 amino acid sequence (combined overlap) | $X_1X_2SX_3X_4X_5X_6$<br>$X_1$ = W, S, or G; $X_2$ = A or T; $X_3$ = T or N; $X_4$ = R or L; $X_5$ = H, A, or E; $X_6$ = T or S | 351 |
| LCDR3 amino acid sequence (combined overlap) | $X_1X_2X_3X_4X_5X_6$PPT<br>$X_1$ = Q or H; $X_2$ = Q or N; $X_3$ = H, Y, or D; $X_4$ = Y or H; $X_5$ = S or R; $X_6$ = T, S, or Y | 352 |

TABLE 2E

Group I CDR Consensus sequences-common sequences

| Description | Sequence | SEQ ID NO: |
|---|---|---|
| HCDR1 amino acid sequence (common sequence) | DY | 353 |
| HCDR2 amino acid sequence (common sequence) | DPEX$_1$GG<br>$X_1$ = T or S | 354 |
| HCDR3 amino acid sequence (common sequence) | Y | 355 |
| LCDR1 amino acid sequence (common sequence) | S | 356 |
| LCDR2 amino acid sequence (common sequence) | $X_1X_2$S<br>$X_1$ = W, S, or G; $X_2$ = A or T | 357 |
| LCDR3 amino acid sequence (common sequence) | $X_1X_2X_3X_4$PPT<br>$X_1$ = H, Y, or D; $X_2$ = Y or H; $X_3$ = S or R; $X_4$ = T, S, or Y | 358 |

TABLE 3A

Group II CDR Consensus sequences-IMGT definition based

| Description | Sequence | SEQ ID NO: |
|---|---|---|
| HCDR1 amino acid sequence (IMGT definition) | GFTFSSYG | 359 |
| HCDR2 amino acid sequence (IMGT definition) | ISRX$_1$SIYT<br>$X_1$ = G or R | 360 |
| HCDR3 amino acid sequence (IMGT definition) | ARLSLYDYDGARYTMDY | 361 |
| LCDR1 amino acid sequence (IMGT definition) | QDVGTA | 362 |
| LCDR2 amino acid sequence (IMGT definition) | WAS | 363 |
| LCDR3 amino acid sequence (IMGT definition) | QQYSSYHT | 364 |

TABLE 3B

Group II CDR Consensus sequences-Kabat definition based

| Description | Sequence | SEQ ID NO: |
|---|---|---|
| HCDR1 amino acid sequence (Kabat definition) | SYGMS | 365 |
| HCDR2 amino acid sequence (Kabat definition) | TISRX$_1$SIYTYYPDSVX$_2$G X$_1$ = G or R; X$_2$ = K or Q | 366 |
| HCDR3 amino acid sequence (Kabat definition) | LSLYDYDGARYTMDY | 367 |
| LCDR1 amino acid sequence (Kabat definition) | KASQDVGTAVA | 368 |
| LCDR2 amino acid sequence (Kabat definition) | WASTRHT | 369 |
| LCDR3 amino acid sequence (Kabat definition) | QQYSSYHT | 370 |

TABLE 3C

Group II CDR Consensus sequences-Chothia definition based

| Description | Sequence | SEQ ID NO: |
|---|---|---|
| HCDR1 amino acid sequence (Chothia definition) | GFTFSSY | 371 |
| HCDR2 amino acid sequence (Chothia definition) | SRX$_1$SIY X$_1$ = G or R | 372 |
| HCDR3 amino acid sequence (Chothia definition) | LSLYDYDGARYTMDY | 373 |
| LCDR1 amino acid sequence (Chothia definition) | SQDVGTA | 374 |
| LCDR2 amino acid sequence (Chothia definition) | WAS | 375 |
| LCDR3 amino acid sequence (Chothia definition) | YSSYHT | 376 |

TABLE 3D

Group II CDR Consensus sequences-combined overlap

| Description | Sequence | SEQ ID NO: |
|---|---|---|
| HCDR1 amino acid sequence (combined overlap) | GFTFSSYGMS | 377 |
| HCDR2 amino acid sequence (combined overlap) | TISRX$_1$SIYTYYPDSVX$_2$G X$_1$ = G or R; X$_2$ = K or Q | 378 |
| HCDR3 amino acid sequence (combined overlap) | ARLSLYDYDGARYTMDY | 379 |
| LCDR1 amino acid sequence (combined overlap) | KASQDVGTAVA | 380 |
| LCDR2 amino acid sequence (combined overlap) | WASTRHT | 381 |

TABLE 3D-continued

Group II CDR Consensus sequences-combined overlap

| Description | Sequence | SEQ ID NO: |
|---|---|---|
| LCDR3 amino acid sequence (combined overlap) | QQYSSYHT | 382 |

TABLE 3E

Group II CDR Consensus sequences-common sequences

| Description | Sequence | SEQ ID NO: |
|---|---|---|
| HCDR1 amino acid sequence (common sequence) | SY | 383 |
| HCDR2 amino acid sequence (common sequence) | SRX$_1$SIY<br>X$_1$ = G or R | 384 |
| HCDR3 amino acid sequence (common sequence) | LSLYDYDGARYTMDY | 385 |
| LCDR1 amino acid sequence (common sequence) | QDVGTA | 386 |
| LCDR2 amino acid sequence (common sequence) | WAS | 387 |
| LCDR3 amino acid sequence (common sequence) | YSSYHT | 388 |

TABLE 4A

Group III CDR Consensus sequences-IMGT definition based

| Description | Sequence | SEQ ID NO: |
|---|---|---|
| HCDR1 amino acid sequence (IMGT definition) | GYX$_1$FX$_2$X$_3$YX$_4$<br>X$_1$ = N or T; X$_2$ = K or T; X$_3$ = S or D; X$_4$ = G or Y | 389 |
| HCDR2 amino acid sequence (IMGT definition) | IX$_1$PGSGX$_2$T<br>X$_1$ = Y or F; X$_2$ = N or S | 390 |
| HCDR3 amino acid sequence (IMGT definition) | YG | 391 |
| LCDR1 amino acid sequence (IMGT definition) | S | 392 |
| LCDR2 amino acid sequence (IMGT definition) | X$_1$X$_2$S<br>X$_1$ = R or A; X$_2$ = V or T | 393 |
| LCDR3 amino acid sequence (IMGT definition) | X$_1$QX$_2$X$_3$X$_4$X$_5$PX$_6$T<br>X$_1$ = M or Q; X$_2$ = H or W; X$_3$ = L or S; X$_4$ = E or S; X$_5$ = Y or N; X$_6$ = F or L | 394 |

TABLE 4B

Group III CDR Consensus sequences-Kabat definition based

| Description | Sequence | SEQ ID NO: |
|---|---|---|
| HCDR1 amino acid sequence (Kabat definition) | $X_1YX_2IX_3$<br>$X_1$ = S or D; $X_2$ = G or Y; $X_3$ = S or N | 395 |
| HCDR2 amino acid sequence (Kabat definition) | $X_1IX_2PGSGX_3TYYNEKX_4KG$<br>$X_1$ = E or W; $X_2$ = Y or F; $X_3$ = N or S; $X_4$ = L or F | 396 |
| HCDR3 amino acid sequence (Kabat definition) | YG | 397 |
| LCDR1 amino acid sequence (Kabat definition) | SS | 398 |
| LCDR2 amino acid sequence (Kabat definition) | $X_1X_2SX_3LAS$<br>$X_1$ = R or A; $X_2$ = V or T; $X_3$ = N or Y | 399 |
| LCDR3 amino acid sequence (Kabat definition) | $X_1QX_2X_3X_4X_5PX_6T$<br>$X_1$ = M or Q; $X_2$ = H or W; $X_3$ = L or S; $X_4$ = E or S; $X_5$ = Y or N; $X_6$ = F or L | 400 |

TABLE 4C

Group III CDR Consensus sequences-Chothia definition based

| Description | Sequence | SEQ ID NO: |
|---|---|---|
| HCDR1 amino acid sequence (Chothia definition) | $GYX_1FX_2X_3Y$<br>$X_1$ = N or T; $X_2$ = K or T; $X_3$ = S or D | 401 |
| HCDR2 amino acid sequence (Chothia definition) | $X_1PGSGX_2$<br>$X_1$ = Y or F; $X_2$ = N or S | 402 |
| HCDR3 amino acid sequence (Chothia definition) | YG | 403 |
| LCDR1 amino acid sequence (Chothia definition) | S | 404 |
| LCDR2 amino acid sequence (Chothia definition) | $X_1X_2S$<br>$X_1$ = R or A; $X_2$ = V or T | 405 |
| LCDR3 amino acid sequence (Chothia definition) | $X_1X_2X_3X_4PX_5T$<br>$X_1$ = H or W; $X_2$ = L or S; $X_3$ = E or S; $X_4$ = Y or N; $X_5$ = F or L | 406 |

TABLE 4D

Group III CDR Consensus sequences-combined overlap

| Description | Sequence | SEQ ID NO: |
|---|---|---|
| HCDR1 amino acid sequence (combined overlap) | $GYX_1FX_2X_3YX_4IX_5$<br>$X_1$ = N or T; $X_2$ = K or T; $X_3$ = S or D; | 407 |

TABLE 4D-continued

Group III CDR Consensus sequences-combined overlap

| Description | Sequence | SEQ ID NO: |
|---|---|---|
| | $X_4$ = G or Y; $X_5$ = S or N | |
| HCDR2 amino acid sequence (combined overlap) | $X_1IX_2PGSGX_3TYYNEKX_4KG$<br>$X_1$ = E or W; $X_2$ = Y or F; $X_3$ = N or S; $X_4$ = L or F | 408 |
| HCDR3 amino acid sequence (combined overlap) | YG | 409 |
| LCDR1 amino acid sequence (combined overlap) | SS | 410 |
| LCDR2 amino acid sequence (combined overlap) | $X_1X_2SX_3LAS$<br>$X_1$ = R or A; $X_2$ = V or T; $X_3$ = N or Y | 411 |
| LCDR3 amino acid sequence (combined overlap) | $X_1QX_2X_3X_4X_5PX_6T$<br>$X_1$ = M or Q; $X_2$ = H or W; $X_3$ = L or S; $X_4$ = E or S; $X_5$ = Y or N; $X_6$ = F or L | 412 |

TABLE 4E

Group III CDR Consensus sequences-common sequences

| Description | Sequence | SEQ ID NO: |
|---|---|---|
| HCDR1 amino acid sequence (common sequence) | $X_1Y$<br>$X_1$ = S or D | 413 |
| HCDR2 amino acid sequence (common sequence) | $X_1PGSGX_2$<br>$X_1$ = Y or F; $X_2$ = N or S | 414 |
| HCDR3 amino acid sequence (common sequence) | YG | 415 |
| LCDR1 amino acid sequence (common sequence) | S | 416 |
| LCDR2 amino acid sequence (common sequence) | $X_1X_2S$<br>$X_1$ = W or A; $X_2$ = A or T | 417 |
| LCDR3 amino acid sequence (common sequence) | $X_1X_2X_3X_4PX_5T$<br>$X_1$ = H or W; $X_2$ = L or S; $X_3$ = E or S; $X_4$ = Y or N; $X_5$ = F or L | 418 |

TABLE 5A

Group IV CDR Consensus sequences-IMGT definition based

| Description | Sequence | SEQ ID NO: |
|---|---|---|
| HCDR1 amino acid sequence (IMGT definition) | $GYX_1FTX_2YX_3$<br>$X_1$ = T or A; $X_2$ = S or N; $X_3$ = W or L | 419 |

TABLE 5A-continued

Group IV CDR Consensus sequences-IMGT definition based

| Description | Sequence | SEQ ID NO: |
|---|---|---|
| HCDR2 amino acid sequence (IMGT definition) | INPX$_1$X$_2$GGT<br>X$_1$ = S or G; X$_2$ = N or S | 420 |
| HCDR3 amino acid sequence (IMGT definition) | ARX$_1$GX$_2$YY<br>X$_1$ = G or W; X$_2$ = I F | 421 |
| LCDR1 amino acid sequence (IMGT definition) | S | 422 |
| LCDR2 amino acid sequence (IMGT definition) | X$_1$X$_2$S<br>X$_1$ = R or A; X$_2$ = V or A | 423 |
| LCDR3 amino acid sequence (IMGT definition) | X$_1$QX$_2$X$_3$X$_4$YPX$_5$T<br>X$_1$ = M or L; X$_2$ = H or Y; X$_3$ = L or A; X$_4$ = E or S; X$_5$ = F or L | 424 |

TABLE 5B

Group IV CDR Consensus sequences-Kabat definition based

| Description | Sequence | SEQ ID NO: |
|---|---|---|
| HCDR1 amino acid sequence (Kabat definition) | X$_1$YX$_2$X$_3$X$_4$<br>X$_1$ = S or N; X$_2$ = W or L; X$_3$ = M or I; X$_4$ = H or E | 425 |
| HCDR2 amino acid sequence (Kabat definition) | X$_1$INPX$_2$X$_3$GGTNYNEKFKX$_4$<br>X$_1$ = N or V; X$_2$ = S or G; X$_3$ = N or S; X$_4$ = S or G | 426 |
| HCDR3 amino acid sequence (Kabat definition) | GX$_1$YY<br>X$_1$ = I or F | 427 |
| LCDR1 amino acid sequence (Kabat definition) | RX$_1$S<br>X$_1$ = S or A | 428 |
| LCDR2 amino acid sequence (Kabat definition) | X$_1$X$_2$SX$_3$LX$_4$S<br>X$_1$ = R or A; X$_2$ = V or A; X$_3$ = N or T; X$_4$ = A or D | 429 |
| LCDR3 amino acid sequence (Kabat definition) | X$_1$QX$_2$X$_3$X$_4$YPX$_5$T<br>X$_1$ = M or L; X$_2$ = H or Y; X$_3$ = L or A; X$_4$ = E or S; X$_5$ = F or L | 430 |

TABLE 5C

Group IV CDR Consensus sequences-Chothia definition based

| Description | Sequence | SEQ ID NO: |
|---|---|---|
| HCDR1 amino acid sequence (Chothia definition) | GYX$_1$FTX$_2$Y<br>X$_1$ = T or A; X$_2$ = S or N | 431 |

TABLE 5C-continued

Group IV CDR Consensus sequences-Chothia definition based

| Description | Sequence | SEQ ID NO: |
|---|---|---|
| HCDR2 amino acid sequence (Chothia definition) | NPX$_1$X$_2$GG<br>X$_1$ = S or G; X$_2$ = N or S | 432 |
| HCDR3 amino acid sequence (Chothia definition) | GX$_1$YY<br>X$_1$ = I or F | 433 |
| LCDR1 amino acid sequence (Chothia definition) | S | 434 |
| LCDR2 amino acid sequence (Chothia definition) | X$_1$X$_2$S<br>X$_1$ = R or A; X$_2$ = V or A | 435 |
| LCDR3 amino acid sequence (Chothia definition) | X$_1$X$_2$X$_3$YPX$_4$T<br>X$_1$ = H or Y; X$_2$ = L or A; X$_3$ = E or S;<br>X$_4$ = F or L | 436 |

TABLE 5D

Group IV CDR Consensus sequences-combined overlap

| Description | Sequence | SEQ ID NO: |
|---|---|---|
| HCDR1 amino acid sequence (combined overlap) | GYX$_1$FTX$_2$YX$_3$X$_4$X$_5$<br>X$_1$ = T or A; X$_2$ = S or N; X$_3$ = W or L;<br>X$_4$ = M or I; X$_5$ = H or E | 437 |
| HCDR2 amino acid sequence (combined overlap) | X$_1$INPX$_2$X$_3$GGTNYNEKFKX$_4$<br>X$_1$ = N or V; X$_2$ = S or G; X$_3$ = N or S;<br>X$_4$ = S or G | 438 |
| HCDR3 amino acid sequence (combined overlap) | ARX$_1$GX$_2$YY<br>X$_1$ = G or W; X$_2$ = I or F | 439 |
| LCDR1 amino acid sequence (combined overlap) | RX$_1$S<br>X$_1$ = S or A | 440 |
| LCDR2 amino acid sequence (combined overlap) | X$_1$X$_2$SX$_3$LX$_4$S<br>X$_1$ = R or A; X$_2$ = V or A; X$_3$ = N or T;<br>X$_4$ = A or D | 441 |
| LCDR3 amino acid sequence (combined overlap) | X$_1$QX$_2$X$_3$X$_4$YPX$_5$T<br>X$_1$ = M or L; X$_2$ = H or Y; X$_3$ = L or A;<br>X$_4$ = E or S; X$_5$ = F or L | 442 |

TABLE 5E

Group IV CDR Consensus sequences-common sequences

| Description | Sequence | SEQ ID NO: |
|---|---|---|
| HCDR1 amino acid sequence (common sequence) | X$_1$Y<br>X$_1$ = S or N | 443 |

TABLE 5E-continued

Group IV CDR Consensus sequences-common sequences

| Description | Sequence | SEQ ID NO: |
|---|---|---|
| HCDR2 amino acid sequence (common sequence) | NPX$_1$X$_2$GG<br>X$_1$ = S or G; X$_2$ = N or S | 444 |
| HCDR3 amino acid sequence (common sequence) | GX$_1$YY<br>X$_1$ = I or F | 445 |
| LCDR1 amino acid sequence (common sequence) | S | 446 |
| LCDR2 amino acid sequence (common sequence) | X$_1$X$_2$S<br>X$_1$ = R or A; X$_2$ = V or A | 447 |
| LCDR3 amino acid sequence (common sequence) | X$_1$X$_2$X$_3$YPX$_4$T<br>X$_1$ = H or Y; X$_2$ = L or A; X$_3$ = E or S; X$_4$ = F or L | 448 |

In some embodiments, an anti AQP3 antibody or functional fragment thereof comprises a variable heavy (VH) and a variable light (VL) chain sequence selected from those set forth in Table 1A-1J. In some embodiments, the anti AQP3 antibody or functional fragment comprises the VH and VL of antibody A. In other embodiments, the anti AQP3 antibody or functional fragment comprises the VH and VL of antibody B. In other embodiments, the anti AQP3 antibody or functional fragment comprises the VH and VL of antibody C. In other embodiments, the anti AQP3 antibody or functional fragment comprises the VH and VL of antibody D. In other embodiments, the anti AQP3 antibody or functional fragment comprises the VH and VL of antibody E. In other embodiments, the anti AQP3 antibody or functional fragment comprises the VH and VL of antibody F. In other embodiments, the anti AQP3 antibody or functional fragment comprises the VH and VL of antibody G. In other embodiments, the anti AQP3 antibody or functional fragment comprises the VH and VL of antibody H. In other embodiments, the anti AQP3 antibody or functional fragment comprises the VH and VL of antibody J. In other embodiments, the anti AQP3 antibody or functional fragment comprises the VH and VL of antibody K.

In some embodiments, an antibody or functional fragment thereof can compete with another anti AQP3 antibody or functional fragment thereof of the present invention for binding to AQP3, e.g., human AQP3 expressed on the surface of HEK293 cells, HaCaT cells, or A431 cells, or mouse AQP3 expressed on the surface of HEK293 cells, PAM212 cells, or mouse macrophage cells. Assays that can be used to measure competition include ELISA and FACS assays.

In one example of a competition assay, cells expressing AQP3 on their surface (e.g., HEK293 cells) are adhered onto a solid surface, e.g., a microwell plate, by contacting the plate with a suspension of AQP3 expressing cells (e.g., over night at 4° C.). The plate is washed (e.g., 0.1% Tween 20 in PBS) and blocked (e.g., in Superblock, Thermo Scientific, Rockford, Ill.). A mixture of sub-saturating amount of a biotinylated first antibody (80 ng/mL) (the "reference" antibody) or competing anti AQP3 antibody (the "test" antibody) in serial dilution (e.g., at a concentration of 2.8 µg/mL, 8.3 µg/mL, or 25 µg/mL) in ELISA buffer (e.g., 1% BSA and 0.1% Tween 20 in PBS) is added to wells and plates are incubated for 1 hour with gentle shaking. The reference antibody can be an antibody of the invention, e.g., antibody A, B, C, D, E, F, G, H, J, or K. The plate is washed, 1 µg/mL HRP-conjugated Streptavidin diluted in ELISA buffer is added to each well and the plates incubated for 1 hour. Plates are washed and bound antibodies are detected by addition of substrate (e.g., TMB, Biofx Laboratories Inc., Owings Mills, Md.). The reaction is terminated by addition of stop buffer (e.g., Bio FX Stop Reagents, Biofx Laboratories Inc., Owings Mills, Md.) and the absorbance is measured at 650 nm using microplate reader (e.g., VERSAmax, Molecular Devices, Sunnyvale, Calif.). Variations on this competition assay can also be used to test competition between a first anti AQP3 antibody of the present invention and a second AQP3 antibody of the present invention. Other formats for competition assays are known in the art and can be employed.

In various embodiments of the above-described competition assay, a test anti AQP3 antibody of the present invention that competes with a reference AQP3 antibody of the present invention reduces the binding of the reference anti AQP3 antibody by at least 30%, by at least 40%, by at least 50%, by at least 60%, by at least 70%, by at least 80%, by at least 90%, by at least 95%, by at least 99% or by a percentage ranging between any of the foregoing values (e.g., a test anti AQP3 antibody of the present invention reduces the binding of a labeled reference anti AQP3 antibody of the present invention by 50% to 70%) when the test anti-AQP3 antibody is used at a concentration of 0.08 µg/mL, 0.4 µg/mL, 2 µg/mL, 10 µg/mL, 50 µg/mL, 100 µg/mL or at a concentration ranging between any of the foregoing values (e.g., at a concentration ranging from 2 µg/mL to 10 µg/m L).

In other embodiments of the above-described competition assay, a test anti AQP3 antibody of the present invention reduces the binding of a labeled reference anti AQP3 antibody by at least 40%, by at least 50%, by at least 60%, by at least 70%, by at least 80%, by at least 90%, or by a percentage ranging between any of the foregoing values (e.g., a test anti AQP3 antibody of the present invention reduces the binding of a labeled reference anti AQP3 antibody of the present invention by 50% to 70%) when the test anti AQP3 antibody is used at a concentration of 0.4 µg/mL, 2 µg/mL, 10 µg/mL, 50 µg/mL, 250 µg/mL or at a concentration ranging between any of the foregoing values (e.g., at a concentration ranging from 2 µg/mL to 10 µg/mL).

In some aspects, the present invention relates to the following (1) to (71).

(1) An anti AQP3 antibody specifically recognizing the extracellular domain of aquaporin 3 (AQP3) or a functional fragment thereof.

(2) The antibody or functional fragment thereof described in above 1, in which the extracellular domain is loop C.

(3) The antibody or functional fragment thereof described in above (1) or (2) specifically binding to an oligopeptide composed of ten amino acid residues at the C-terminal side of loop C that are adjacent to the boundary to the transmembrane region IV.

(4) The antibody or functional fragment thereof described in above (3), in which the amino acid sequence of the oligopeptide composed of ten amino acid residues at the C-terminal side of loop C, that are adjacent to the boundary to the transmembrane region IV, is ATYPSGHLDM (SEQ ID NO: 1).

(5) The antibody or functional fragment thereof described in any one of above (1) to (4), which is a mouse antibody, a rat antibody, a rabbit antibody, a guinea pig antibody, a sheep antibody, a goat antibody, a donkey antibody, a chicken antibody, or a camel antibody.

(6) The antibody or functional fragment thereof described in any one of above (1) to (5), which is a mouse antibody.

(7) The antibody or functional fragment thereof described in any one of above (1) to (6), which is labeled with a reporter material.

(8) The antibody or functional fragment thereof described in above (7), in which the reporter material is selected from the group consisting of a radioactive isotope, a metal micro particle, an enzyme, a fluorescent material, and a luminescent material.

(9) The antibody or a functional fragment thereof described in any one of above (1) to (8), which is immobilized on a solid support.

(10) The antibody or functional fragment thereof described in above (9), in which the solid support is selected from the group consisting of a micro plate, a glass plate, a plastic plate, a syringe, a vial, a column, a magnetic particle, a micro bead made of resin, a porous membrane, a porous carrier, and a microchip.

(11) The antibody or functional fragment thereof described in any one of above (1) to (10) specifically binding to AQP3 derived from a human and/or a mouse.

(12) The antibody or functional fragment thereof described in any one of above (1) to (11), which specifically binds to AQP3 derived from human.

(13) The antibody or functional fragment thereof described in any one of above (1) to (12), in which the antibody is an immunoglobulin molecule of IgG or IgM.

(14) The antibody or functional fragment thereof described in any one of above (1) to (13), in which the antibody is an immunoglobulin molecule of IgG.

(15) The antibody or functional fragment thereof described in any one of above (1) to (14) having an inhibitory activity on function of AQP3.

(16) The antibody or a functional fragment thereof described in above (15), in which the function of AQP3 is at least one activity selected from the group consisting of an activity of transporting (permeating) a low molecular weight material by AQP3, an activity of promoting cell proliferation of AQP3-expressing cells, an activity of promoting cell migration of AQP3-expressing cells, and an activity of inducing an inflammatory response and a disorder response associated with AQP3.

(17) The antibody or functional fragment thereof described in any one of above (1) to (16), in which the antibody is a monoclonal antibody.

(18) The antibody or functional fragment thereof described in above (17), in which heavy chain CDR1, CDR2, and CDR3 are composed of the amino acid sequence represented by SEQ ID NO: 10, SEQ ID NO: 11, and SEQ ID NO: 12, respectively, and light chain CDR1, CDR2, and CDR3 are composed of the amino acid sequence represented by SEQ ID NO: 13, SEQ ID NO: 14, and SEQ ID NO: 15, respectively.

(19) The antibody or functional fragment thereof described in above (17) or (18), in which the heavy chain variable region is composed of the amino acid sequence represented by SEQ ID NO: 4 and the light chain variable region is composed of the amino acid sequence represented by SEQ ID NO: 5.

(20) The antibody or functional fragment thereof described in above (17), in which heavy chain CDR1, CDR2, and CDR3 are composed of the amino acid sequence represented by SEQ ID NO: 16, SEQ ID NO: 17, and SEQ ID NO: 18, respectively, and light chain CDR1, CDR2, and CDR3 are composed of the amino acid sequence represented by SEQ ID NO: 19, SEQ ID NO: 20, and SEQ ID NO: 21, respectively.

(21) The antibody or functional fragment thereof described in above (17) or (20), in which the heavy chain variable region is composed of the amino acid sequence represented by SEQ ID NO: 6 and the light chain variable region is composed of the amino acid sequence represented by SEQ ID NO: 7.

(22) The antibody or functional fragment thereof described in above (17), in which heavy chain CDR1, CDR2, and CDR3 are composed of the amino acid sequence represented by SEQ ID NO: 22, SEQ ID NO: 23, and SEQ ID NO: 24, respectively, and light chain CDR1, CDR2, and CDR3 are composed of the amino acid sequence represented by SEQ ID NO: 25, SEQ ID NO: 26, and SEQ ID NO: 27, respectively.

(23) The antibody or functional fragment thereof described in above (17) or (22), in which the heavy chain variable region is composed of the amino acid sequence represented by SEQ ID NO: 8 and the light chain variable region is composed of the amino acid sequence represented by SEQ ID NO: 9.

(24) The monoclonal antibody described in any one of above (1), (7), (18), (20) and (22), in which the antibody is a chimeric antibody or a humanized antibody having a constant region of a human antibody.

(25) A composition comprising the antibody or fragment thereof described in any one of above (1) to (24).

(26) The composition described in above (25), which is a reagent for detecting AQP3.

(27) The composition described in above (25), which is a reagent for identifying, separating, or purifying AQP3-expressing cells.

(28) The composition described in above (25) or (26), which is a reagent for measuring an expression amount of AQP3.

(29) A kit comprising the composition described in any one of above (25) to (28).

(30) A composition comprising the monoclonal antibody or fragment thereof described in above 9 or 10, in which the monoclonal antibody or a functional fragment thereof has an inhibitory activity on function of AQP3.
(31) The composition described in above (30), in which the function of AQP3 is at least one activity selected from the group consisting of an activity of transporting a low molecular weight material by AQP3, an activity of promoting cell proliferation of AQP3-expressing cells, and an activity of promoting cell migration of AQP3-expressing cells.
(32) The composition described in above (30) or (31) which is a pharmaceutical composition further including a pharmaceutically acceptable carrier.
(33) The composition described in above (31) or (32) for use in treating cancer.
(34) The composition described in above (33), in which the cancer is cancer selected from the group consisting of colorectal cancer, cervical cancer, liver cancer, lung cancer, esophageal cancer, kidney cancer, stomach cancer, tongue cancer, skin cancer, and breast cancer.
(35) The composition described in above (33) or (34), in which the treatment is selected from the group consisting of suppression of a progress (proliferation) of cancer, suppression of tumor angiogenesis, suppression of infiltration, suppression of metastasis, suppression of energy metabolism in cancer tissues, and improvement of prognosis of a patient.
(36) The composition described in above (31) or (32), for use in preventing and/or treating a skin disorder.
(37) The composition described in above (36), in which the skin disorder is selected from the group consisting of psoriasis, actinic keratosis, ichthyosis, and seborrheic dermatitis.
(38) The composition described in above (31) or (32) for use in preventing and/or treating an inflammatory disorder.
(39) The composition described in above (38), in which the inflammatory disorder is selected from the group consisting of atopic dermatitis, psoriasis, asthma, chronic obstructive pulmonary disease, and hepatitis (e.g., acute hepatitis or acute hepatic disorder).
(40) The composition described in above (31) or (32), for use in treating an abnormality in bowel movement.
(41) The composition described in above (40), in which the abnormality in bowel movement is constipation.
(42) A method for detecting AQP3 comprising a step of contacting a sample with the antibody or fragment thereof described in any one of above (1) to (24), or with the composition described in above (25) or (26).
(43) The method described in above (42), in which it is carried out by using the kit described in above (29).
(44) The method described in above (42) or (43), in which the sample contains a cell, a living body tissue, an organ, or an individual subject.
(45) The method described in above (44), in which the sample contains a cell, a living body tissue, or an organ, and which is carried out in vitro.
(46) The method described in above (44), which is carried out in vivo (optionally with the proviso that a case of having an individual human or an individual animal as a sample is excluded).
(47) A method for separating and/or purifying AQP3-expressing cells from a sample comprising AQP3-expressing cells, the method comprising a step of contacting the sample with the antibody or a functional fragment thereof described in any one of above (1) to (24), or with the composition described in above (25) or (27).
(48) The method described in above (47), which is carried out by using the kit described in above (29).
(49) The method described in above (47) or (48), in which the sample is a sample containing living cells.
(50) A method for measuring AQP3 comprising a step of contacting a sample with the antibody or a functional fragment thereof described in any one of above (1) to (24), or with the composition described in above (25), (26), or (28).
(51) The method described in above (46), which is carried out by using the kit described in above (29).
(52) The method described in above (50) or (51), in which the sample contains a cell or a cell extract.
(53) A method for inhibiting at least one function of AQP3 comprising a step of contacting a sample including AQP3 with the antibody or a functional fragment thereof described in any one of above (1) to (24), or with the composition described in above (25).
(54) The method described in above (53), in which the sample containing AQP3 is a reconstituted membrane containing recombinant AQP3, or a cell group, living body tissues, an organ, or an individual containing AQP3-expressing cells.
(55) The method described in above (53) or (54), in which the contacting step is a step of contacting the sample with the monoclonal antibody or a functional fragment thereof described in any one of above (17) to (24) or with a composition containing the monoclonal antibody described in any one of above (17) to (24).
(56) The method described in above (55), in which the monoclonal antibody described in any one of above (17) to (24) or a functional fragment thereof has an activity of inhibiting at least one function of AQP3.
(57) The method described in above (56), in which the function of AQP3 is at least one activity selected from the group consisting of an activity of transporting a low molecular weight material by AQP3, an activity of promoting cell proliferation of AQP3-expressing cells, an activity of promoting cell migration of AQP3-expressing cells, and an activity of inducing an inflammatory response and a disorder response associated with AQP3.
(58) A method for inhibiting transport of a low molecular weight material across a membrane comprising a step of contacting a sample having a membrane including AQP3 with the antibody or a functional fragment thereof described in any one of above (1) to (24) or with the composition described in above (25).
(59) The method described in above (58), in which the membrane containing AQP3 is a reconstituted membrane containing recombinant AQP3 or a biological membrane of AQP3-expressing cells.
(60) The method described in above (58) or (59), in which the contacting step is a step of contacting with the monoclonal antibody or a functional fragment thereof described in any one of above (17) to (24) or with a composition containing the monoclonal antibody described in any one of above (17) to (24).
(61) The method described in above (60), in which the monoclonal antibody described in any one of above (17) to (24) or a functional fragment thereof has an activity of inhibiting a function of AQP3.

(62) The method described in above (61), in which the function of AQP3 is an activity of transporting a low molecular weight material by AQP3.
(63) The method described in any one of above (58) to (62), in which the low molecular weight material is selected from the group consisting of water molecule, glycerol, and hydrogen peroxide.
(64) A method for prevention and/or treatment of a disorder associated with AQP3 including a step of administering the composition described in any one of above (30) to (39) to a subject who is in need of treatment.
(65) The method described in above (64), in which the disorder associated with AQP3 is associated with an increased expression level of AQP3.
(66) The method described in above (65), in which the disorder associated with AQP3 is selected from the group consisting of cancer, a skin disorder, and an inflammatory disorder.
(67) A method of ameliorating an abnormality in bowel movement including a step of administering the composition described in above (30) to (32), (40), or (41) to a subject with an abnormality in bowel movement in which the abnormality in bowel movement is constipation.
(68) The composition described in above (31) or (32), which is for use in a method of treating a disorder associated with AQP3.
(69) The monoclonal antibody described in any one of above (17) to (24) or a functional fragment thereof, which is for use in a method of treating a disorder associated with AQP3.
(70) Use of the composition described in above (31) or (32) for producing a pharmaceutical composition for preventing and/or treating a disorder associated with AQP3.
(71) Use of the monoclonal antibody or a functional fragment thereof described in any one of above (17) to (24) for producing a pharmaceutical composition for preventing and/or treating a disorder associated with AQP3.

Advantageous Effects of Invention

With an anti AQP3 antibody or a functional fragment thereof of the present invention which specifically recognizes the extracellular domain of AQP3, detection of AQP3-expressing cells or measurement of AQP3 expression level can be carried out. Furthermore, because an anti AQP3 antibody or a functional fragment thereof of the present invention can specifically bind to AQP3 present in cell membrane of living cells, staining of tissues or an organ containing AQP3-expressing cells or separation and purification of AQP3-expressing cells can be carried out. Furthermore, because in some embodiments an anti AQP3 antibody or a functional fragment thereof of the present invention can not only recognize specifically a peptide included in loop C of AQP3 but can also specifically bind to AQP3, it can inhibit one or more functions of AQP3. By inhibiting one or more functions of AQP3, it is possible to prevent and/or treat a disorder associated with AQP3 which is associated with an increase in AQP3 expression level. In a case in which the disorder associated with AQP3 is cancer, it is possible to have suppression of a progress (proliferation) of cancer, suppression of tumor angiogenesis, suppression of infiltration, suppression of metastasis, suppression of energy metabolism in cancer tissues, improvement of prognosis of a cancer patient, or a combination of the foregoing. It is also possible to alleviate an abnormality in bowel movement which is associated with an increase in AQP3 expression level.

BRIEF DESCRIPTION OF DRAWINGS

FIG. 1 is a diagram illustrating the molecular structure of aquaporin. It has a transmembrane structure of traversing, from the N-terminal to the C-terminal, the membrane six times and, in the five regions connected between the six transmembrane domains of transmembrane domains I to VI, five loops (loop A to loop E) are included. Among those loops, loop A, loop C, and loop E are present at the extracellular side while loop B and loop D are present at the intracellular side, respectively. The N-terminal region and the C-terminal region are all included in the intracellular domain. Two NPAs shown in the drawing indicate an NPA box consisting of three amino acid residues of asparagine-proline-alanine. The NPA box is present inside an aquaporin molecule and it is known to be widely preserved among biospecies.

FIG. 2 is a diagram showing the result of testing the binding property of anti AQP3 antibodies of the present invention to a peptide having the amino acid sequence of SEQ ID NO:1. Left panel shows the results for antibodies C, E, H, J, and a negative control IgG antibody (IgG). Right panel shows the results for antibodies B, G, K, A, D, and F.

FIG. 3 is a diagram showing the result of testing the binding property of anti AQP3 antibodies of the present invention to cell lysate of AQP3 overexpressing HEK293T cells (AQP3). Cell lysate from HEK293T cells not overexpressing AQP3 was used as control (N.C.).

FIG. 4 is a diagram showing the result of testing the binding property of an anti AQP3 antibody of the present invention to mouse macrophage cells. Used is antibody J, which is one of the anti AQP3 antibodies of the present invention.

FIG. 5A is a diagram showing the result of testing the binding property of an anti AQP3 antibody of the present invention to mouse epithelial cells (PAM212 cells). Used is antibody J, which is one of the anti AQP3 antibodies of the present invention.

FIG. 5B is a diagram showing the result of testing the binding property of antibodies A, B, C, D, E, F, G, H, and J to mouse epithelial cells (PAM212 cells).

FIG. 5C is a diagram showing the result of testing the binding property of antibodies A, B, C, D, E, F, G, H, and J to human epithelial cells (HaCaT cells).

FIG. 6A is a diagram showing the result of testing the binding property of antibody G, which is one of the anti AQP3 antibodies of the present invention, to human epithelial cells (HaCaT cells).

FIG. 6B is a diagram showing the result of testing the binding property of antibody H, which is one of the anti AQP3 antibodies of the present invention, to human epithelial cells (HaCaT cells).

FIG. 6C is a diagram showing the result of testing the binding property of antibody J, which is one of the anti AQP3 antibodies of the present invention, to human epithelial cells (HaCaT cells).

FIG. 6D is a diagram showing the result of testing the binding property of antibody E to HEK293 cells overexpressing mouse AQP3.

FIG. 6E is a diagram showing the result of testing the binding property of antibody H to HEK293 cells overexpressing mouse AQP3.

FIG. 6F is a diagram showing the result of testing the binding property of antibody J to HEK293 cells overexpressing mouse AQP3.

FIG. 6G is a diagram showing the result of testing the binding properties of antibody E to HEK293 cells overexpressing mouse AQP3.

FIG. 6H is a diagram showing the result of testing the binding properties of antibody E to HEK293 cells overexpressing human AQP3.

FIG. 7A is a diagram showing the result of carrying out immunostaining for AQP3-expressing cells (mouse macrophages) by using an anti AQP3 antibody of the present invention. As anti AQP3 antibodies of the present invention, antibody H and antibody J were used.

FIG. 7B is a diagram showing the result of carrying out immunostaining for AQP3-expressing cells (mouse macrophages) (top panel) and AQP3 knock-out cells by using an anti AQP3 antibody of the present invention. As an anti AQP3 antibody of the present invention, antibody J was used.

FIG. 8A is a diagram showing the result of testing the activity on cell proliferation of an anti AQP3 antibody of the present invention by using mouse epithelial cells (PAM212 cells). As anti AQP3 antibodies of the present invention, antibody G and antibody J were used.

FIG. 8B is a diagram showing the result of testing the activity on cell proliferation of an anti AQP3 antibody of the present invention by using mouse epithelial cells (PAM212 cells). An anti AQP3 antibody of the present invention, antibody J was used.

FIG. 8C is a diagram showing the result of testing the activity on cell proliferation of an anti AQP3 antibody of the present invention by using mouse epithelial cells (PAM212 cells). As anti AQP3 antibodies of the present invention, antibodies A, B, C, D, E, F, G, H, and J were used.

FIG. 9 is a diagram showing the result of testing the activity on cell proliferation of an anti AQP3 antibody of the present invention by using human epithelial cells (HaCaT cells). As anti AQP3 antibodies of the present invention, antibody G, antibody H, and antibody J were used.

FIG. 10 is a diagram showing the result of testing the activity on cell proliferation of anti AQP3 antibodies of the present invention by using human epithelioid carcinoma cells (A431 cells). As anti AQP3 antibodies of the present invention, antibody G, antibody H, and antibody J were used.

FIG. 11 is a diagram showing the result of testing the functional inhibition effect of an anti AQP3 antibody of the present invention on the hydrogen peroxide permeation function in mouse macrophage cells as AQP3-expressing cells. As an anti AQP3 antibody of the present invention, antibody J was used.

FIG. 12 is a diagram showing the result of testing the functional inhibition effect of anti AQP3 antibodies of the present invention on the hydrogen peroxide permeation function in mouse macrophage cells as AQP3-expressing cells. As anti AQP3 antibodies of the present invention, antibodies A, B, C, D, E, F, G, H, and J were used.

FIG. 13 is a diagram showing the result of testing the functional inhibition effect of an anti AQP3 antibody of the present invention on the LPS responsive p65 activation (p65 phosphorylation) in mouse macrophage cells as AQP3-expressing cells. As an anti AQP3 antibody of the present invention, antibody J was used.

FIG. 14A is a diagram showing the result of testing the inhibitory effect of an anti AQP3 antibody of the present invention on acute liver disorder (inflammatory response and disorder response) which was caused in a mouse by treatment with carbon tetrachloride. The test was carried out by having the AST level in blood serum as an indicator. As an anti AQP3 antibody of the present invention, antibody J was used.

FIG. 14B is a diagram showing the result of testing the inhibitory effect of the anti AQP3 antibody of the present invention on acute liver disorder (inflammatory response and disorder response) which was caused in a mouse by treatment with carbon tetrachloride. The test was carried out by having the ALT level in blood serum as an indicator. As an anti AQP3 antibody of the present invention, antibody J was used.

FIG. 15A is a diagram showing the result of testing the inhibitory effect of an anti AQP3 antibody of the present invention on acute liver disorder (inflammatory response and disorder response) which was caused in a mouse by treatment with carbon tetrachloride. The test was carried out by having the TNF-α mRNA expression level in a RNA sample, which was derived from liver, as an indicator. As an anti AQP3 antibody of the present invention, antibody J was used.

FIG. 15B is a diagram showing the result of testing the inhibitory effect of an anti AQP3 antibody of the present invention on acute liver disorder (inflammatory response and disorder response) which was caused in a mouse by treatment with carbon tetrachloride. The test was carried out by having the IL-6 mRNA expression level in a RNA sample, which was derived from liver, as an indicator. As an anti AQP3 antibody of the present invention, antibody J was used.

DESCRIPTION OF EMBODIMENTS (1) Preparation of an Anti AQP3 Antibody Specifically Recognizing Extracellular Domain of AQP3

Because there are three extracellular domains in AQP3, such as loop A, loop C, and loop E, by having at least one AQP3 fragment of them as an immunogen, a host animal can be immunized. In the case of human AQP3, in the polypeptide consisting of full-length 292 amino acid residues (UniProt accession: Q92482), positions 50 to 53 (loop A), positions 131 to 157 (loop C), and positions 210 to 244 (loop E; all positions represent the position from N-terminal side) form each of the extracellular domains. The immunogen is preferably an AQP3 fragment of loop C. Particularly preferably, a polypeptide composed of ten amino acid residues, which is the C-terminal part of loop C and adjacent to the boundary to the transmembrane domain IV, is used as an immunogen. The C-terminal part of loop C adjacent to the boundary to the transmembrane domain IV has the amino acid sequence ATYPSGHLDM (SEQ ID NO: 1) in both human and mouse.

Oligopeptides can be chemically synthesized by well-known standard methods. Furthermore, they can be simply obtained by using a custom-made synthesis service that is commercially available.

As for the immunogen, an oligopeptide itself can be used for immunization, or it is also possible that immunization can be carried out by using reconstituted membrane or recombinant body cells which provide a polypeptide containing the oligopeptide to a membrane. When the immunogen is prepared in the form of a transmembrane protein containing the oligopeptide part, the preparation is preferably carried out by using a baculovirus display method. In that case, a polypeptide containing the oligopeptide can be expressed on a membrane surface of baculovirus and immunization of a host animal can be carried out by using the baculovirus itself as an immunogen to induce an antibody. Those immunogens may be used for immunization either singly or a combination of them may be used simultaneously.

In some embodiments, the host animal is immunized with a peptide whose amino acid sequence consists of the amino acid sequence of SEQ ID NO:1 in combination with AQP3 overexpressing cells. For example, AQP3 overexpressing cells can be HaCaT cells, PAM212 cells, mouse macrophages, or HEK293 cells overexpressing AQP3 or a combination thereof. In another embodiment, the AQP3 overexpressing cells are AQP3 overexpressing CHO cells, e.g., CHO cells expressing mouse or human AQP3 under the control of the CMV promoter. Exemplary vectors that can be used include pCMV6-AC (Origene sc322406) (human AQP3) and pCMV6-Entry-Myc-DDK (Origene MR203989) (mouse AQP3). In some embodiments, the AQP3 overexpressing cells comprise a combination of CHO cells overexpressing mouse AQP3 and CHO cells overexpressing human AQP3.

Preferred examples of the host animal to be immunized include, although not particularly limited, animals like mouse, rat, rabbit, guinea pig, sheep, goat, donkey, chicken, and camel. More preferably, the host animal is a mouse or a rat, and particularly preferably a mouse. For example, reference can be made to the methods described in WO 2015/179360 A. An anti-blood serum containing an anti AQP3 antibody can be produced by a well-known standard method. Anti AQP3 antibodies can be any class of the five kinds of immunoglobulin molecules (IgG, IgM, IgA, IgD, and IgE). Anti AQP3 antibodies are preferably IgG or IgM, and more preferably IgG. Among the IgG subclasses, IgG2 has lower ADCC activity and IgG4 has lower CDC activity. As such, when it is desired to use an antibody having low cell damaging property, it is preferable to use, among IgGs, an antibody of subclass IgG2 or IgG4.

(2) Preparation of an Anti AQP3 Monoclonal Antibody (Anti AQP3 mAb)

An anti AQP3 mAb can be produced as a monoclonal antibody by cloning after fusion of antibody-producing cells obtained during a preparation process as described above in (1) with myeloma cells. Alternatively, according to a genetic engineering method, it can be produced by expressing the chemically-synthesized antibody gene in E. coli or the like. The method for fusing antibody-producing cells and myeloma cells, the method for screening desired cells from the cell group containing the fused cells, the method for monoclonizing the cells selected by screening, and the method for producing mAb from clones can be all carried out according to well-known standard methods. Synthesis of a desired mAb based on sequence information can be also carried out according to well-known standard methods. As it is described in detail in the examples that are given below, monoclonal antibodies that are representative examples of the anti AQP3 mAbs of the present invention have the amino acid sequences of the heavy chain and light chain CDRs or the amino acid sequences of the heavy chain and light chain variable regions that are specifically disclosed. A mAb can be also prepared as a non-secretion type recombinant mAb which consists of an amino acid sequence obtained by removing the signal sequence from each variable region of the heavy chain and light chain. The recombinant mAb with removed signal sequence can accumulate in a host cell without being secreted from the host cell expressing the recombinant mAb into a culture supernatant. The signal sequence can be predicted from the amino acid sequence information, and, for example, it can be predicted by using software for predicting signal sequence. Exemplary software for predicting signal sequence includes Signal P, PRORT II, and the like.

(3) Preparation of Inhibitory Anti AQP3 mAb

Among anti AQP3 antibodies, an antibody having an inhibitory activity for the function of AQP3 is referred herein to as an inhibitory anti AQP3 antibody. In the case of a monoclonal antibody, it is referred to as an inhibitory anti AQP3 mAb, in particular. Herein, the function of AQP3 indicates at least one activity selected from the group consisting of an activity of transporting (permeating) a low molecular weight material by AQP3, an activity of promoting cell proliferation of AQP3-expressing cells, and an activity of promoting cell migration of AQP3-expressing cells. Herein, the low molecular weight material indicates at least one material selected from the group consisting of water molecule, glycerol, and hydrogen peroxide. Presence or absence of the desired inhibitory activity of an anti AQP3 antibody can be determined by having, as an indicator, a decrease in at least one of the cell migration activity and/or cell proliferation activity by 10% or more, 20% or more, or 30% or more according to extracellular addition of a sufficient amount of the anti AQP3 antibody to the cells which constitutively express AQP3 (PAM212 cells, HaCaT cells, A431 cells, or the like) compared to a control without the addition. Alternatively, the determination can be made by having, as an indicator, a decrease in the hydrogen peroxide permeating activity of cells by 10% or more, 20% or more, or 30% or more according to extracellular addition of a sufficient amount of the anti AQP3 antibody to the cells which constitutively express AQP3 (mouse macrophage cells or the like) compared to a control without the addition.

(4) Functional Fragment of an Antibody

As long as sufficient specificity and affinity for AQP3 are exhibited, an antibody of the present invention is not necessarily required to maintain the whole structure of an immunoglobulin molecule, and it can be a functional fragment of the antibody (antigen binding fragment). Because the antigen binding property of an antibody is decided by a variable part of the antibody, the constant region part of an immunoglobulin molecule may not be necessarily present. As such, examples of a functional fragment of an antibody of the present invention include Fab, Fab', F(ab')$_2$, which are a fragment consisting of a variable part of an immunoglobulin molecule, Fd obtained by removing VL from Fab, single-chain Fv fragment (scFv) and a dimer thereof, i.e. a diabody. Alternatively, a single domain antibody (sdAb) obtained by removing VL from scFv, or the like can be also used, but the functional fragment of the antibody is not limited to them.

A functional fragment of an antibody can be prepared by a known technique. For example, fragmentation can be carried out by an enzyme treatment of an immunoglobulin molecule. According to degradation of an immunoglobulin molecule with papain, a Fab is obtained. According to degradation with pepsin, a F(ab')$_2$ is obtained, and according to a reducing treatment of a F(ab')$_2$, a Fab' is obtained. Furthermore, it is also possible, according to a genetic engineering technique, to produce a scFv by linking a heavy chain variable part (VH) to a light chain variable part (VL) of an antibody via a linker peptide with sufficient mobility.

(5) Antibody Labeled with Reporter Material

Depending on a case, an anti AQP3 antibody or a functional fragment thereof of the present invention is used in a state where it is labeled with a reporter material. The reporter material can be any kind as long as it can label the anti AQP3 antibody or a functional fragment thereof while they maintain a desired function. A material capable of generating a signal for quantitative measurement of the present of AQP3 is more preferable. Examples thereof include a radioactive isotope, a metal micro particle, an enzyme, a fluorescent material, and a luminescent material. When a radioactive isotope, a fluorescent material, or a luminescent material is used as a reporter material, the radioactivity, fluorescence, or luminescence generated from them can be quantitatively measured as a signal. When the reporter material is an enzyme, after application to a suitable substrate, the pigment that is finally generated, color, fluorescence, or luminescence derived from fluorescent material or luminescent material can be measured as a signal. Examples of radioactive isotopes include $^3$H and $^{125}$I. Examples of fluorescent materials include fluorescein and derivatives thereof (for example, FITC), tetramethyl rhodamine (TAM RA) and derivatives thereof (for example, TRITC), Cy3, Cy5, Texas Red, phycoerythrin (PE), and quantum dots. Examples of luminescent materials include a luminol derivative, an acridinium derivative, aequorin, and a ruthenium complex. Examples of metal micro particles include gold nano particles and nano particles composed of an alloy of gold and platinum. Examples of reporter enzymes include horseradish peroxidase (HRP), β-galactosidase (β-GAL), alkali phosphatase (ALP), glucose oxidase (GOD), luciferase, and aequorin. By using each enzyme in combination with a suitable substrate, analysis based on light-emission method, colorimetric method, or fluorescence method can be made. For a quantitative analysis, an antibody or a functional fragment thereof of the present invention, which is labeled with a reporter material, is preferably used.

(6) Antibody Immobilized on Solid Support

Depending on a case, an anti AQP3 antibody or a functional fragment thereof of the present invention can be used in a state where it is immobilized on a solid support. The solid support can be any material as long as it can immobilize an antibody or a functional fragment thereof while they remain in a state of maintaining a desired activity. It is preferably a material composed of an inactive material which does not have any influence on the biological analysis using an antibody. Examples of solid supports include a micro plate, a glass plate, a plastic plate, a syringe, a vial, a column, a magnetic particle, a micro bead made of resin, a porous membrane, a porous carrier, and a microchip. The micro plate, syringe, vial, column, and microchip are all preferably made of an inactive resin. Solid supports can be also made of glass.

(7) Antibody Specifically Binding to AQP3 Derived from Human and/or Mouse

An anti AQP3 antibody or a functional fragment thereof of the present invention binds to the extracellular domain of AQP3, in particular, loop C (second extracellular domain) in some embodiments. The amino acid sequence of loop C exhibits high conservation among biospecies. Both the amino acid sequence of human loop C and the amino acid sequence of mouse loop C (positions 131 to 157 from the N-terminal side for both human and mouse) have high homology as it is described below.

```
Human:
                                     (SEQ ID NO: 2)
ADNQLFVSGPNGTAGIFATYPSGHLDM Mouse:
                                     (SEQ ID NO: 3)
ANNELFVSGPNGTAGIFATYPSGHLDM
```

Due to the above reason, an anti AQP3 antibody or a functional fragment thereof of the present invention, which binds to loop C as the extracellular domain, is highly likely to bind specifically to human AQP3 and also mouse AQP3. In some aspects, the present invention relates to antibodies which can be obtained by using the polypeptide (oligopeptide) composed of ten amino acid residues at the C-terminal side of loop C as an immunogen. The oligopeptide composed of ten amino acid residues has an amino acid sequence consisting of ATYPSGHLDM (SEQ ID NO: 1), and the human sequence and mouse sequence are in complete match in that part. Due to this reason, it is highly likely that an anti AQP3 antibody or a functional fragment thereof which is obtained according to the examples of the present invention not only specifically recognizes human AQP3 but also specifically recognizes mouse AQP3. Actually, according to the testing performed on individual mAbs described in the examples, it appears that mAbs of the disclosure can generally recognize both of them. Furthermore, an inhibitory anti AQP mAb of the present invention and a functional fragment thereof can in some embodiments inhibit the function of AQP3 for both human AQP3 and mouse AQP3.

In some embodiments, anti AQP3 antibodies and functional fragments thereof do not specifically bind to one or more human aquaporins other than AQP3, for example, one or more of AQP0 (Accession no. NP_036196.1), APQ1 (Accession no. NP_932766.1), AQP2 (Accession no. NP_000477.1), AQP4 (Accession no. NP_001641.1), AQP5 (Accession no. NP_001642.1), AQP6 (Accession no. NP_001643.2), AQP7 (Accession no. NP_001161.1), AQP8 (Accession no. NP_001160.2), AQP9 (Accession no. NP_066190.2), AQP10 (Accession no. NP_536354.2), AQP11 (Accession no. NP_766627.1), and AQP12 (Accession no. NP_945349.1).

(8) Variable Region of Antibody Molecules and Complementarity-Determining Regions in Variable Regions An immunoglobulin molecule is a hetero tetramer molecule which is basically composed of two heavy chain polypeptides and two light chain polypeptides. Each of the heavy chain and light chain contains a variable region and a constant region. The heavy chain variable region and light chain variable region of an antibody consist of three CDRs (complementarity-determining regions) and four FRs (framework regions), and FR1, CDR1, FR2, CDR2, FR3, CDR3, and FR4 are arranged in the order, from the amino terminal to the carboxy terminal. When the amino acid sequence information of an antibody molecule is determined by a known technique, location of a variable region or a constant region can be predicted based on the sequence information. Furthermore, predicting the sequence of CDR1, CDR2, and CDR3 in a variable region can be also similarly carried out by known methods.

(9) Preparation of Antibody Molecules

A representative anti AQP3 mAb of the present invention is an mAb of which heavy chain variable region consists of the amino acid sequence represented by SEQ ID NO: 4 and light chain variable region consists of the amino acid sequence represented by SEQ ID NO: 5, an mAb of which heavy chain variable region consists of the amino acid sequence represented by SEQ ID NO: 6 and light chain variable region consists of the amino acid sequence represented by SEQ ID NO: 7, or an mAb of which heavy chain variable region consists of the amino acid sequence represented by SEQ ID NO: 8 and light chain variable region consists of the amino acid sequence represented by SEQ ID NO: 9.

An anti AQP3 antibody of the present invention can be produced as a monoclonal antibody by, after cloning the antibody gene from hybridoma or artificially synthesizing the antibody gene based on the amino acid sequence information of the antibody polypeptide, introducing the antibody gene to a suitable expression vector, and introducing the vector to a host using a gene recombination technique.

In that case, a promoter, an enhancer, a polyadenylation signal, or the like can be suitably arranged in the vector. As for the vector, any vector can be used as long as it uses a replicable host cells like bacteria, yeast, and animal cells, and a commercially available vector can be suitably used depending on a host. The expression vector can be introduced to a host cell by a known method for transforming the host cells. Examples of the method include an electroporation method, a DEAE-dextran method, and a calcium phosphate method.

The host cell is not particularly limited, but a eukaryotic cell is preferably used. Examples thereof include yeast and cultured cells derived from an animal (HEK293 cells, CHO cells, COS cells, and MEF, etc.).

Purification of a produced antibody can be carried out by using a method for separation and purification that is generally employed for proteins. For example, it can be suitably carried out by suitably combining affinity chromatography, other chromatography, filtration, ultrafiltration, salting-out, dialysis, and the like.

(10) Modified Products of Antibodies

An anti AQP3 mAb of the present invention may be a sequence-modified product of an antibody having the amino acid sequences described in the above section or Table 1 or Table 6. For example, by having an antibody of which heavy chain variable region consists of the amino acid sequence represented by SEQ ID NO: 4 and light chain variable region consists of the amino acid sequence represented by SEQ ID NO: 5 as a starting point for modification, and within a range in which the specific binding property to the extracellular domain of AQP3 is substantially maintained (within a range in which a specific binding property substantially equivalent to the specific binding property of the original antibody is maintained), a modification may be present within each variable region of the heavy chain and light chain. In each of the amino acid sequence described above, it is also possible that one or several, for example one to ten, preferably one to five, more preferably one or two, and even more preferably one amino acid residue is deleted, substituted, inserted, or added. Furthermore, when calculation is made by using a tool like BLAST, the modification may be present within a range in which there is sequence homology of at least 85% or more, preferably 90% or more, more preferably 95% or more, and particularly preferably 97% or more. However, for any modified product, there is preferably no modification of the amino acid sequence of the CDRs (such that each CDR has the same amino acid sequence as that of the antibody before modification). Namely, in some embodiments, with regard to a modified polypeptide of the heavy chain variable region which consists of the amino acid sequence represented by SEQ ID NO: 4, modification on sequence is not present for CDR1 which consists of the amino acid sequence of SEQ ID NO: 10, CDR2 which consists of the amino acid sequence of SEQ ID NO: 11, and CDR3 which consists of the amino acid sequence of SEQ ID NO: 12. Similarly, in some embodiments, with regard to a modified polypeptide of the light chain variable region which consists of the amino acid sequence represented by SEQ ID NO: 5, modification on sequence is not present for CDR1 which consists of the amino acid sequence of SEQ ID NO: 13, CDR2 which consists of the amino acid sequence of SEQ ID NO: 14, and CDR3 which consists of the amino acid sequence of SEQ ID NO: 15. The same can apply to a modified polypeptide of the heavy chain variable region which consists of the amino acid sequence represented by SEQ ID NO: 6, a modified polypeptide of the light chain variable region which consists of the amino acid sequence represented by SEQ ID NO: 7, a modified polypeptide of the heavy chain variable region which consists of the amino acid sequence represented by SEQ ID NO: 8, and a modified polypeptide of the light chain variable region which consists of the amino acid sequence represented by SEQ ID NO: 9.

It is widely known that the CDR sequence is a major factor for determining an epitope of an antibody. An anti AQP3 mAb of the present invention preferably has, even for the sequence-modified product described above, completely preserved CDRs present in total number of 6 as it is included in the heavy chain and light chain. As such, it is reasonably expected to have a specific binding property for the same epitope as the anti AQP3 mAb before modification. Furthermore, as long as it binds to the same epitope, it is also reasonably expected that, even when the anti AQP3 mAb is the above described sequence-modified product, it has the activity of inhibiting the function of AQP3 as the antibody before modification.

(11) Chimeric Antibodies and Humanized Antibodies

An anti AQP3 mAb of the present invention can be an artificially-modified gene recombination type antibody for the purpose of reducing the heteroantigenicity to a human or the like. Examples of those antibodies include a chimeric antibody and a humanized antibody. These modified antibodies can be produced by known methods.

A chimeric antibody can be prepared by linking the DNA encoding the variable region (V) of an anti AQP3 mAb of the present invention to the DNA encoding a constant (C) region of a human antibody, introducing the resultant construct to an expression vector, and introducing the vector to a host.

A humanized antibody can be obtained by grafting CDRs of an antibody of a mammal other than a human, such as CDRs of a mouse antibody, to a human acceptor antibody (CDR grafting). Production thereof can be suitably carried out by applying a common technique for gene recombination. For example, it is possible that a DNA sequence designed to encode an amino acid sequence for linking each CDR of a mouse anti AQP3 mAb and a framework region of a human antibody is synthesized by PCR method by using several oligonucleotides as a primer, which have been prepared such that they have an overlapped region at terminal regions of both the CDR and FR. For example, it can be carried out by a method described in WO 98/13388 A. The FR of the variable region of a human antibody can be obtained from published DNA data base or the like.

As for the constant region of a chimeric antibody and a humanized antibody, the constant region of a human antibody can be used. For example, Cγ1, Cγ2, Cγ3, and Cγ4 are preferably used for the heavy chain while OK and CA are preferably used for the light chain.

Because chimeric antibodies and humanized antibodies have reduced heteroantigenicity in the human body, they have long half-life in a living body of a human and are useful as an effective ingredient of the pharmaceutical composition of the present invention (agent for prevention and/or treatment). Methods of antibody humanization are known in the art. See, e.g., Riechmann et al., 1988, Nature 332:323-7; U.S. Pat. Nos. 5,530,101; 5,585,089; 5,693,761; 5,693,762;

and 6,180,370 to Queen et al; EP239400; PCT publication WO 91/09967; U.S. Pat. No. 5,225,539; EP592106; EP519596; Padlan, 1991, Mol. Immunol., 28:489-498; Studnicka et al, 1994, Prot. Eng. 7:805-814; Roguska et al, 1994, Proc. Natl. Acad. Sci. 91:969-973; and U.S. Pat. No. 5,565,332

In some embodiments, the anti AQP3 antibodies an functional fragments thereof can be antibodies or antibody fragments whose sequence has been modified to alter at least one constant region-mediated biological effector function relative to the corresponding wild type sequence.

For example, in some embodiments, an anti AQP3 antibody of the present invention can be modified to reduce at least one constant region-mediated biological effector function relative to an unmodified antibody, e.g., reduced binding to the Fc receptor (FcγR). FcγR binding can be reduced by mutating the immunoglobulin constant region segment of the antibody at particular regions necessary for FcγR interactions (see e.g., Canffeld and Morrison, 1991, J. Exp. Med. 173:1483-1491; and Lund et al., 1991, J. Immunol. 147: 2657-2662). Reduction in FcγR binding ability of the antibody can also reduce other effector functions which rely on FcγR interactions, such as opsonization, phagocytosis and antigen-dependent cellular cytotoxicity ("ADCC"). In other embodiments, an anti AQP3 antibody of the present invention can be modified to acquire or improve at least one constant region-mediated biological effector function relative to an unmodified antibody, e.g., to enhance FcγR interactions (see, e.g., US 2006/0134709). For example, an anti AQP3 antibody of the present invention can have a constant region that binds FcγRIIA, FcγRJIB and/or FcγRIIIA with greater affinity than the corresponding wild type constant region.

Thus, antibodies of the present invention can have alterations in biological activity that result in increased or decreased opsonization, phagocytosis, or ADCC. Such alterations are known in the art. For example, modifications in antibodies that reduce ADCC activity are described in U.S. Pat. No. 5,834,597. An exemplary ADCC lowering variant corresponds to "mutant 3" shown in FIG. 4 of U.S. Pat. No. 5,834,597, in which residue 236 is deleted and residues 234, 235 and 237 (using EU numbering) are substituted with alanines.

(12) Reagents for Detecting AQP3

From the viewpoint that an anti AQP3 antibody or a functional fragment thereof of the present invention has an ability of specifically binding to AQP3, a composition containing the antibody or a functional fragment thereof can be provided. This composition can be provided as a reagent for detecting AQP3. Herein, an anti AQP3 antibody or a functional fragment thereof to be contained in a reagent may also be one which is labeled with a reporter material as it has been described in above (5). When it is labeled with a reporter material, detection can be carried out without using a secondary antibody. As another embodiment, an antibody or a functional fragment thereof to be contained in a reagent may be bound or adsorbed onto a solid support such as magnetic micro particles. In a case in which the anti AQP3 antibody or a functional fragment thereof of the present invention is contained as a solution in the reagent, the concentration thereof can be suitably set depending on the purpose of the reagent or mode of use. For example, it can be set within a range of 1 ng/mL to 10 mg/mL, 100 ng/mL to 1 mg/mL, or 1 μg/mL to 300 μg/mL. Furthermore, although the reagent may be used as a stock solution by itself, it can also be used in a diluted state (10 times to 10,000 times) depending on the purpose. As for the solvent, water or a buffer solution can be suitably used.

(13) Reagents for Identification, Separation, and Purification of AQP3-Expressing Cells An anti AQP3 antibody or a functional fragment thereof of the present invention specifically recognizes and binds to the extracellular domain of AQP3, more specifically, the epitope within loop C in some embodiments. From the viewpoint that it can bind to the extracellular domain of an AQP3 molecule, it can be also used for a system in which living cells are employed as a sample. Even for a case of carrying out immunohistological staining, it is not necessary to perform fixing or dialysis of tissue or cells. Accordingly, regardless of the state of cells to be a sample, an anti AQP3 antibody or a functional fragment thereof of the present invention can be used for the identification of AQP3-expressing cells. In particular, when isolated living cells like hematocyte cells are employed as a sample, an anti AQP3 antibody or a functional fragment thereof of the present invention can be used for separation or purification of the AQP3-expressing cells according to combination with a suitable instrument like a flow cytometer. When it is used for separation or purification of the AQP3-expressing cells, an anti AQP3 antibody or a functional fragment thereof labeled with a reporter material as described in above (5) are suitably used. As for the reporter material, a fluorescent pigment is preferable. Examples thereof include FITC, PE/RD1, ECD, PC5, PC7, and APC/Cy3. Alternatively, for separation or purification of the AQP3-expressing cells, an anti AQP3 antibody or a functional fragment thereof immobilized onto a solid phase such as magnetic micro particles can be also used. After binding to the anti AQP3 antibody or a functional fragment thereof immobilized onto a solid phase, the AQP3-expressing cells can be specifically separated by utilizing magnetic force or the like. After the separation, the antibody or a functional fragment thereof can be dissociated from the cells based on adjustment of salt strength or the like. As such, according to this order, the separation or purification of the AQP3-expressing cells can be completed. For the identification, separation, or purification of the AQP3-expressing cells, the composition containing the anti AQP3 antibody or a functional fragment thereof of the present invention is provided as a reagent for detecting AQP3. The reagent may be produced and used as it is described in above (12).

(14) Reagents for Measuring Expression Amount of AQP3

An anti AQP3 antibody or a functional fragment thereof of the present invention can be used as a component of the reagent for detecting AQP3 as described in above (12). Herein, if the anti AQP3 antibody or a functional fragment thereof is labeled with a reporter material as described in above (5) and the reporter material generates a signal allowing quantitative measurement, not only the presence or absence of AQP3 as a target but also the expression amount of AQP3 can be quantitatively measured. Furthermore, even in a case in which an anti AQP3 antibody labeled with a reporter material or a functional fragment thereof is not used, by using in combination a secondary antibody that is labeled with a reporter material which generates a signal allowing quantitative measurement, an anti AQP3 antibody or a functional fragment thereof of the present invention can be used for the measurement of the expression amount of AQP3. For this purpose, a composition containing an anti AQP3 antibody or a functional fragment thereof of the present invention is provided as a reagent for measuring the expression amount of AQP3. The reagent may be suitably produced and used as it is described in the example of above (12).

(15) Antibody Drug Conjugates

The present invention provides antibody drug conjugates (ADCs) comprising an anti AQP3 antibody of the present invention or functional fragment thereof conjugated to a cytotoxic agent. Linkers and processes for making ADCs are known in the art and can be used to make an ADC of the present invention. See, e.g., Tsuchikama and An, 2018, Protein & Cell, 9(1):33-46; Deonarain et al., 2015, Expert Opin Drug Discov. 10(5):463-81; Singh et al., 2015, Pharm Res. 2015 November; 32(11):3541-71. The ADCS of the disclosure can be included in pharmaceutical compositions for use in treating cancer.

Exemplary cytotoxic agents include, for example, auristatins, camptothecins, calicheamicins, duocarmycins, etoposides, maytansinoids (e.g., DM1, DM2, DM3, DM4), taxanes, benzodiazepines (e.g., pyrrolo[I,4]benzodiazepines, indolinobenzodiazepines, and oxazolidinobenzodiazepines including pyrrolo[I,4]benzodiazepine dimers, indolinobenzodiazepine dimers, and oxazolidinobenzodiazepine dimers) and *vinca* alkaloids. Techniques for conjugating therapeutic agents to proteins, and in particular to antibodies, are well-known. (See, e.g., Alley et al., 2010, Current Opinion in Chemical Biology 14: 1-9; Senter, 2008, Cancer J., 14(3): 154-169.) Typically, the therapeutic agent is conjugated to the antibody via a linker unit. The linker unit can be cleavable or non-cleavable. For example, the therapeutic agent can be attached to the antibody with a cleavable linker that is sensitive to cleavage in the intracellular environment of an AQP3 expressing cancer cell but is not substantially sensitive to the extracellular environment, such that the conjugate is cleaved from the antibody when it is internalized by the AQP3 expressing cancer cell (e.g., in the endosomal, lysosomal environment, or in the caveolear environment). In another example, the therapeutic agent can be conjugated to the antibody via a non-cleavable linker and drug release is by total antibody degradation following internalization by the AQP3 expressing cancer cell.

Typically, the ADC will comprise a linker region between the cytotoxic agent and the anti AQP3 antibody. As noted supra, typically, the linker can be cleavable under intracellular conditions, such that cleavage of the linker releases the therapeutic agent from the antibody in the intracellular environment (e.g., within a lysosome or endosome or caveolea). The linker can be, e.g., a peptidyl linker that is cleaved by an intracellular peptidase or protease enzyme, including a lysosomal or endosomal protease. Cleaving agents can include cathepsins B and D and plasmin (see, e.g., Dubowchik and Walker, 1999, Pharm. Therapeutics 83:67-123). Most typical are peptidyl linkers that are cleavable by enzymes that are present in AQP3 expressing cells. For example, a peptidyl linker that is cleavable by the thiol-dependent protease cathepsin-B, which is highly expressed in cancerous tissue, can be used (e.g., a linker comprising a Phe-Leu or a Val-Cit peptide). The linker can also be a carbohydrate linker, including a sugar linker that is cleaved by an intracellular glycosidase (e.g., a glucuronide linker cleavable by a glucuronidase).

The linker also can be a non-cleavable linker, such as an maleimido-alkylene- or maleimide-aryl linker that is directly attached to the therapeutic agent and released by proteolytic degradation of the antibody.

The anti AQP3 antibody can be conjugated to the linker via a heteroatom of the antibody. These heteroatoms can be present on the antibody in its natural state or can be introduced into the antibody. In some aspects, the anti AQP3 antibody will be conjugated to the linker via a nitrogen atom of a lysine residue. In other aspects, the anti AQP3 antibody will be conjugated to the linker via a sulfur atom of a cysteine residue. The cysteine residue can be naturally-occurring or one that is engineered into the antibody. Methods of conjugating linkers and drug-linkers to antibodies via lysine and cysteine residues are known in the art.

Exemplary antibody-drug conjugates include auristatin based antibody-drug conjugates (i.e., the drug component is an auristatin drug). Auristatins bind tubulin, have been shown to interfere with microtubule dynamics and nuclear and cellular division, and have anticancer activity. Typically the auristatin based antibody-drug conjugate comprises a linker between the auristatin drug and the anti AQP3 antibody. The linker can be, for example, a cleavable linker (e.g., a peptidyl linker, a carbohydrate linker) or a non-cleavable linker (e.g., linker released by degradation of the antibody). Auristatins include MMAF, and MMAE. The synthesis and structure of exemplary auristatins are described in U.S. Pat. Nos. 7,659,241, 7,498,298, 2009-0111756, 2009-0018086, and U.S. Pat. No. 7,968,687.

Other exemplary antibody-drug conjugates include maytansinoid antibody-drug conjugates (i.e., the drug component is a maytansinoid drug), and benzodiazepine antibody drug conjugates (i.e., the drug component is a benzodiazepine (e.g., pyrrolo[I,4]benzodiazepine dimers (PBD dimer), indolinobenzodiazepine dimers, and oxazolidinobenzodiazepine dimers)).

(16) Kits Obtained by Including a Composition Containing an Anti AQP3 Antibody or Functional Fragment Thereof As described in above (12) to (14), by using an anti AQP3 antibody or a functional fragment thereof of the present invention, a reagent for detecting AQP3, a reagent for identification, separation, or purification of AQP3-expressing cells, and a reagent for measuring an expression amount of AQP3 can be prepared. In accordance with respective purpose, those reagents can be used for forming a kit, together with an additional component. The kit is suitably combined with constitutional elements such as AQP3 or a fragment thereof as a positive control, AQP3 with known concentration as a standard material, a secondary antibody, an enzyme substrate, a co-factor, an assistant component, a non-specific protein sample as a negative control, a buffer solution, a preservative, a diluent, a user guide book, or the like. A buffer solution for blocking or washing can be also added as a suitable constitutional element of the kit.

(17) Compositions Containing an Inhibitory Anti AQP3 mAb or Functional Fragment Thereof and Compositions as AQP3 Inhibitors An anti AQP3 antibody, a functional fragment thereof, or ADC of the present invention specifically recognizes and binds to the extracellular domain of AQP3, in particular, the epitope in loop C in some embodiments. As it is specifically described in the examples given below, an anti AQP3 mAb of the present invention which binds to the epitope can inhibit at least one function of AQP3 such as the channel function (for example, hydrogen peroxide permeating property) of AQP3 or function of promoting cell proliferation of AQP3 in AQP3-expressing cells. Namely, an anti AQP3 antibody of the present invention can be regarded as an inhibitory anti AQP3 antibody. As such, it is possible to provide a composition which contains an inhibitory anti AQP3 mAb of the present invention or a functional fragment thereof. Furthermore, this composition can be used as an AQP3 inhibitor.

(18) Compositions for Treatment of Cancer

An increased expression level of AQP3 is confirmed in each of skin cancer, colorectal cancer, cervical cancer, liver cancer, lung cancer, esophageal cancer, kidney cancer, stomach cancer, tongue cancer, and the like. Furthermore, as it is described in the examples given below, proliferation of human cancer cell lines, in which AQP3 is expressed, can be inhibited. Accordingly, a composition containing an inhibitory anti AQP3 mAb of the present invention or a functional fragment thereof, an ADC of the present invention, or an AQP3 inhibitor can be used as a composition for treating any one of the above cancers. Furthermore, as it has been suggested that the function of AQP3 is associated with a progress level of cancer, tumor angiogenesis, infiltration property, metastasis, and energy metabolism of cancer tissues, or the like, the composition for treating cancer can be also regarded as a composition for inhibiting cancer proliferation, a composition for inhibiting angiogenesis in cancer, a composition for inhibiting cancer infiltration, and/or a composition for inhibiting/preventing cancer metastasis.

A composition for treating cancer of the present invention can be prepared in a formulation such as a solution for injection or the like. Basically, such a composition for treating cancer can be systemically administered by injection or dropwise addition. However, in a case in which it is used for the purpose of treating cancer or preventing metastasis or the like, topical administration can be also carried out. Those preparations can be prepared by known methods. When it is prepared in a preparation for injection, for example, production can be carried out by dissolving or diluting an inhibitory anti AQP3 mAb of the present invention or a functional fragment thereof, or an ADC of the present invention, which has been aseptically preserved, in water, physiological saline, or buffer solution for injection.

An effective dose of an inhibitory anti AQP3 mAb of the present invention or a functional fragment thereof or an ADC of the present invention, which becomes an effective ingredient of the treatment composition of the present invention, suitably varies depending on various conditions including a state, a symptom, or the like of a patient. In general, a single dose is determined within a range of 0.1 to 10 mg of anti AQP3 mAb/kg of body weight, and it is administered by subcutaneous injection, intravenous injection, intraperitoneal injection, or the like. The administration interval also suitably varies depending on various conditions including a state, a symptom, or the like of a patient. In general, the administration is made once for 1 to 4 weeks, but it is also possible that, after having several weekly administrations, no administration is made for a certain period, or, after one to several initial administrations, administration can be continued at the same pace while the dose is cut down to half or the like.

(19) Compositions for Preventing and/or Treating Skin Disorders

A composition containing an inhibitory anti AQP3 mAb of the present invention or a functional fragment thereof or the AQP3 inhibitor can be used, based on a mechanism of inhibiting the function of AQP3 in cells of skin tissues like keratinocyte, as a composition for preventing and/or treating a skin disorder. Specific examples of the skin disorder include psoriasis, actinic keratosis, ichthyosis, and seborrheic dermatitis. Other than that, for curing or ameliorating keratinocyte proliferative skin abnormality, a composition containing an inhibitory anti AQP3 mAb of the present invention or a functional fragment thereof or a composition for treatment of the present invention which is obtained by containing an AQP3 inhibitor can be used.

(20) Compositions for Preventing and/or Treating Inflammatory Disorders

A composition containing an inhibitory anti AQP3 mAb of the present invention or a functional fragment thereof or an AQP3 inhibitor can be used, based on a mechanism of reducing an inflammatory response according to inhibition of the function of AQP3, as a composition for preventing and/or treating an inflammatory disorder. Specific examples of the inflammatory disorder include atopic dermatitis, psoriasis, asthma, and chronic obstructive lung disease, and hepatitis. Examples of the hepatitis include acute hepatitis and acute liver disorder. Other than that, for preventing, curing, or ameliorating an inflammatory disorder accompanying increased expression of AQP3, a composition containing an inhibitory anti AQP3 mAb of the present invention or a functional fragment thereof or a composition for preventing and/or treating an inflammatory disorder obtained by containing the AQP3 inhibitor can be used.

(21) Compositions for Alleviating Abnormality in Bowel Movement

It is widely known that AQP3 is expressed in intestinal epithelial cells, and it is suggested that the expression level of AQP3 has an influence on the transport amount of moisture inside and outside an intestine. Specifically, it is suggested that the reduced expression level of AQP3 can cause diarrhea by increasing the moisture inside an intestine, while the increased expression level of AQP3 can cause constipation by reducing the moisture inside an intestine. As such, a composition containing an inhibitory anti AQP3 mAb of the present invention or a functional fragment thereof or an AQP3 inhibitor can be used, based on a mechanism of inhibiting the function of AQP3, as a composition for alleviating an abnormality in bowel movement, in particular, as a composition for alleviating constipation. The composition may be prepared and used in the form of an enteric tablet or a suppository, for example. The enteric tablet or suppository can be suitably prepared by a known method. It is not necessary to carry out the administration continuously or periodically, and it can be carried out with a suitable interval depending on a change in symptoms or the like.

(22) Preparation of Compositions for Preventing and/or Treating Skin Disorders or Inflammatory Disorders of the Present Invention An inhibitory anti AQP mAb of the present invention or a functional fragment thereof can be provided as, together with a pharmaceutically acceptable carrier or the like, a composition for prevention and/or treatment. Also for a case in which a skin disorder or an inflammatory disorder is a subject, it can be basically and suitably prepared as a pharmaceutical composition (composition for prevention and/or treatment) like the composition for treating cancer that is described in above (18). The pharmaceutical composition can have a formulation like injection solution or the like. It may also have the form like aqueous solution, suspension, or emulsion. The pharmaceutical composition may contain a pharmaceutically acceptable diluent, aid, carrier, or the like including salts, buffering agents, adjuvants, or the like. Those preparations can be prepared by known methods. When it is produced in the form of a preparation for injection, the production can be made by dissolving or diluting a dried product or a preserved solution of the inhibitory anti AQP mAb or a functional fragment thereof, which has been aseptically preserved, with physiological saline or a buffer solution for subcutaneous injection or intravenous injection. Alternatively, it is also possible to enhance the water solubility by encapsulating the inhibitory anti AQP mAb or a functional fragment thereof by cyclodextrins.

(23) Assistant Components for Compositions for Preventing and/or Treating Skin Disorders or Inflammatory Disorders of the Present Invention A composition containing an inhibitory anti AQP3 mAb of the present invention or a functional fragment thereof, or a composition for prevention or treatment containing an inhibitory anti AQP3 mAb may have a possibility of developing aggregation or precipitation of the anti AQP3 mAb or a functional fragment thereof, as it is often presented as a problem when other antibody preparations are developed while the preparation is a liquid preparation and concentration of the effective ingredient is high or the like. For the purpose of preventing the aggregation or precipitation, one or more than one assistant components may be included in the composition. Examples of the assistant components include saccharides such as monosaccharides, disaccharides, or oligosaccharides, sugar alcohols, salts, and surfactants. More specific examples thereof include sucrose, sodium chloride, and polyoxyethylene sorbitan monolaurate.

(24) Administration Forms of Compositions for Preventing and/or Treating Skin Disorders or Inflammatory Disorders of the Present Invention An effective dose of an inhibitory anti AQP mAb or a functional fragment thereof, which becomes an effective ingredient of a composition for prevention and/or treatment of the present invention, suitably varies depending on various conditions including a state, a symptom, or the like of a patient. The administration dose suitably varies depending on various conditions including a state, a symptom, or the like of a patient. However, the dose as exemplified in the above (18) can be set, for example. The administration interval can be also set similar to the example of the above (18), but it is not necessary to carry out the administration continuously or periodically, and it can be carried out with a suitable interval depending on a change in symptoms or the like. It is needless to say that plural administrations would not be necessary if healing or remission is achieved by single administration. When there is recurrence or worsening of symptoms, the administration can be initiated again.

The administration period can be suitably adjusted depending on a disease condition of a patient. Although the administration dose during the administration period can be suitably adjusted, it is preferable that a constant amount is continuously administered or it is preferable to have administration form in which, after administration of relatively high dose only at initial administration stage, a shift to constant administration of less amount for maintenance is made.

EXAMPLES

Hereinbelow, the present invention is more specifically described by Examples, but the present invention is not limited by those examples at all.

Example 1: Sequence Determination of Oligopeptide Used as Immunogen

To obtain an anti AQP3 antibody which specifically recognizes the extracellular domain of AQP3, the inventors of the present invention conducted multiple computer modeling studies on the structure of AQP3, in particular, the structure of loop A, loop C, and loop E constituting the extracellular domain, and, as a result, selected as an immunogen a fragment (oligopeptide) composed of the amino acid sequence of SEQ ID NO: 1, which constitutes a part of loop C (extracellular second loop). The amino acid sequence of SEQ ID NO: 1 is a sequence which corresponds to positions 148 to 157 of the human AQP3 polypeptide, and it is composed of ten amino acid residues at the C-terminal side of loop C that are adjacent to the boundary to the transmembrane domain IV.

Example 2: Immunization and Selection of Antibody

The oligopeptide composed of the amino acid sequence of SEQ ID NO: 1 was produced as a synthetic peptide. Furthermore, cells which overexpress the AQP3 polypeptide including that amino acid sequence (AQP3-overexpressing cells) were separately produced. Then, the synthetic peptide was combined with AQP3-overexpressing cells, and used as an immunogen.

A suspension of the above immunogen was immunized together with an adjuvant into the abdominal cavity of a mouse of the C57BL/6 line. After that, immune cells were collected from the immunized mouse and the antibody gene phage library was constructed. The phage library was introduced to CHO-K1 cells, and the recombinant antibodies were displayed in the cell membrane of the transformed CHO-K1 cells. Initial patterning was also carried out by using the transformed cells and the synthetic peptide, and patterning using AQP3-solubilizing protein was carried out subsequently. Using several screenings, AQP3-binding colonies were selected. Finally, clones having AQP3-specific binding activity were immunoglobulized (IgG) to obtain ten clones and ten anti AQP3 mAb (antibodies A, B, C, D, E, F, G, H, J, and K) that are derived from those 10 clones.

Meanwhile, when the oligopeptide derived from loop E was used as an immunogen, a clone exhibiting a significant binding activity for AQP3 was not obtained.

Example 3: Binding Property of Anti AQP3 Antibodies to AQP3

A. Antibody Binding to Immunogen Peptide

Binding of antibodies A, B, C, D, E, F, G, H, J, and K to the peptide used for immunization (SEQ ID NO:1) was tested in an ELISA assay. Results are shown in FIG. 2. Antibodies B, C, E, G, H, J, and K were observed to bind the peptide. Antibodies A, D, and F, in contrast to the other antibodies, did not strongly bind the peptide in this assay. Thus, antibodies A, D, and F may therefore bind to AQP3 at a different epitope.

B. Antibody Binding to AQP3 Containing Cell Lysate Measured by ELISA

Cell lysate from HEK293T cells overexpressing mouse AQP3 and a myc-biotinylated tag was used in an ELISA assay to measure the binding of antibodies A, B, C, D, E, F, G, H, J, and K to AQP3. Cell lysate from HEK293T cells overexpressing the myc-biotinylated tag but not AQP3 was used as control. Results are shown in FIG. 3. Each of antibodies A, B, C, D, E, F, G, H, J, and K showed binding to AQP3.

C. Antibody Binding to AQP3 Expressing Cells

By using mouse epithelial cells (PAM212), mouse macrophage cells, human epithelial cells (HaCaT), and HEK293 cells as AQP3-expressing cells, the binding properties of the anti AQP3 antibodies A, B, C, D, E, F, G, H, J, and K to cells were measured.

PAM212 and macrophage cells were reacted with each anti AQP3 antibody (0.1, 1, or 10 μg/mL) at 4° C. for 1 hour. After washing the cells, a fluorescent-labeled anti mouse secondary antibody was added and the reaction was allowed to occur additionally for 1 hour (4° C.). By measuring the fluorescence intensity, the binding property of each anti AQP3 antibody to cells was obtained.

The result obtained by using the mouse macrophage cells and antibody J is shown in FIG. 4.

The testing was also carried out using solvent (Veh) or a non-specific IgG (IgG) controls. In FIG. 4, the vertical axis represents fluorescence intensity, and the mean fluorescence intensity of each sample is represented by bar height together with standard error. From all cases in which antibody J was used at any concentration of 0.1, 1, and 10 μg/mL, significantly increased fluorescence intensity was recognized compared to the controls (Veh and IgG) (in the drawing, ** represents the presence of a significant difference of P<0.01). It was found that antibody J specifically recognizes the mouse AQP3 on cell surface so that antibody J and mouse macrophage cells bind to each other.

The result obtained by using PAM212 cells, which are mouse epithelial cells, and antibody J is shown in FIG. 5A.

The testing was also carried out using solvent (Veh) or a non-specific IgG (IgG) controls. In FIG. 5A, the vertical axis represents fluorescence intensity, and the mean fluorescence intensity of each sample is represented by bar height together with standard error. From all cases in which antibody J was used at any concentration of 0.1, 1, and 10 μg/mL, significantly increased fluorescence intensity was recognized compared to the controls (Veh and IgG) (in the drawing, ** represents the presence of a significant difference of P<0.01). It was found that antibody J specifically recognizes the mouse AQP3 on cell surface so that antibody J and PAM212 cells bind to each other.

The assay was also performed using PAM212 cells and antibodies A, B, C, D, E, F, G, H, and J at a concentration of 10 μg/mL. Results are shown in FIG. 5B. Binding of antibodies C, D, E, G, and J to PAM212 cells was statistically significant.

The assay was also performed using HaCaT cells and antibodies A, B, C, D, E, F, G, H, and J at a concentration of 10 μg/mL. Results are shown in FIG. 5C. Binding of antibodies C, D, E, H, and J to HaCaT cells was statistically significant. The results obtained by performing a FACS assay using HaCaT, which are human epithelial cells, and antibody G, antibody H, or antibody J are shown in FIG. 6A-6C, respectively.

HaCaT cells were treated with Cell Dissociation Buffer for 30 minutes at 37° C., and then dislodged and collected. Then, the cells were reacted with 10 μg/mL anti AQP3 antibody at 4° C. for 1 hour. After washing the cells, a fluorescent-labeled anti mouse secondary antibody was added and the reaction was allowed to occur additionally for 1 hour (4° C.). Then, by using a flow cytometer, fluorescence intensity was measured (FIG. 6A to FIG. 6C). FIG. 6A represents the result of a case in which antibody G was used, FIG. 6B represents the result of a case in which antibody H was used, and FIG. 6C represents the result of a case in which antibody J was used. Each panel shows a histogram in which the horizontal axis represents fluorescence intensity and the vertical axis represents the cell number distribution when the mode value is set at 100. The histogram expressed with bold line represents a case in which the anti AQP3 antibody was used while the histogram expressed with thin gray line represents a case as a control in which the anti AQP3 antibody was not used (addition of non-specific IgG). In the drawing, the range represented by a horizontal bar indicates the fluorescence intensity that is exhibited by the AQP3 antibody positive cell group. Ratio (%) of the cells included in this range (=cells showing positive staining by anti AQP3 antibody) is also shown in the drawing.

From all cases in which any of antibody G, antibody H, and antibody J was used, a clear increase in fluorescence intensity was recognized compared to the control, and thus it was found that the anti AQP3 antibodies have a binding activity for human AQP3 on cell surface.

A FACS assay was also performed using HEK293 cells stably overexpressing mouse AQP3. Cells were incubated with antibody E, H, J, or negative control IgG at a concentration of 10 μg/mL for one hour and then sorted by FACS. Separately, HEK293 cells stably overexpressing human AQP3 were incubated with antibody E at a concentration of 10 μg/mL for one hour and then sorted by FACS. The results are shown in FIGS. 6D-6H. Each of antibodies E, H, and J were found to bind to AQP3 overexpressed on surface of HEK293 cells.

From the above, several anti AQP3 antibodies of the present invention were found to bind to the mouse macrophage cells, mouse epithelial cells (PAM212 cells), and human epithelial cells (HaCaT cells).

Example 4: Immunostaining

By using mouse macrophage cells as AQP3-expressing cells, an immunohistochemistry analysis was made to see whether or not anti AQP3 antibodies can be used for immunostaining.

Blocking was carried out for a plate adhered with mouse macrophage cells, and then a reaction with 10 μg/mL anti AQP3 antibody was carried out for 1 hour at 4° C. After washing the cells, a fluorescent-labeled anti mouse secondary antibody was added and the reaction was allowed to occur additionally for 1 hour (4° C.). As a control, a test not using the anti AQP3 antibody was also carried out. Furthermore, to have a clear location of cell nucleus, staining using DAPI was also carried out. Observation of the fluorescence staining was carried out by a confocal fluorescence microscope. The result obtained by using antibody H and antibody J is shown in FIG. 7A, together with the result of the control having no antibody. In FIG. 7A, the left panel shows an observation image of a case in which there was no antibody (anti AQP3 antibody was not present, only secondary antibody was present), the center panel shows an observation image of a case in which antibody H was used, and the right panel shows an observation image of a case in which antibody J was used. From all panels, a signal derived from DAPI with a dot-like shape showing the location of cell nucleus was recognized. Meanwhile, when antibody H or antibody J was used, a signal which appears to wrap around the edge of cell shape by enclosing the dot-like shape signal resulting from DAPI staining was also recognized. However, when the antibody was not present, a signal which appears to enclose the dot-like shape signal resulting from DAPI staining was not recognized at all.

Only a faint signal was observed when the immunostaining was performed using antibody J and mouse macrophage cells from AQP3 knock-out mice (Ma et al., 2000, PNAS, 97(8):4386-4391), showing that antibody J specifically binds to AQP3 expressing macrophage cells (FIG. 7B).

From the above, it was shown that the tested anti AQP3 antibodies of the present invention are antibodies which can be used for an immunohistochemistry analysis.

Example 5: Activity of Inhibiting Cell Proliferation

By using mouse epithelial cells (PAM212), mouse macrophage as mouse AQP3-expressing cells, human epithelial cells (HaCaT), or human epithelioid carcinoma cells (A431), the activity of inhibiting cell proliferation by an anti AQP3 antibody was measured.

Each of PAM212, HaCaT, and A431 were suspended in DMEM medium containing 1% FBS and seeded on a 96-well plate (5,000 cells/well). On the day after the seeding, DMEM medium containing anti AQP3 antibody (0.1, 1, or 10 μg/mL) was added and culture was continued for additional 2 days. The cell number was compared by using a reagent for measuring living cells (Nacalai Tesque Inc.) and measuring absorbance at 450 nm.

FIG. 8A and FIG. 8B represent a result obtained from a case in which PAM212 AQP3-expressing cells were used. The result obtained by using antibody G or antibody J is shown in FIG. 8A, together with the result of testing non-specific IgG as a control (non-specific IgG was added at 10 μg/mL; Control). In FIG. 8A, the vertical axis shows the absorbance at 450 nm, and the absorbance level was expressed by bar height, together with standard error (same for FIG. 8B, FIG. 9, and FIG. 10). The asterisk (*) in the drawing indicates that there is a significant difference of $P<0.01$ compared to the control. When antibody G or antibody J (10 μg/mL) was used, a significant inhibitory activity for PAM212 cell proliferation was observed.

Concentration-dependent effect of the anti AQP3 antibody J on the inhibitory activity for PAM212 cell proliferation was analyzed and is shown in FIG. 8B. Number of the living cells when antibody J was used at 0.1, 1, or 10 μg/mL is shown in FIG. 8B, together with the result of a non-specific IgG as a control (non-specific IgG was added at 10 μg/mL; Ct). The inhibitory activity for cell proliferation was increased by antibody J in a concentration-dependent manner. In FIG. 8B, the asterisk (*) described for the case in which in antibody J was used at 1 and 10 μg/mL indicates that there is a significant difference of $P<0.01$ compared to the control.

FIG. 8C. shows the effect of antibodies A, B, C, D, E, F, G, H, J, and a negative control IgG antibody at a concentration of 10 μg/mL on PAM212 cell growth. At the tested concentration, antibodies B, C, E, and J significantly inhibited cell growth.

FIG. 9 represents a result obtained from a case in which HaCaT cells were used as a material of human AQP3-expressing cells. The result obtained by using antibody G, antibody H, or antibody J is shown in FIG. 9, together with the result of testing a non-specific IgG as a control (non-specific IgG was added at 10 μg/mL; Control). In FIG. 9, the asterisks (*) and (**) indicate that there is a significant difference of $P<0.05$ or $P<0.01$, respectively, compared to the control. When antibody G, antibody H, or antibody J were used (10 μg/mL), a significant inhibitory activity for HaCaT cell proliferation was shown.

FIG. 10 represents a result obtained from a case in which A431 cells were used as a material of human AQP3-expressing cells. The result obtained by using antibody G, antibody H, or antibody J is shown in FIG. 10, together with the result of testing a non-specific IgG as a control (non-specific IgG was added at 10 μg/mL; Control). In FIG. 10, the asterisk (*) indicates that there is a significant difference of $P<0.05$ compared to the control. When antibody G, antibody H, or antibody J was used (10 μg/mL), a significant inhibitory activity for A431 cell proliferation was observed. Because A431 cells are a human squamous epithelial carcinoma cell line, the effect of inhibiting proliferation into AQP3-expressing cancer cells by the anti AQP3 antibodies was exhibited.

From the above, it was clearly shown that, at least with antibody G, antibody H, and antibody J among the anti AQP3 antibodies of the present invention, the significant inhibitory activity on the cell proliferation in AQP3-expressing cells including cancer cells is exhibited when co-culture of the anti AQP3 antibody and AQP3-expressing cells is carried out.

Example 6: Activity of Inhibiting Hydrogen Peroxide Permeation

By using mouse macrophage as mouse AQP3-expressing cells, an activity of inhibiting the hydrogen peroxide permeation property (incorporating property) by an anti AQP3 antibody was measured.

Mouse macrophages were suspended in DMEM medium containing 1% FBS and seeded on a 96-well plate (10,000 cells/well). On the day after the seeding, DMEM medium containing antibody J (10 μg/mL) as an anti AQP3 antibody or 10 μg/mL control IgG antibody (Ct-IgG: IgG antibody not having specific binding property to AQP3) was added and co-culture was additionally continued overnight. To the culture, hydrogen peroxide (100 μM) or lipopolysaccharide (LPS) (300 ng/mL) was added, and the amount of reactive oxygen species (ROS) in the cells was measured. The ROS amount in the cells was evaluated by, after staining the cells by adding CM-$H_2$DCFDA reagent (Invitrogen, 50 μM, for 20 minutes), measuring the fluorescence intensity derived from CM2DCF before and after the addition. If hydrogen peroxide as one kind of ROS permeates into the cell, it is possible to perform a measurement in which increased fluorescence intensity is taken as an indicator of an increased ROS amount in cells. Addition of LPS has a function of increasing artificially the ROS amount in cells.

FIG. 11 shows the fluorescence intensity derived from CM2DCF when antibody J was added to a co-culture system (Ab) or a solvent was added to a co-culture system (Veh), for a case in which hydrogen peroxide was added ($H_2O_2$), a case in which lipopolysaccharide was added (LPS), or a case in which both $H_2O_2$ and LPS were not added (Ct) to the co-culture system. The vertical axis represents a relative value of the fluorescence intensity. A case of applying a solvent to the cells which have been added with Ct-IgG antibody (left bars in the drawing) is set at 100%, and the relative fluorescence intensity at each condition is represented by bar height, together with standard error. In the drawing, the asterisk (**) indicates that there is a significant difference of $P<0.01$ among the comparisons, and it is clearly shown that, when hydrogen peroxide was added or LPS was added, the ROS amount in cells significantly increased compared to Veh group added with a solvent, and, at any conditions of adding hydrogen peroxide or adding LPS, if antibody J was present during the co-culture, the ROS amount in cells significantly decreased compared to a case in which antibody J was absent.

FIG. 12 shows the results of an $H_2O_2$ transport assay performed using antibodies A, B, C, D, E, F, G, H, and J. Antibodies C, D, E, H, and J have an activity of significantly suppressing the incorporation of hydrogen peroxide to the inside of AQP3-expressing cells.

Example 7: Cell Signal Inhibitory Activity

It is known that, in mouse macrophage, p65/NFκB is phosphorylated and activated in accordance with the stimulation by LPS. To determine whether or not the cell signal responding to LPS is inhibited by an anti AQP3 antibody in mouse macrophage, which is a mouse AQP3-expressing cell, a test was carried out.

Mouse macrophages were suspended in DMEM medium containing 1% FBS and seeded on a 60 mm dish ($2\times10^6$ cells/dish). On the day after the seeding, DMEM medium containing antibody J (10 μg/mL) as an anti AQP3 antibody or 10 μg/mL control IgG antibody (non-specific IgG antibody) was added and co-culture was additionally continued overnight (in FIG. 13 showing the result, the former condition was described as "anti-AQP3 +", while the latter condition was described as "anti-AQP3–"). Each cultured product under both conditions was subjected to a treatment with LPS (100 ng/mL, for 1 hour) or a no treatment with LPS (in FIG. 13 showing the result, the former condition was described as "LPS +", while the latter condition was described as "LPS –"). According to the addition/no addition of the anti AQP3 antibody and the treatment/no treatment with LPS, four treatment groups were created with the mouse macrophage as a sample. From each cell of the four treatment groups, proteins were extracted, and phosphorylation state of p65/NFκB was determined by immunoblotting for each group. FIG. 13 shows the result of carrying out immunoblotting by using an antibody which is specific to each of non-phosphorylated p65 (p65) and phosphorylated p65 (P-p65).

While phosphorylated p65 was strongly induced by LPS treatment at the condition of "anti-AQP3 –" (compare the top panel signals of the left most column with the second column from the right side), at the condition "anti-AQP3+" in which an anti AQP3 antibody was present, induction of phosphorylated p65 (P-p65) by LPS treatment was inhibited (compare the top panel signals of the second column from the left side with the right most column, and, for comparison between conditions regarding LPS addition, compare the top panel signals of the two right columns).

For the intracellular signal in which LPS-induced p65/NFκB is involved with the phosphorylation and activation in AQP3-expressing cells, antibody J has an inhibitory activity.

Example 8: Inhibitory Activity on Liver Disorder (Acute Hepatitis and Acute Liver Disorder)

A test was carried out to determine in an animal subject the anti-inflammatory activity of an anti AQP3 antibody of the present invention (inflammation inhibiting activity and disorder inhibiting activity).

A mouse was used as a test material. The mouse was administered intravenously with an anti AQP3 antibody (antibody J) (5 μg/g of body weight). On the day after the administration, carbon tetrachloride ($CCl_4$), which is a chemical for inducing a liver disorder (acute hepatitis and acute liver disorder), was administered (0.5 μL/g of body weight). 24 Hours after administering the carbon tetrachloride, blood serum and a liver RNA sample were collected. Blood serum AST value, blood serum ALT value, accumulation level of liver TNF-α mRNA, and accumulation level of liver IL-6 mRNA, as an indicator of the degree of the liver disorder, were evaluated. The analysis results using the blood sample and the analysis using the liver RNA sample are shown in FIG. 14 and FIG. 15, respectively.

FIG. 14A shows the analysis result of blood serum AST level. In the drawing, the vertical axis represents the AST level [IU/L], each spot represented by "o" shows an individual measurement value, and the horizontal bar indicates a median value. Ct means a control that has not been subjected to a treatment with carbon tetrachloride. In the carbon tetrachloride treatment group ($CCl_4$), Ab represents a group which has been treated in advance with an anti AQP3 antibody (antibody J) and Veh represents a group which has not been treated with an anti AQP3 antibody. In the drawing, the asterisk (*) indicates that there is a significant difference of $p<0.01$ between the carbon tetrachloride treatment group (both of Veh group and Ab group) and the control group (Ct), and also there is a significant difference of $p<0.01$ between Veh group and Ab group within the carbon tetrachloride treatment group.

FIG. 14B shows the analysis result of blood serum ALT level. In the drawing, the vertical axis represents the ALT level [IU/L], each spot represented by "o" shows an individual measurement value, and the horizontal bar indicates a median value. Ct means a control that has not been subjected to a treatment with carbon tetrachloride. In the carbon tetrachloride treatment group ($CCl_4$), Ab represents a group which has been treated in advance with an anti AQP3 antibody (antibody J) and Veh represents a group which has not been treated with an anti AQP3 antibody. In the drawing, the asterisk (*) indicates that there is a significant difference of $p<0.01$ between the carbon tetrachloride treatment group (both of Veh group and Ab group) and the control group (Ct), and also there is a significant difference of $p<0.01$ between Veh group and Ab group within the carbon tetrachloride treatment group.

It is widely known that both the blood serum AST value and blood serum ALT value can be an indicator of a liver disorder (acute hepatitis and acute liver disorder). From the above test results, it is understood that, in a mouse which has been treated in advance with an anti AQP3 antibody of the present invention, a liver disorder and/or liver inflammation reaction that is caused later by carbon tetrachloride can be prevented or inhibited.

FIG. 15A shows the analysis result of accumulation level of TNF-α mRNA in a liver homogenates. In the drawing, the vertical axis represents the TNF-α expression level, which was obtained by dividing the accumulation level of TNF-α mRNA by 18s rRNA level as a control. In the drawing, TNF-α expression level is shown by bar height together with standard error. Ct means a control that has not been subjected to a treatment with carbon tetrachloride. In the carbon tetrachloride treatment group ($CCl_4$), Ab represents a group which has been treated in advance with an anti AQP3 antibody (antibody J) and Veh represents a group which has not been treated with an anti AQP3 antibody. In the drawing, the asterisk (*) indicates that there is a significant difference of $p<0.01$ between Veh group and the control group (Ct), and also between Veh group and Ab group.

FIG. 15B shows the analysis result of accumulation level of IL-6 mRNA in a liver homogenates. In the drawing, the vertical axis represents the IL-6 expression level, which was obtained by dividing the accumulation level of IL-6 mRNA by 18s rRNA level as a control. In the drawing, IL-6 expression level is shown by bar height together with standard error. Ct means a control that has not been subjected to a treatment with carbon tetrachloride. In the carbon tetrachloride treatment group ($CCl_4$), Ab represents a group which has been treated in advance with an anti AQP3 antibody (antibody J) and Veh represents a group which has not been treated with an anti AQP3 antibody. In the drawing, the asterisk (*) indicates that there is a significant difference of $p<0.01$ between Veh group and the control group (Ct), and also between Veh group and Ab group.

It is widely known that expression of TNF-α or IL-6 in liver is an indicator of a liver disorder (acute hepatitis and acute liver disorder). From the above test results, it is understood that, in a mouse which has been treated in advance with an anti AQP3 antibody of the present invention, a liver disorder and/or liver inflammation reaction that is caused later by carbon tetrachloride can be prevented or inhibited.

For a case of an individual animal which may have a liver disorder (acute hepatitis and acute liver disorder), an occurrence of liver disorder or inflammatory response can be prevented or inhibited by an anti AQP3 antibody of the present invention.

Example 9: Sequence Analysis of Anti AQP3 Antibody

Among ten anti AQP3 antibodies (antibodies A, B, C, D, E, F, G, H, J, and K) derived from 10 clones, which have been obtained in the examples of the present invention, the amino acid sequence of the heavy chain and light chain was determined for each antibody. The heavy chain and light chain sequences (without the predicted signal sequences, which are the same for antibodies A, B, C, D, E, F, G, H, J, and K, and which are discussed below with respect to antibodies F, H, and J) are shown in Table 6.

TABLE 6

Heavy Chain (HC) and Light Chain (LC) Sequences

| Description | Sequence | SEQ ID NO: |
|---|---|---|
| Antibody A HC | QVQLQQPGAELVRPGASVTLSCKASGYTFTDYEMHWVKQTPV HGLEWIGGVDPETGGTGYNQKFRGKAILTADKSSTAYMELR SLTSEDSAVYYCARHGGSFYAMDYWGQGTSVTVSSAKTTAPS VYPLAPVCGDTTGSSVTLGCLVKGYFPEPVTLTWNSGSLSSG VHTFPAVLQSDLYTLSSSVTVTSSTWPSQSITCNVAHPASST KVDKKIEPRGPTIKPCPPCKCPAPNLLGGPSVFIFPPKIKDV LMISLSPIVTCVVVDVSEDDPDVQISWFVNNVEVHTAQTQTH REDYNSTLRVVSALPIQHQDWMSGKEFKCKVNNKDLPAPIER TISKPKGSVRAPQVYVLPPPEEEMTKKQVTLTCMVTDFMPED IYVEWTNNGKTELNYKNTEPVLDSDGSYFMYSKLRVEKKNWV ERNSYSCSVVHEGLHNHHTTKSFSRTPGK | 449 |
| Antibody A LC | DIVMTQSPKFMSTSVGDRVSITCKASQDVSTAVAWYQQKPGQ SPKLLIYWASTRHTGVPDRFTGSGSGTDYTLTISSVQAEDLA LYYCQQHYSTPPTFGGGTKLELKRADAAPTVSIFPPSSEQLT SGGASVVCFLNNFYPKDINVKWKIDGSERQNGVLNSWTDQDS KDSTYSMSSTLTLTKDEYERHNSYTCEATHKTSTSPIVKSFN RNEC | 450 |
| Antibody B HC | EVQLVESGGDLVKPGGSLKLSCAASGFTFSSYGMSWVRQTPD KRLEWVATISRGSIYTYYPDSVKGRFTISRDNAKNTLYLQMS SLKSEDTAMYYCARLSLYDYDGARYTMDYWGQGTSVTVSSAK TTAPSVYPLAPVCGDTTGSSVTLGCLVKGYFPEPVTLTWNSG SLSSGVHTFPAVLQSDLYTLSSSVTVTSSTWPSQSITCNVAH PASSTKVDKKIEPRGPTIKPCPPCKCPAPNLLGGPSVFIFPP KIKDVLMISLSPIVTCVVVDVSEDDPDVQISWFVNNVEVHTA QTQTHREDYNSTLRVVSALPIQHQDWMSGKEFKCKVNNKDLP APIERTISKPKGSVRAPQVYVLPPPEEEMTKKQVTLTCMVTD FMPEDIYVEWTNNGKTELNYKNTEPVLDSDGSYFMYSKLRVE KKNWVERNSYSCSVVHEGLHNHHTTKSFSRTPGK | 451 |
| Antibody B LC | DTVMTQSPKFMSTSVGDRVSITCKASQDVGTAVAWYQQKPGQ SPKLLIYWASTRHTGVPDRFTGSGSGTDFTLTTSNVQSEDLA DYFCQQYSSYHTFGAGTKLELKRADAAPTVSIFPPSSEQLTS GGASVVCFLNNFYPKDINVKWKIDGSERQNGVLNSWTDQDSK DSTYSMSSTLTLTKDEYERHNSYTCEATHKTSTSPIVKSFNR NEC | 452 |
| Antibody C HC | QVQLKQSGAELARPGASVKLSCKASGYNFKSYGISWVKQRTG QGLEWIGEIYPGSGNTYYNEKLKGKATLTADKSSSTAYMELR SLTSEDSAVYFCARTYGYDSFPWFAYWGQGTLVTVSSAKTTA PSVYPLAPVCGDTTGSSVTLGCLVKGYFPEPVTLTWNSGSLS SGVHTFPAVLQSDLYTLSSSVTVTSSTWPSQSITCNVAHPAS STKVDKKIEPRGPTIKPCPPCKCPAPNLLGGPSVFIFPPKIK DVLMISLSPIVTCVVVDVSEDDPDVQISWFVNNVEVHTAQTQ THREDYNSTLRVVSALPIQHQDWMSGKEFKCKVNNKDLPAPI ERTISKPKGSVRAPQVYVLPPPEEEMTKKQVTLTCMVTDFMP EDIYVEWTNNGKTELNYKNTEPVLDSDGSYFMYSKLRVEKKN WVERNSYSCSVVHEGLHNHHTTKSFSRTPGK | 453 |
| Antibody C LC | DIVMTQAAPSVPVTPGESVSISCRSSKSLLHSNGNTYLYWFL QRPGQSPQLLIYRVSNLASGVPDRFSGSGSGTAFTLRISRVE AEDEGVYYCMQHLEYPFTFGAGTKLEIKRADAAPTVSIFPPS SEQLTSGGASVVCFLNNFYPKDINVKWKIDGSERQNGVLNSW TDQDSKDSTYSMSSTLTLTKDEYERHNSYTCEATHKTSTSPI VKSFNRNEC | 454 |
| Antibody D HC | EVQLQQSGAELVRPGASVTLSCKASGYTFTDYEMHWVQQTPV HGLEWIGGIDPETGGTGYNQKFKGKAILTADKSSSTAYMELR SLTSEDSAVYFCTRHGSYAMDYWGQGTSVTVSSAKTTAPSVY PLAPVCGDTTGSSVTLGCLVKGYFPEPVTLTWNSGSLSSGVH TFPAVLQSDLYTLSSSVTVTSSTWPSQSITCNVAHPASSTKV DKKIEPRGPTIKPCPPCKCPAPNLLGGPSVFIFPPKIKDVLM ISLSPIVTCVVVDVSEDDPDVQISWFVNNVEVHTAQTQTHRE | 455 |

TABLE 6-continued

Heavy Chain (HC) and Light Chain (LC) Sequences

| Description | Sequence | SEQ ID NO: |
|---|---|---|
| | DYNSTLRVVSALPIQHQDWMSGKEFKCKVNNKDLPAPIERTI SKPKGSVRAPQVYVLPPPEEEMTKKQVTLTCMVTDFMPEDIY VEWTNMGKTELNYKNTEPVLDSDGSYFMYSKLRVEKKNWVER NSYSCSVVHEGLHNHHTTKSFSRTPGK | |
| Antibody D LC | DIVMTQSPKFMSTSVGDRVSITCKASQDVSTAVAWYQQKPGQ SPKLLIYWASTRHTGVPDRFTGSGSGTDYTLTISSVQAEDLA LYYCQQHYSTPPTFGGGTRLEIKRADAAPTVSIFPPSSEQLT SGGASVVCFLNNFYPKDINVKWKIDGSERQNGVLNSWTDQDS KDSTYSMSSTLTLTKDEYERHNSYTCEATHKTSTSPIVKSFN RNEC | 456 |
| Antibody E HC | EVKLLESGAELVRPGASVTLSCKASGYTFTDYEMHWVKQTPV HGLEWIGGIDPESGGTGYNQKFKGKAILTADKSSSTAYMELR SLTSEDSAVYFCTRSGYYGSPLLDYWGQGTTLTVSSAKTTAP SVYPLAPVCGDTTGSSVTLGCLVKGYFPEPVTLTWNSGSLSS GVHTFPAVLQSDLYTLSSSVTVTSSTWPSQSITCNVAHPASS TKVDKKIEPRGPTIKPCPPCKCPAPNLLGGPSVFIFPPKIKD VLMISLSPIVTCVVVDVSEDDPDVQISWFVNNVEVKTAQTQT HREDYNSTLRVVSALPIQHQDWMSGKEFKCKVNNKDLPAPIE RTISKPKGSVRAPQVYVLPPPEEEMTKKQVTLTCMVTDFMPE DIYVEWTNNGKTELNYKNTEPVLDSDGSYFMYSKLRVEKKNW VERNSYSCSVVHEGLHMHHTTKSFSRTPGK | 457 |
| Antibody E LC | QIVLSQSPAIMSASLGERVTMTCTASSSVSSSYLHWYQQKPG SSPKLWIYSTSNLASGVPARFSGSGSGTSYSLTISSMEAEDA ATYYCHQYHRSPPTFGAGTKLEIKRADAAPTVSIFPPSSEQL TSGGASVVCFLNNFYPKDINVKWKIDGSERQMGVLNSWTDQD SKDSTYSMSSTLTLTKDEYERHNSYTCEATHKTSTSPIVKSF NRNEC | 458 |
| Antibody F HC | QVQLKESGPELVKPGASVKISCKASGYTFTDYYINWVKQRPG QGLEWIGWIFPGSGSTYYNEKFKGKATLTVDKSSSTAYMLLS SLTSEDSAVYFCADYGSSYRYFDVWGAGTTVTVSSAKTTAPS VYPLAPVCGDTTGSSVTLGCLVKGYFPEPVTLTWNSGSLSSG VHTFPAVLQSDLYTLSSSVTVTSSTWPSQSITCNVAHPASST KVDKKIEPRGPTTKPCPPCKCPAPNLLGGPSVFTFPPPKTKDV LMISLSPIVTCVVVDVSEDDPDVQISWFVNNVEVHTAQTQTH REDYNSTLRVVSALPIQHQDWMSGKEFKCKVNNKDLPAPIER TISKPKGSVRAPQVYVLPPPEEEMTKKQVTLTCMVTDFMPED IYVEWTNNGKTELNYKNTEPVLDSDGSYFMYSKLRVEKKNWV ERNSYSCSVVHEGLHNHHTTKSFSRTPGK | 459 |
| Antibody F LC | DIVMTQSPAILSASPGEKVTMTCRASSSVSYMHWYQQKPGSS PKPWIYATSYLASGVPARFSGSGSGTSYSLTIGRVEAEDAAT YYCQQWSSNPLTFGAGTKLELKRADAAPTVSIFPPSSEQLTS GGASVVCFLNKFYPKDINVKWKIDGSERQNGVLNSWTDQDSK DSTYSMSSTLTLTKDEYERHNSYTCEATHKTSTSPIVKSFNR NEC | 460 |
| Antibody G HC | QVQLKQSGAELVRPGASVTLSCKASGYTFTDYEMHWVKQTPV HGLEWIGGIDPETGGTAYNQKFKGKAILTADKSSSTAYMELR SLTSEDSAVYYCTRWGAITSFVALRGFAYWGQGTLVTVSSAK TTAPSVYPLAPVCGDTTGSSVTLGCLVKGYFPEPVTLTWNSG SLSSGVHTFPAVLQSDLYTLSSSVTVTSSTWPSQSITCNVAH PASSTKVDKKIEPRGPTIKPCPPCKCPAPNLLGGPSVFIFPP KIKDVLMISLSPIVTCVVVDVSEDDPDVQISWFVNNVEVHTA QTQTHREDYNSTLRVVSALPIQHQDWMSGKEFKCKVNNKDLP APTERTISKPKGSVRAPQVYVLPPPEEEMTKKQVTLTCMVTD FMPEDIYVEWTNNGKTELNYKNTEPVLDSDGSYFMYSKLRVE KKNWVERNSYSCSVVHEGLHNHHTTKSFSRTPGK | 461 |
| Antibody G LC | DTQMTQSPSSLSVSAGEKVTMSCKSSQSLLNSGNQKNYLAWY QQKPGQPPKLLIYGASTRESGVPDRFTGSGSGTDFTLTTSSV QAEDLAVYYCQNDHSYPPTFGAGTKLELKRADAAPTVSIFPP SSEQLTSGGASVVCFLNNFYPKDINVKWKIDGSERQNGVLNS WTDQDSKDSTYSMSSTLTLTKDEYERHNSYTCEATHKTSTSP IVKSFNRNEC | 462 |
| Antibody H HC | EVKLVESGGDLVKPGGSLKLSCAASGFTFSSYGMSWVRQTPD KRLEWVATISRRSIYTYYPDSVQGRFTISRDNAKNTLYLQMS SLKSEDTAMYYCARLSLYDYDGARYTMDYWGQGTSVTVSSAK TTAPSVYPLAPVCGDTTGSSVTLGCLVKGYFPEPVTLTWNSG SLSSGVHTFPAVLQSDLYTLSSSVTVTSSTWPSQSITCNVAH PASSTKVDKKIEPRGPTIKPCPPCKCPAPNLLGGPSVFIFPP | 463 |

TABLE 6-continued

Heavy Chain (HC) and Light Chain (LC) Sequences

| Description | Sequence | SEQ ID NO: |
|---|---|---|
| | KIKDVLMISLSPIVTCVVVDVSEDDPDVQISWFVNNVEVHTA QTQTHREDYNSTLRVVSALPIQHQDWMSGKEFKCKVNNKDLP APIERTISKPKGSVRAPQVYVLPPPEEEMTKKQVTLTCMVTD FMPEDIYVEWTNNGKTELNYKNTEPVLDSDGSYFMYSKLRVE KKNWVERNSYSCSVVHEGLHNHHTTKSFSRTPGK | |
| Antibody H LC | DIKMTQSPKFMSTSVGDRVSITCKASQDVGTAVAWYQQKPGQ SPKLLIYWASTRHTGVPDRFTGSGSGTDFTLTISNVQSEDLA DYFCQQYSSYHTFGAGTKLEIKRADAAPTVSIFPPSSEQLTS GGASVVCFLNNEYPKDINVKWKIDGSERQNGVLNSWTDQDSK DSTYSMSSTLTLTKDEYERHNSYTCEATHKTSTSPIVKSFNR NEC | 464 |
| Antibody J HC | QVHLQQSGTELVKPGASVKLSCEASGYTFTSYWMHWVKQRPG QGLEWIGNINPSNGGTNYNEKFKSKATLTVDKSSSTAYMQLS SLTSEDSAVYYCARGGIYYGNYDYYAMDYWGQGTSVTVSSAK TTAPSVYPLAPVCGDTTGSSVTLGCLVKGYFPEPVTLTWNSG SLSSGVHTFPAVLQSDLYTLSSSVTVTSSTWPSQSITCNVAH PASSTKVDKKIEPRGPTIKPCPPCKCPAPNLLGGPSVFIFPP KIKDVLMISLSPIVTCVVVDVSEDDPDVQISWFVNNVEVHTA QTQTHREDYNSTLRVVSALPIQHQDWMSGKEFKCKVNNKDLP APIERTISKPKGSVRAPQVYVLPPPEEEMTKKQVTLTCMVTD FMPEDIYVEWTNNGKTELNYKNTEPVLDSDGSYFMYSKLRVE KKNWVERNSYSCSVVHEGLHNHHTTKSFSRTPGK | 465 |
| Antibody J LC | DIVMTQAAPSVPVTPGESVSISCRSSKSLLHSNGNTYLYWFL QRPGQSPQLLIYRVSNLASGVPDRFSGSGSGTAFTLRISRVE AEDVGVYYCMQHLEYPPTFGGGTKLEIKRADAAPTVSIFPPS SEQLTSGGASVVCFLNNFYPKDINVKWKIDGSERQNGVLNSW TDQDSKDSTYSMSSTLTLTKDEYERHNSYTCEATHKTSTSPI VKSFNRNEC | 466 |
| Antibody K HC | QVQLKQSGAELVRPGTSVKVSCKASGYAFTNYLIEWVKQRPG QGLEWIGVINPGSGGTNYNEKFKGKATLTADKSSSTAYMQLS SLTSEDSAVYFCARWGFYYAMDYWGQGTSVTVSSAKTTAPSV YPLAPVCGDTTGSSVTLGCLVKGYFPEPVTLTWNSGSLSSGV HTFPAVLQSDLYTLSSSVTVTSSTWPSQSITCNVAHPASSTK VDKKIEPRGPTIKPCPPCKCPAPNLLGGPSVFIFPPKIKDVL MISLSPIVTCVVVDVSEDDPDVQISWFVNNVEVHTAQTQTHR EDYNSTLRVVSALPIQHQDWMSGKEFKCKVNNKDLPAPIERT ISKPKGSVRAPQVYVLPPPEEEMTKKQVTLTCMVTDFMPEDI YVEWTNNGKTELNYKNTEPVLDSDGSYFMYSKLRVEKKNWVE RNSYSCSVVHEGLHNHHTTKSFSRTPGK | 467 |
| Antibody K LC | DIVMTQSPSSLSASLGERVSLTCRASQEISGYLSWLQQKPDG TIKRLIYAASTLDSGVPKRFSGSRSGSDYSLTISSLESEDFA DYYCLQYASYPLTFGAGTKLEIKRADAAPTVSIFPPSSEQLT SGGASVVCFLNNFYPKDINVKWKIDGSERQNGVLNSWTDQDS KDSTYSMSSTLTLTKDEYERHNSYTCEATHKTSTSPIVKSFN RNEC | 468 |

Furthermore, by combining the determined amino acid sequence information with a known analytical technique, sequences of the variable region, CDR, and signal peptide included in each chain of the immunoglobulin molecule were determined.

(1) Antibody F

The heavy chain variable region of antibody F has the amino acid sequence that is represented by SEQ ID NO: 4.

When counting is made from the N-terminal side, the region composed of 19 amino acid residues starting from the methionine residue at position 6 to the serine residue at position 24 in the amino acid sequence is believed to be a signal peptide.

In this heavy chain variable region, CDR1 (IMGT definition) has an amino acid sequence of GYTFTDYY (SEQ ID NO: 10), CDR2 (IMGT definition) has an amino acid sequence of IFPGSGST (SEQ ID NO: 11), and CDR3 (IMGT definition) has an amino acid sequence of ADYGSSYRYFDV (SEQ ID NO: 12), respectively.

The light chain variable region of antibody F has the amino acid sequence that is represented by SEQ ID NO: 5.

When counting is made from the N-terminal side, the region composed of 20 amino acid residues starting from the methionine residue at position 6 to the glycine residue at position 25 in the amino acid sequence is believed to be a signal peptide.

In this light chain variable region, CDR1 (IMGT definition) has an amino acid sequence of SSVSY (SEQ ID NO: 13), CDR2 (IMGT definition) has an amino acid sequence of ATS (SEQ ID NO: 14), and CDR3 (IMGT definition) has an amino acid sequence of QQWSSNPLT (SEQ ID NO: 15), respectively.

(2) Antibody H

The heavy chain variable region of antibody H has the amino acid sequence that is represented by SEQ ID NO: 6.

When counting is made from the N-terminal side, the region composed of 19 amino acid residues starting from the methionine residue at position 6 to the serine residue at position 24 in the amino acid sequence is believed to be a signal peptide.

In this heavy chain variable region, CDR1 (IMGT definition) has an amino acid sequence of GFTYSSYG (SEQ ID NO: 16), CDR2 (IMGT definition) has an amino acid sequence of ISRRSIYT (SEQ ID NO: 17), and CDR3 (IMGT definition) has an amino acid sequence of ARLSLYDYDGARYTMDY (SEQ ID NO: 18), respectively.

The light chain variable region of antibody H has the amino acid sequence that is represented by SEQ ID NO: 7.

When counting is made from the N-terminal side, the region composed of 20 amino acid residues starting from the methionine residue at position 6 to the glycine residue at position 25 in the amino acid sequence is believed to be a signal peptide.

In this light chain variable region, CDR1 (IMGT definition) has an amino acid sequence of QDVGTA (SEQ ID NO: 19), CDR2 (IMGT definition) has an amino acid sequence of WAS (SEQ ID NO: 20), and CDR3 (IMGT definition) has an amino acid sequence of QQYSSYHT (SEQ ID NO: 21), respectively.

(3) Antibody J

The heavy chain variable region of antibody J has the amino acid sequence that is represented by SEQ ID NO: 8.

When counting is made from the N-terminal side, the region composed of 19 amino acid residues starting from the methionine residue at position 6 to the serine residue at position 24 in the amino acid sequence is believed to be a signal peptide.

In this heavy chain variable region, CDR1 (IMGT definition) has an amino acid sequence GYTFTSYW (SEQ ID NO: 22). CDR2 (IMGT definition) has an amino acid sequence INPSNGGT (SEQ ID NO: 23), and CDR3 (IMGT definition) has an amino acid sequence of ARGGIYYGNYDYYAMDY (SEQ ID NO: 24), respectively.

The light chain variable region of antibody J has the amino acid sequence that is represented by SEQ ID NO: 9.

When counting is made from the N-terminal side, the region composed of 20 amino acid residues starting from the methionine residue at position 6 to the glycine residue at position 25 in the amino acid sequence is believed to be a signal peptide.

In this light chain variable region, CDR1 (IMGT definition) has an amino acid sequence of KSLLHSNGNTY (SEQ ID NO: 25), CDR2 (IMGT definition) has an amino acid sequence of RVS (SEQ ID NO: 26), and CDR3 (IMGT definition) has an amino acid sequence of MQHLEYPFT (SEQ ID NO: 27), respectively.

(4) Summary of Results and Discussion

It is evident from the sequence information that antibodies A, B, C, D, E, F, G, H, J, and K are different antibodies, each derived from an independent clone.

Several of the antibodies were shown to bind specifically to both the mouse AQP3 and human AQP3 as an antigen (in particular, they can bind to a peptide fragment composed of the amino acid sequence of SEQ ID NO: 1, which is included in loop C). In addition, several of the antibodies were shown to be an inhibitory anti AQP3 mAb. Inhibitory anti AQP3 antibodies of the present invention have at least one suppressive activity selected from suppressing the function of permeating a low molecular weight molecule, which is responsible by AQP3 (for example, function of permeating hydrogen peroxide), suppressing the cellular function of AQP3-expressing cells (for example, function of cell proliferation), and suppressing an inflammatory response or a disorder response that is associated with AQP3.

Successful obtainment of multiple inhibitory antibodies derived from independent clones means that the epitope constituted with a region composed of the amino acid sequence of SEQ ID NO: 1, which is included in loop C as one of the extracellular domains of AQP3, is important, and, by selecting an anti AQP3 antibody that can specifically recognize the epitope, even more independent inhibitory anti AQP3 antibodies can be selected. The present invention provides an antibody which recognizes the extracellular domain of AQP3 and can directly bind to AQP3 from the outside of a cell, and it can also provide an anti AQP3 mAb which has not been known in a related art. In addition, without being limited thereto, the present invention provides plural molecules of an inhibitory anti AQP3 antibody, and gives clear information about the epitope included in the extracellular domain of AQP3, thus allowing new obtainment of an inhibitory anti AQP3 antibody.

INDUSTRIAL APPLICABILITY

The anti AQP3 monoclonal antibodies of the present invention specifically recognizing the extracellular domain of AQP3 enables highly-sensitive detection of AQP3, and from the viewpoint that it can be also used for identification, separation, and purification of living cells which express AQP3, it allows various analyses relating to AQP3, and thus has an industrial applicability. Furthermore, because anti AQP3 monoclonal antibodies of the present invention can have an inhibitory activity on at least one function of AQP3 like inhibiting the function of permeating a low molecular weight molecule that is responsible by AQP3, inhibiting the cellular function of AQP3-expressing cells (cell proliferation or the like), and inhibiting an occurrence of an inflammatory response in liver or the like, they can be used for prevention or treatment of various disorders, and thus have an industrial applicability.

Specific Embodiments

While various specific embodiments have been illustrated and described, it will be appreciated that various changes can be made without departing from the spirit and scope of the disclosure(s). The present disclosure is exemplified by the numbered embodiments set forth below.

1. An anti AQP3 antibody or a functional fragment thereof that specifically binds to an oligopeptide whose amino acid sequence consists of ATYPSGHLDM (SEQ ID NO:1).

2. The antibody or functional fragment thereof according to embodiment 1, which specifically binds to human AQP3.

3. The antibody or functional fragment thereof according to embodiment 1 or embodiment 2, which specifically binds to mouse AQP3.

4. An anti AQP3 antibody or a functional fragment thereof that specifically binds to the extracellular domain of human AQP3 and/or the extracellular domain of mouse AQP3.

5. The antibody or functional fragment thereof according to any one of embodiments 1 to 3, which specifically binds to the extracellular domain of human AQP3 and/or the extracellular domain of mouse AQP3.

6. The antibody or functional fragment thereof according to embodiment 4 or embodiment 5, which specifically binds to the extracellular domain of human AQP3.

7. The antibody or functional fragment thereof according to any one of embodiments 4 to 6, which specifically binds to the extracellular domain of mouse AQP3.

8. The antibody or functional fragment thereof according to any one of embodiments 4 to 7, which specifically binds to the extracellular domain of AQP3 expressed on the surface of PAM212 cells.

9. The antibody or functional fragment thereof according to any one of embodiments 4 to 8, which specifically binds to the extracellular domain of AQP3 expressed on the surface of mouse macrophages.

10. The antibody or functional fragment thereof according to any one of embodiments 3 to 9, which specifically binds to the extracellular domain of AQP3 expressed on the surface of HEK293 cells.

11. The antibody or functional fragment thereof according to any one of embodiments 1 to 10 having an inhibitory activity on at least one function of human AQP3.

12. The antibody or functional fragment thereof according to any one of embodiments 1 to 11 having an inhibitory activity on at least one function of mouse AQP3.

13. The antibody or functional fragment thereof according to any one of embodiments 1 to 12, which inhibits proliferation of one or more of PAM212 cells, HaCaT cells, and A431 cells.

14. The antibody or functional fragment thereof according to embodiment 13, which inhibits proliferation of PAM212 cells.

15. The antibody or functional fragment thereof according to embodiment 13 or embodiment 14, which inhibits proliferation of HaCaT cells.

16. The antibody or functional fragment thereof according to any one of embodiments 13 to 15, which inhibits proliferation of A431 cells.

17. The antibody or functional fragment thereof according to any one of embodiments 13 to 16, wherein proliferation is measured according to the assay described in Example 5.

18. The antibody or functional fragment thereof according to any one of embodiments 13 to 17, which inhibits proliferation by at least 10% relative to an IgG control antibody that does not specifically bind AQP3.

19. The antibody or functional fragment thereof according to embodiment 18, which inhibits proliferation by at least 20% relative to an IgG control antibody that does not specifically bind AQP3.

20. The antibody or functional fragment thereof according to embodiment 19, which inhibits proliferation by at least 30% relative to an IgG control antibody that does not specifically bind AQP3.

21. The antibody or functional fragment thereof according to embodiment 18, which inhibits proliferation by about 10% to about 30% relative to an IgG control antibody that does not specifically bind AQP3.

22. The antibody or functional fragment thereof according to any one of embodiments 1 to 21, which inhibits $H_2O_2$ transport.

23. The antibody or functional fragment thereof according to embodiment 22, wherein inhibition of $H_2O_2$ transport is measured according to the assay described in Example 6.

24. The antibody or functional fragment thereof according to embodiment 22 or embodiment 23, which inhibits $H_2O_2$ transport by at least 10% relative to an IgG control antibody that does not specifically bind AQP3.

25. The antibody or functional fragment thereof according to embodiment 24, which inhibits $H_2O_2$ transport by at least 20% relative to an IgG control antibody that does not specifically bind AQP3.

26. The antibody or functional fragment thereof according to embodiment 24, which inhibits $H_2O_2$ transport by at least 30% relative to an IgG control antibody that does not specifically bind AQP3.

27. The antibody or functional fragment thereof according to embodiment 24, which inhibits $H_2O_2$ transport by about 10% to about 30% relative to an IgG control antibody that does not specifically bind AQP3.

28. The antibody or functional fragment thereof according to any one of embodiments 1 to 27, which inhibits phosphorylation of p65.

29. The antibody or functional fragment thereof according to embodiment 28, wherein inhibition of phosphorylation of p65 is measured according to the assay described in Example 7.

30. The antibody or functional fragment thereof according to any one of embodiments 1 to 29, which inhibits a liver inflammatory response in mice treated with carbon tetrachloride.

31. The antibody or function fragment thereof according to embodiment 30, wherein the liver inflammatory response in mice treated with carbon tetrachloride is measured according to the assay described in Example 8.

32. An anti AQP3 antibody or a functional fragment thereof comprising a heavy chain complementarity determining region 1 (HCDR1), a heavy chain complementarity determining region 2 (HCRD2), a heavy chain complementarity determining region 3 (HCDR3), a light chain complementarity determining region 1 (LCDR1), a light chain complementarity determining region 2 (LCDR2), and a light chain complementarity determining region 3 (LCDR3) comprising amino acid sequences selected from the sequences set forth in one of Tables 2A-5E.

33. The antibody or functional fragment thereof according to embodiment 32, comprising HCDR1, HCDR2, HCDR3, LCDR1, LCDR2, and LCDR3 sequences as set forth in Table 2A.

34. The antibody or functional fragment thereof according to embodiment 32, comprising HCDR1, HCDR2, HCDR3, LCDR1, LCDR2, and LCDR3 sequences as set forth in Table 2B.

35. The antibody or functional fragment thereof according to embodiment 32, comprising HCDR1, HCDR2, HCDR3, LCDR1, LCDR2, and LCDR3 sequences as set forth in Table 2C.

36. The antibody or functional fragment thereof according to embodiment 32, comprising HCDR1, HCDR2, HCDR3, LCDR1, LCDR2, and LCDR3 sequences as set forth in Table 2D.

37. The antibody or functional fragment thereof according to embodiment 32, comprising HCDR1, HCDR2, HCDR3, LCDR1, LCDR2, and LCDR3 sequences as set forth in Table 2E.

38. The antibody or functional fragment thereof according to embodiment 32, comprising HCDR1, HCDR2, HCDR3, LCDR1, LCDR2, and LCDR3 sequences as set forth in Table 3A.

39. The antibody or functional fragment thereof according to embodiment 32, comprising HCDR1, HCDR2, HCDR3, LCDR1, LCDR2, and LCDR3 sequences as set forth in Table 3B.

40. The antibody or functional fragment thereof according to embodiment 32, comprising HCDR1, HCDR2, HCDR3, LCDR1, LCDR2, and LCDR3 sequences as set forth in Table 3C.

41. The antibody or functional fragment thereof according to embodiment 32, comprising HCDR1, HCDR2, HCDR3, LCDR1, LCDR2, and LCDR3 sequences as set forth in Table 3D.

42. The antibody or functional fragment thereof according to embodiment 32, comprising HCDR1, HCDR2, HCDR3, LCDR1, LCDR2, and LCDR3 sequences as set forth in Table 3E.

43. The antibody or functional fragment thereof according to embodiment 32, comprising HCDR1, HCDR2, HCDR3, LCDR1, LCDR2, and LCDR3 sequences as set forth in Table 4A.

44. The antibody or functional fragment thereof according to embodiment 32, comprising HCDR1, HCDR2, HCDR3, LCDR1, LCDR2, and LCDR3 sequences as set forth in Table 4B.

45. The antibody or functional fragment thereof according to embodiment 32, comprising HCDR1, HCDR2, HCDR3, LCDR1, LCDR2, and LCDR3 sequences as set forth in Table 4C.

46. The antibody or functional fragment thereof according to embodiment 32, comprising HCDR1, HCDR2, HCDR3, LCDR1, LCDR2, and LCDR3 sequences as set forth in Table 4D.

47. The antibody or functional fragment thereof according to embodiment 32, comprising HCDR1, HCDR2, HCDR3, LCDR1, LCDR2, and LCDR3 sequences as set forth in Table 4E.

48. The antibody or functional fragment thereof according to embodiment 32, comprising HCDR1, HCDR2, HCDR3, LCDR1, LCDR2, and LCDR3 sequences as set forth in Table 5A.

49. The antibody or functional fragment thereof according to embodiment 32, comprising HCDR1, HCDR2, HCDR3, LCDR1, LCDR2, and LCDR3 sequences as set forth in Table 5B.

50. The antibody or functional fragment thereof according to embodiment 32, comprising HCDR1, HCDR2, HCDR3, LCDR1, LCDR2, and LCDR3 sequences as set forth in Table 5C.

51. The antibody or functional fragment thereof according to embodiment 32, comprising HCDR1, HCDR2, HCDR3, LCDR1, LCDR2, and LCDR3 sequences as set forth in Table 5D.

52. The antibody or functional fragment thereof according to embodiment 32, comprising HCDR1, HCDR2, HCDR3, LCDR1, LCDR2, and LCDR3 sequences as set forth in Table 5E.

53. The antibody or functional fragment thereof according to embodiment 32, comprising complementarity determining region (CDR) sequences of antibody A, antibody B, antibody C, antibody D, antibody E, antibody F, antibody G, antibody H, antibody J, or antibody K.

54. The antibody or functional fragment thereof according to embodiment 53, comprising CDR sequences of antibody A.

55. The antibody or functional fragment thereof according to embodiment 53, comprising CDR sequences of antibody B.

56. The antibody or functional fragment thereof according to embodiment 53, comprising CDR sequences of antibody C.

57. The antibody or functional fragment thereof according to embodiment 53, comprising CDR sequences of antibody D.

58. The antibody or functional fragment thereof according to embodiment 53, comprising CDR sequences of antibody E.

59. The antibody or functional fragment thereof according to embodiment 53, comprising CDR sequences of antibody F.

60. The antibody or functional fragment thereof according to embodiment 53, comprising CDR sequences of antibody G.

61. The antibody or functional fragment thereof according to embodiment 53, comprising CDR sequences of antibody H.

62. The antibody or functional fragment thereof according to embodiment 53, comprising CDR sequences of antibody J.

63. The antibody or functional fragment thereof according to embodiment 53, comprising CDR sequences of antibody K.

64. The antibody or functional fragment thereof according to any one of embodiments 53 to 63, wherein the CDR sequences are defined by IMGT numbering, as set forth in Tables 1A-1J.

65. The antibody or functional fragment thereof according to any one of embodiments 53 to 63, wherein the CDR sequences are defined by Kabat numbering, as set forth in Tables 1A-1J.

66. The antibody or functional fragment thereof according to any one of embodiments 53 to 63, wherein the CDR sequences are defined by Chothia numbering, as set forth in Tables 1A-1J.

67. The antibody or functional fragment thereof according to any one of embodiments 53 to 63, wherein the CDR sequences are defined by the IMGT, Kabat, and Chothia common sequences, as set forth in Tables 1A-1J.

68. The antibody or functional fragment thereof according to any one of embodiments 53 to 63, wherein the CDR sequences are defined by the IMGT, Kabat, and Chothia combined overlap sequences, as set forth in Tables 1A-1J.

69. The antibody or functional fragment thereof according to embodiment 32, comprising variable heavy (VH) and variable light (VH) chain sequences of antibody A, antibody B, antibody C, antibody D, antibody E, antibody F, antibody G, antibody H, antibody J, or antibody K.

70. The antibody or functional fragment thereof according to embodiment 69, which comprises the VH and VL sequence of antibody A, as set forth in Table 1A.

71. The antibody or functional fragment thereof according to embodiment 69, which comprises the VH and VL sequence of antibody B, as set forth in Table 1B.

72. The antibody or functional fragment thereof according to embodiment 69, which comprises the VH and VL sequence of antibody C, as set forth in Table 10.

73. The antibody or functional fragment thereof according to embodiment 69, which comprises the VH and VL sequence of antibody D, as set forth in Table 1D.

74. The antibody or functional fragment thereof according to embodiment 69, which comprises the VH and VL sequence of antibody E, as set forth in Table 1E.

75. The antibody or functional fragment thereof according to embodiment 69, which comprises the VH and VL sequence of antibody F, as set forth in Table 1F.

76. The antibody or functional fragment thereof according to embodiment 69, which comprises the VH and VL sequence of antibody G, as set forth in Table 1G.

77. The antibody or functional fragment thereof according to embodiment 69, which comprises the VH and VL sequence of antibody H, as set forth in Table 1H.

78. The antibody or functional fragment thereof according to embodiment 69, which comprises the VH and VL sequence of antibody J, as set forth in Table 1I.

79. The antibody or functional fragment thereof according to embodiment 69, which comprises the VH and VL sequence of antibody K, as set forth in Table 1J.

80. An antibody or functional fragment thereof that competes with the antibody or functional fragment thereof according to any one of embodiments 1 to 79 for binding to human AQP3.

81. The antibody or functional fragment thereof according to embodiment 80, wherein the competition is for binding to cell surface expressed human AQP3.

82. The antibody or functional fragment thereof according to embodiment 80, wherein the competition is for binding to human AQP3 expressed on the surface of HEK293 cells.

83. An antibody or functional fragment thereof that competes with the antibody or functional fragment thereof according to any one of embodiments 1 to 79 for binding to mouse AQP3.

84. The antibody or functional fragment thereof according to embodiment 83, wherein the competition is for binding to cell surface expressed mouse AQP3.

85. The antibody or functional fragment thereof according to embodiment 84, wherein the competition is for binding to mouse AQP3 expressed on the surface of HEK293 cells.

86. The antibody or functional fragment thereof according to embodiment 84, wherein the competition is for binding to mouse AQP3 expressed on the surface of PAM212 cells.

87. The antibody or functional fragment thereof according to embodiment 84, wherein the competition is for binding to mouse AQP3 expressed on the surface of mouse macrophage cells.

88. The antibody or functional fragment thereof according to any one of embodiments 1 to 87, which does not specifically bind to one or more human aquaporins other than AQP3 ("non-AQP3 aquaporins").

89. The antibody or functional fragment thereof according to embodiment 88, wherein the non-AQP3 aquaporins are selected from AQP0, APQ1, AQP2, AQP4, AQP5, AQP6, AQP7, AQP8, AQP9, AQP10, AQP11, and AQP12.

90. The antibody or functional fragment thereof according to embodiment 89, wherein the one or more non-AQP3 aquaporins comprises AQP0.

91. The antibody or functional fragment thereof according to any one of embodiments 88 to 90, wherein the one or more non-AQP3 aquaporins comprises AQP1.

92. The antibody or functional fragment thereof according to any one of embodiments 88 to 91, wherein the one or more non-AQP3 aquaporins comprises AQP2.

93. The antibody or functional fragment thereof according to any one of embodiments 88 to 92, wherein the one or more non-AQP3 aquaporins comprises AQP4.

94. The antibody or functional fragment thereof according to any one of embodiments 88 to 93, wherein the one or more non-AQP3 aquaporins comprises AQP5.

95. The antibody or functional fragment thereof according to any one of embodiments 88 to 94, wherein the one or more non-AQP3 aquaporins comprises AQP6.

96. The antibody or functional fragment thereof according to any one of embodiments 88 to 95, wherein the one or more non-AQP3 aquaporins comprises AQP7.

97. The antibody or functional fragment thereof according to any one of embodiments 88 to 96, wherein the one or more non-AQP3 aquaporins comprises AQP8.

98. The antibody or functional fragment thereof according to any one of embodiments 88 to 97, wherein the one or more non-AQP3 aquaporins comprises AQP9.

99. The antibody or functional fragment thereof according to any one of embodiments 88 to 98, wherein the one or more non-AQP3 aquaporins comprises AQP10.

100. The antibody or functional fragment thereof according to any one of embodiments 88 to 99, wherein the one or more non-AQP3 aquaporins comprises AQP11.

101. The antibody or functional fragment thereof according to any one of embodiments 88 to 100, wherein the one or more non-AQP3 aquaporins comprises AQP12.

102. The antibody or functional fragment thereof according to any one of embodiments 1 to 101, wherein the antibody is an immunoglobulin molecule of IgG.

103. The antibody or functional fragment thereof according to any one of embodiments 1 to 102, wherein the antibody is a monoclonal antibody.

104. The antibody or functional fragment thereof according to any one of embodiments 1 to 103, wherein the antibody or functional fragment thereof is a chimeric antibody or a humanized antibody having a constant region of a human antibody.

105. The antibody or functional fragment thereof according to embodiment 104, wherein the antibody or functional fragment thereof is a chimeric antibody.

106. The antibody or functional fragment thereof according to embodiment 104, wherein the antibody or functional fragment thereof is a humanized antibody having a constant region of a human antibody.

107. The antibody or functional fragment thereof according to any one of embodiments 1 to 106, which is an antibody.

108. The antibody or functional fragment thereof according to embodiment 107, which is a monospecific antibody.

109. The antibody or functional fragment thereof according to embodiment 107, which is a multispecific antibody.

110. The antibody or functional fragment thereof according to any one of embodiments 1 to 106, which is a functional fragment of an antibody.

111. The antibody or functional fragment thereof according to embodiment 110, which is a functional fragment selected from F(ab')2, Fab, Fab' and Fv.

112. The antibody or functional fragment thereof according to any one of embodiments 1 to 111, which is labeled with a reporter material.

113. The antibody or a functional fragment thereof according to any one of embodiments 1 to 112, which is immobilized on a solid support.

114. An antibody drug conjugate (ADC) comprising the antibody or a functional fragment thereof according to any one of embodiments 1 to 111 conjugated to a cytotoxic agent.

115. The ADC of embodiment 114, wherein the cytotoxic agent comprises an alkylating agent.

116. The ADC of embodiment 115, wherein the alkylating agent comprises cisplatin, carboplatin, oxaliplatin, mechlorethamine, cyclophosphamide, melphalan, chlorambucil, ifosfamide busulfan, N-Nitroso-N-methylurea (MNU), carmustine (BCNU), lomustine (CCNU), semustine (MeCCNU), fotemustine, streptozotocin, dacarbazine, mitozolomide, temozolomide, thiotepa, mytomycin, diaziquone (AZQ), procarbazine or hexamethylmelamine.

117. The ADC of embodiment 114, wherein the cytotoxic agent comprises an antimetabolite.

118. The ADC of embodiment 117, wherein the antimetabolite comprises methotrexate, pemetrexed, capecitabine, cytarabine, gemcitabine, decitabine, azacitidine, fludarabine, nelarabine, cladribine, clofarabine, or pentostatin.

119. The ADC of embodiment 114, wherein the cytotoxic agent comprises an antimicrotubule agent.

120. The ADC of embodiment 119, wherein the antimicrotubule agent comprises paclitaxel, docetaxel, vincristine, vinorelbine, vinblastine, vindesine, vinflunine, monomethyl auristatin E, or monomethyl auristatin F.

121. The ADC of embodiment 114, wherein the cytotoxic agent comprises a topoisomerase inhibitor.

122. The ADC of embodiment 121, wherein the topoisomerase inhibitor comprises irinotecan, topotecan, etoposide, doxorubicin, mitoxantrone, teniposide, novobiocin, merbarone, or aclarubicin.

123. The ADC of embodiment 114, wherein the cytotoxic agent comprises a cytotoxic antibiotic.

124. The ADC of embodiment 123, wherein the cytotoxic antibiotic comprises doxorubicin, daunorubicin, epirubicin idarubicin, pirarubicin, aclarubicin, mitoxantrone, or bleomycin.

125. A composition comprising the antibody or fragment thereof according to any one of embodiments 1 to 113.

126. The composition according to embodiment 125, which is a reagent for detecting AQP3.

127. The composition according to embodiment 125, which is a reagent for identifying, separating, or purifying AQP3-expressing cells.

128. The composition according to embodiment 125 or 126, which is a reagent for measuring an expression amount of AQP3.

129. A kit comprising the composition according to any one of embodiments 126 to 128.

130. A composition comprising the monoclonal antibody or fragment thereof according to any one of embodiments 1 to 112, wherein the monoclonal antibody or a functional fragment thereof has an inhibitory activity on at least one function of AQP3.

131. The composition according to embodiment 130, which is a pharmaceutical composition further including a pharmaceutically acceptable carrier.

132. A composition comprising the ADC according to any one of embodiments 114 to 124 and a pharmaceutically acceptable carrier.

133. The composition according to embodiment 131 or embodiment 132 for use in treating cancer.

134. The composition according to embodiment 133, wherein the cancer is cancer selected from the group consisting of colorectal cancer, cervical cancer, liver cancer, lung cancer, esophageal cancer, kidney cancer, stomach cancer, tongue cancer, skin cancer, and breast cancer.

135. The composition according to embodiment 131, for use in preventing and/or treating a skin disorder.

136. The composition according to embodiment 135, wherein the skin disorder is selected from the group consisting of psoriasis, actinic keratosis, ichthyosis, and seborrheic dermatitis.

137. The composition according to embodiment 131 for use in preventing and/or treating an inflammatory disorder.

138. The composition according to embodiment 137, wherein the inflammatory disorder is selected from the group consisting of atopic dermatitis, psoriasis, asthma, chronic obstructive pulmonary disease, and hepatitis.

139. A method for detecting AQP3 comprising a step of contacting a sample with the antibody or fragment thereof according to any one of embodiments 1 to 113, or with the composition according to embodiment 125 or 126.

140. A method for separating and/or purifying AQP3-expressing cells comprising a step of contacting a sample including cells with the antibody or a functional fragment thereof according to any one of embodiments 1 to 113, or with the composition according to any one of embodiments 125 to 127.

141. A method for measuring AQP3 comprising a step of contacting a sample with the antibody or a functional fragment thereof according to any one of embodiments 1 to 113, or with the composition according to embodiment 125, 126, or 128.

142. A method for inhibiting at least one function of AQP3 comprising a step of contacting a sample including AQP3 with the antibody or a functional fragment thereof according to any one of embodiments 1 to 113, or with the composition according to embodiment 130.

143. A method for inhibiting transport of a low molecular weight material across a membrane comprising a step of contacting a sample having a membrane including AQP3 with the antibody or a functional fragment thereof according to any one of embodiments 1 to 113, or with the composition according to embodiment 130.

144. A method of treating a subject having cancer comprising administering a therapeutically effective amount of the antibody or functional fragment thereof according to any one of embodiments 1 to 112, the ADC of any one of embodiments 114 to 124, or the composition of embodiment 131 or embodiment 132 to the subject.

145. The method according to embodiment 144, wherein the cancer is cancer selected from the group consisting of colorectal cancer, cervical cancer, liver cancer, lung cancer, esophageal cancer, kidney cancer, stomach cancer, tongue cancer, skin cancer, and breast cancer.

146. A method of preventing and/or treating a skin disorder in a subject comprising administering a therapeutically effective amount of the antibody or functional fragment thereof according to any one of embodiments 1 to 112 or the composition of embodiment 131 to the subject.

147. The method of embodiment 146, wherein the skin disorder is selected from the group consisting of psoriasis, actinic keratosis, ichthyosis, and seborrheic dermatitis.

148. The method of embodiment 146 or embodiment 147, which is a method of treating a skin disorder.

149. A method of preventing and/or treating an inflammatory disorder in a subject comprising administering a therapeutically effective amount of the antibody or functional fragment thereof according to any one of embodiments 1 to 112 or the composition of embodiment 131 to the subject.

150. The method according to embodiment 149, wherein the inflammatory disorder is selected from the group consisting of atopic dermatitis, psoriasis, asthma, chronic obstructive pulmonary disease, and hepatitis.

151. The method of embodiment 149 or embodiment 150, which is a method of treating an inflammatory disorder.

152. A method for generating an anti AQP3 antibody, comprising immunizing a non-human mammal with a combination of (i) a peptide whose amino acid sequence consists of the amino acid sequence of SEQ ID NO:1 and (ii) AQP3 overexpressing cells.

153. The method of embodiment 152, wherein the mammal is a mouse.

154. The method of embodiment 152 or embodiment 153, wherein the AQP3 overexpressing cells comprise HaCaT cells, PAM212 cells, mouse macrophages, or HEK293 cells overexpressing AQP3 or a combination thereof.

155. The method of embodiment 152 or embodiment 153, wherein the AQP3 overexpressing cells comprise CHO cells overexpressing AQP3.

156. The method of embodiment 155, wherein the CHO cells overexpressing AQP3 comprise CHO cells overexpressing mouse AQP3.

157. The method of embodiment 156, wherein the mouse AQP3 is expressed in the CHO cells using a CMV promoter.

158. The method of any one of embodiments 155 to 157, wherein the CHO cells overexpressing AQP3 comprise CHO cells overexpressing human AQP3.

159. The method of embodiment 158, wherein the human AQP3 is expressed in the CHO cells using a CMV promoter.

160. The method of any one of embodiments 152 to 159, which further comprises collecting immune cells from the immunized mammal, generating an antibody library using mRNA from the immune cells, and identifying one or more anti AQP3 antibodies from the antibody library.

The present disclosure if further exemplified by the additional numbered embodiments set forth below.

1'. An anti AQP3 antibody specifically recognizing the extracellular domain of aquaporin 3 (AQP3) or a functional fragment thereof.

2'. The antibody or functional fragment thereof according to embodiment 1', wherein the extracellular domain is loop C.

3'. The antibody or functional fragment thereof according to embodiment 1' or 2' specifically binding to an oligopeptide composed of ten amino acid residues at the C-terminal side of loop C that are adjacent to the boundary to the transmembrane region IV.

4'. The antibody or functional fragment thereof according to any one of embodiments 1' to 3', which is labeled with a reporter material.

5'. The antibody or a functional fragment thereof according to any one of embodiments 1' to 4', which is immobilized on a solid support.

6'. The antibody or functional fragment thereof according to any one of embodiments 1' to 5' specifically binding to AQP3 derived from a human and/or a mouse.

7'. The antibody or functional fragment thereof according to any one of embodiments 1' to 6', wherein the antibody is an immunoglobulin molecule of IgG.

8'. The antibody or functional fragment thereof according to any one of embodiments 1' to 7' having an inhibitory activity on at least one function of AQP3.

9'. The antibody or functional fragment thereof according to any one of embodiments 1' to 8', wherein the antibody is a monoclonal antibody.

10'. The monoclonal antibody according to embodiment 9', wherein the antibody or functional fragment thereof is a chimeric antibody or a humanized antibody having a constant region of a human antibody.

11'. A composition comprising the antibody or fragment thereof according to any one of embodiments 1' to 10'.

12'. The composition according to embodiment 11', which is a reagent for detecting AQP3.

13'. The composition according to embodiment 11', which is a reagent for identifying, separating, or purifying AQP3-expressing cells.

14'. The composition according to embodiment 11' or 12', which is a reagent for measuring an expression amount of AQP3.

15'. A kit comprising the composition according to any one of embodiments 12' to 14'.

16'. A composition comprising the monoclonal antibody or fragment thereof according to embodiment 9' or 10', wherein the monoclonal antibody or a functional fragment thereof has an inhibitory activity on at least one function of AQP3.

17'. The composition according to embodiment 16', which is a pharmaceutical composition further including a pharmaceutically acceptable carrier.

18'. The composition according to embodiment 17' for use in treating cancer.

19'. The composition according to embodiment 18', wherein the cancer is cancer selected from the group consisting of colorectal cancer, cervical cancer, liver cancer, lung cancer, esophageal cancer, kidney cancer, stomach cancer, tongue cancer, skin cancer, and breast cancer.

20'. The composition according to embodiment 16', wherein it is used for preventing and/or treating a skin disorder.

21'. The composition according to embodiment 20', wherein the skin disorder is selected from the group consisting of psoriasis, actinic keratosis, ichthyosis, and seborrheic dermatitis.

22'. The composition according to embodiment 16' for use in preventing and/or treating an inflammatory disorder.

23'. The composition according to embodiment 22', wherein the inflammatory disorder is selected from the group consisting of atopic dermatitis, psoriasis, asthma, chronic obstructive pulmonary disease, and hepatitis.

24'. A method for detecting AQP3 comprising a step of contacting a sample with the antibody or fragment thereof according to any one of embodiments 1' to 10', or with the composition according to embodiment 11' or 12'.

25'. A method for separating and/or purifying AQP3-expressing cells comprising a step of contacting a sample including cells with the antibody or a functional fragment thereof according to any one of embodiments 1' to 10', or with the composition according to embodiment 11' or 12'.

26'. A method for measuring AQP3 comprising a step of contacting a sample with the antibody or a functional fragment thereof according to any one of embodiments 1' to 10', or with the composition according to embodiment 11', 12', or 14'.

27'. A method for inhibiting at least one function of AQP3 comprising a step of contacting a sample including AQP3 with the antibody or a functional fragment thereof according to any one of embodiments 1' to 10', or with the composition according to embodiment 16'.

28'. A method for inhibiting transport of a low molecular weight material across a membrane comprising a step of contacting a sample having a membrane including AQP3 with the antibody or a functional fragment thereof according to any one of embodiments 1' to 10', or with the composition according to embodiment 16'.

The invention claimed is:

1. An anti AQP3 antibody or a functional fragment thereof comprising a heavy chain complementarity determining region 1 (HCDR1), a heavy chain complementarity determining region 2 (HCRD2), a heavy chain complementarity determining region 3 (HCDR3), a light chain complementarity determining region 1 (LCDR1), a light chain complementarity determining region 2 (LCDR2), and a light chain complementarity determining region 3 (LCDR3) comprising amino acid sequences of:
   (i) SEQ ID NOs:28-33, respectively;
   (ii) SEQ ID Nos: 34-39, respectively;
   (iii) SEQ ID NOs:40-45, respectively;
   (iv) SEQ ID NOs:46-51, respectively;
   (v) SEQ ID NOs:52-57, respectively;
   (vi) SEQ ID NOs:58-63, respectively;
   (vii) SEQ ID NOs:64-69, respectively;
   (viii) SEQ ID NOs:70-75, respectively;
   (ix) SEQ ID NOs:76-81, respectively;
   (x) SEQ ID NOs:82-87, respectively;
   (xi) SEQ ID NOs:88-93, respectively;
   (xii) SEQ ID NOs:94-99, respectively;
   (xiii) SEQ ID NOs:100-105, respectively;
   (xiv) SEQ ID NOs:106-110 and 469, respectively;
   (xv) SEQ ID NOs:111-116, respectively;
   (xvi) SEQ ID NOs:117-122, respectively;
   (xvii) SEQ ID NOs:123-128, respectively;
   (xviii) SEQ ID NOs:129-134, respectively;
   (xix) SEQ ID NOs:135-140, respectively;
   SEQ ID NOs:141-146, respectively;
   (xxi) SEQ ID NOs:147-152, respectively;
   (xxii) SEQ ID NOs:153-158, respectively;
   (xxiii) SEQ ID NOs:159-164, respectively;
   (xxiv) SEQ ID NOs:165-170, respectively;
   (xxv) SEQ ID NOs:171-176, respectively;
   (xxvi) SEQ ID NOs:10-15, respectively;
   (xxvii) SEQ ID NOs:207-212, respectively;
   (xxviii) SEQ ID NOs:213-218, respectively;
   (xxix) SEQ ID NOs:219-224, respectively;
   (xxx) SEQ ID NOs:225-230, respectively;
   (xxxi) SEQ ID NOs:177-182, respectively;
   (xxxii) SEQ ID NOs:183-188, respectively;
   (xxxiii) SEQ ID NOs:189-194, respectively;
   (xxxiv) SEQ ID NOs:195-200, respectively;
   (xxxv) SEQ ID NOs:201-206, respectively;
   (xxxvi) SEQ ID NOs:16-21, respectively;
   (xxxvii) SEQ ID NOs:231-236, respectively;
   (xxxviii) SEQ ID NOs:237-242, respectively;
   (xxxix) SEQ ID NOs:243-248, respectively;
   (xl) SEQ ID NOs:249-254, respectively;
   (xli) SEQ ID NOs:22-27, respectively;
   (xlii) SEQ ID NOs:255-260, respectively;
   (xliii) SEQ ID NOs:261-266, respectively;
   (xliv) SEQ ID NOs:267-272, respectively;
   (xlv) SEQ ID NOs:273-278, respectively;
   (xlvi) SEQ ID NOs:279-284, respectively;
   (xlvii) SEQ ID NOs:285-290, respectively;
   (xlviii) SEQ ID NOs:291-296, respectively;
   (xlix) SEQ ID NOs:297-302, respectively; or
   (l) SEQ ID NOs:303-308, respectively.

2. The antibody or functional fragment thereof according to claim 1, wherein the HCDR1, HCDR2, HCDR3, LCDR1, LCDR2, and LCDR3 comprise the amino acid sequences of SEQ ID NOs:28-33, respectively.

3. The antibody or functional fragment thereof according to claim 1, wherein the HCDR1, HCDR2, HCDR3, LCDR1, LCDR2, and LCDR3 comprise the amino acid sequences of SEQ ID NOs:58-63, respectively.

4. The antibody or functional fragment thereof according to claim 1, wherein the HCDR1, HCDR2, HCDR3, LCDR1, LCDR2, and LCDR3 comprise the amino acid sequences of SEQ ID NOs:88-93, respectively.

5. The antibody or functional fragment thereof according to claim 1, wherein the HCDR1, HCDR2, HCDR3, LCDR1, LCDR2, and LCDR3 comprise the amino acid sequences of SEQ ID NOs:117-122.

6. The antibody or functional fragment thereof according to claim 1, wherein the HCDR1, HCDR2, HCDR3, LCDR1, LCDR2, and LCDR3 comprise the amino acid sequences of SEQ ID NOs:147-152, respectively.

7. The antibody or functional fragment thereof according to claim 1, wherein the HCDR1, HCDR2, HCDR3, LCDR1, LCDR2, and LCDR3 comprise the amino acid sequences of SEQ ID NOs:10-15, respectively.

8. The antibody or functional fragment thereof according to claim 1, wherein the HCDR1, HCDR2, HCDR3, LCDR1, LCDR2, and LCDR3 comprise the amino acid sequences of SEQ ID NOs:177-182, respectively.

9. The antibody or functional fragment thereof according to claim 1, wherein the HCDR1, HCDR2, HCDR3, LCDR1, LCDR2, and LCDR3 comprise the amino acid sequences of SEQ ID NOs:16-21, respectively.

10. The antibody or functional fragment thereof according to claim 1, wherein the HCDR1, HCDR2, HCDR3, LCDR1, LCDR2, and LCDR3 comprise the amino acid sequences of SEQ ID NOs:22-27, respectively.

11. The antibody or functional fragment thereof according to claim 1, wherein the HCDR1, HCDR2, HCDR3, LCDR1, LCDR2, and LCDR3 comprise the amino acid sequences of SEQ ID NOs:279-284, respectively.

12. The antibody or functional fragment thereof according to claim 1, comprising variable heavy (VH) and variable light (VL) chain sequences of:
   (i) SEQ ID NOs:309 and 310, respectively;
   (ii) SEQ ID NOs:311 and 312, respectively;
   (iii) SEQ ID NOs:313 and 314, respectively;
   (iv) SEQ ID NOs:315 and 316, respectively;
   (v) SEQ ID NOs:317 and 318, respectively;
   (vi) SEQ ID NOs:321 and 322, respectively;
   (vii) SEQ ID NOs:319 and 320, respectively;
   (viii) SEQ ID NOs:323 and 324, respectively;
   (ix) SEQ ID NOs:325 and 326, respectively; or
   (x) SEQ ID NOs:327 and 328, respectively.

13. The antibody or functional fragment thereof according to claim 1, wherein the antibody is a monoclonal antibody.

14. The antibody or functional fragment thereof according to claim 1, wherein the antibody or functional fragment thereof is a chimeric antibody or a humanized antibody having a constant region of a human antibody.

15. An antibody drug conjugate (ADC) comprising the antibody or a functional fragment thereof according to claim 1 conjugated to a cytotoxic agent.

16. A composition comprising the antibody or functional fragment thereof according to claim 1 and a pharmaceutically acceptable carrier.

17. The antibody or functional fragment thereof according to claim 1, which is an antibody.

18. The antibody or functional fragment thereof according to claim 17, which is a monospecific antibody.

19. The antibody or functional fragment thereof according to claim 17, which is a multispecific antibody.

20. The antibody or functional fragment thereof according to claim 1, which is a functional fragment of an antibody.

21. The antibody or functional fragment thereof according to claim 20, which is a functional fragment selected from F(ab')$_2$, Fab, Fab' and Fv.

22. A method of treating a subject having cancer comprising administering a therapeutically effective amount of the antibody of claim 1 or a functional fragment thereof to the subject.

23. The method of claim 22, wherein the cancer is colorectal cancer, cervical cancer, liver cancer, lung cancer, esophageal cancer, kidney cancer, stomach cancer, tongue cancer, skin cancer, or breast cancer.

24. A method of preventing and/or treating a skin disorder in a subject comprising administering a therapeutically effective amount of the antibody of claim 1 or a functional fragment thereof to the subject.

25. The method of claim 24, wherein the skin disorder is psoriasis, actinic keratosis, ichthyosis, or seborrheic dermatitis.

26. A method of preventing and/or treating an inflammatory disorder in a subject comprising administering a therapeutically effective amount of the antibody or claim 1 or a functional fragment thereof to the subject.

27. The method of claim 26, wherein the inflammatory disorder is atopic dermatitis, psoriasis, asthma, chronic obstructive pulmonary disease, or hepatitis.

28. A method for generating an anti AQP3 antibody, comprising immunizing a c57BL/6 mouse with a combination of (i) a peptide whose amino acid sequence consists of the amino acid sequence of SEQ ID NO:1 and (ii) AQP3 overexpressing cells.

* * * * *

SEQUENCE LISTING

```
<160> NUMBER OF SEQ ID NOS: 469

<210> SEQ ID NO 1
<211> LENGTH: 10
<212> TYPE: PRT
<213> ORGANISM: Artificial Sequence
<220> FEATURE:
```

<223> OTHER INFORMATION: Immunogen

<400> SEQUENCE: 1

Ala Thr Tyr Pro Ser Gly His Leu Asp Met
1               5                   10

<210> SEQ ID NO 2
<211> LENGTH: 27
<212> TYPE: PRT
<213> ORGANISM: Homo sapiens

<400> SEQUENCE: 2

Ala Asp Asn Gln Leu Phe Val Ser Gly Pro Asn Gly Thr Ala Gly Ile
1               5                   10                  15

Phe Ala Thr Tyr Pro Ser Gly His Leu Asp Met
            20                  25

<210> SEQ ID NO 3
<211> LENGTH: 27
<212> TYPE: PRT
<213> ORGANISM: Mus musculus

<400> SEQUENCE: 3

Ala Asn Asn Glu Leu Phe Val Ser Gly Pro Asn Gly Thr Ala Gly Ile
1               5                   10                  15

Phe Ala Thr Tyr Pro Ser Gly His Leu Asp Met
            20                  25

<210> SEQ ID NO 4
<211> LENGTH: 139
<212> TYPE: PRT
<213> ORGANISM: Artificial Sequence
<220> FEATURE:
<223> OTHER INFORMATION: mAb_F H_chain variable region

<400> SEQUENCE: 4

Lys Leu Ala Ala Thr Met Lys His Leu Trp Phe Phe Leu Leu Leu Val
1               5                   10                  15

Ala Ala Pro Arg Trp Val Leu Ser Gln Val Gln Leu Lys Glu Ser Gly
                20                  25                  30

Pro Glu Leu Val Lys Pro Gly Ala Ser Val Lys Ile Ser Cys Lys Ala
            35                  40                  45

Ser Gly Tyr Thr Phe Thr Asp Tyr Tyr Ile Asn Trp Val Lys Gln Arg
        50                  55                  60

Pro Gly Gln Gly Leu Glu Trp Ile Gly Trp Ile Phe Pro Gly Ser Gly
65                  70                  75                  80

Ser Thr Tyr Tyr Asn Glu Lys Phe Lys Gly Lys Ala Thr Leu Thr Val
                85                  90                  95

Asp Lys Ser Ser Ser Thr Ala Tyr Met Leu Leu Ser Ser Leu Thr Ser
            100                 105                 110

Glu Asp Ser Ala Val Tyr Phe Cys Ala Asp Tyr Gly Ser Ser Tyr Arg
        115                 120                 125

Tyr Phe Asp Val Trp Gly Ala Gly Thr Thr Val
    130                 135

<210> SEQ ID NO 5
<211> LENGTH: 130
<212> TYPE: PRT
<213> ORGANISM: Artificial Sequence
<220> FEATURE:
<223> OTHER INFORMATION: mAb_F L_chain variable region -continued

<400> SEQUENCE: 5

Lys Leu Ala Ala Thr Met Arg Leu Leu Ala Gln Leu Leu Gly Leu Leu
1               5                   10                  15

Met Leu Trp Val Pro Gly Ser Ser Gly Asp Ile Val Met Thr Gln Ser
            20                  25                  30

Pro Ala Ile Leu Ser Ala Ser Pro Gly Glu Lys Val Thr Met Thr Cys
        35                  40                  45

Arg Ala Ser Ser Ser Val Ser Tyr Met His Trp Tyr Gln Gln Lys Pro
    50                  55                  60

Gly Ser Ser Pro Lys Pro Trp Ile Tyr Ala Thr Ser Tyr Leu Ala Ser
65                  70                  75                  80

Gly Val Pro Ala Arg Phe Ser Gly Ser Gly Ser Gly Thr Ser Tyr Ser
                85                  90                  95

Leu Thr Ile Gly Arg Val Glu Ala Glu Asp Ala Ala Thr Tyr Tyr Cys
            100                 105                 110

Gln Gln Trp Ser Ser Asn Pro Leu Thr Phe Gly Ala Gly Thr Lys Leu
        115                 120                 125

Glu Leu
    130

<210> SEQ ID NO 6
<211> LENGTH: 144
<212> TYPE: PRT
<213> ORGANISM: Artificial Sequence
<220> FEATURE:
<223> OTHER INFORMATION: mAb_H H_chain variable region

<400> SEQUENCE: 6

Lys Leu Ala Ala Thr Met Lys His Leu Trp Phe Phe Leu Leu Leu Val
1               5                   10                  15

Ala Ala Pro Arg Trp Val Leu Ser Glu Val Lys Leu Val Glu Ser Gly
            20                  25                  30

Gly Asp Leu Val Lys Pro Gly Gly Ser Leu Lys Leu Ser Cys Ala Ala
        35                  40                  45

Ser Gly Phe Thr Phe Ser Ser Tyr Gly Met Ser Trp Val Arg Gln Thr
    50                  55                  60

Pro Asp Lys Arg Leu Glu Trp Val Ala Thr Ile Ser Arg Arg Ser Ile
65                  70                  75                  80

Tyr Thr Tyr Tyr Pro Asp Ser Val Gln Gly Arg Phe Thr Ile Ser Arg
                85                  90                  95

Asp Asn Ala Lys Asn Thr Leu Tyr Leu Gln Met Ser Ser Leu Lys Ser
            100                 105                 110

Glu Asp Thr Ala Met Tyr Tyr Cys Ala Arg Leu Ser Leu Tyr Asp Tyr
        115                 120                 125

Asp Gly Ala Arg Tyr Thr Met Asp Tyr Trp Gly Gln Gly Thr Ser Val
    130                 135                 140

<210> SEQ ID NO 7
<211> LENGTH: 130
<212> TYPE: PRT
<213> ORGANISM: Artificial Sequence
<220> FEATURE:
<223> OTHER INFORMATION: mAb_H L_chain variable region

<400> SEQUENCE: 7

Lys Leu Ala Ala Thr Met Arg Leu Leu Ala Gln Leu Leu Gly Leu Leu
1               5                   10                  15

Met Leu Trp Val Pro Gly Ser Ser Gly Asp Ile Lys Met Thr Gln Ser
            20                  25                  30

Pro Lys Phe Met Ser Thr Ser Val Gly Asp Arg Val Ser Ile Thr Cys
            35                  40                  45

Lys Ala Ser Gln Asp Val Gly Thr Ala Val Ala Trp Tyr Gln Gln Lys
        50                  55                  60

Pro Gly Gln Ser Pro Lys Leu Leu Ile Tyr Trp Ala Ser Thr Arg His
65                  70                  75                  80

Thr Gly Val Pro Asp Arg Phe Thr Gly Ser Gly Ser Gly Thr Asp Phe
                85                  90                  95

Thr Leu Thr Ile Ser Asn Val Gln Ser Glu Asp Leu Ala Asp Tyr Phe
            100                 105                 110

Cys Gln Gln Tyr Ser Ser Tyr His Thr Phe Gly Ala Gly Thr Lys Leu
        115                 120                 125

Glu Ile
    130

<210> SEQ ID NO 8
<211> LENGTH: 144
<212> TYPE: PRT
<213> ORGANISM: Artificial Sequence
<220> FEATURE:
<223> OTHER INFORMATION: mAb_J H_chain variable region

<400> SEQUENCE: 8

Lys Leu Ala Ala Thr Met Lys His Leu Trp Phe Phe Leu Leu Leu Val
1               5                   10                  15

Ala Ala Pro Arg Trp Val Leu Ser Gln Val His Leu Gln Gln Ser Gly
            20                  25                  30

Thr Glu Leu Val Lys Pro Gly Ala Ser Val Lys Leu Ser Cys Glu Ala
            35                  40                  45

Ser Gly Tyr Thr Phe Thr Ser Tyr Trp Met His Trp Val Lys Gln Arg
        50                  55                  60

Pro Gly Gln Gly Leu Glu Trp Ile Gly Asn Ile Asn Pro Ser Asn Gly
65                  70                  75                  80

Gly Thr Asn Tyr Asn Glu Lys Phe Lys Ser Lys Ala Thr Leu Thr Val
                85                  90                  95

Asp Lys Ser Ser Ser Thr Ala Tyr Met Gln Leu Ser Ser Leu Thr Ser
            100                 105                 110

Glu Asp Ser Ala Val Tyr Tyr Cys Ala Arg Gly Gly Ile Tyr Tyr Gly
        115                 120                 125

Asn Tyr Asp Tyr Tyr Ala Met Asp Tyr Trp Gly Gln Gly Thr Ser Val
    130                 135                 140

<210> SEQ ID NO 9
<211> LENGTH: 136
<212> TYPE: PRT
<213> ORGANISM: Artificial Sequence
<220> FEATURE:
<223> OTHER INFORMATION: mAb_J L_chain variable region

<400> SEQUENCE: 9

Lys Leu Ala Ala Thr Met Arg Leu Leu Ala Gln Leu Leu Gly Leu Leu
1               5                   10                  15

Met Leu Trp Val Pro Gly Ser Ser Gly Asp Ile Val Met Thr Gln Ala
            20                  25                  30

Ala Pro Ser Val Pro Val Thr Pro Gly Glu Ser Val Ser Ile Ser Cys

```
                35                  40                  45
Arg Ser Ser Lys Ser Leu Leu His Ser Asn Gly Asn Thr Tyr Leu Tyr
    50                  55                  60

Trp Phe Leu Gln Arg Pro Gly Gln Ser Pro Gln Leu Leu Ile Tyr Arg
65                  70                  75                  80

Val Ser Asn Leu Ala Ser Gly Val Pro Asp Arg Phe Ser Gly Ser Gly
                85                  90                  95

Ser Gly Thr Ala Phe Thr Leu Arg Ile Ser Arg Val Glu Ala Glu Asp
            100                 105                 110

Val Gly Val Tyr Tyr Cys Met Gln His Leu Glu Tyr Pro Phe Thr Phe
        115                 120                 125

Gly Gly Gly Thr Lys Leu Glu Ile
    130                 135

<210> SEQ ID NO 10
<211> LENGTH: 8
<212> TYPE: PRT
<213> ORGANISM: Artificial Sequence
<220> FEATURE:
<223> OTHER INFORMATION: mAb_F HCDR1 amino acid sequence (IMGT
      definition)

<400> SEQUENCE: 10

Gly Tyr Thr Phe Thr Asp Tyr Tyr
1               5

<210> SEQ ID NO 11
<211> LENGTH: 8
<212> TYPE: PRT
<213> ORGANISM: Artificial Sequence
<220> FEATURE:
<223> OTHER INFORMATION: mAb_F  HCDR2 amino acid sequence (IMGT
      definition)

<400> SEQUENCE: 11

Ile Phe Pro Gly Ser Gly Ser Thr
1               5

<210> SEQ ID NO 12
<211> LENGTH: 12
<212> TYPE: PRT
<213> ORGANISM: Artificial Sequence
<220> FEATURE:
<223> OTHER INFORMATION: mAb_F  HCDR3 amino acid sequence (IMGT
      definition)

<400> SEQUENCE: 12

Ala Asp Tyr Gly Ser Ser Tyr Arg Tyr Phe Asp Val
1               5                   10

<210> SEQ ID NO 13
<211> LENGTH: 5
<212> TYPE: PRT
<213> ORGANISM: Artificial Sequence
<220> FEATURE:
<223> OTHER INFORMATION: mAb_F  LCDR1 amino acid sequence (IMGT
      definition)

<400> SEQUENCE: 13

Ser Ser Val Ser Tyr
1               5

<210> SEQ ID NO 14
<211> LENGTH: 3
```

```
<212> TYPE: PRT
<213> ORGANISM: Artificial Sequence
<220> FEATURE:
<223> OTHER INFORMATION: mAb_F  LCDR2 amino acid sequence (IMGT
      definition)

<400> SEQUENCE: 14

Ala Thr Ser
1

<210> SEQ ID NO 15
<211> LENGTH: 9
<212> TYPE: PRT
<213> ORGANISM: Artificial Sequence
<220> FEATURE:
<223> OTHER INFORMATION: mAb_F  LCDR3 amino acid sequence (IMGT
      definition)

<400> SEQUENCE: 15

Gln Gln Trp Ser Ser Asn Pro Leu Thr
1               5

<210> SEQ ID NO 16
<211> LENGTH: 8
<212> TYPE: PRT
<213> ORGANISM: Artificial Sequence
<220> FEATURE:
<223> OTHER INFORMATION: mAb_H HCDR1 amino acid sequence (IMGT
      definition)

<400> SEQUENCE: 16

Gly Phe Thr Phe Ser Ser Tyr Gly
1               5

<210> SEQ ID NO 17
<211> LENGTH: 8
<212> TYPE: PRT
<213> ORGANISM: Artificial Sequence
<220> FEATURE:
<223> OTHER INFORMATION: mAb_H HCDR2 amino acid sequence (IMGT
      definition)

<400> SEQUENCE: 17

Ile Ser Arg Arg Ser Ile Tyr Thr
1               5

<210> SEQ ID NO 18
<211> LENGTH: 17
<212> TYPE: PRT
<213> ORGANISM: Artificial Sequence
<220> FEATURE:
<223> OTHER INFORMATION: mAb_H HCDR3 amino acid sequence (IMGT
      definition)

<400> SEQUENCE: 18

Ala Arg Leu Ser Leu Tyr Asp Tyr Asp Gly Ala Arg Tyr Thr Met Asp
1               5                   10                  15

Tyr

<210> SEQ ID NO 19
<211> LENGTH: 6
<212> TYPE: PRT
<213> ORGANISM: Artificial Sequence
<220> FEATURE:
<223> OTHER INFORMATION: mAb_H LCDR1 amino acid sequence (IMGT
      definition)

<400> SEQUENCE: 19
```

```
Gln Asp Val Gly Thr Ala
1               5

<210> SEQ ID NO 20
<211> LENGTH: 3
<212> TYPE: PRT
<213> ORGANISM: Artificial Sequence
<220> FEATURE:
<223> OTHER INFORMATION: mAb_H LCDR2 amino acid sequence (IMGT
      definition)

<400> SEQUENCE: 20

Trp Ala Ser
1

<210> SEQ ID NO 21
<211> LENGTH: 8
<212> TYPE: PRT
<213> ORGANISM: Artificial Sequence
<220> FEATURE:
<223> OTHER INFORMATION: mAb_H LCDR3 amino acid sequence (IMGT
      definition)

<400> SEQUENCE: 21

Gln Gln Tyr Ser Ser Tyr His Thr
1               5

<210> SEQ ID NO 22
<211> LENGTH: 8
<212> TYPE: PRT
<213> ORGANISM: Artificial Sequence
<220> FEATURE:
<223> OTHER INFORMATION: mAb_J HCDR1 amino acid sequence (IMGT
      definition)

<400> SEQUENCE: 22

Gly Tyr Thr Phe Thr Ser Tyr Trp
1               5

<210> SEQ ID NO 23
<211> LENGTH: 8
<212> TYPE: PRT
<213> ORGANISM: Artificial Sequence
<220> FEATURE:
<223> OTHER INFORMATION: mAb_J HCDR2 amino acid sequence (IMGT
      definition)

<400> SEQUENCE: 23

Ile Asn Pro Ser Asn Gly Gly Thr
1               5

<210> SEQ ID NO 24
<211> LENGTH: 17
<212> TYPE: PRT
<213> ORGANISM: Artificial Sequence
<220> FEATURE:
<223> OTHER INFORMATION: mAb_J HCDR3 amino acid sequence (IMGT
      definition)

<400> SEQUENCE: 24

Ala Arg Gly Gly Ile Tyr Tyr Gly Asn Tyr Asp Tyr Tyr Ala Met Asp
1               5                   10                  15

Tyr

<210> SEQ ID NO 25
<211> LENGTH: 11
```

```
<212> TYPE: PRT
<213> ORGANISM: Artificial Sequence
<220> FEATURE:
<223> OTHER INFORMATION: mAb_J LCDR1 amino acid sequence (IMGT
      definition)

<400> SEQUENCE: 25

Lys Ser Leu Leu His Ser Asn Gly Asn Thr Tyr
1               5                   10

<210> SEQ ID NO 26
<211> LENGTH: 3
<212> TYPE: PRT
<213> ORGANISM: Artificial Sequence
<220> FEATURE:
<223> OTHER INFORMATION: mAb_J LCDR2 amino acid sequence (IMGT
      definition)

<400> SEQUENCE: 26

Arg Val Ser
1

<210> SEQ ID NO 27
<211> LENGTH: 9
<212> TYPE: PRT
<213> ORGANISM: Artificial Sequence
<220> FEATURE:
<223> OTHER INFORMATION: mAb_J LCDR3 amino acid sequence (IMGT
      definition)

<400> SEQUENCE: 27

Met Gln His Leu Glu Tyr Pro Phe Thr
1               5

<210> SEQ ID NO 28
<211> LENGTH: 8
<212> TYPE: PRT
<213> ORGANISM: Artificial Sequence
<220> FEATURE:
<223> OTHER INFORMATION: mAb_A HCDR1 amino acid sequence (IMGT
      definition)

<400> SEQUENCE: 28

Gly Tyr Thr Phe Thr Asp Tyr Glu
1               5

<210> SEQ ID NO 29
<211> LENGTH: 8
<212> TYPE: PRT
<213> ORGANISM: Artificial Sequence
<220> FEATURE:
<223> OTHER INFORMATION: mAb_A HCDR2 amino acid sequence (IMGT
      definition)

<400> SEQUENCE: 29

Val Asp Pro Glu Thr Gly Gly Thr
1               5

<210> SEQ ID NO 30
<211> LENGTH: 12
<212> TYPE: PRT
<213> ORGANISM: Artificial Sequence
<220> FEATURE:
<223> OTHER INFORMATION: mAb_A HCDR3 amino acid sequence (IMGT
      definition)

<400> SEQUENCE: 30

Ala Arg His Gly Gly Ser Phe Tyr Ala Met Asp Tyr
```

```
1               5                    10
```

```
<210> SEQ ID NO 31
<211> LENGTH: 6
<212> TYPE: PRT
<213> ORGANISM: Artificial Sequence
<220> FEATURE:
<223> OTHER INFORMATION: mAb_A LCDR1 amino acid sequence (IMGT
      definition)

<400> SEQUENCE: 31

Gln Asp Val Ser Thr Ala
1               5

<210> SEQ ID NO 32
<211> LENGTH: 3
<212> TYPE: PRT
<213> ORGANISM: Artificial Sequence
<220> FEATURE:
<223> OTHER INFORMATION: mAb_A LCDR2 amino acid sequence (IMGT
      definition)

<400> SEQUENCE: 32

Trp Ala Ser
1

<210> SEQ ID NO 33
<211> LENGTH: 9
<212> TYPE: PRT
<213> ORGANISM: Artificial Sequence
<220> FEATURE:
<223> OTHER INFORMATION: mAb_A LCDR3 amino acid sequence (IMGT
      definition)

<400> SEQUENCE: 33

Gln Gln His Tyr Ser Thr Pro Pro Thr
1               5

<210> SEQ ID NO 34
<211> LENGTH: 5
<212> TYPE: PRT
<213> ORGANISM: Artificial Sequence
<220> FEATURE:
<223> OTHER INFORMATION: mAb_A HCDR1 amino acid sequence (Kabat
      definition)

<400> SEQUENCE: 34

Asp Tyr Glu Met His
1               5

<210> SEQ ID NO 35
<211> LENGTH: 17
<212> TYPE: PRT
<213> ORGANISM: Artificial Sequence
<220> FEATURE:
<223> OTHER INFORMATION: mAb_A HCDR2 amino acid sequence (Kabat
      definition)

<400> SEQUENCE: 35

Gly Val Asp Pro Glu Thr Gly Gly Thr Gly Tyr Asn Gln Lys Phe Arg
1               5                   10                  15

Gly

<210> SEQ ID NO 36
<211> LENGTH: 10
<212> TYPE: PRT
<213> ORGANISM: Artificial Sequence
```

```
<220> FEATURE:
<223> OTHER INFORMATION: mAb_A HCDR3 amino acid sequence (Kabat
      definition)

<400> SEQUENCE: 36

His Gly Gly Ser Phe Tyr Ala Met Asp Tyr
1               5                   10

<210> SEQ ID NO 37
<211> LENGTH: 11
<212> TYPE: PRT
<213> ORGANISM: Artificial Sequence
<220> FEATURE:
<223> OTHER INFORMATION: mAb_A LCDR1 amino acid sequence (Kabat
      definition)

<400> SEQUENCE: 37

Lys Ala Ser Gln Asp Val Ser Thr Ala Val Ala
1               5                   10

<210> SEQ ID NO 38
<211> LENGTH: 7
<212> TYPE: PRT
<213> ORGANISM: Artificial Sequence
<220> FEATURE:
<223> OTHER INFORMATION: mAb_A LCDR2 amino acid sequence (Kabat
      definition)

<400> SEQUENCE: 38

Trp Ala Ser Thr Arg His Thr
1               5

<210> SEQ ID NO 39
<211> LENGTH: 9
<212> TYPE: PRT
<213> ORGANISM: Artificial Sequence
<220> FEATURE:
<223> OTHER INFORMATION: mAb_A LCDR3 amino acid sequence (Kabat
      definition)

<400> SEQUENCE: 39

Gln Gln His Tyr Ser Thr Pro Pro Thr
1               5

<210> SEQ ID NO 40
<211> LENGTH: 7
<212> TYPE: PRT
<213> ORGANISM: Artificial Sequence
<220> FEATURE:
<223> OTHER INFORMATION: mAb_A HCDR1 amino acid sequence (Chothia
      definition)

<400> SEQUENCE: 40

Gly Tyr Thr Phe Thr Asp Tyr
1               5

<210> SEQ ID NO 41
<211> LENGTH: 6
<212> TYPE: PRT
<213> ORGANISM: Artificial Sequence
<220> FEATURE:
<223> OTHER INFORMATION: mAb_A HCDR2 amino acid sequence (Chothia
      definition)

<400> SEQUENCE: 41

Asp Pro Glu Thr Gly Gly
1               5
```

<210> SEQ ID NO 42
<211> LENGTH: 10
<212> TYPE: PRT
<213> ORGANISM: Artificial Sequence
<220> FEATURE:
<223> OTHER INFORMATION: mAb_A HCDR3 amino acid sequence (Chothia
      definition)

<400> SEQUENCE: 42

His Gly Gly Ser Phe Tyr Ala Met Asp Tyr
1               5                   10

<210> SEQ ID NO 43
<211> LENGTH: 7
<212> TYPE: PRT
<213> ORGANISM: Artificial Sequence
<220> FEATURE:
<223> OTHER INFORMATION: mAb_A LCDR1 amino acid sequence (Chothia
      definition)

<400> SEQUENCE: 43

Ser Gln Asp Val Ser Thr Ala
1               5

<210> SEQ ID NO 44
<211> LENGTH: 3
<212> TYPE: PRT
<213> ORGANISM: Artificial Sequence
<220> FEATURE:
<223> OTHER INFORMATION: mAb_A LCDR2 amino acid sequence (Chothia
      definition)

<400> SEQUENCE: 44

Trp Ala Ser
1

<210> SEQ ID NO 45
<211> LENGTH: 7
<212> TYPE: PRT
<213> ORGANISM: Artificial Sequence
<220> FEATURE:
<223> OTHER INFORMATION: mAb_A LCDR3 amino acid sequence (Chothia
      definition)

<400> SEQUENCE: 45

His Tyr Ser Thr Pro Pro Thr
1               5

<210> SEQ ID NO 46
<211> LENGTH: 2
<212> TYPE: PRT
<213> ORGANISM: Artificial Sequence
<220> FEATURE:
<223> OTHER INFORMATION: mAb_A HCDR1 amino acid sequence (IMGT, Kabat,
      and Chothia common sequences)

<400> SEQUENCE: 46

Asp Tyr
1

<210> SEQ ID NO 47
<211> LENGTH: 6
<212> TYPE: PRT
<213> ORGANISM: Artificial Sequence
<220> FEATURE:
<223> OTHER INFORMATION: mAb_A HCDR2 amino acid sequence (IMGT, Kabat,
      and Chothia common sequences)

```
<400> SEQUENCE: 47

Asp Pro Glu Thr Gly Gly
1               5

<210> SEQ ID NO 48
<211> LENGTH: 10
<212> TYPE: PRT
<213> ORGANISM: Artificial Sequence
<220> FEATURE:
<223> OTHER INFORMATION: mAb_A HCDR3 amino acid sequence (IMGT, Kabat,
      and Chothia common sequences definition)

<400> SEQUENCE: 48

His Gly Gly Ser Phe Tyr Ala Met Asp Tyr
1               5                   10

<210> SEQ ID NO 49
<211> LENGTH: 6
<212> TYPE: PRT
<213> ORGANISM: Artificial Sequence
<220> FEATURE:
<223> OTHER INFORMATION: mAb_A LCDR1 amino acid sequence (IMGT, Kabat,
      and Chothia common sequences)

<400> SEQUENCE: 49

Gln Asp Val Ser Thr Ala
1               5

<210> SEQ ID NO 50
<211> LENGTH: 3
<212> TYPE: PRT
<213> ORGANISM: Artificial Sequence
<220> FEATURE:
<223> OTHER INFORMATION: mAb_A LCDR2 amino acid sequence (IMGT, Kabat,
      and Chothia common sequences)

<400> SEQUENCE: 50

Trp Ala Ser
1

<210> SEQ ID NO 51
<211> LENGTH: 7
<212> TYPE: PRT
<213> ORGANISM: Artificial Sequence
<220> FEATURE:
<223> OTHER INFORMATION: mAb_A LCDR3 amino acid sequence (IMGT, Kabat,
      and Chothia common sequences)

<400> SEQUENCE: 51

His Tyr Ser Thr Pro Pro Thr
1               5

<210> SEQ ID NO 52
<211> LENGTH: 10
<212> TYPE: PRT
<213> ORGANISM: Artificial Sequence
<220> FEATURE:
<223> OTHER INFORMATION: mAb_A HCDR1 amino acid sequence (IMGT, Kabat,
      and Chothia combined overlap sequences)

<400> SEQUENCE: 52

Gly Tyr Thr Phe Thr Asp Tyr Glu Met His
1               5                   10

<210> SEQ ID NO 53
<211> LENGTH: 17
<212> TYPE: PRT
```

<213> ORGANISM: Artificial Sequence
<220> FEATURE:
<223> OTHER INFORMATION: mAb_A HCDR2 amino acid sequence (IMGT, Kabat,
      and Chothia combined overlap sequences)

<400> SEQUENCE: 53

Gly Val Asp Pro Glu Thr Gly Gly Thr Gly Tyr Asn Gln Lys Phe Arg
1               5                   10                  15
Gly

<210> SEQ ID NO 54
<211> LENGTH: 12
<212> TYPE: PRT
<213> ORGANISM: Artificial Sequence
<220> FEATURE:
<223> OTHER INFORMATION: mAb_A HCDR3 amino acid sequence (IMGT, Kabat,
      and Chothia combined overlap sequences)

<400> SEQUENCE: 54

Ala Arg His Gly Gly Ser Phe Tyr Ala Met Asp Tyr
1               5                   10

<210> SEQ ID NO 55
<211> LENGTH: 11
<212> TYPE: PRT
<213> ORGANISM: Artificial Sequence
<220> FEATURE:
<223> OTHER INFORMATION: mAb_A LCDR1 amino acid sequence (IMGT, Kabat,
      and Chothia combined overlap sequences)

<400> SEQUENCE: 55

Lys Ala Ser Gln Asp Val Ser Thr Ala Val Ala
1               5                   10

<210> SEQ ID NO 56
<211> LENGTH: 7
<212> TYPE: PRT
<213> ORGANISM: Artificial Sequence
<220> FEATURE:
<223> OTHER INFORMATION: mAb_A LCDR2 amino acid sequence (IMGT, Kabat,
      and Chothia combined overlap sequences)

<400> SEQUENCE: 56

Trp Ala Ser Thr Arg His Thr
1               5

<210> SEQ ID NO 57
<211> LENGTH: 9
<212> TYPE: PRT
<213> ORGANISM: Artificial Sequence
<220> FEATURE:
<223> OTHER INFORMATION: mAb_A LCDR3 amino acid sequence (IMGT, Kabat,
      and Chothia combined overlap sequences)

<400> SEQUENCE: 57

Gln Gln His Tyr Ser Thr Pro Pro Thr
1               5

<210> SEQ ID NO 58
<211> LENGTH: 8
<212> TYPE: PRT
<213> ORGANISM: Artificial Sequence
<220> FEATURE:
<223> OTHER INFORMATION: mAb_B HCDR1 amino acid sequence (IMGT
      definition)

<400> SEQUENCE: 58

Gly Phe Thr Phe Ser Ser Tyr Gly
1               5

<210> SEQ ID NO 59
<211> LENGTH: 8
<212> TYPE: PRT
<213> ORGANISM: Artificial Sequence
<220> FEATURE:
<223> OTHER INFORMATION: mAb_B HCDR2 amino acid sequence (IMGT
      definition)

<400> SEQUENCE: 59

Ile Ser Arg Gly Ser Ile Tyr Thr
1               5

<210> SEQ ID NO 60
<211> LENGTH: 17
<212> TYPE: PRT
<213> ORGANISM: Artificial Sequence
<220> FEATURE:
<223> OTHER INFORMATION: mAb_B HCDR3 amino acid sequence (IMGT
      definition)

<400> SEQUENCE: 60

Ala Arg Leu Ser Leu Tyr Asp Tyr Asp Gly Ala Arg Tyr Thr Met Asp
1               5                   10                  15

Tyr

<210> SEQ ID NO 61
<211> LENGTH: 6
<212> TYPE: PRT
<213> ORGANISM: Artificial Sequence
<220> FEATURE:
<223> OTHER INFORMATION: mAb_B LCDR1 amino acid sequence (IMGT
      definition)

<400> SEQUENCE: 61

Gln Asp Val Gly Thr Ala
1               5

<210> SEQ ID NO 62
<211> LENGTH: 3
<212> TYPE: PRT
<213> ORGANISM: Artificial Sequence
<220> FEATURE:
<223> OTHER INFORMATION: mAb_B LCDR2 amino acid sequence (IMGT
      definition)

<400> SEQUENCE: 62

Trp Ala Ser
1

<210> SEQ ID NO 63
<211> LENGTH: 8
<212> TYPE: PRT
<213> ORGANISM: Artificial Sequence
<220> FEATURE:
<223> OTHER INFORMATION: mAb_B LCDR3 amino acid sequence (IMGT
      definition)

<400> SEQUENCE: 63

Gln Gln Tyr Ser Ser Tyr His Thr
1               5

<210> SEQ ID NO 64
<211> LENGTH: 5
<212> TYPE: PRT

```
<213> ORGANISM: Artificial Sequence
<220> FEATURE:
<223> OTHER INFORMATION: mAb_B HCDR1 amino acid sequence (Kabat
      definition)

<400> SEQUENCE: 64

Ser Tyr Gly Met Ser
1               5

<210> SEQ ID NO 65
<211> LENGTH: 17
<212> TYPE: PRT
<213> ORGANISM: Artificial Sequence
<220> FEATURE:
<223> OTHER INFORMATION: mAb_B HCDR2 amino acid sequence (Kabat
      definition)

<400> SEQUENCE: 65

Thr Ile Ser Arg Gly Ser Ile Tyr Thr Tyr Tyr Pro Asp Ser Val Lys
1               5                   10                  15

Gly

<210> SEQ ID NO 66
<211> LENGTH: 15
<212> TYPE: PRT
<213> ORGANISM: Artificial Sequence
<220> FEATURE:
<223> OTHER INFORMATION: mAb_B HCDR3 amino acid sequence (Kabat
      definition)

<400> SEQUENCE: 66

Leu Ser Leu Tyr Asp Tyr Asp Gly Ala Arg Tyr Thr Met Asp Tyr
1               5                   10                  15

<210> SEQ ID NO 67
<211> LENGTH: 11
<212> TYPE: PRT
<213> ORGANISM: Artificial Sequence
<220> FEATURE:
<223> OTHER INFORMATION: mAb_B LCDR1 amino acid sequence (Kabat
      definition)

<400> SEQUENCE: 67

Lys Ala Ser Gln Asp Val Gly Thr Ala Val Ala
1               5                   10

<210> SEQ ID NO 68
<211> LENGTH: 7
<212> TYPE: PRT
<213> ORGANISM: Artificial Sequence
<220> FEATURE:
<223> OTHER INFORMATION: mAb_B LCDR2 amino acid sequence (Kabat
      definition)

<400> SEQUENCE: 68

Trp Ala Ser Thr Arg His Thr
1               5

<210> SEQ ID NO 69
<211> LENGTH: 8
<212> TYPE: PRT
<213> ORGANISM: Artificial Sequence
<220> FEATURE:
<223> OTHER INFORMATION: mAb_B LCDR3 amino acid sequence (Kabat
      definition)

<400> SEQUENCE: 69
```

```
Gln Gln Tyr Ser Ser Tyr His Thr
1               5

<210> SEQ ID NO 70
<211> LENGTH: 7
<212> TYPE: PRT
<213> ORGANISM: Artificial Sequence
<220> FEATURE:
<223> OTHER INFORMATION: mAb_B HCDR1 amino acid sequence (Chothia
      definition)

<400> SEQUENCE: 70

Gly Phe Thr Phe Ser Ser Tyr
1               5

<210> SEQ ID NO 71
<211> LENGTH: 6
<212> TYPE: PRT
<213> ORGANISM: Artificial Sequence
<220> FEATURE:
<223> OTHER INFORMATION: mAb_B HCDR2 amino acid sequence (Chothia
      definition)

<400> SEQUENCE: 71

Ser Arg Gly Ser Ile Tyr
1               5

<210> SEQ ID NO 72
<211> LENGTH: 15
<212> TYPE: PRT
<213> ORGANISM: Artificial Sequence
<220> FEATURE:
<223> OTHER INFORMATION: mAb_B HCDR3 amino acid sequence (Chothia
      definition)

<400> SEQUENCE: 72

Leu Ser Leu Tyr Asp Tyr Asp Gly Ala Arg Tyr Thr Met Asp Tyr
1               5                   10                  15

<210> SEQ ID NO 73
<211> LENGTH: 7
<212> TYPE: PRT
<213> ORGANISM: Artificial Sequence
<220> FEATURE:
<223> OTHER INFORMATION: mAb_B LCDR1 amino acid sequence (Chothia
      definition)

<400> SEQUENCE: 73

Ser Gln Asp Val Gly Thr Ala
1               5

<210> SEQ ID NO 74
<211> LENGTH: 3
<212> TYPE: PRT
<213> ORGANISM: Artificial Sequence
<220> FEATURE:
<223> OTHER INFORMATION: mAb_B LCDR2 amino acid sequence (Chothia
      definition)

<400> SEQUENCE: 74

Trp Ala Ser
1

<210> SEQ ID NO 75
<211> LENGTH: 6
<212> TYPE: PRT
<213> ORGANISM: Artificial Sequence
<220> FEATURE:
```

```
<223> OTHER INFORMATION: mAb_B LCDR3 amino acid sequence (Chothia
      definition)

<400> SEQUENCE: 75

Tyr Ser Ser Tyr His Thr
1               5

<210> SEQ ID NO 76
<211> LENGTH: 2
<212> TYPE: PRT
<213> ORGANISM: Artificial Sequence
<220> FEATURE:
<223> OTHER INFORMATION: mAb_B HCDR1 amino acid sequence (IMGT, Kabat,
      and Chothia common sequences)

<400> SEQUENCE: 76

Ser Tyr
1

<210> SEQ ID NO 77
<211> LENGTH: 6
<212> TYPE: PRT
<213> ORGANISM: Artificial Sequence
<220> FEATURE:
<223> OTHER INFORMATION: mAb_B HCDR2 amino acid sequence (IMGT, Kabat,
      and Chothia common sequences)

<400> SEQUENCE: 77

Ser Arg Gly Ser Ile Tyr
1               5

<210> SEQ ID NO 78
<211> LENGTH: 15
<212> TYPE: PRT
<213> ORGANISM: Artificial Sequence
<220> FEATURE:
<223> OTHER INFORMATION: mAb_B HCDR3 amino acid sequence (IMGT, Kabat,
      and Chothia common sequences definition)

<400> SEQUENCE: 78

Leu Ser Leu Tyr Asp Tyr Asp Gly Ala Arg Tyr Thr Met Asp Tyr
1               5                   10                  15

<210> SEQ ID NO 79
<211> LENGTH: 6
<212> TYPE: PRT
<213> ORGANISM: Artificial Sequence
<220> FEATURE:
<223> OTHER INFORMATION: mAb_B LCDR1 amino acid sequence (IMGT, Kabat,
      and Chothia common sequences)

<400> SEQUENCE: 79

Gln Asp Val Gly Thr Ala
1               5

<210> SEQ ID NO 80
<211> LENGTH: 3
<212> TYPE: PRT
<213> ORGANISM: Artificial Sequence
<220> FEATURE:
<223> OTHER INFORMATION: mAb_B LCDR2 amino acid sequence (IMGT, Kabat,
      and Chothia common sequences)

<400> SEQUENCE: 80

Trp Ala Ser
1
```

```
<210> SEQ ID NO 81
<211> LENGTH: 6
<212> TYPE: PRT
<213> ORGANISM: Artificial Sequence
<220> FEATURE:
<223> OTHER INFORMATION: mAb_B LCDR3 amino acid sequence (IMGT, Kabat,
      and Chothia common sequences)

<400> SEQUENCE: 81

Tyr Ser Ser Tyr His Thr
1               5

<210> SEQ ID NO 82
<211> LENGTH: 10
<212> TYPE: PRT
<213> ORGANISM: Artificial Sequence
<220> FEATURE:
<223> OTHER INFORMATION: mAb_B HCDR1 amino acid sequence (IMGT, Kabat,
      and Chothia combined overlap sequences)

<400> SEQUENCE: 82

Gly Phe Thr Phe Ser Ser Tyr Gly Met Ser
1               5                   10

<210> SEQ ID NO 83
<211> LENGTH: 17
<212> TYPE: PRT
<213> ORGANISM: Artificial Sequence
<220> FEATURE:
<223> OTHER INFORMATION: mAb_B HCDR2 amino acid sequence (IMGT, Kabat,
      and Chothia combined overlap sequences)

<400> SEQUENCE: 83

Thr Ile Ser Arg Gly Ser Ile Tyr Thr Tyr Tyr Pro Asp Ser Val Lys
1               5                   10                  15

Gly

<210> SEQ ID NO 84
<211> LENGTH: 17
<212> TYPE: PRT
<213> ORGANISM: Artificial Sequence
<220> FEATURE:
<223> OTHER INFORMATION: mAb_B HCDR3 amino acid sequence (IMGT, Kabat,
      and Chothia combined overlap sequences)

<400> SEQUENCE: 84

Ala Arg Leu Ser Leu Tyr Asp Tyr Asp Gly Ala Arg Tyr Thr Met Asp
1               5                   10                  15

Tyr

<210> SEQ ID NO 85
<211> LENGTH: 11
<212> TYPE: PRT
<213> ORGANISM: Artificial Sequence
<220> FEATURE:
<223> OTHER INFORMATION: mAb_B LCDR1 amino acid sequence (IMGT, Kabat,
      and Chothia combined overlap sequences)

<400> SEQUENCE: 85

Lys Ala Ser Gln Asp Val Gly Thr Ala Val Ala
1               5                   10

<210> SEQ ID NO 86
<211> LENGTH: 7
<212> TYPE: PRT
<213> ORGANISM: Artificial Sequence
<220> FEATURE:
```

<223> OTHER INFORMATION: mAb_B LCDR2 amino acid sequence (IMGT, Kabat,
      and Chothia combined overlap sequences)

<400> SEQUENCE: 86

Trp Ala Ser Thr Arg His Thr
1               5

<210> SEQ ID NO 87
<211> LENGTH: 8
<212> TYPE: PRT
<213> ORGANISM: Artificial Sequence
<220> FEATURE:
<223> OTHER INFORMATION: mAb_B LCDR3 amino acid sequence (IMGT, Kabat,
      and Chothia combined overlap sequences)

<400> SEQUENCE: 87

Gln Gln Tyr Ser Ser Tyr His Thr
1               5

<210> SEQ ID NO 88
<211> LENGTH: 8
<212> TYPE: PRT
<213> ORGANISM: Artificial Sequence
<220> FEATURE:
<223> OTHER INFORMATION: mAb_C HCDR1 amino acid sequence (IMGT
      definition)

<400> SEQUENCE: 88

Gly Tyr Asn Phe Lys Ser Tyr Gly
1               5

<210> SEQ ID NO 89
<211> LENGTH: 8
<212> TYPE: PRT
<213> ORGANISM: Artificial Sequence
<220> FEATURE:
<223> OTHER INFORMATION: mAb_C HCDR2 amino acid sequence (IMGT
      definition)

<400> SEQUENCE: 89

Ile Tyr Pro Gly Ser Gly Asn Thr
1               5

<210> SEQ ID NO 90
<211> LENGTH: 14
<212> TYPE: PRT
<213> ORGANISM: Artificial Sequence
<220> FEATURE:
<223> OTHER INFORMATION: mAb_C HCDR3 amino acid sequence (IMGT
      definition)

<400> SEQUENCE: 90

Ala Arg Thr Tyr Gly Tyr Asp Ser Phe Pro Trp Phe Ala Tyr
1               5                   10

<210> SEQ ID NO 91
<211> LENGTH: 11
<212> TYPE: PRT
<213> ORGANISM: Artificial Sequence
<220> FEATURE:
<223> OTHER INFORMATION: mAb_C LCDR1 amino acid sequence (IMGT
      definition)

<400> SEQUENCE: 91

Lys Ser Leu Leu His Ser Asn Gly Asn Thr Tyr
1               5                   10

```
<210> SEQ ID NO 92
<211> LENGTH: 3
<212> TYPE: PRT
<213> ORGANISM: Artificial Sequence
<220> FEATURE:
<223> OTHER INFORMATION: mAb_C LCDR2 amino acid sequence (IMGT
      definition)

<400> SEQUENCE: 92

Arg Val Ser
1

<210> SEQ ID NO 93
<211> LENGTH: 9
<212> TYPE: PRT
<213> ORGANISM: Artificial Sequence
<220> FEATURE:
<223> OTHER INFORMATION: mAb_C LCDR3 amino acid sequence (IMGT
      definition)

<400> SEQUENCE: 93

Met Gln His Leu Glu Tyr Pro Phe Thr
1               5

<210> SEQ ID NO 94
<211> LENGTH: 5
<212> TYPE: PRT
<213> ORGANISM: Artificial Sequence
<220> FEATURE:
<223> OTHER INFORMATION: mAb_C HCDR1 amino acid sequence (Kabat
      definition)

<400> SEQUENCE: 94

Ser Tyr Gly Ile Ser
1               5

<210> SEQ ID NO 95
<211> LENGTH: 17
<212> TYPE: PRT
<213> ORGANISM: Artificial Sequence
<220> FEATURE:
<223> OTHER INFORMATION: mAb_C HCDR2 amino acid sequence (Kabat
      definition)

<400> SEQUENCE: 95

Glu Ile Tyr Pro Gly Ser Gly Asn Thr Tyr Tyr Asn Glu Lys Leu Lys
1               5                   10                  15

Gly

<210> SEQ ID NO 96
<211> LENGTH: 12
<212> TYPE: PRT
<213> ORGANISM: Artificial Sequence
<220> FEATURE:
<223> OTHER INFORMATION: mAb_C HCDR3 amino acid sequence (Kabat
      definition)

<400> SEQUENCE: 96

Thr Tyr Gly Tyr Asp Ser Phe Pro Trp Phe Ala Tyr
1               5                   10

<210> SEQ ID NO 97
<211> LENGTH: 16
<212> TYPE: PRT
<213> ORGANISM: Artificial Sequence
<220> FEATURE:
<223> OTHER INFORMATION: mAb_C LCDR1 amino acid sequence (Kabat
      definition)
```

```
<400> SEQUENCE: 97

Arg Ser Ser Lys Ser Leu Leu His Ser Asn Gly Asn Thr Tyr Leu Tyr
1               5                   10                  15

<210> SEQ ID NO 98
<211> LENGTH: 7
<212> TYPE: PRT
<213> ORGANISM: Artificial Sequence
<220> FEATURE:
<223> OTHER INFORMATION: mAb_C LCDR2 amino acid sequence (Kabat
      definition)

<400> SEQUENCE: 98

Arg Val Ser Asn Leu Ala Ser
1               5

<210> SEQ ID NO 99
<211> LENGTH: 9
<212> TYPE: PRT
<213> ORGANISM: Artificial Sequence
<220> FEATURE:
<223> OTHER INFORMATION: mAb_C LCDR3 amino acid sequence (Kabat
      definition)

<400> SEQUENCE: 99

Met Gln His Leu Glu Tyr Pro Phe Thr
1               5

<210> SEQ ID NO 100
<211> LENGTH: 7
<212> TYPE: PRT
<213> ORGANISM: Artificial Sequence
<220> FEATURE:
<223> OTHER INFORMATION: mAb_C HCDR1 amino acid sequence (Chothia
      definition)

<400> SEQUENCE: 100

Gly Tyr Asn Phe Lys Ser Tyr
1               5

<210> SEQ ID NO 101
<211> LENGTH: 6
<212> TYPE: PRT
<213> ORGANISM: Artificial Sequence
<220> FEATURE:
<223> OTHER INFORMATION: mAb_C HCDR2 amino acid sequence (Chothia
      definition)

<400> SEQUENCE: 101

Tyr Pro Gly Ser Gly Asn
1               5

<210> SEQ ID NO 102
<211> LENGTH: 12
<212> TYPE: PRT
<213> ORGANISM: Artificial Sequence
<220> FEATURE:
<223> OTHER INFORMATION: mAb_C HCDR3 amino acid sequence (Chothia
      definition)

<400> SEQUENCE: 102

Thr Tyr Gly Tyr Asp Ser Phe Pro Trp Phe Ala Tyr
1               5                   10

<210> SEQ ID NO 103
<211> LENGTH: 12
```

```
<212> TYPE: PRT
<213> ORGANISM: Artificial Sequence
<220> FEATURE:
<223> OTHER INFORMATION: mAb_C LCDR1 amino acid sequence (Chothia
      definition)

<400> SEQUENCE: 103

Ser Lys Ser Leu Leu His Ser Asn Gly Asn Thr Tyr
1               5                   10

<210> SEQ ID NO 104
<211> LENGTH: 3
<212> TYPE: PRT
<213> ORGANISM: Artificial Sequence
<220> FEATURE:
<223> OTHER INFORMATION: mAb_C LCDR2 amino acid sequence (Chothia
      definition)

<400> SEQUENCE: 104

Arg Val Ser
1

<210> SEQ ID NO 105
<211> LENGTH: 7
<212> TYPE: PRT
<213> ORGANISM: Artificial Sequence
<220> FEATURE:
<223> OTHER INFORMATION: mAb_C LCDR3 amino acid sequence (Chothia
      definition)

<400> SEQUENCE: 105

His Leu Glu Tyr Pro Phe Thr
1               5

<210> SEQ ID NO 106
<211> LENGTH: 2
<212> TYPE: PRT
<213> ORGANISM: Artificial Sequence
<220> FEATURE:
<223> OTHER INFORMATION: mAb_C HCDR1 amino acid sequence (IMGT, Kabat,
      and Chothia common sequences)

<400> SEQUENCE: 106

Ser Tyr
1

<210> SEQ ID NO 107
<211> LENGTH: 6
<212> TYPE: PRT
<213> ORGANISM: Artificial Sequence
<220> FEATURE:
<223> OTHER INFORMATION: mAb_C HCDR2 amino acid sequence (IMGT, Kabat,
      and Chothia common sequences)

<400> SEQUENCE: 107

Tyr Pro Gly Ser Gly Asn
1               5

<210> SEQ ID NO 108
<211> LENGTH: 12
<212> TYPE: PRT
<213> ORGANISM: Artificial Sequence
<220> FEATURE:
<223> OTHER INFORMATION: mAb_C HCDR3 amino acid sequence (IMGT, Kabat,
      and Chothia common sequences definition)

<400> SEQUENCE: 108

Thr Tyr Gly Tyr Asp Ser Phe Pro Trp Phe Ala Tyr
```

```
<210> SEQ ID NO 109
<211> LENGTH: 11
<212> TYPE: PRT
<213> ORGANISM: Artificial Sequence
<220> FEATURE:
<223> OTHER INFORMATION: mAb_C LCDR1 amino acid sequence (IMGT, Kabat,
      and Chothia common sequences)

<400> SEQUENCE: 109

Lys Ser Leu Leu His Ser Asn Gly Asn Thr Tyr
1               5                   10

<210> SEQ ID NO 110
<211> LENGTH: 3
<212> TYPE: PRT
<213> ORGANISM: Artificial Sequence
<220> FEATURE:
<223> OTHER INFORMATION: mAb_C LCDR2 amino acid sequence (IMGT, Kabat,
      and Chothia common sequences)

<400> SEQUENCE: 110

Trp Ala Ser
1

<210> SEQ ID NO 111
<211> LENGTH: 10
<212> TYPE: PRT
<213> ORGANISM: Artificial Sequence
<220> FEATURE:
<223> OTHER INFORMATION: mAb_C HCDR1 amino acid sequence (IMGT, Kabat,
      and Chothia combined overlap sequences)

<400> SEQUENCE: 111

Gly Tyr Asn Phe Lys Ser Tyr Gly Ile Ser
1               5                   10

<210> SEQ ID NO 112
<211> LENGTH: 17
<212> TYPE: PRT
<213> ORGANISM: Artificial Sequence
<220> FEATURE:
<223> OTHER INFORMATION: mAb_C HCDR2 amino acid sequence (IMGT, Kabat,
      and Chothia combined overlap sequences)

<400> SEQUENCE: 112

Glu Ile Tyr Pro Gly Ser Gly Asn Thr Tyr Tyr Asn Glu Lys Leu Lys
1               5                   10                  15

Gly

<210> SEQ ID NO 113
<211> LENGTH: 14
<212> TYPE: PRT
<213> ORGANISM: Artificial Sequence
<220> FEATURE:
<223> OTHER INFORMATION: mAb_C HCDR3 amino acid sequence (IMGT, Kabat,
      and Chothia combined overlap sequences)

<400> SEQUENCE: 113

Ala Arg Thr Tyr Gly Tyr Asp Ser Phe Pro Trp Phe Ala Tyr
1               5                   10

<210> SEQ ID NO 114
<211> LENGTH: 16
<212> TYPE: PRT
<213> ORGANISM: Artificial Sequence
```

```
<220> FEATURE:
<223> OTHER INFORMATION: mAb_C LCDR1 amino acid sequence (IMGT, Kabat,
      and Chothia combined overlap sequences)

<400> SEQUENCE: 114

Arg Ser Ser Lys Ser Leu Leu His Ser Asn Gly Asn Thr Tyr Leu Tyr
1               5                   10                  15

<210> SEQ ID NO 115
<211> LENGTH: 7
<212> TYPE: PRT
<213> ORGANISM: Artificial Sequence
<220> FEATURE:
<223> OTHER INFORMATION: mAb_C LCDR2 amino acid sequence (IMGT, Kabat,
      and Chothia combined overlap sequences)

<400> SEQUENCE: 115

Arg Val Ser Asn Leu Ala Ser
1               5

<210> SEQ ID NO 116
<211> LENGTH: 9
<212> TYPE: PRT
<213> ORGANISM: Artificial Sequence
<220> FEATURE:
<223> OTHER INFORMATION: mAb_C LCDR3 amino acid sequence (IMGT, Kabat,
      and Chothia combined overlap sequences)

<400> SEQUENCE: 116

Met Gln His Leu Glu Tyr Pro Phe Thr
1               5

<210> SEQ ID NO 117
<211> LENGTH: 8
<212> TYPE: PRT
<213> ORGANISM: Artificial Sequence
<220> FEATURE:
<223> OTHER INFORMATION: mAb_D HCDR1 amino acid sequence (IMGT
      definition)

<400> SEQUENCE: 117

Gly Tyr Thr Phe Thr Asp Tyr Glu
1               5

<210> SEQ ID NO 118
<211> LENGTH: 8
<212> TYPE: PRT
<213> ORGANISM: Artificial Sequence
<220> FEATURE:
<223> OTHER INFORMATION: mAb_D HCDR2 amino acid sequence (IMGT
      definition)

<400> SEQUENCE: 118

Ile Asp Pro Glu Thr Gly Gly Thr
1               5

<210> SEQ ID NO 119
<211> LENGTH: 10
<212> TYPE: PRT
<213> ORGANISM: Artificial Sequence
<220> FEATURE:
<223> OTHER INFORMATION: mAb_D HCDR3 amino acid sequence (IMGT
      definition)

<400> SEQUENCE: 119

Thr Arg His Gly Ser Tyr Ala Met Asp Tyr
1               5                   10
```

<210> SEQ ID NO 120
<211> LENGTH: 6
<212> TYPE: PRT
<213> ORGANISM: Artificial Sequence
<220> FEATURE:
<223> OTHER INFORMATION: mAb_D LCDR1 amino acid sequence (IMGT
      definition)

<400> SEQUENCE: 120

Gln Asp Val Ser Thr Ala
1               5

<210> SEQ ID NO 121
<211> LENGTH: 3
<212> TYPE: PRT
<213> ORGANISM: Artificial Sequence
<220> FEATURE:
<223> OTHER INFORMATION: mAb_D LCDR2 amino acid sequence (IMGT
      definition)

<400> SEQUENCE: 121

Trp Ala Ser
1

<210> SEQ ID NO 122
<211> LENGTH: 9
<212> TYPE: PRT
<213> ORGANISM: Artificial Sequence
<220> FEATURE:
<223> OTHER INFORMATION: mAb_D LCDR3 amino acid sequence (IMGT
      definition)

<400> SEQUENCE: 122

Gln Gln His Tyr Ser Thr Pro Pro Thr
1               5

<210> SEQ ID NO 123
<211> LENGTH: 5
<212> TYPE: PRT
<213> ORGANISM: Artificial Sequence
<220> FEATURE:
<223> OTHER INFORMATION: mAb_D HCDR1 amino acid sequence (Kabat
      definition)

<400> SEQUENCE: 123

Asp Tyr Glu Met His
1               5

<210> SEQ ID NO 124
<211> LENGTH: 17
<212> TYPE: PRT
<213> ORGANISM: Artificial Sequence
<220> FEATURE:
<223> OTHER INFORMATION: mAb_D HCDR2 amino acid sequence (Kabat
      definition)

<400> SEQUENCE: 124

Gly Ile Asp Pro Glu Thr Gly Gly Thr Gly Tyr Asn Gln Lys Phe Lys
1               5                   10                  15

Gly

<210> SEQ ID NO 125
<211> LENGTH: 8
<212> TYPE: PRT
<213> ORGANISM: Artificial Sequence
<220> FEATURE:
<223> OTHER INFORMATION: mAb_D HCDR3 amino acid sequence (Kabat -continued definition)

<400> SEQUENCE: 125

His Gly Ser Tyr Ala Met Asp Tyr
1               5

<210> SEQ ID NO 126
<211> LENGTH: 11
<212> TYPE: PRT
<213> ORGANISM: Artificial Sequence
<220> FEATURE:
<223> OTHER INFORMATION: mAb_D LCDR1 amino acid sequence (Kabat
      definition)

<400> SEQUENCE: 126

Lys Ala Ser Gln Asp Val Ser Thr Ala Val Ala
1               5                   10

<210> SEQ ID NO 127
<211> LENGTH: 7
<212> TYPE: PRT
<213> ORGANISM: Artificial Sequence
<220> FEATURE:
<223> OTHER INFORMATION: mAb_D LCDR2 amino acid sequence (Kabat
      definition)

<400> SEQUENCE: 127

Trp Ala Ser Thr Arg His Thr
1               5

<210> SEQ ID NO 128
<211> LENGTH: 9
<212> TYPE: PRT
<213> ORGANISM: Artificial Sequence
<220> FEATURE:
<223> OTHER INFORMATION: mAb_D LCDR3 amino acid sequence (Kabat
      definition)

<400> SEQUENCE: 128

Gln Gln His Tyr Ser Thr Pro Pro Thr
1               5

<210> SEQ ID NO 129
<211> LENGTH: 7
<212> TYPE: PRT
<213> ORGANISM: Artificial Sequence
<220> FEATURE:
<223> OTHER INFORMATION: mAb_D HCDR1 amino acid sequence (Chothia
      definition)

<400> SEQUENCE: 129

Gly Tyr Thr Phe Thr Asp Tyr
1               5

<210> SEQ ID NO 130
<211> LENGTH: 6
<212> TYPE: PRT
<213> ORGANISM: Artificial Sequence
<220> FEATURE:
<223> OTHER INFORMATION: mAb_D HCDR2 amino acid sequence (Chothia
      definition)

<400> SEQUENCE: 130

Asp Pro Glu Thr Gly Gly
1               5

<210> SEQ ID NO 131

```
<211> LENGTH: 8
<212> TYPE: PRT
<213> ORGANISM: Artificial Sequence
<220> FEATURE:
<223> OTHER INFORMATION: mAb_D HCDR3 amino acid sequence (Chothia
      definition)

<400> SEQUENCE: 131

His Gly Ser Tyr Ala Met Asp Tyr
1               5

<210> SEQ ID NO 132
<211> LENGTH: 7
<212> TYPE: PRT
<213> ORGANISM: Artificial Sequence
<220> FEATURE:
<223> OTHER INFORMATION: mAb_D LCDR1 amino acid sequence (Chothia
      definition)

<400> SEQUENCE: 132

Ser Gln Asp Val Ser Thr Ala
1               5

<210> SEQ ID NO 133
<211> LENGTH: 3
<212> TYPE: PRT
<213> ORGANISM: Artificial Sequence
<220> FEATURE:
<223> OTHER INFORMATION: mAb_D LCDR2 amino acid sequence (Chothia
      definition)

<400> SEQUENCE: 133

Trp Ala Ser
1

<210> SEQ ID NO 134
<211> LENGTH: 7
<212> TYPE: PRT
<213> ORGANISM: Artificial Sequence
<220> FEATURE:
<223> OTHER INFORMATION: mAb_D LCDR3 amino acid sequence (Chothia
      definition)

<400> SEQUENCE: 134

His Tyr Ser Thr Pro Pro Thr
1               5

<210> SEQ ID NO 135
<211> LENGTH: 2
<212> TYPE: PRT
<213> ORGANISM: Artificial Sequence
<220> FEATURE:
<223> OTHER INFORMATION: mAb_D HCDR1 amino acid sequence (IMGT, Kabat,
      and Chothia common sequences)

<400> SEQUENCE: 135

Asp Tyr
1

<210> SEQ ID NO 136
<211> LENGTH: 6
<212> TYPE: PRT
<213> ORGANISM: Artificial Sequence
<220> FEATURE:
<223> OTHER INFORMATION: mAb_D HCDR2 amino acid sequence (IMGT, Kabat,
      and Chothia common sequences)

<400> SEQUENCE: 136
```

```
Asp Pro Glu Thr Gly Gly
1               5
```

<210> SEQ ID NO 137
<211> LENGTH: 8
<212> TYPE: PRT
<213> ORGANISM: Artificial Sequence
<220> FEATURE:
<223> OTHER INFORMATION: mAb_D HCDR3 amino acid sequence (IMGT, Kabat,
      and Chothia common sequences definition)

<400> SEQUENCE: 137

```
His Gly Ser Tyr Ala Met Asp Tyr
1               5
```

<210> SEQ ID NO 138
<211> LENGTH: 6
<212> TYPE: PRT
<213> ORGANISM: Artificial Sequence
<220> FEATURE:
<223> OTHER INFORMATION: mAb_D LCDR1 amino acid sequence (IMGT, Kabat,
      and Chothia common sequences)

<400> SEQUENCE: 138

```
Gln Asp Val Ser Thr Ala
1               5
```

<210> SEQ ID NO 139
<211> LENGTH: 3
<212> TYPE: PRT
<213> ORGANISM: Artificial Sequence
<220> FEATURE:
<223> OTHER INFORMATION: mAb_D LCDR2 amino acid sequence (IMGT, Kabat,
      and Chothia common sequences)

<400> SEQUENCE: 139

```
Trp Ala Ser
1
```

<210> SEQ ID NO 140
<211> LENGTH: 7
<212> TYPE: PRT
<213> ORGANISM: Artificial Sequence
<220> FEATURE:
<223> OTHER INFORMATION: mAb_D LCDR3 amino acid sequence (IMGT, Kabat,
      and Chothia common sequences)

<400> SEQUENCE: 140

```
His Tyr Ser Thr Pro Pro Thr
1               5
```

<210> SEQ ID NO 141
<211> LENGTH: 10
<212> TYPE: PRT
<213> ORGANISM: Artificial Sequence
<220> FEATURE:
<223> OTHER INFORMATION: mAb_D HCDR1 amino acid sequence (IMGT, Kabat,
      and Chothia combined overlap sequences)

<400> SEQUENCE: 141

```
Gly Tyr Thr Phe Thr Asp Tyr Glu Met His
1               5                   10
```

<210> SEQ ID NO 142
<211> LENGTH: 17
<212> TYPE: PRT
<213> ORGANISM: Artificial Sequence
<220> FEATURE:

```
<223> OTHER INFORMATION: mAb_D HCDR2 amino acid sequence (IMGT, Kabat,
      and Chothia combined overlap sequences)

<400> SEQUENCE: 142

Gly Ile Asp Pro Glu Thr Gly Gly Thr Gly Tyr Asn Gln Lys Phe Lys
1               5                   10                  15

Gly

<210> SEQ ID NO 143
<211> LENGTH: 10
<212> TYPE: PRT
<213> ORGANISM: Artificial Sequence
<220> FEATURE:
<223> OTHER INFORMATION: mAb_D HCDR3 amino acid sequence (IMGT, Kabat,
      and Chothia combined overlap sequences)

<400> SEQUENCE: 143

Thr Arg His Gly Ser Tyr Ala Met Asp Tyr
1               5                   10

<210> SEQ ID NO 144
<211> LENGTH: 11
<212> TYPE: PRT
<213> ORGANISM: Artificial Sequence
<220> FEATURE:
<223> OTHER INFORMATION: mAb_D LCDR1 amino acid sequence (IMGT, Kabat,
      and Chothia combined overlap sequences)

<400> SEQUENCE: 144

Lys Ala Ser Gln Asp Val Ser Thr Ala Val Ala
1               5                   10

<210> SEQ ID NO 145
<211> LENGTH: 7
<212> TYPE: PRT
<213> ORGANISM: Artificial Sequence
<220> FEATURE:
<223> OTHER INFORMATION: mAb_D LCDR2 amino acid sequence (IMGT, Kabat,
      and Chothia combined overlap sequences)

<400> SEQUENCE: 145

Trp Ala Ser Thr Arg His Thr
1               5

<210> SEQ ID NO 146
<211> LENGTH: 9
<212> TYPE: PRT
<213> ORGANISM: Artificial Sequence
<220> FEATURE:
<223> OTHER INFORMATION: mAb_D LCDR3 amino acid sequence (IMGT, Kabat,
      and Chothia combined overlap sequences)

<400> SEQUENCE: 146

Gln Gln His Tyr Ser Thr Pro Pro Thr
1               5

<210> SEQ ID NO 147
<211> LENGTH: 8
<212> TYPE: PRT
<213> ORGANISM: Artificial Sequence
<220> FEATURE:
<223> OTHER INFORMATION: mAb_E HCDR1 amino acid sequence (IMGT
      definition)

<400> SEQUENCE: 147

Gly Tyr Thr Phe Thr Asp Tyr Glu
1               5
```

<210> SEQ ID NO 148
<211> LENGTH: 8
<212> TYPE: PRT
<213> ORGANISM: Artificial Sequence
<220> FEATURE:
<223> OTHER INFORMATION: mAb_E HCDR2 amino acid sequence (IMGT
      definition)

<400> SEQUENCE: 148

Ile Asp Pro Glu Ser Gly Gly Thr
1               5

<210> SEQ ID NO 149
<211> LENGTH: 13
<212> TYPE: PRT
<213> ORGANISM: Artificial Sequence
<220> FEATURE:
<223> OTHER INFORMATION: mAb_E HCDR3 amino acid sequence (IMGT
      definition)

<400> SEQUENCE: 149

Thr Arg Ser Gly Tyr Tyr Gly Ser Pro Leu Leu Asp Tyr
1               5                   10

<210> SEQ ID NO 150
<211> LENGTH: 7
<212> TYPE: PRT
<213> ORGANISM: Artificial Sequence
<220> FEATURE:
<223> OTHER INFORMATION: mAb_E LCDR1 amino acid sequence (IMGT
      definition)

<400> SEQUENCE: 150

Ser Ser Val Ser Ser Ser Tyr
1               5

<210> SEQ ID NO 151
<211> LENGTH: 3
<212> TYPE: PRT
<213> ORGANISM: Artificial Sequence
<220> FEATURE:
<223> OTHER INFORMATION: mAb_E LCDR2 amino acid sequence (IMGT
      definition)

<400> SEQUENCE: 151

Ser Thr Ser
1

<210> SEQ ID NO 152
<211> LENGTH: 9
<212> TYPE: PRT
<213> ORGANISM: Artificial Sequence
<220> FEATURE:
<223> OTHER INFORMATION: mAb_E LCDR3 amino acid sequence (IMGT
      definition)

<400> SEQUENCE: 152

His Gln Tyr His Arg Ser Pro Pro Thr
1               5

<210> SEQ ID NO 153
<211> LENGTH: 5
<212> TYPE: PRT
<213> ORGANISM: Artificial Sequence
<220> FEATURE:
<223> OTHER INFORMATION: mAb_E HCDR1 amino acid sequence (Kabat
      definition)

<400> SEQUENCE: 153

Asp Tyr Glu Met His
1               5

<210> SEQ ID NO 154
<211> LENGTH: 17
<212> TYPE: PRT
<213> ORGANISM: Artificial Sequence
<220> FEATURE:
<223> OTHER INFORMATION: mAb_E HCDR2 amino acid sequence (Kabat
      definition)

<400> SEQUENCE: 154

Gly Ile Asp Pro Glu Ser Gly Gly Thr Gly Tyr Asn Gln Lys Phe Lys
1               5                   10                  15

Gly

<210> SEQ ID NO 155
<211> LENGTH: 11
<212> TYPE: PRT
<213> ORGANISM: Artificial Sequence
<220> FEATURE:
<223> OTHER INFORMATION: mAb_E HCDR3 amino acid sequence (Kabat
      definition)

<400> SEQUENCE: 155

Ser Gly Tyr Tyr Gly Ser Pro Leu Leu Asp Tyr
1               5                   10

<210> SEQ ID NO 156
<211> LENGTH: 12
<212> TYPE: PRT
<213> ORGANISM: Artificial Sequence
<220> FEATURE:
<223> OTHER INFORMATION: mAb_E LCDR1 amino acid sequence (Kabat
      definition)

<400> SEQUENCE: 156

Thr Ala Ser Ser Ser Val Ser Ser Ser Tyr Leu His
1               5                   10

<210> SEQ ID NO 157
<211> LENGTH: 7
<212> TYPE: PRT
<213> ORGANISM: Artificial Sequence
<220> FEATURE:
<223> OTHER INFORMATION: mAb_E LCDR2 amino acid sequence (Kabat
      definition)

<400> SEQUENCE: 157

Ser Thr Ser Asn Leu Ala Ser
1               5

<210> SEQ ID NO 158
<211> LENGTH: 9
<212> TYPE: PRT
<213> ORGANISM: Artificial Sequence
<220> FEATURE:
<223> OTHER INFORMATION: mAb_E LCDR3 amino acid sequence (Kabat
      definition)

<400> SEQUENCE: 158

His Gln Tyr His Arg Ser Pro Pro Thr
1               5

```
<210> SEQ ID NO 159
<211> LENGTH: 7
<212> TYPE: PRT
<213> ORGANISM: Artificial Sequence
<220> FEATURE:
<223> OTHER INFORMATION: mAb_E HCDR1 amino acid sequence (Chothia
      definition)

<400> SEQUENCE: 159

Gly Tyr Thr Phe Thr Asp Tyr
1               5

<210> SEQ ID NO 160
<211> LENGTH: 6
<212> TYPE: PRT
<213> ORGANISM: Artificial Sequence
<220> FEATURE:
<223> OTHER INFORMATION: mAb_E HCDR2 amino acid sequence (Chothia
      definition)

<400> SEQUENCE: 160

Asp Pro Glu Ser Gly Gly
1               5

<210> SEQ ID NO 161
<211> LENGTH: 11
<212> TYPE: PRT
<213> ORGANISM: Artificial Sequence
<220> FEATURE:
<223> OTHER INFORMATION: mAb_E HCDR3 amino acid sequence (Chothia
      definition)

<400> SEQUENCE: 161

Ser Gly Tyr Tyr Gly Ser Pro Leu Leu Asp Tyr
1               5                   10

<210> SEQ ID NO 162
<211> LENGTH: 8
<212> TYPE: PRT
<213> ORGANISM: Artificial Sequence
<220> FEATURE:
<223> OTHER INFORMATION: mAb_E LCDR1 amino acid sequence (Chothia
      definition)

<400> SEQUENCE: 162

Ser Ser Ser Val Ser Ser Ser Tyr
1               5

<210> SEQ ID NO 163
<211> LENGTH: 3
<212> TYPE: PRT
<213> ORGANISM: Artificial Sequence
<220> FEATURE:
<223> OTHER INFORMATION: mAb_E LCDR2 amino acid sequence (Chothia
      definition)

<400> SEQUENCE: 163

Ser Thr Ser
1

<210> SEQ ID NO 164
<211> LENGTH: 7
<212> TYPE: PRT
<213> ORGANISM: Artificial Sequence
<220> FEATURE:
<223> OTHER INFORMATION: mAb_E LCDR3 amino acid sequence (Chothia
      definition)

<400> SEQUENCE: 164
```

```
Tyr His Arg Ser Pro Pro Thr
1               5

<210> SEQ ID NO 165
<211> LENGTH: 2
<212> TYPE: PRT
<213> ORGANISM: Artificial Sequence
<220> FEATURE:
<223> OTHER INFORMATION: mAb_E HCDR1 amino acid sequence (IMGT, Kabat,
      and Chothia common sequences)

<400> SEQUENCE: 165

Asp Tyr
1

<210> SEQ ID NO 166
<211> LENGTH: 6
<212> TYPE: PRT
<213> ORGANISM: Artificial Sequence
<220> FEATURE:
<223> OTHER INFORMATION: mAb_E HCDR2 amino acid sequence (IMGT, Kabat,
      and Chothia common sequences)

<400> SEQUENCE: 166

Asp Pro Glu Ser Gly Gly
1               5

<210> SEQ ID NO 167
<211> LENGTH: 11
<212> TYPE: PRT
<213> ORGANISM: Artificial Sequence
<220> FEATURE:
<223> OTHER INFORMATION: mAb_E HCDR3 amino acid sequence (IMGT, Kabat,
      and Chothia common sequences definition)

<400> SEQUENCE: 167

Ser Gly Tyr Tyr Gly Ser Pro Leu Leu Asp Tyr
1               5                   10

<210> SEQ ID NO 168
<211> LENGTH: 8
<212> TYPE: PRT
<213> ORGANISM: Artificial Sequence
<220> FEATURE:
<223> OTHER INFORMATION: mAb_E LCDR1 amino acid sequence (IMGT, Kabat,
      and Chothia common sequences)

<400> SEQUENCE: 168

Ser Ser Ser Val Ser Ser Ser Tyr
1               5

<210> SEQ ID NO 169
<211> LENGTH: 3
<212> TYPE: PRT
<213> ORGANISM: Artificial Sequence
<220> FEATURE:
<223> OTHER INFORMATION: mAb_E LCDR2 amino acid sequence (IMGT, Kabat,
      and Chothia common sequences)

<400> SEQUENCE: 169

Ser Thr Ser
1

<210> SEQ ID NO 170
<211> LENGTH: 7
<212> TYPE: PRT
<213> ORGANISM: Artificial Sequence
```

```
<220> FEATURE:
<223> OTHER INFORMATION: mAb_E LCDR3 amino acid sequence (IMGT, Kabat,
      and Chothia common sequences)

<400> SEQUENCE: 170

Tyr His Arg Ser Pro Pro Thr
1               5

<210> SEQ ID NO 171
<211> LENGTH: 10
<212> TYPE: PRT
<213> ORGANISM: Artificial Sequence
<220> FEATURE:
<223> OTHER INFORMATION: mAb_E HCDR1 amino acid sequence (IMGT, Kabat,
      and Chothia combined overlap sequences)

<400> SEQUENCE: 171

Gly Tyr Thr Phe Thr Asp Tyr Glu Met His
1               5                   10

<210> SEQ ID NO 172
<211> LENGTH: 17
<212> TYPE: PRT
<213> ORGANISM: Artificial Sequence
<220> FEATURE:
<223> OTHER INFORMATION: mAb_E HCDR2 amino acid sequence (IMGT, Kabat,
      and Chothia combined overlap sequences)

<400> SEQUENCE: 172

Gly Ile Asp Pro Glu Ser Gly Gly Thr Gly Tyr Asn Gln Lys Phe Lys
1               5                   10                  15

Gly

<210> SEQ ID NO 173
<211> LENGTH: 13
<212> TYPE: PRT
<213> ORGANISM: Artificial Sequence
<220> FEATURE:
<223> OTHER INFORMATION: mAb_E HCDR3 amino acid sequence (IMGT, Kabat,
      and Chothia combined overlap sequences)

<400> SEQUENCE: 173

Thr Arg Ser Gly Tyr Tyr Gly Ser Pro Leu Leu Asp Tyr
1               5                   10

<210> SEQ ID NO 174
<211> LENGTH: 12
<212> TYPE: PRT
<213> ORGANISM: Artificial Sequence
<220> FEATURE:
<223> OTHER INFORMATION: mAb_E LCDR1 amino acid sequence (IMGT, Kabat,
      and Chothia combined overlap sequences)

<400> SEQUENCE: 174

Thr Ala Ser Ser Ser Val Ser Ser Ser Tyr Leu His
1               5                   10

<210> SEQ ID NO 175
<211> LENGTH: 7
<212> TYPE: PRT
<213> ORGANISM: Artificial Sequence
<220> FEATURE:
<223> OTHER INFORMATION: mAb_E LCDR2 amino acid sequence (IMGT, Kabat,
      and Chothia combined overlap sequences)

<400> SEQUENCE: 175

Ser Thr Ser Asn Leu Ala Ser
```

```
1               5

<210> SEQ ID NO 176
<211> LENGTH: 9
<212> TYPE: PRT
<213> ORGANISM: Artificial Sequence
<220> FEATURE:
<223> OTHER INFORMATION: mAb_E LCDR3 amino acid sequence (IMGT, Kabat,
      and Chothia combined overlap sequences)

<400> SEQUENCE: 176

His Gln Tyr His Arg Ser Pro Pro Thr
1               5

<210> SEQ ID NO 177
<211> LENGTH: 8
<212> TYPE: PRT
<213> ORGANISM: Artificial Sequence
<220> FEATURE:
<223> OTHER INFORMATION: mAb_G HCDR1 amino acid sequence (IMGT
      definition)

<400> SEQUENCE: 177

Gly Tyr Thr Phe Thr Asp Tyr Glu
1               5

<210> SEQ ID NO 178
<211> LENGTH: 8
<212> TYPE: PRT
<213> ORGANISM: Artificial Sequence
<220> FEATURE:
<223> OTHER INFORMATION: mAb_G HCDR2 amino acid sequence (IMGT
      definition)

<400> SEQUENCE: 178

Ile Asp Pro Glu Thr Gly Gly Thr
1               5

<210> SEQ ID NO 179
<211> LENGTH: 17
<212> TYPE: PRT
<213> ORGANISM: Artificial Sequence
<220> FEATURE:
<223> OTHER INFORMATION: mAb_G HCDR3 amino acid sequence (IMGT
      definition)

<400> SEQUENCE: 179

Thr Arg Trp Gly Ala Ile Thr Ser Phe Val Ala Leu Arg Gly Phe Ala
1               5                   10                  15

Tyr

<210> SEQ ID NO 180
<211> LENGTH: 12
<212> TYPE: PRT
<213> ORGANISM: Artificial Sequence
<220> FEATURE:
<223> OTHER INFORMATION: mAb_G LCDR1 amino acid sequence (IMGT
      definition)

<400> SEQUENCE: 180

Gln Ser Leu Leu Asn Ser Gly Asn Gln Lys Asn Tyr
1               5                   10

<210> SEQ ID NO 181
<211> LENGTH: 3
<212> TYPE: PRT
<213> ORGANISM: Artificial Sequence
```

```
<220> FEATURE:
<223> OTHER INFORMATION: mAb_G LCDR2 amino acid sequence (IMGT
      definition)

<400> SEQUENCE: 181

Gly Ala Ser
1

<210> SEQ ID NO 182
<211> LENGTH: 9
<212> TYPE: PRT
<213> ORGANISM: Artificial Sequence
<220> FEATURE:
<223> OTHER INFORMATION: mAb_G LCDR3 amino acid sequence (IMGT
      definition)

<400> SEQUENCE: 182

Gln Asn Asp His Ser Tyr Pro Pro Thr
1               5

<210> SEQ ID NO 183
<211> LENGTH: 5
<212> TYPE: PRT
<213> ORGANISM: Artificial Sequence
<220> FEATURE:
<223> OTHER INFORMATION: mAb_G HCDR1 amino acid sequence (Kabat
      definition)

<400> SEQUENCE: 183

Asp Tyr Glu Met His
1               5

<210> SEQ ID NO 184
<211> LENGTH: 17
<212> TYPE: PRT
<213> ORGANISM: Artificial Sequence
<220> FEATURE:
<223> OTHER INFORMATION: mAb_G HCDR2 amino acid sequence (Kabat
      definition)

<400> SEQUENCE: 184

Gly Ile Asp Pro Glu Thr Gly Gly Thr Ala Tyr Asn Gln Lys Phe Lys
1               5                   10                  15

Gly

<210> SEQ ID NO 185
<211> LENGTH: 15
<212> TYPE: PRT
<213> ORGANISM: Artificial Sequence
<220> FEATURE:
<223> OTHER INFORMATION: mAb_G HCDR3 amino acid sequence (Kabat
      definition)

<400> SEQUENCE: 185

Trp Gly Ala Ile Thr Ser Phe Val Ala Leu Arg Gly Phe Ala Tyr
1               5                   10                  15

<210> SEQ ID NO 186
<211> LENGTH: 17
<212> TYPE: PRT
<213> ORGANISM: Artificial Sequence
<220> FEATURE:
<223> OTHER INFORMATION: mAb_G LCDR1 amino acid sequence (Kabat
      definition)

<400> SEQUENCE: 186

Lys Ser Ser Gln Ser Leu Leu Asn Ser Gly Asn Gln Lys Asn Tyr Leu
```

<210> SEQ ID NO 187
<211> LENGTH: 7
<212> TYPE: PRT
<213> ORGANISM: Artificial Sequence
<220> FEATURE:
<223> OTHER INFORMATION: mAb_G LCDR2 amino acid sequence (Kabat definition)

<400> SEQUENCE: 187

Gly Ala Ser Thr Arg Glu Ser
1               5

<210> SEQ ID NO 188
<211> LENGTH: 9
<212> TYPE: PRT
<213> ORGANISM: Artificial Sequence
<220> FEATURE:
<223> OTHER INFORMATION: mAb_G LCDR3 amino acid sequence (Kabat definition)

<400> SEQUENCE: 188

Gln Asn Asp His Ser Tyr Pro Pro Thr
1               5

<210> SEQ ID NO 189
<211> LENGTH: 7
<212> TYPE: PRT
<213> ORGANISM: Artificial Sequence
<220> FEATURE:
<223> OTHER INFORMATION: mAb_G HCDR1 amino acid sequence (Chothia definition)

<400> SEQUENCE: 189

Gly Tyr Thr Phe Thr Asp Tyr
1               5

<210> SEQ ID NO 190
<211> LENGTH: 6
<212> TYPE: PRT
<213> ORGANISM: Artificial Sequence
<220> FEATURE:
<223> OTHER INFORMATION: mAb_G HCDR2 amino acid sequence (Chothia definition)

<400> SEQUENCE: 190

Asp Pro Glu Thr Gly Gly
1               5

<210> SEQ ID NO 191
<211> LENGTH: 15
<212> TYPE: PRT
<213> ORGANISM: Artificial Sequence
<220> FEATURE:
<223> OTHER INFORMATION: mAb_G HCDR3 amino acid sequence (Chothia definition)

<400> SEQUENCE: 191

Trp Gly Ala Ile Thr Ser Phe Val Ala Leu Arg Gly Phe Ala Tyr
1               5                   10                  15

<210> SEQ ID NO 192
<211> LENGTH: 13
<212> TYPE: PRT
<213> ORGANISM: Artificial Sequence
<220> FEATURE:
<223> OTHER INFORMATION: mAb_G LCDR1 amino acid sequence (Chothia
      definition)

<400> SEQUENCE: 192

Ser Gln Ser Leu Leu Asn Ser Gly Asn Gln Lys Asn Tyr
1               5                   10

<210> SEQ ID NO 193
<211> LENGTH: 3
<212> TYPE: PRT
<213> ORGANISM: Artificial Sequence
<220> FEATURE:
<223> OTHER INFORMATION: mAb_G LCDR2 amino acid sequence (Chothia
      definition)

<400> SEQUENCE: 193

Gly Ala Ser
1

<210> SEQ ID NO 194
<211> LENGTH: 7
<212> TYPE: PRT
<213> ORGANISM: Artificial Sequence
<220> FEATURE:
<223> OTHER INFORMATION: mAb_G LCDR3 amino acid sequence (Chothia
      definition)

<400> SEQUENCE: 194

Asp His Ser Tyr Pro Pro Thr
1               5

<210> SEQ ID NO 195
<211> LENGTH: 2
<212> TYPE: PRT
<213> ORGANISM: Artificial Sequence
<220> FEATURE:
<223> OTHER INFORMATION: mAb_G HCDR1 amino acid sequence (IMGT, Kabat,
      and Chothia common sequences)

<400> SEQUENCE: 195

Asp Tyr
1

<210> SEQ ID NO 196
<211> LENGTH: 6
<212> TYPE: PRT
<213> ORGANISM: Artificial Sequence
<220> FEATURE:
<223> OTHER INFORMATION: mAb_G HCDR2 amino acid sequence (IMGT, Kabat,
      and Chothia common sequences)

<400> SEQUENCE: 196

Asp Pro Glu Thr Gly Gly
1               5

<210> SEQ ID NO 197
<211> LENGTH: 15
<212> TYPE: PRT
<213> ORGANISM: Artificial Sequence
<220> FEATURE:
<223> OTHER INFORMATION: mAb_G HCDR3 amino acid sequence (IMGT, Kabat,
      and Chothia common sequences definition)

<400> SEQUENCE: 197

Trp Gly Ala Ile Thr Ser Phe Val Ala Leu Arg Gly Phe Ala Tyr
1               5                   10                  15

<210> SEQ ID NO 198
<211> LENGTH: 12
<212> TYPE: PRT
<213> ORGANISM: Artificial Sequence
<220> FEATURE:
<223> OTHER INFORMATION: mAb_G LCDR1 amino acid sequence (IMGT, Kabat, and Chothia common sequences)

<400> SEQUENCE: 198

Gln Ser Leu Leu Asn Ser Gly Asn Gln Lys Asn Tyr
1               5                   10

<210> SEQ ID NO 199
<211> LENGTH: 3
<212> TYPE: PRT
<213> ORGANISM: Artificial Sequence
<220> FEATURE:
<223> OTHER INFORMATION: mAb_G LCDR2 amino acid sequence (IMGT, Kabat, and Chothia common sequences)

<400> SEQUENCE: 199

Gly Ala Ser
1

<210> SEQ ID NO 200
<211> LENGTH: 7
<212> TYPE: PRT
<213> ORGANISM: Artificial Sequence
<220> FEATURE:
<223> OTHER INFORMATION: mAb_G LCDR3 amino acid sequence (IMGT, Kabat, and Chothia common sequences)

<400> SEQUENCE: 200

Asp His Ser Tyr Pro Pro Thr
1               5

<210> SEQ ID NO 201
<211> LENGTH: 10
<212> TYPE: PRT
<213> ORGANISM: Artificial Sequence
<220> FEATURE:
<223> OTHER INFORMATION: mAb_G HCDR1 amino acid sequence (IMGT, Kabat, and Chothia combined overlap sequences)

<400> SEQUENCE: 201

Gly Tyr Thr Phe Thr Asp Tyr Glu Met His
1               5                   10

<210> SEQ ID NO 202
<211> LENGTH: 17
<212> TYPE: PRT
<213> ORGANISM: Artificial Sequence
<220> FEATURE:
<223> OTHER INFORMATION: mAb_G HCDR2 amino acid sequence (IMGT, Kabat, and Chothia combined overlap sequences)

<400> SEQUENCE: 202

Gly Ile Asp Pro Glu Thr Gly Gly Thr Ala Tyr Asn Gln Lys Phe Lys
1               5                   10                  15

Gly

<210> SEQ ID NO 203
<211> LENGTH: 17
<212> TYPE: PRT
<213> ORGANISM: Artificial Sequence
<220> FEATURE:
<223> OTHER INFORMATION: mAb_G HCDR3 amino acid sequence (IMGT, Kabat, and Chothia combined overlap sequences)

<400> SEQUENCE: 203

Thr Arg Trp Gly Ala Ile Thr Ser Phe Val Ala Leu Arg Gly Phe Ala
1               5                   10                  15
Tyr

<210> SEQ ID NO 204
<211> LENGTH: 17
<212> TYPE: PRT
<213> ORGANISM: Artificial Sequence
<220> FEATURE:
<223> OTHER INFORMATION: mAb_G LCDR1 amino acid sequence (IMGT, Kabat,
      and Chothia combined overlap sequences)

<400> SEQUENCE: 204

Lys Ser Ser Gln Ser Leu Leu Asn Ser Gly Asn Gln Lys Asn Tyr Leu
1               5                   10                  15
Ala

<210> SEQ ID NO 205
<211> LENGTH: 7
<212> TYPE: PRT
<213> ORGANISM: Artificial Sequence
<220> FEATURE:
<223> OTHER INFORMATION: mAb_G LCDR2 amino acid sequence (IMGT, Kabat,
      and Chothia combined overlap sequences)

<400> SEQUENCE: 205

Gly Ala Ser Thr Arg Glu Ser
1               5

<210> SEQ ID NO 206
<211> LENGTH: 9
<212> TYPE: PRT
<213> ORGANISM: Artificial Sequence
<220> FEATURE:
<223> OTHER INFORMATION: mAb_G LCDR3 amino acid sequence (IMGT, Kabat,
      and Chothia combined overlap sequences)

<400> SEQUENCE: 206

Gln Asn Asp His Ser Tyr Pro Pro Thr
1               5

<210> SEQ ID NO 207
<211> LENGTH: 5
<212> TYPE: PRT
<213> ORGANISM: Artificial Sequence
<220> FEATURE:
<223> OTHER INFORMATION: mAb_F HCDR1 amino acid sequence (Kabat
      definition)

<400> SEQUENCE: 207

Asp Tyr Tyr Ile Asn
1               5

<210> SEQ ID NO 208
<211> LENGTH: 17
<212> TYPE: PRT
<213> ORGANISM: Artificial Sequence
<220> FEATURE:
<223> OTHER INFORMATION: mAb_F HCDR2 amino acid sequence (Kabat
      definition)

<400> SEQUENCE: 208

Trp Ile Phe Pro Gly Ser Gly Ser Thr Tyr Tyr Asn Glu Lys Phe Lys

-continued

```
1               5                   10                  15

Gly

<210> SEQ ID NO 209
<211> LENGTH: 10
<212> TYPE: PRT
<213> ORGANISM: Artificial Sequence
<220> FEATURE:
<223> OTHER INFORMATION: mAb_F HCDR3 amino acid sequence (Kabat
      definition)

<400> SEQUENCE: 209

Tyr Gly Ser Ser Tyr Arg Tyr Phe Asp Val
1               5                   10

<210> SEQ ID NO 210
<211> LENGTH: 10
<212> TYPE: PRT
<213> ORGANISM: Artificial Sequence
<220> FEATURE:
<223> OTHER INFORMATION: mAb_F LCDR1 amino acid sequence (Kabat
      definition)

<400> SEQUENCE: 210

Arg Ala Ser Ser Ser Val Ser Tyr Met His
1               5                   10

<210> SEQ ID NO 211
<211> LENGTH: 7
<212> TYPE: PRT
<213> ORGANISM: Artificial Sequence
<220> FEATURE:
<223> OTHER INFORMATION: mAb_F LCDR2 amino acid sequence (Kabat
      definition)

<400> SEQUENCE: 211

Ala Thr Ser Tyr Leu Ala Ser
1               5

<210> SEQ ID NO 212
<211> LENGTH: 9
<212> TYPE: PRT
<213> ORGANISM: Artificial Sequence
<220> FEATURE:
<223> OTHER INFORMATION: mAb_F LCDR3 amino acid sequence (Kabat
      definition)

<400> SEQUENCE: 212

Gln Gln Trp Ser Ser Asn Pro Leu Thr
1               5

<210> SEQ ID NO 213
<211> LENGTH: 7
<212> TYPE: PRT
<213> ORGANISM: Artificial Sequence
<220> FEATURE:
<223> OTHER INFORMATION: mAb_F HCDR1 amino acid sequence (Chothia
      definition)

<400> SEQUENCE: 213

Gly Tyr Thr Phe Thr Asp Tyr
1               5

<210> SEQ ID NO 214
<211> LENGTH: 6
<212> TYPE: PRT
<213> ORGANISM: Artificial Sequence
```

```
<220> FEATURE:
<223> OTHER INFORMATION: mAb_F HCDR2 amino acid sequence (Chothia
      definition)

<400> SEQUENCE: 214

Phe Pro Gly Ser Gly Ser
1               5

<210> SEQ ID NO 215
<211> LENGTH: 10
<212> TYPE: PRT
<213> ORGANISM: Artificial Sequence
<220> FEATURE:
<223> OTHER INFORMATION: mAb_F HCDR3 amino acid sequence (Chothia
      definition)

<400> SEQUENCE: 215

Tyr Gly Ser Ser Tyr Arg Tyr Phe Asp Val
1               5                   10

<210> SEQ ID NO 216
<211> LENGTH: 6
<212> TYPE: PRT
<213> ORGANISM: Artificial Sequence
<220> FEATURE:
<223> OTHER INFORMATION: mAb_F LCDR1 amino acid sequence (Chothia
      definition)

<400> SEQUENCE: 216

Ser Ser Ser Val Ser Tyr
1               5

<210> SEQ ID NO 217
<211> LENGTH: 3
<212> TYPE: PRT
<213> ORGANISM: Artificial Sequence
<220> FEATURE:
<223> OTHER INFORMATION: mAb_F LCDR2 amino acid sequence (Chothia
      definition)

<400> SEQUENCE: 217

Ala Thr Ser
1

<210> SEQ ID NO 218
<211> LENGTH: 7
<212> TYPE: PRT
<213> ORGANISM: Artificial Sequence
<220> FEATURE:
<223> OTHER INFORMATION: mAb_F LCDR3 amino acid sequence (Chothia
      definition)

<400> SEQUENCE: 218

Trp Ser Ser Asn Pro Leu Thr
1               5

<210> SEQ ID NO 219
<211> LENGTH: 2
<212> TYPE: PRT
<213> ORGANISM: Artificial Sequence
<220> FEATURE:
<223> OTHER INFORMATION: mAb_F HCDR1 amino acid sequence (IMGT, Kabat,
      and Chothia common sequences)

<400> SEQUENCE: 219

Asp Tyr
1
```

```
<210> SEQ ID NO 220
<211> LENGTH: 6
<212> TYPE: PRT
<213> ORGANISM: Artificial Sequence
<220> FEATURE:
<223> OTHER INFORMATION: mAb_F HCDR2 amino acid sequence (IMGT, Kabat,
      and Chothia common sequences)

<400> SEQUENCE: 220

Phe Pro Gly Ser Gly Ser
1               5

<210> SEQ ID NO 221
<211> LENGTH: 10
<212> TYPE: PRT
<213> ORGANISM: Artificial Sequence
<220> FEATURE:
<223> OTHER INFORMATION: mAb_F HCDR3 amino acid sequence (IMGT, Kabat,
      and Chothia common sequences definition)

<400> SEQUENCE: 221

Tyr Gly Ser Ser Tyr Arg Tyr Phe Asp Val
1               5                   10

<210> SEQ ID NO 222
<211> LENGTH: 5
<212> TYPE: PRT
<213> ORGANISM: Artificial Sequence
<220> FEATURE:
<223> OTHER INFORMATION: mAb_F HCDR3 amino acid sequence (IMGT, Kabat,
      and Chothia common sequences definition)

<400> SEQUENCE: 222

Ser Ser Val Ser Tyr
1               5

<210> SEQ ID NO 223
<211> LENGTH: 3
<212> TYPE: PRT
<213> ORGANISM: Artificial Sequence
<220> FEATURE:
<223> OTHER INFORMATION: mAb_F LCDR2 amino acid sequence (IMGT, Kabat,
      and Chothia common sequences)

<400> SEQUENCE: 223

Ala Thr Ser
1

<210> SEQ ID NO 224
<211> LENGTH: 7
<212> TYPE: PRT
<213> ORGANISM: Artificial Sequence
<220> FEATURE:
<223> OTHER INFORMATION: mAb_F LCDR3 amino acid sequence (IMGT, Kabat,
      and Chothia common sequences)

<400> SEQUENCE: 224

Trp Ser Ser Asn Pro Leu Thr
1               5

<210> SEQ ID NO 225
<211> LENGTH: 10
<212> TYPE: PRT
<213> ORGANISM: Artificial Sequence
<220> FEATURE:
<223> OTHER INFORMATION: mAb_F HCDR1 amino acid sequence (IMGT, Kabat,
      and Chothia combined overlap sequences)
```

```
<400> SEQUENCE: 225

Gly Tyr Thr Phe Thr Asp Tyr Tyr Ile Asn
1               5                   10

<210> SEQ ID NO 226
<211> LENGTH: 17
<212> TYPE: PRT
<213> ORGANISM: Artificial Sequence
<220> FEATURE:
<223> OTHER INFORMATION: mAb_F HCDR2 amino acid sequence (IMGT, Kabat,
      and Chothia combined overlap sequences)

<400> SEQUENCE: 226

Trp Ile Phe Pro Gly Ser Gly Ser Thr Tyr Tyr Asn Glu Lys Phe Lys
1               5                   10                  15
Gly

<210> SEQ ID NO 227
<211> LENGTH: 12
<212> TYPE: PRT
<213> ORGANISM: Artificial Sequence
<220> FEATURE:
<223> OTHER INFORMATION: mAb_F HCDR3 amino acid sequence (IMGT, Kabat,
      and Chothia combined overlap sequences

<400> SEQUENCE: 227

Ala Asp Tyr Gly Ser Ser Tyr Arg Tyr Phe Asp Val
1               5                   10

<210> SEQ ID NO 228
<211> LENGTH: 10
<212> TYPE: PRT
<213> ORGANISM: Artificial Sequence
<220> FEATURE:
<223> OTHER INFORMATION: mAb_F LCDR1 amino acid sequence (IMGT, Kabat,
      and Chothia combined overlap sequences)

<400> SEQUENCE: 228

Arg Ala Ser Ser Ser Val Ser Tyr Met His
1               5                   10

<210> SEQ ID NO 229
<211> LENGTH: 7
<212> TYPE: PRT
<213> ORGANISM: Artificial Sequence
<220> FEATURE:
<223> OTHER INFORMATION: mAb_F LCDR2 amino acid sequence (IMGT, Kabat,
      and Chothia combined overlap sequences)

<400> SEQUENCE: 229

Ala Thr Ser Tyr Leu Ala Ser
1               5

<210> SEQ ID NO 230
<211> LENGTH: 9
<212> TYPE: PRT
<213> ORGANISM: Artificial Sequence
<220> FEATURE:
<223> OTHER INFORMATION: mAb_F LCDR3 amino acid sequence (IMGT, Kabat,
      and Chothia combined overlap sequences)

<400> SEQUENCE: 230

Gln Gln Trp Ser Ser Asn Pro Leu Thr
1               5

<210> SEQ ID NO 231
```

```
<211> LENGTH: 5
<212> TYPE: PRT
<213> ORGANISM: Artificial Sequence
<220> FEATURE:
<223> OTHER INFORMATION: mAb_H HCDR1 amino acid sequence (Kabat
      definition)

<400> SEQUENCE: 231

Ser Tyr Gly Met Ser
1               5

<210> SEQ ID NO 232
<211> LENGTH: 17
<212> TYPE: PRT
<213> ORGANISM: Artificial Sequence
<220> FEATURE:
<223> OTHER INFORMATION: mAb_H HCDR2 amino acid sequence (Kabat
      definition)

<400> SEQUENCE: 232

Thr Ile Ser Arg Arg Ser Ile Tyr Thr Tyr Tyr Pro Asp Ser Val Gln
1               5                   10                  15

Gly

<210> SEQ ID NO 233
<211> LENGTH: 15
<212> TYPE: PRT
<213> ORGANISM: Artificial Sequence
<220> FEATURE:
<223> OTHER INFORMATION: mAb_H HCDR3 amino acid sequence (Kabat
      definition)

<400> SEQUENCE: 233

Leu Ser Leu Tyr Asp Tyr Asp Gly Ala Arg Tyr Thr Met Asp Tyr
1               5                   10                  15

<210> SEQ ID NO 234
<211> LENGTH: 11
<212> TYPE: PRT
<213> ORGANISM: Artificial Sequence
<220> FEATURE:
<223> OTHER INFORMATION: mAb_H LCDR1 amino acid sequence (Kabat
      definition)

<400> SEQUENCE: 234

Lys Ala Ser Gln Asp Val Gly Thr Ala Val Ala
1               5                   10

<210> SEQ ID NO 235
<211> LENGTH: 7
<212> TYPE: PRT
<213> ORGANISM: Artificial Sequence
<220> FEATURE:
<223> OTHER INFORMATION: mAb_H LCDR2 amino acid sequence (Kabat
      definition)

<400> SEQUENCE: 235

Trp Ala Ser Thr Arg His Thr
1               5

<210> SEQ ID NO 236
<211> LENGTH: 8
<212> TYPE: PRT
<213> ORGANISM: Artificial Sequence
<220> FEATURE:
<223> OTHER INFORMATION: mAb_H LCDR3 amino acid sequence (Kabat
      definition)
```

```
<400> SEQUENCE: 236

Gln Gln Tyr Ser Ser Tyr His Thr
1               5

<210> SEQ ID NO 237
<211> LENGTH: 7
<212> TYPE: PRT
<213> ORGANISM: Artificial Sequence
<220> FEATURE:
<223> OTHER INFORMATION: mAb_H HCDR1 amino acid sequence (Chothia
      definition)

<400> SEQUENCE: 237

Gly Phe Thr Phe Ser Ser Tyr
1               5

<210> SEQ ID NO 238
<211> LENGTH: 6
<212> TYPE: PRT
<213> ORGANISM: Artificial Sequence
<220> FEATURE:
<223> OTHER INFORMATION: mAb_H HCDR2 amino acid sequence (Chothia
      definition)

<400> SEQUENCE: 238

Ser Arg Arg Ser Ile Tyr
1               5

<210> SEQ ID NO 239
<211> LENGTH: 15
<212> TYPE: PRT
<213> ORGANISM: Artificial Sequence
<220> FEATURE:
<223> OTHER INFORMATION: mAb_H HCDR3 amino acid sequence (Chothia
      definition)

<400> SEQUENCE: 239

Leu Ser Leu Tyr Asp Tyr Asp Gly Ala Arg Tyr Thr Met Asp Tyr
1               5                   10                  15

<210> SEQ ID NO 240
<211> LENGTH: 7
<212> TYPE: PRT
<213> ORGANISM: Artificial Sequence
<220> FEATURE:
<223> OTHER INFORMATION: mAb_H LCDR1 amino acid sequence (Chothia
      definition)

<400> SEQUENCE: 240

Ser Gln Asp Val Gly Thr Ala
1               5

<210> SEQ ID NO 241
<211> LENGTH: 3
<212> TYPE: PRT
<213> ORGANISM: Artificial Sequence
<220> FEATURE:
<223> OTHER INFORMATION: mAb_H LCDR2 amino acid sequence (Chothia
      definition)

<400> SEQUENCE: 241

Trp Ala Ser
1

<210> SEQ ID NO 242
<211> LENGTH: 6
<212> TYPE: PRT
```

```
<213> ORGANISM: Artificial Sequence
<220> FEATURE:
<223> OTHER INFORMATION: mAb_H LCDR3 amino acid sequence (Chothia
      definition)

<400> SEQUENCE: 242

Tyr Ser Ser Tyr His Thr
1               5

<210> SEQ ID NO 243
<211> LENGTH: 2
<212> TYPE: PRT
<213> ORGANISM: Artificial Sequence
<220> FEATURE:
<223> OTHER INFORMATION: mAb_H HCDR1 amino acid sequence (IMGT, Kabat,
      and Chothia common sequences)

<400> SEQUENCE: 243

Ser Tyr
1

<210> SEQ ID NO 244
<211> LENGTH: 6
<212> TYPE: PRT
<213> ORGANISM: Artificial Sequence
<220> FEATURE:
<223> OTHER INFORMATION: mAb_H HCDR2 amino acid sequence (IMGT, Kabat,
      and Chothia common sequences)

<400> SEQUENCE: 244

Ser Arg Arg Ser Ile Tyr
1               5

<210> SEQ ID NO 245
<211> LENGTH: 15
<212> TYPE: PRT
<213> ORGANISM: Artificial Sequence
<220> FEATURE:
<223> OTHER INFORMATION: mAb_H HCDR3 amino acid sequence (IMGT, Kabat,
      and Chothia common sequences definition)

<400> SEQUENCE: 245

Leu Ser Leu Tyr Asp Tyr Asp Gly Ala Arg Tyr Thr Met Asp Tyr
1               5                   10                  15

<210> SEQ ID NO 246
<211> LENGTH: 6
<212> TYPE: PRT
<213> ORGANISM: Artificial Sequence
<220> FEATURE:
<223> OTHER INFORMATION: mAb_H LCDR1 amino acid sequence (IMGT, Kabat,
      and Chothia common sequences)

<400> SEQUENCE: 246

Gln Asp Val Gly Thr Ala
1               5

<210> SEQ ID NO 247
<211> LENGTH: 3
<212> TYPE: PRT
<213> ORGANISM: Artificial Sequence
<220> FEATURE:
<223> OTHER INFORMATION: mAb_H LCDR2 amino acid sequence (IMGT, Kabat,
      and Chothia common sequences)

<400> SEQUENCE: 247

Trp Ala Ser
1
```

<210> SEQ ID NO 248
<211> LENGTH: 6
<212> TYPE: PRT
<213> ORGANISM: Artificial Sequence
<220> FEATURE:
<223> OTHER INFORMATION: mAb_H LCDR3 amino acid sequence (IMGT, Kabat, and Chothia common sequences)

<400> SEQUENCE: 248

Tyr Ser Ser Tyr His Thr
1               5

<210> SEQ ID NO 249
<211> LENGTH: 10
<212> TYPE: PRT
<213> ORGANISM: Artificial Sequence
<220> FEATURE:
<223> OTHER INFORMATION: mAb_H HCDR1 amino acid sequence (IMGT, Kabat, and Chothia combined overlap sequences)

<400> SEQUENCE: 249

Gly Phe Thr Phe Ser Ser Tyr Gly Met Ser
1               5                   10

<210> SEQ ID NO 250
<211> LENGTH: 17
<212> TYPE: PRT
<213> ORGANISM: Artificial Sequence
<220> FEATURE:
<223> OTHER INFORMATION: mAb_H HCDR2 amino acid sequence (IMGT, Kabat, and Chothia combined overlap sequences)

<400> SEQUENCE: 250

Thr Ile Ser Arg Arg Ser Ile Tyr Thr Tyr Tyr Pro Asp Ser Val Gln
1               5                   10                  15

Gly

<210> SEQ ID NO 251
<211> LENGTH: 17
<212> TYPE: PRT
<213> ORGANISM: Artificial Sequence
<220> FEATURE:
<223> OTHER INFORMATION: mAb_H HCDR3 amino acid sequence (IMGT, Kabat, and Chothia combined overlap sequences)

<400> SEQUENCE: 251

Ala Arg Leu Ser Leu Tyr Asp Tyr Asp Gly Ala Arg Tyr Thr Met Asp
1               5                   10                  15

Tyr

<210> SEQ ID NO 252
<211> LENGTH: 11
<212> TYPE: PRT
<213> ORGANISM: Artificial Sequence
<220> FEATURE:
<223> OTHER INFORMATION: mAb_H LCDR1 amino acid sequence (IMGT, Kabat, and Chothia combined overlap sequences)

<400> SEQUENCE: 252

Lys Ala Ser Gln Asp Val Gly Thr Ala Val Ala
1               5                   10

<210> SEQ ID NO 253
<211> LENGTH: 7
<212> TYPE: PRT

<213> ORGANISM: Artificial Sequence
<220> FEATURE:
<223> OTHER INFORMATION: mAb_H LCDR2 amino acid sequence (IMGT, Kabat, and Chothia combined overlap sequences)

<400> SEQUENCE: 253

Trp Ala Ser Thr Arg His Thr
1               5

<210> SEQ ID NO 254
<211> LENGTH: 8
<212> TYPE: PRT
<213> ORGANISM: Artificial Sequence
<220> FEATURE:
<223> OTHER INFORMATION: mAb_H LCDR3 amino acid sequence (IMGT, Kabat, and Chothia combined overlap sequences)

<400> SEQUENCE: 254

Gln Gln Tyr Ser Ser Tyr His Thr
1               5

<210> SEQ ID NO 255
<211> LENGTH: 5
<212> TYPE: PRT
<213> ORGANISM: Artificial Sequence
<220> FEATURE:
<223> OTHER INFORMATION: mAb_J HCDR1 amino acid sequence (Kabat definition)

<400> SEQUENCE: 255

Ser Tyr Trp Met His
1               5

<210> SEQ ID NO 256
<211> LENGTH: 17
<212> TYPE: PRT
<213> ORGANISM: Artificial Sequence
<220> FEATURE:
<223> OTHER INFORMATION: mAb_J HCDR2 amino acid sequence (Kabat definition)

<400> SEQUENCE: 256

Asn Ile Asn Pro Ser Asn Gly Gly Thr Asn Tyr Asn Glu Lys Phe Lys
1               5                   10                  15

Ser

<210> SEQ ID NO 257
<211> LENGTH: 15
<212> TYPE: PRT
<213> ORGANISM: Artificial Sequence
<220> FEATURE:
<223> OTHER INFORMATION: mAb_J HCDR3 amino acid sequence (Kabat definition)

<400> SEQUENCE: 257

Gly Gly Ile Tyr Tyr Gly Asn Tyr Asp Tyr Tyr Ala Met Asp Tyr
1               5                   10                  15

<210> SEQ ID NO 258
<211> LENGTH: 16
<212> TYPE: PRT
<213> ORGANISM: Artificial Sequence
<220> FEATURE:
<223> OTHER INFORMATION: mAb_J LCDR1 amino acid sequence (Kabat definition)

<400> SEQUENCE: 258

Arg Ser Ser Lys Ser Leu Leu His Ser Asn Gly Asn Thr Tyr Leu Tyr
1               5                   10                  15

<210> SEQ ID NO 259
<211> LENGTH: 7
<212> TYPE: PRT
<213> ORGANISM: Artificial Sequence
<220> FEATURE:
<223> OTHER INFORMATION: mAb_J LCDR2 amino acid sequence (Kabat
      definition)

<400> SEQUENCE: 259

Arg Val Ser Asn Leu Ala Ser
1               5

<210> SEQ ID NO 260
<211> LENGTH: 9
<212> TYPE: PRT
<213> ORGANISM: Artificial Sequence
<220> FEATURE:
<223> OTHER INFORMATION: mAb_J LCDR3 amino acid sequence (Kabat
      definition)

<400> SEQUENCE: 260

Met Gln His Leu Glu Tyr Pro Phe Thr
1               5

<210> SEQ ID NO 261
<211> LENGTH: 7
<212> TYPE: PRT
<213> ORGANISM: Artificial Sequence
<220> FEATURE:
<223> OTHER INFORMATION: mAb_J HCDR1 amino acid sequence (Chothia
      definition)

<400> SEQUENCE: 261

Gly Tyr Thr Phe Thr Ser Tyr
1               5

<210> SEQ ID NO 262
<211> LENGTH: 6
<212> TYPE: PRT
<213> ORGANISM: Artificial Sequence
<220> FEATURE:
<223> OTHER INFORMATION: mAb_J HCDR2 amino acid sequence (Chothia
      definition)

<400> SEQUENCE: 262

Asn Pro Ser Asn Gly Gly
1               5

<210> SEQ ID NO 263
<211> LENGTH: 15
<212> TYPE: PRT
<213> ORGANISM: Artificial Sequence
<220> FEATURE:
<223> OTHER INFORMATION: mAb_J HCDR3 amino acid sequence (Chothia
      definition)

<400> SEQUENCE: 263

Gly Gly Ile Tyr Tyr Gly Asn Tyr Asp Tyr Tyr Ala Met Asp Tyr
1               5                   10                  15

<210> SEQ ID NO 264
<211> LENGTH: 12
<212> TYPE: PRT
<213> ORGANISM: Artificial Sequence
<220> FEATURE:

```
<223> OTHER INFORMATION: mAb_J LCDR1 amino acid sequence (Chothia
      definition)

<400> SEQUENCE: 264

Ser Lys Ser Leu Leu His Ser Asn Gly Asn Thr Tyr
1               5                   10

<210> SEQ ID NO 265
<211> LENGTH: 3
<212> TYPE: PRT
<213> ORGANISM: Artificial Sequence
<220> FEATURE:
<223> OTHER INFORMATION: mAb_J LCDR2 amino acid sequence (Chothia
      definition)

<400> SEQUENCE: 265

Arg Val Ser
1

<210> SEQ ID NO 266
<211> LENGTH: 7
<212> TYPE: PRT
<213> ORGANISM: Artificial Sequence
<220> FEATURE:
<223> OTHER INFORMATION: mAb_J LCDR3 amino acid sequence (Chothia
      definition)

<400> SEQUENCE: 266

His Leu Glu Tyr Pro Phe Thr
1               5

<210> SEQ ID NO 267
<211> LENGTH: 2
<212> TYPE: PRT
<213> ORGANISM: Artificial Sequence
<220> FEATURE:
<223> OTHER INFORMATION: mAb_J HCDR1 amino acid sequence (IMGT, Kabat,
      and Chothia common sequences)

<400> SEQUENCE: 267

Ser Tyr
1

<210> SEQ ID NO 268
<211> LENGTH: 6
<212> TYPE: PRT
<213> ORGANISM: Artificial Sequence
<220> FEATURE:
<223> OTHER INFORMATION: mAb_J HCDR2 amino acid sequence (IMGT, Kabat,
      and Chothia common sequences)

<400> SEQUENCE: 268

Asn Pro Ser Asn Gly Gly
1               5

<210> SEQ ID NO 269
<211> LENGTH: 15
<212> TYPE: PRT
<213> ORGANISM: Artificial Sequence
<220> FEATURE:
<223> OTHER INFORMATION: mAb_J HCDR3 amino acid sequence (IMGT, Kabat,
      and Chothia common sequences definition)

<400> SEQUENCE: 269

Gly Gly Ile Tyr Tyr Gly Asn Tyr Asp Tyr Tyr Ala Met Asp Tyr
1               5                   10                  15
```

```
<210> SEQ ID NO 270
<211> LENGTH: 11
<212> TYPE: PRT
<213> ORGANISM: Artificial Sequence
<220> FEATURE:
<223> OTHER INFORMATION: mAb_J LCDR1 amino acid sequence (IMGT, Kabat,
      and Chothia common sequences)

<400> SEQUENCE: 270

Lys Ser Leu Leu His Ser Asn Gly Asn Thr Tyr
1               5                   10

<210> SEQ ID NO 271
<211> LENGTH: 3
<212> TYPE: PRT
<213> ORGANISM: Artificial Sequence
<220> FEATURE:
<223> OTHER INFORMATION: mAb_J LCDR2 amino acid sequence (IMGT, Kabat,
      and Chothia common sequences)

<400> SEQUENCE: 271

Arg Val Ser
1

<210> SEQ ID NO 272
<211> LENGTH: 7
<212> TYPE: PRT
<213> ORGANISM: Artificial Sequence
<220> FEATURE:
<223> OTHER INFORMATION: mAb_J LCDR3 amino acid sequence (IMGT, Kabat,
      and Chothia common sequences)

<400> SEQUENCE: 272

His Leu Glu Tyr Pro Phe Thr
1               5

<210> SEQ ID NO 273
<211> LENGTH: 10
<212> TYPE: PRT
<213> ORGANISM: Artificial Sequence
<220> FEATURE:
<223> OTHER INFORMATION: mAb_J HCDR1 amino acid sequence (IMGT, Kabat,
      and Chothia combined overlap sequences)

<400> SEQUENCE: 273

Gly Tyr Thr Phe Thr Ser Tyr Trp Met His
1               5                   10

<210> SEQ ID NO 274
<211> LENGTH: 17
<212> TYPE: PRT
<213> ORGANISM: Artificial Sequence
<220> FEATURE:
<223> OTHER INFORMATION: mAb_J HCDR2 amino acid sequence (IMGT, Kabat,
      and Chothia combined overlap sequences)

<400> SEQUENCE: 274

Asn Ile Asn Pro Ser Asn Gly Gly Thr Asn Tyr Asn Glu Lys Phe Lys
1               5                   10                  15

Ser

<210> SEQ ID NO 275
<211> LENGTH: 17
<212> TYPE: PRT
<213> ORGANISM: Artificial Sequence
<220> FEATURE:
<223> OTHER INFORMATION: mAb_J HCDR3 amino acid sequence (IMGT, Kabat,
      and Chothia combined overlap sequences)
```

-continued

<400> SEQUENCE: 275

Ala Arg Gly Gly Ile Tyr Tyr Gly Asn Tyr Asp Tyr Tyr Ala Met Asp
1               5                   10                  15
Tyr

<210> SEQ ID NO 276
<211> LENGTH: 16
<212> TYPE: PRT
<213> ORGANISM: Artificial Sequence
<220> FEATURE:
<223> OTHER INFORMATION: mAb_J LCDR1 amino acid sequence (IMGT, Kabat,
      and Chothia combined overlap sequences)

<400> SEQUENCE: 276

Arg Ser Ser Lys Ser Leu Leu His Ser Asn Gly Asn Thr Tyr Leu Tyr
1               5                   10                  15

<210> SEQ ID NO 277
<211> LENGTH: 7
<212> TYPE: PRT
<213> ORGANISM: Artificial Sequence
<220> FEATURE:
<223> OTHER INFORMATION: mAb_J LCDR2 amino acid sequence (IMGT, Kabat,
      and Chothia combined overlap sequences)

<400> SEQUENCE: 277

Arg Val Ser Asn Leu Ala Ser
1               5

<210> SEQ ID NO 278
<211> LENGTH: 9
<212> TYPE: PRT
<213> ORGANISM: Artificial Sequence
<220> FEATURE:
<223> OTHER INFORMATION: mAb_J LCDR3 amino acid sequence (IMGT, Kabat,
      and Chothia combined overlap sequences)

<400> SEQUENCE: 278

Met Gln His Leu Glu Tyr Pro Phe Thr
1               5

<210> SEQ ID NO 279
<211> LENGTH: 8
<212> TYPE: PRT
<213> ORGANISM: Artificial Sequence
<220> FEATURE:
<223> OTHER INFORMATION: mAb_K HCDR1 amino acid sequence (IMGT
      definition)

<400> SEQUENCE: 279

Gly Tyr Ala Phe Thr Asn Tyr Leu
1               5

<210> SEQ ID NO 280
<211> LENGTH: 8
<212> TYPE: PRT
<213> ORGANISM: Artificial Sequence
<220> FEATURE:
<223> OTHER INFORMATION: mAb_K HCDR2 amino acid sequence (IMGT
      definition)

<400> SEQUENCE: 280

Ile Asn Pro Gly Ser Gly Gly Thr
1               5

```
<210> SEQ ID NO 281
<211> LENGTH: 11
<212> TYPE: PRT
<213> ORGANISM: Artificial Sequence
<220> FEATURE:
<223> OTHER INFORMATION: mAb_K HCDR3 amino acid sequence (IMGT
      definition)

<400> SEQUENCE: 281

Ala Arg Trp Gly Phe Tyr Tyr Ala Met Asp Tyr
1               5                   10

<210> SEQ ID NO 282
<211> LENGTH: 6
<212> TYPE: PRT
<213> ORGANISM: Artificial Sequence
<220> FEATURE:
<223> OTHER INFORMATION: mAb_K LCDR1 amino acid sequence (IMGT
      definition)

<400> SEQUENCE: 282

Gln Glu Ile Ser Gly Tyr
1               5

<210> SEQ ID NO 283
<211> LENGTH: 3
<212> TYPE: PRT
<213> ORGANISM: Artificial Sequence
<220> FEATURE:
<223> OTHER INFORMATION: mAb_K LCDR2 amino acid sequence (IMGT
      definition)

<400> SEQUENCE: 283

Ala Ala Ser
1

<210> SEQ ID NO 284
<211> LENGTH: 9
<212> TYPE: PRT
<213> ORGANISM: Artificial Sequence
<220> FEATURE:
<223> OTHER INFORMATION: mAb_K LCDR3 amino acid sequence (IMGT
      definition)

<400> SEQUENCE: 284

Leu Gln Tyr Ala Ser Tyr Pro Leu Thr
1               5

<210> SEQ ID NO 285
<211> LENGTH: 5
<212> TYPE: PRT
<213> ORGANISM: Artificial Sequence
<220> FEATURE:
<223> OTHER INFORMATION: mAb_K HCDR1 amino acid sequence (Kabat
      definition)

<400> SEQUENCE: 285

Asn Tyr Leu Ile Glu
1               5

<210> SEQ ID NO 286
<211> LENGTH: 17
<212> TYPE: PRT
<213> ORGANISM: Artificial Sequence
<220> FEATURE:
<223> OTHER INFORMATION: mAb_K HCDR2 amino acid sequence (Kabat
      definition)

<400> SEQUENCE: 286
```

Val Ile Asn Pro Gly Ser Gly Gly Thr Asn Tyr Asn Glu Lys Phe Lys
1               5                   10                  15

Gly

<210> SEQ ID NO 287
<211> LENGTH: 9
<212> TYPE: PRT
<213> ORGANISM: Artificial Sequence
<220> FEATURE:
<223> OTHER INFORMATION: mAb_K HCDR3 amino acid sequence (Kabat
      definition)

<400> SEQUENCE: 287

Trp Gly Phe Tyr Tyr Ala Met Asp Tyr
1               5

<210> SEQ ID NO 288
<211> LENGTH: 11
<212> TYPE: PRT
<213> ORGANISM: Artificial Sequence
<220> FEATURE:
<223> OTHER INFORMATION: mAb_K LCDR1 amino acid sequence (Kabat
      definition)

<400> SEQUENCE: 288

Arg Ala Ser Gln Glu Ile Ser Gly Tyr Leu Ser
1               5                   10

<210> SEQ ID NO 289
<211> LENGTH: 7
<212> TYPE: PRT
<213> ORGANISM: Artificial Sequence
<220> FEATURE:
<223> OTHER INFORMATION: mAb_K LCDR2 amino acid sequence (Kabat
      definition)

<400> SEQUENCE: 289

Ala Ala Ser Thr Leu Asp Ser
1               5

<210> SEQ ID NO 290
<211> LENGTH: 9
<212> TYPE: PRT
<213> ORGANISM: Artificial Sequence
<220> FEATURE:
<223> OTHER INFORMATION: mAb_K LCDR3 amino acid sequence (Kabat
      definition)

<400> SEQUENCE: 290

Leu Gln Tyr Ala Ser Tyr Pro Leu Thr
1               5

<210> SEQ ID NO 291
<211> LENGTH: 7
<212> TYPE: PRT
<213> ORGANISM: Artificial Sequence
<220> FEATURE:
<223> OTHER INFORMATION: mAb_K HCDR1 amino acid sequence (Chothia
      definition)

<400> SEQUENCE: 291

Gly Tyr Ala Phe Thr Asn Tyr
1               5

<210> SEQ ID NO 292
<211> LENGTH: 7

<212> TYPE: PRT
<213> ORGANISM: Artificial Sequence
<220> FEATURE:
<223> OTHER INFORMATION: mAb_K HCDR2 amino acid sequence (Chothia
      definition)

<400> SEQUENCE: 292

Ile Asn Pro Gly Ser Gly Gly
1               5

<210> SEQ ID NO 293
<211> LENGTH: 9
<212> TYPE: PRT
<213> ORGANISM: Artificial Sequence
<220> FEATURE:
<223> OTHER INFORMATION: mAb_K HCDR3 amino acid sequence (Chothia
      definition)

<400> SEQUENCE: 293

Trp Gly Phe Tyr Tyr Ala Met Asp Tyr
1               5

<210> SEQ ID NO 294
<211> LENGTH: 7
<212> TYPE: PRT
<213> ORGANISM: Artificial Sequence
<220> FEATURE:
<223> OTHER INFORMATION: mAb_K LCDR1 amino acid sequence (Chothia
      definition)

<400> SEQUENCE: 294

Ser Gln Glu Ile Ser Gly Tyr
1               5

<210> SEQ ID NO 295
<211> LENGTH: 3
<212> TYPE: PRT
<213> ORGANISM: Artificial Sequence
<220> FEATURE:
<223> OTHER INFORMATION: mAb_K LCDR2 amino acid sequence (Chothia
      definition)

<400> SEQUENCE: 295

Ala Ala Ser
1

<210> SEQ ID NO 296
<211> LENGTH: 7
<212> TYPE: PRT
<213> ORGANISM: Artificial Sequence
<220> FEATURE:
<223> OTHER INFORMATION: mAb_K LCDR3 amino acid sequence (Chothia
      definition)

<400> SEQUENCE: 296

Tyr Ala Ser Tyr Pro Leu Thr
1               5

<210> SEQ ID NO 297
<211> LENGTH: 2
<212> TYPE: PRT
<213> ORGANISM: Artificial Sequence
<220> FEATURE:
<223> OTHER INFORMATION: mAb_K HCDR1 amino acid sequence (IMGT, Kabat,
      and Chothia common sequences)

<400> SEQUENCE: 297

Asn Tyr

```
<210> SEQ ID NO 298
<211> LENGTH: 7
<212> TYPE: PRT
<213> ORGANISM: Artificial Sequence
<220> FEATURE:
<223> OTHER INFORMATION: mAb_K HCDR2 amino acid sequence (IMGT, Kabat,
      and Chothia common sequences)

<400> SEQUENCE: 298

Ile Asn Pro Gly Ser Gly Gly
1               5

<210> SEQ ID NO 299
<211> LENGTH: 9
<212> TYPE: PRT
<213> ORGANISM: Artificial Sequence
<220> FEATURE:
<223> OTHER INFORMATION: mAb_K HCDR3 amino acid sequence (IMGT, Kabat,
      and Chothia common sequences definition)

<400> SEQUENCE: 299

Trp Gly Phe Tyr Tyr Ala Met Asp Tyr
1               5

<210> SEQ ID NO 300
<211> LENGTH: 6
<212> TYPE: PRT
<213> ORGANISM: Artificial Sequence
<220> FEATURE:
<223> OTHER INFORMATION: mAb_K LCDR1 amino acid sequence (IMGT, Kabat,
      and Chothia common sequences)

<400> SEQUENCE: 300

Gln Glu Ile Ser Gly Tyr
1               5

<210> SEQ ID NO 301
<211> LENGTH: 3
<212> TYPE: PRT
<213> ORGANISM: Artificial Sequence
<220> FEATURE:
<223> OTHER INFORMATION: mAb_K LCDR2 amino acid sequence (IMGT, Kabat,
      and Chothia common sequences)

<400> SEQUENCE: 301

Ala Ala Ser
1

<210> SEQ ID NO 302
<211> LENGTH: 7
<212> TYPE: PRT
<213> ORGANISM: Artificial Sequence
<220> FEATURE:
<223> OTHER INFORMATION: mAb_K LCDR3 amino acid sequence (IMGT, Kabat,
      and Chothia common sequences)

<400> SEQUENCE: 302

Tyr Ala Ser Tyr Pro Leu Thr
1               5

<210> SEQ ID NO 303
<211> LENGTH: 10
<212> TYPE: PRT
<213> ORGANISM: Artificial Sequence
<220> FEATURE:
<223> OTHER INFORMATION: mAb_K HCDR1 amino acid sequence (IMGT, Kabat,
``` and Chothia combined overlap sequences)

<400> SEQUENCE: 303

Gly Tyr Ala Phe Thr Asn Tyr Leu Ile Glu
1               5                   10

<210> SEQ ID NO 304
<211> LENGTH: 17
<212> TYPE: PRT
<213> ORGANISM: Artificial Sequence
<220> FEATURE:
<223> OTHER INFORMATION: mAb_K HCDR2 amino acid sequence (IMGT, Kabat,
      and Chothia combined overlap sequences)

<400> SEQUENCE: 304

Val Ile Asn Pro Gly Ser Gly Gly Thr Asn Tyr Asn Glu Lys Phe Lys
1               5                   10                  15

Gly

<210> SEQ ID NO 305
<211> LENGTH: 11
<212> TYPE: PRT
<213> ORGANISM: Artificial Sequence
<220> FEATURE:
<223> OTHER INFORMATION: mAb_K HCDR3 amino acid sequence (IMGT, Kabat,
      and Chothia combined overlap sequences)

<400> SEQUENCE: 305

Ala Arg Trp Gly Phe Tyr Tyr Ala Met Asp Tyr
1               5                   10

<210> SEQ ID NO 306
<211> LENGTH: 11
<212> TYPE: PRT
<213> ORGANISM: Artificial Sequence
<220> FEATURE:
<223> OTHER INFORMATION: mAb_K LCDR1 amino acid sequence (IMGT, Kabat,
      and Chothia combined overlap sequences)

<400> SEQUENCE: 306

Arg Ala Ser Gln Glu Ile Ser Gly Tyr Leu Ser
1               5                   10

<210> SEQ ID NO 307
<211> LENGTH: 7
<212> TYPE: PRT
<213> ORGANISM: Artificial Sequence
<220> FEATURE:
<223> OTHER INFORMATION: mAb_K LCDR2 amino acid sequence (IMGT, Kabat,
      and Chothia combined overlap sequences)

<400> SEQUENCE: 307

Ala Ala Ser Thr Leu Asp Ser
1               5

<210> SEQ ID NO 308
<211> LENGTH: 9
<212> TYPE: PRT
<213> ORGANISM: Artificial Sequence
<220> FEATURE:
<223> OTHER INFORMATION: mAb_K LCDR3 amino acid sequence (IMGT, Kabat,
      and Chothia combined overlap sequences)

<400> SEQUENCE: 308

Leu Gln Tyr Ala Ser Tyr Pro Leu Thr
1               5

<210> SEQ ID NO 309
<211> LENGTH: 119
<212> TYPE: PRT
<213> ORGANISM: Artificial Sequence
<220> FEATURE:
<223> OTHER INFORMATION: mAb_A VH amino acid sequence (predicted mature)

<400> SEQUENCE: 309

Gln Val Gln Leu Gln Gln Pro Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Val Lys Gln Thr Pro Val His Gly Leu Glu Trp Ile
        35                  40                  45

Gly Gly Val Asp Pro Glu Thr Gly Gly Thr Gly Tyr Asn Gln Lys Phe
    50                  55                  60

Arg Gly Lys Ala Ile Leu Thr Ala Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg His Gly Gly Ser Phe Tyr Ala Met Asp Tyr Trp Gly Gln Gly
            100                 105                 110

Thr Ser Val Thr Val Ser Ser
        115

<210> SEQ ID NO 310
<211> LENGTH: 119
<212> TYPE: PRT
<213> ORGANISM: Artificial Sequence
<220> FEATURE:
<223> OTHER INFORMATION: mAb_A VL amino acid sequence (predicted mature)

<400> SEQUENCE: 310

Gln Val Gln Leu Gln Gln Pro Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Val Lys Gln Thr Pro Val His Gly Leu Glu Trp Ile
        35                  40                  45

Gly Gly Val Asp Pro Glu Thr Gly Gly Thr Gly Tyr Asn Gln Lys Phe
    50                  55                  60

Arg Gly Lys Ala Ile Leu Thr Ala Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg His Gly Gly Ser Phe Tyr Ala Met Asp Tyr Trp Gly Gln Gly
            100                 105                 110

Thr Ser Val Thr Val Ser Ser
        115

<210> SEQ ID NO 311
<211> LENGTH: 124
<212> TYPE: PRT
<213> ORGANISM: Artificial Sequence
<220> FEATURE:
<223> OTHER INFORMATION: mAb_B VH amino acid sequence (predicted mature)

<400> SEQUENCE: 311

Glu Val Gln Leu Val Glu Ser Gly Gly Asp Leu Val Lys Pro Gly Gly

```
                1               5                   10                  15
Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
            35                  40                  45

Ala Thr Ile Ser Arg Gly Ser Ile Tyr Thr Tyr Tyr Pro Asp Ser Val
        50                  55                  60

Lys Gly Arg Phe Thr Ile Ser Arg Asp Asn Ala Lys Asn Thr Leu Tyr
65                      70                  75                  80

Leu Gln Met Ser Ser Leu Lys Ser Glu Asp Thr Ala Met Tyr Tyr Cys
                    85                  90                  95

Ala Arg Leu Ser Leu Tyr Asp Tyr Asp Gly Ala Arg Tyr Thr Met Asp
                100                 105                 110

Tyr Trp Gly Gln Gly Thr Ser Val Thr Val Ser Ser
                115                 120

<210> SEQ ID NO 312
<211> LENGTH: 106
<212> TYPE: PRT
<213> ORGANISM: Artificial Sequence
<220> FEATURE:
<223> OTHER INFORMATION: mAb_B VL amino acid sequence (predicted mature)

<400> SEQUENCE: 312

Asp Ile Val Met Thr Gln Ser Pro Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
        50                  55                  60

Ser Gly Ser Gly Thr Asp Phe Thr Leu Thr Ile Ser Asn Val Gln Ser
65                      70                  75                  80

Glu Asp Leu Ala Asp Tyr Phe Cys Gln Gln Tyr Ser Ser Tyr His Thr
                    85                  90                  95

Phe Gly Ala Gly Thr Lys Leu Glu Leu Lys
                100                 105

<210> SEQ ID NO 313
<211> LENGTH: 121
<212> TYPE: PRT
<213> ORGANISM: Artificial Sequence
<220> FEATURE:
<223> OTHER INFORMATION: mAb_C VH amino acid sequence (predicted mature)

<400> SEQUENCE: 313

Gln Val Gln Leu Lys Gln Ser Gly Ala Glu Leu Ala Arg Pro Gly Ala
1               5                   10                  15

Ser Val Lys Leu Ser Cys Lys Ala Ser Gly Tyr Asn Phe Lys Ser Tyr
            20                  25                  30

Gly Ile Ser Trp Val Lys Gln Arg Thr Gly Gln Gly Leu Glu Trp Ile
            35                  40                  45

Gly Glu Ile Tyr Pro Gly Ser Gly Asn Thr Tyr Tyr Asn Glu Lys Leu
        50                  55                  60

Lys Gly Lys Ala Thr Leu Thr Ala Asp Lys Ser Ser Ser Thr Ala Tyr
65                      70                  75                  80
```

```
Met Glu Leu Arg Ser Leu Thr Ser Glu Asp Ser Ala Val Tyr Phe Cys
                85                  90                  95

Ala Arg Thr Tyr Gly Tyr Asp Ser Phe Pro Trp Phe Ala Tyr Trp Gly
            100                 105                 110

Gln Gly Thr Leu Val Thr Val Ser Ser
        115                 120

<210> SEQ ID NO 314
<211> LENGTH: 112
<212> TYPE: PRT
<213> ORGANISM: Artificial Sequence
<220> FEATURE:
<223> OTHER INFORMATION: mAb_C VL amino acid sequence (predicted mature)

<400> SEQUENCE: 314

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Val Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ala Gly Thr Lys Leu Glu Ile Lys
            100                 105                 110

<210> SEQ ID NO 315
<211> LENGTH: 117
<212> TYPE: PRT
<213> ORGANISM: Artificial Sequence
<220> FEATURE:
<223> OTHER INFORMATION: mAb_D VH amino acid sequence (predicted mature)

<400> SEQUENCE: 315

Glu Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Val Gln Gln Thr Pro Val His Gly Leu Glu Trp Ile
        35                  40                  45

Gly Gly Ile Asp Pro Glu Thr Gly Gly Thr Gly Tyr Asn Gln Lys Phe
    50                  55                  60

Lys Gly Lys Ala Ile Leu Thr Ala Asp Lys Ser Ser Thr Ala Tyr
65                  70                  75                  80

Met Glu Leu Arg Ser Leu Thr Ser Glu Asp Ser Ala Val Tyr Phe Cys
                85                  90                  95

Thr Arg His Gly Ser Tyr Ala Met Asp Tyr Trp Gly Gln Gly Thr Ser
            100                 105                 110

Val Thr Val Ser Ser
        115

<210> SEQ ID NO 316
<211> LENGTH: 107
<212> TYPE: PRT
<213> ORGANISM: Artificial Sequence
```

```
<220> FEATURE:
<223> OTHER INFORMATION: mAb_D VL amino acid sequence (predicted mature)

<400> SEQUENCE: 316

Asp Ile Val Met Thr Gln Ser Pro Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Ser Thr Pro Pro
                85                  90                  95

Thr Phe Gly Gly Gly Thr Arg Leu Glu Ile Lys
            100                 105

<210> SEQ ID NO 317
<211> LENGTH: 120
<212> TYPE: PRT
<213> ORGANISM: Artificial Sequence
<220> FEATURE:
<223> OTHER INFORMATION: mAb_E VH amino acid sequence (predicted mature)

<400> SEQUENCE: 317

Glu Val Lys Leu Leu Glu Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Val Lys Gln Thr Pro Val His Gly Leu Glu Trp Ile
        35                  40                  45

Gly Gly Ile Asp Pro Glu Ser Gly Gly Thr Gly Tyr Asn Gln Lys Phe
50                  55                  60

Lys Gly Lys Ala Ile Leu Thr Ala Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Thr Arg Ser Gly Tyr Tyr Gly Ser Pro Leu Leu Asp Tyr Trp Gly Gln
            100                 105                 110

Gly Thr Thr Leu Thr Val Ser Ser
        115                 120

<210> SEQ ID NO 318
<211> LENGTH: 108
<212> TYPE: PRT
<213> ORGANISM: Artificial Sequence
<220> FEATURE:
<223> OTHER INFORMATION: mAb_E VL amino acid sequence (predicted mature)

<400> SEQUENCE: 318

Gln Ile Val Leu Ser Gln Ser Pro Ala Ile Met Ser Ala Ser Leu Gly
1               5                   10                  15

Glu Arg Val Thr Met Thr Cys Thr Ala Ser Ser Ser Val Ser Ser Ser
            20                  25                  30

Tyr Leu His Trp Tyr Gln Gln Lys Pro Gly Ser Ser Pro Lys Leu Trp
        35                  40                  45
```

```
Ile Tyr Ser Thr Ser Asn Leu Ala Ser Gly Val Pro Ala Arg Phe Ser
    50                  55                  60
Gly Ser Gly Ser Gly Thr Ser Tyr Ser Leu Thr Ile Ser Ser Met Glu
65                  70                  75                  80
Ala Glu Asp Ala Ala Thr Tyr Tyr Cys His Gln Tyr His Arg Ser Pro
                85                  90                  95
Pro Thr Phe Gly Ala Gly Thr Lys Leu Glu Ile Lys
                100                 105
```

<210> SEQ ID NO 319
<211> LENGTH: 124
<212> TYPE: PRT
<213> ORGANISM: Artificial Sequence
<220> FEATURE:
<223> OTHER INFORMATION: mAb_G VH amino acid sequence (predicted mature)

<400> SEQUENCE: 319

```
Gln Val Gln Leu Lys Gln Ser Gly Ala Glu Leu Val Arg Pro Gly Ala
1               5                   10                  15
Ser Val Thr Leu Ser Cys Lys Ala Ser Gly Tyr Thr Phe Thr Asp Tyr
                20                  25                  30
Glu Met His Trp Val Lys Gln Thr Pro Val His Gly Leu Glu Trp Ile
                35                  40                  45
Gly Gly Ile Asp Pro Glu Thr Gly Gly Thr Ala Tyr Asn Gln Lys Phe
    50                  55                  60
Lys Gly Lys Ala Ile Leu Thr Ala Asp Lys Ser Ser Thr Ala Tyr
65                  70                  75                  80
Met Glu Leu Arg Ser Leu Thr Ser Glu Asp Ser Ala Val Tyr Tyr Cys
                85                  90                  95
Thr Arg Trp Gly Ala Ile Thr Ser Phe Val Ala Leu Arg Gly Phe Ala
                100                 105                 110
Tyr Trp Gly Gln Gly Thr Leu Val Thr Val Ser Ser
            115                 120
```

<210> SEQ ID NO 320
<211> LENGTH: 113
<212> TYPE: PRT
<213> ORGANISM: Artificial Sequence
<220> FEATURE:
<223> OTHER INFORMATION: mAb_G VL amino acid sequence (predicted mature)

<400> SEQUENCE: 320

```
Asp Ile Gln Met Thr Gln Ser Pro Ser Ser Leu Ser Val Ser Ala Gly
1               5                   10                  15
Glu Lys Val Thr Met Ser Cys Lys Ser Ser Gln Ser Leu Leu Asn Ser
                20                  25                  30
Gly Asn Gln Lys Asn Tyr Leu Ala Trp Tyr Gln Gln Lys Pro Gly Gln
                35                  40                  45
Pro Pro Lys Leu Leu Ile Tyr Gly Ala Ser Thr Arg Glu Ser Gly Val
    50                  55                  60
Pro Asp Arg Phe Thr Gly Ser Gly Ser Gly Thr Asp Phe Thr Leu Thr
65                  70                  75                  80
Ile Ser Ser Val Gln Ala Glu Asp Leu Ala Val Tyr Tyr Cys Gln Asn
                85                  90                  95
Asp His Ser Tyr Pro Pro Thr Phe Gly Ala Gly Thr Lys Leu Glu Leu
                100                 105                 110
Lys
```

<210> SEQ ID NO 321
<211> LENGTH: 119
<212> TYPE: PRT
<213> ORGANISM: Artificial Sequence
<220> FEATURE:
<223> OTHER INFORMATION: mAb_F VH amino acid sequence (predicted mature)

<400> SEQUENCE: 321

Gln Val Gln Leu Lys Glu Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Asn Trp Val Lys Gln Arg Pro Gly Gln Gly Leu Glu Trp Ile
        35                  40                  45

Gly Trp Ile Phe Pro Gly Ser Gly Ser Thr Tyr Asn Glu Lys Phe
    50                  55                  60

Lys Gly Lys Ala Thr Leu Thr Val Asp Lys Ser Ser Thr Ala Tyr
65                  70                  75                  80

Met Leu Leu Ser Ser Leu Thr Ser Glu Asp Ser Ala Val Tyr Phe Cys
                85                  90                  95

Ala Asp Tyr Gly Ser Ser Tyr Arg Tyr Phe Asp Val Trp Gly Ala Gly
            100                 105                 110

Thr Thr Val Thr Val Ser Ser
        115

<210> SEQ ID NO 322
<211> LENGTH: 106
<212> TYPE: PRT
<213> ORGANISM: Artificial Sequence
<220> FEATURE:
<223> OTHER INFORMATION: mAb_F VL amino acid sequence (predicted mature)

<400> SEQUENCE: 322

Asp Ile Val Met Thr Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Thr Ser Tyr Leu Ala Ser Gly Val Pro Ala Arg Phe Ser Gly Ser
    50                  55                  60

Gly Ser Gly Thr Ser Tyr Ser Leu Thr Ile Gly Arg Val Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105

<210> SEQ ID NO 323
<211> LENGTH: 124
<212> TYPE: PRT
<213> ORGANISM: Artificial Sequence
<220> FEATURE:
<223> OTHER INFORMATION: mAb_H VH amino acid sequence (predicted mature)

<400> SEQUENCE: 323

Glu Val Lys Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr

```
                    20                  25                  30

Gly Met Ser Trp Val Arg Gln Thr Pro Asp Lys Arg Leu Glu Trp Val
            35                  40                  45

Ala Thr Ile Ser Arg Arg Ser Ile Tyr Thr Tyr Tyr Pro Asp Ser Val
        50                  55                  60

Gln Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                85                  90                  95

Ala Arg Leu Ser Leu Tyr Asp Tyr Asp Gly Ala Arg Tyr Thr Met Asp
            100                 105                 110

Tyr Trp Gly Gln Gly Thr Ser Val Thr Val Ser Ser
            115                 120

<210> SEQ ID NO 324
<211> LENGTH: 106
<212> TYPE: PRT
<213> ORGANISM: Artificial Sequence
<220> FEATURE:
<223> OTHER INFORMATION: mAb_H L amino acid sequence (predicted mature)

<400> SEQUENCE: 324

Asp Ile Lys Met Thr Gln Ser Pro Lys Phe Met Ser Thr Ser Val Gly
 1               5                  10                  15

Asp Arg Val Ser Ile Thr Cys Lys Ala Ser Gln Asp Val Gly Thr Ala
                20                  25                  30

Val Ala Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
        50                  55                  60

Ser Gly Ser Gly Thr Asp Phe Thr Leu Thr Ile Ser Asn Val Gln Ser
 65                  70                  75                  80

Glu Asp Leu Ala Asp Tyr Phe Cys Gln Gln Tyr Ser Ser Tyr His Thr
                85                  90                  95

Phe Gly Ala Gly Thr Lys Leu Glu Ile Lys
            100                 105

<210> SEQ ID NO 325
<211> LENGTH: 124
<212> TYPE: PRT
<213> ORGANISM: Artificial Sequence
<220> FEATURE:
<223> OTHER INFORMATION: mAb_J VH amino acid sequence (predicted mature)

<400> SEQUENCE: 325

Gln Val His Leu Gln Gln Ser Gly Thr Glu Leu Val Lys Pro Gly Ala
 1               5                  10                  15

Ser Val Lys Leu Ser Cys Glu Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Asn Ile Asn Pro Ser Asn Gly Gly Thr Asn Tyr Asn Glu Lys Phe
        50                  55                  60

Lys Ser Lys Ala Thr Leu Thr Val Asp Lys Ser Ser Ser Thr Ala Tyr
 65                  70                  75                  80

Met Gln Leu Ser Ser Leu Thr Ser Glu Asp Ser Ala Val Tyr Tyr Cys
                85                  90                  95
```

Ala Arg Gly Gly Ile Tyr Tyr Gly Asn Tyr Asp Tyr Tyr Ala Met Asp
            100                 105                 110

Tyr Trp Gly Gln Gly Thr Ser Val Thr Val Ser Ser
        115                 120

<210> SEQ ID NO 326
<211> LENGTH: 112
<212> TYPE: PRT
<213> ORGANISM: Artificial Sequence
<220> FEATURE:
<223> OTHER INFORMATION: mAb_J VL amino acid sequence (predicted mature)

<400> SEQUENCE: 326

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Val Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Leu Glu Ile Lys
            100                 105                 110

<210> SEQ ID NO 327
<211> LENGTH: 118
<212> TYPE: PRT
<213> ORGANISM: Artificial Sequence
<220> FEATURE:
<223> OTHER INFORMATION: mAb_K VH amino acid sequence (predicted mature)

<400> SEQUENCE: 327

Gln Val Gln Leu Lys Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
            20                  25                  30

Leu Ile Glu Trp Val Lys Gln Arg Pro Gly Gln Gly Leu Glu Trp Ile
        35                  40                  45

Gly Val Ile Asn Pro Gly Ser Gly Gly Thr Asn Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Trp Gly Phe Tyr Tyr Ala Met Asp Tyr Trp Gly Gln Gly Thr
            100                 105                 110

Ser Val Thr Val Ser Ser
        115

<210> SEQ ID NO 328
<211> LENGTH: 107
<212> TYPE: PRT
<213> ORGANISM: Artificial Sequence
<220> FEATURE:
<223> OTHER INFORMATION: mAb_K VL amino acid sequence (predicted mature)

<400> SEQUENCE: 328

```
Asp Ile Val Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Tyr Pro Leu
                85                  90                  95

Thr Phe Gly Ala Gly Thr Lys Leu Glu Ile Lys
            100                 105
```

<210> SEQ ID NO 329
<211> LENGTH: 8
<212> TYPE: PRT
<213> ORGANISM: Artificial Sequence
<220> FEATURE:
<223> OTHER INFORMATION: Group I_Ab HCDR1 amino acid sequence (IMGT definition)

<400> SEQUENCE: 329

```
Gly Tyr Thr Phe Thr Asp Tyr Glu
1               5
```

<210> SEQ ID NO 330
<211> LENGTH: 8
<212> TYPE: PRT
<213> ORGANISM: Artificial Sequence
<220> FEATURE:
<223> OTHER INFORMATION: Group I_Ab HCDR2 amino acid sequence (IMGT definition)
<220> FEATURE:
<221> NAME/KEY: MISC_FEATURE
<222> LOCATION: (1)..(1)
<223> OTHER INFORMATION: Xaa = Val or Ile
<220> FEATURE:
<221> NAME/KEY: MISC_FEATURE
<222> LOCATION: (5)..(5)
<223> OTHER INFORMATION: Xaa = Thr or Ser

<400> SEQUENCE: 330

```
Xaa Asp Pro Glu Xaa Gly Gly Thr
1               5
```

<210> SEQ ID NO 331
<211> LENGTH: 1
<212> TYPE: PRT
<213> ORGANISM: Artificial Sequence
<220> FEATURE:
<223> OTHER INFORMATION: Group I_Ab HCDR3 amino acid sequence (IMGT definition)

<400> SEQUENCE: 331

```
Tyr
1
```

<210> SEQ ID NO 332
<211> LENGTH: 1
<212> TYPE: PRT
<213> ORGANISM: Artificial Sequence
<220> FEATURE:

<223> OTHER INFORMATION: Group I_Ab LCDR1 amino acid sequence (IMGT
       definition)

<400> SEQUENCE: 332

Ser
1

<210> SEQ ID NO 333
<211> LENGTH: 3
<212> TYPE: PRT
<213> ORGANISM: Artificial Sequence
<220> FEATURE:
<223> OTHER INFORMATION: Group I_Ab LCDR2 amino acid sequence (IMGT
       definition)
<220> FEATURE:
<221> NAME/KEY: MISC_FEATURE
<222> LOCATION: (1)..(1)
<223> OTHER INFORMATION: Xaa = Trp, Ser or Gly
<220> FEATURE:
<221> NAME/KEY: MISC_FEATURE
<222> LOCATION: (2)..(2)
<223> OTHER INFORMATION: Xaa = Ala or Thr

<400> SEQUENCE: 333

Xaa Xaa Ser
1

<210> SEQ ID NO 334
<211> LENGTH: 9
<212> TYPE: PRT
<213> ORGANISM: Artificial Sequence
<220> FEATURE:
<223> OTHER INFORMATION: Group I_Ab LCDR3 amino acid sequence (IMGT
       definition)
<220> FEATURE:
<221> NAME/KEY: MISC_FEATURE
<222> LOCATION: (1)..(1)
<223> OTHER INFORMATION: Xaa = Gln or His
<220> FEATURE:
<221> NAME/KEY: MISC_FEATURE
<222> LOCATION: (2)..(2)
<223> OTHER INFORMATION: Xaa = Gln or Asn
<220> FEATURE:
<221> NAME/KEY: MISC_FEATURE
<222> LOCATION: (3)..(3)
<223> OTHER INFORMATION: Xaa = His, Tyr or Asp
<220> FEATURE:
<221> NAME/KEY: MISC_FEATURE
<222> LOCATION: (4)..(4)
<223> OTHER INFORMATION: Xaa = Tyr or His
<220> FEATURE:
<221> NAME/KEY: MISC_FEATURE
<222> LOCATION: (5)..(5)
<223> OTHER INFORMATION: Xaa = Ser or Arg
<220> FEATURE:
<221> NAME/KEY: MISC_FEATURE
<222> LOCATION: (6)..(6)
<223> OTHER INFORMATION: Xaa = Thr, Ser or Tyr

<400> SEQUENCE: 334

Xaa Xaa Xaa Xaa Xaa Xaa Pro Pro Thr
1               5

<210> SEQ ID NO 335
<211> LENGTH: 5
<212> TYPE: PRT
<213> ORGANISM: Artificial Sequence
<220> FEATURE:
<223> OTHER INFORMATION: Group I_Ab HCDR1 amino acid sequence (Kabat
       definition)

<400> SEQUENCE: 335

Asp Tyr Glu Met His
1               5

<210> SEQ ID NO 336
<211> LENGTH: 17
<212> TYPE: PRT
<213> ORGANISM: Artificial Sequence
<220> FEATURE:
<223> OTHER INFORMATION: Group I_Ab HCDR2 amino acid sequence (Kabat
      definition)
<220> FEATURE:
<221> NAME/KEY: MISC_FEATURE
<222> LOCATION: (2)..(2)
<223> OTHER INFORMATION: Xaa = Val or Ile
<220> FEATURE:
<221> NAME/KEY: MISC_FEATURE
<222> LOCATION: (6)..(6)
<223> OTHER INFORMATION: Xaa = Thr or Ser
<220> FEATURE:
<221> NAME/KEY: MISC_FEATURE
<222> LOCATION: (10)..(10)
<223> OTHER INFORMATION: Xaa = Gly or Ala
<220> FEATURE:
<221> NAME/KEY: MISC_FEATURE
<222> LOCATION: (16)..(16)
<223> OTHER INFORMATION: Xaa = Arg or Lys

<400> SEQUENCE: 336

Gly Xaa Asp Pro Glu Xaa Gly Gly Thr Xaa Tyr Asn Gln Lys Phe Xaa
1               5                   10                  15

Gly

<210> SEQ ID NO 337
<211> LENGTH: 1
<212> TYPE: PRT
<213> ORGANISM: Artificial Sequence
<220> FEATURE:
<223> OTHER INFORMATION: Group I_Ab HCDR3 amino acid sequence (Kabat
      definition)

<400> SEQUENCE: 337

Tyr
1

<210> SEQ ID NO 338
<211> LENGTH: 1
<212> TYPE: PRT
<213> ORGANISM: Artificial Sequence
<220> FEATURE:
<223> OTHER INFORMATION: Group I_Ab LCDR1 amino acid sequence (Kabat
      definition)

<400> SEQUENCE: 338

Ser
1

<210> SEQ ID NO 339
<211> LENGTH: 7
<212> TYPE: PRT
<213> ORGANISM: Artificial Sequence
<220> FEATURE:
<223> OTHER INFORMATION: Group I_Ab LCDR2 amino acid sequence (Kabat
      definition)
<220> FEATURE:
<221> NAME/KEY: MISC_FEATURE
<222> LOCATION: (1)..(1)
<223> OTHER INFORMATION: Xaa = Trp, Ser or Gly
<220> FEATURE:
<221> NAME/KEY: MISC_FEATURE
<222> LOCATION: (2)..(2)
<223> OTHER INFORMATION: Xaa = Ala or Thr

```
<220> FEATURE:
<221> NAME/KEY: MISC_FEATURE
<222> LOCATION: (4)..(4)
<223> OTHER INFORMATION: Xaa = Thr or Asn
<220> FEATURE:
<221> NAME/KEY: MISC_FEATURE
<222> LOCATION: (5)..(5)
<223> OTHER INFORMATION: Xaa = Arg or Leu
<220> FEATURE:
<221> NAME/KEY: MISC_FEATURE
<222> LOCATION: (6)..(6)
<223> OTHER INFORMATION: Xaa = His, Ala or Glu
<220> FEATURE:
<221> NAME/KEY: MISC_FEATURE
<222> LOCATION: (7)..(7)
<223> OTHER INFORMATION: Xaa = Thr or Ser

<400> SEQUENCE: 339

Xaa Xaa Ser Xaa Xaa Xaa Xaa
1               5

<210> SEQ ID NO 340
<211> LENGTH: 9
<212> TYPE: PRT
<213> ORGANISM: Artificial Sequence
<220> FEATURE:
<223> OTHER INFORMATION: Group I_Ab LCDR3 amino acid sequence (Kabat
      definition)
<220> FEATURE:
<221> NAME/KEY: MISC_FEATURE
<222> LOCATION: (1)..(1)
<223> OTHER INFORMATION: Xaa = Gln or His
<220> FEATURE:
<221> NAME/KEY: MISC_FEATURE
<222> LOCATION: (2)..(2)
<223> OTHER INFORMATION: Xaa = Gln or Asn
<220> FEATURE:
<221> NAME/KEY: MISC_FEATURE
<222> LOCATION: (3)..(3)
<223> OTHER INFORMATION: Xaa = His, Tyr or Asp
<220> FEATURE:
<221> NAME/KEY: MISC_FEATURE
<222> LOCATION: (4)..(4)
<223> OTHER INFORMATION: Xaa = Tyr or His
<220> FEATURE:
<221> NAME/KEY: MISC_FEATURE
<222> LOCATION: (5)..(5)
<223> OTHER INFORMATION: Xaa = Ser or Arg
<220> FEATURE:
<221> NAME/KEY: MISC_FEATURE
<222> LOCATION: (6)..(6)
<223> OTHER INFORMATION: Xaa = Thr, Ser or Tyr

<400> SEQUENCE: 340

Xaa Xaa Xaa Xaa Xaa Xaa Pro Pro Thr
1               5

<210> SEQ ID NO 341
<211> LENGTH: 7
<212> TYPE: PRT
<213> ORGANISM: Artificial Sequence
<220> FEATURE:
<223> OTHER INFORMATION: Group I_Ab HCDR1 amino acid sequence (Chothia
      definition)

<400> SEQUENCE: 341

Gly Tyr Thr Phe Thr Asp Tyr
1               5

<210> SEQ ID NO 342
<211> LENGTH: 6
<212> TYPE: PRT
<213> ORGANISM: Artificial Sequence
```

```
<220> FEATURE:
<223> OTHER INFORMATION: Group I_Ab HCDR2 amino acid sequence (Chothia
      definition)
<220> FEATURE:
<221> NAME/KEY: MISC_FEATURE
<222> LOCATION: (4)..(4)
<223> OTHER INFORMATION: Xaa = Thr or Ser

<400> SEQUENCE: 342

Asp Pro Glu Xaa Gly Gly
1               5

<210> SEQ ID NO 343
<211> LENGTH: 1
<212> TYPE: PRT
<213> ORGANISM: Artificial Sequence
<220> FEATURE:
<223> OTHER INFORMATION: Group I_Ab HCDR3 amino acid sequence (Chothia
      definition)

<400> SEQUENCE: 343

Tyr
1

<210> SEQ ID NO 344
<211> LENGTH: 7
<212> TYPE: PRT
<213> ORGANISM: Artificial Sequence
<220> FEATURE:
<223> OTHER INFORMATION: Group I_Ab LCDR1 amino acid sequence (Chothia
      definition)
<220> FEATURE:
<221> NAME/KEY: MISC_FEATURE
<222> LOCATION: (2)..(2)
<223> OTHER INFORMATION: Xaa = Gln or Ser
<220> FEATURE:
<221> NAME/KEY: MISC_FEATURE
<222> LOCATION: (3)..(3)
<223> OTHER INFORMATION: Xaa = Asp or Ser
<220> FEATURE:
<221> NAME/KEY: MISC_FEATURE
<222> LOCATION: (4)..(4)
<223> OTHER INFORMATION: Xaa = Val or Leu
<220> FEATURE:
<221> NAME/KEY: MISC_FEATURE
<222> LOCATION: (5)..(5)
<223> OTHER INFORMATION: Xaa = Ser or Leu
<220> FEATURE:
<221> NAME/KEY: MISC_FEATURE
<222> LOCATION: (6)..(6)
<223> OTHER INFORMATION: Xaa = Thr, Ser or Asn
<220> FEATURE:
<221> NAME/KEY: MISC_FEATURE
<222> LOCATION: (7)..(7)
<223> OTHER INFORMATION: Xaa = Ala or Ser

<400> SEQUENCE: 344

Ser Xaa Xaa Xaa Xaa Xaa Xaa
1               5

<210> SEQ ID NO 345
<211> LENGTH: 3
<212> TYPE: PRT
<213> ORGANISM: Artificial Sequence
<220> FEATURE:
<223> OTHER INFORMATION: Group I_Ab LCDR2 amino acid sequence (Chothia
      definition)
<220> FEATURE:
<221> NAME/KEY: MISC_FEATURE
<222> LOCATION: (1)..(1)
<223> OTHER INFORMATION: Xaa = Trp, Ser or Gly
<220> FEATURE:
<221> NAME/KEY: MISC_FEATURE
```

```
<222> LOCATION: (2)..(2)
<223> OTHER INFORMATION: Xaa = Ala or Thr

<400> SEQUENCE: 345

Xaa Xaa Ser
1

<210> SEQ ID NO 346
<211> LENGTH: 7
<212> TYPE: PRT
<213> ORGANISM: Artificial Sequence
<220> FEATURE:
<223> OTHER INFORMATION: Group I_Ab LCDR3 amino acid sequence (Chothia
      definition)
<220> FEATURE:
<221> NAME/KEY: MISC_FEATURE
<222> LOCATION: (1)..(1)
<223> OTHER INFORMATION: Xaa = His, Tyr, or Asp
<220> FEATURE:
<221> NAME/KEY: MISC_FEATURE
<222> LOCATION: (2)..(2)
<223> OTHER INFORMATION: Xaa = Tyr or His
<220> FEATURE:
<221> NAME/KEY: MISC_FEATURE
<222> LOCATION: (3)..(3)
<223> OTHER INFORMATION: Xaa = Ser or Arg
<220> FEATURE:
<221> NAME/KEY: MISC_FEATURE
<222> LOCATION: (4)..(4)
<223> OTHER INFORMATION: Xaa = Thr, Ser or Tyr

<400> SEQUENCE: 346

Xaa Xaa Xaa Xaa Pro Pro Thr
1               5

<210> SEQ ID NO 347
<211> LENGTH: 10
<212> TYPE: PRT
<213> ORGANISM: Artificial Sequence
<220> FEATURE:
<223> OTHER INFORMATION: Group I_Ab HCDR1 amino acid sequence (combined
      overlap)

<400> SEQUENCE: 347

Gly Tyr Thr Phe Thr Asp Tyr Glu Met His
1               5                   10

<210> SEQ ID NO 348
<211> LENGTH: 17
<212> TYPE: PRT
<213> ORGANISM: Artificial Sequence
<220> FEATURE:
<223> OTHER INFORMATION: Group I_Ab HCDR2 amino acid sequence (combined
      overlap)
<220> FEATURE:
<221> NAME/KEY: MISC_FEATURE
<222> LOCATION: (2)..(2)
<223> OTHER INFORMATION: Xaa = Val or Ile
<220> FEATURE:
<221> NAME/KEY: MISC_FEATURE
<222> LOCATION: (6)..(6)
<223> OTHER INFORMATION: Xaa = Thr or Ser
<220> FEATURE:
<221> NAME/KEY: MISC_FEATURE
<222> LOCATION: (10)..(10)
<223> OTHER INFORMATION: Xaa = Gly or Ala
<220> FEATURE:
<221> NAME/KEY: MISC_FEATURE
<222> LOCATION: (16)..(16)
<223> OTHER INFORMATION: Xaa = Arg or Lys

<400> SEQUENCE: 348
```

```
Gly Xaa Asp Pro Glu Xaa Gly Gly Thr Xaa Tyr Asn Gln Lys Phe Xaa
1               5                   10                  15
Gly

<210> SEQ ID NO 349
<211> LENGTH: 1
<212> TYPE: PRT
<213> ORGANISM: Artificial Sequence
<220> FEATURE:
<223> OTHER INFORMATION: Group I_Ab HCDR3 amino acid sequence (combined
      overlap)

<400> SEQUENCE: 349

Tyr
1

<210> SEQ ID NO 350
<211> LENGTH: 11
<212> TYPE: PRT
<213> ORGANISM: Artificial Sequence
<220> FEATURE:
<223> OTHER INFORMATION: Group I_Ab LCDR1 amino acid sequence (combined
      overlap)
<220> FEATURE:
<221> NAME/KEY: MISC_FEATURE
<222> LOCATION: (1)..(1)
<223> OTHER INFORMATION: Xaa = Lys or Thr
<220> FEATURE:
<221> NAME/KEY: MISC_FEATURE
<222> LOCATION: (2)..(2)
<223> OTHER INFORMATION: Xaa = Ala or Ser
<220> FEATURE:
<221> NAME/KEY: MISC_FEATURE
<222> LOCATION: (4)..(4)
<223> OTHER INFORMATION: Xaa = Gln or Ser
<220> FEATURE:
<221> NAME/KEY: MISC_FEATURE
<222> LOCATION: (5)..(5)
<223> OTHER INFORMATION: Xaa = Asp or Ser
<220> FEATURE:
<221> NAME/KEY: MISC_FEATURE
<222> LOCATION: (6)..(6)
<223> OTHER INFORMATION: Xaa = Val or Leu
<220> FEATURE:
<221> NAME/KEY: MISC_FEATURE
<222> LOCATION: (7)..(7)
<223> OTHER INFORMATION: Xaa = Ser or Leu
<220> FEATURE:
<221> NAME/KEY: MISC_FEATURE
<222> LOCATION: (8)..(8)
<223> OTHER INFORMATION: Xaa = Thr, Ser or Asn
<220> FEATURE:
<221> NAME/KEY: MISC_FEATURE
<222> LOCATION: (9)..(9)
<223> OTHER INFORMATION: Xaa = Ala or Ser
<220> FEATURE:
<221> NAME/KEY: MISC_FEATURE
<222> LOCATION: (10)..(10)
<223> OTHER INFORMATION: Xaa = Val, Tyr or Gly
<220> FEATURE:
<221> NAME/KEY: MISC_FEATURE
<222> LOCATION: (11)..(11)
<223> OTHER INFORMATION: Xaa = Ala, Leu, or Asn

<400> SEQUENCE: 350

Xaa Xaa Ser Xaa Xaa Xaa Xaa Xaa Xaa Xaa Xaa
1               5                   10

<210> SEQ ID NO 351
<211> LENGTH: 7
<212> TYPE: PRT
<213> ORGANISM: Artificial Sequence
<220> FEATURE:
```

<223> OTHER INFORMATION: Group I_Ab LCDR2 amino acid sequence (combined
      overlap)
<220> FEATURE:
<221> NAME/KEY: MISC_FEATURE
<222> LOCATION: (1)..(1)
<223> OTHER INFORMATION: Xaa = Trp, Ser or Gly
<220> FEATURE:
<221> NAME/KEY: MISC_FEATURE
<222> LOCATION: (2)..(2)
<223> OTHER INFORMATION: Xaa = Ala or Thr
<220> FEATURE:
<221> NAME/KEY: MISC_FEATURE
<222> LOCATION: (4)..(4)
<223> OTHER INFORMATION: Xaa = Thr or Asn
<220> FEATURE:
<221> NAME/KEY: MISC_FEATURE
<222> LOCATION: (5)..(5)
<223> OTHER INFORMATION: Xaa = Arg or Leu
<220> FEATURE:
<221> NAME/KEY: MISC_FEATURE
<222> LOCATION: (6)..(6)
<223> OTHER INFORMATION: Xaa = His, Ala or Glu
<220> FEATURE:
<221> NAME/KEY: MISC_FEATURE
<222> LOCATION: (7)..(7)
<223> OTHER INFORMATION: Xaa = Thr or Ser

<400> SEQUENCE: 351

Xaa Xaa Ser Xaa Xaa Xaa Xaa
1               5

<210> SEQ ID NO 352
<211> LENGTH: 9
<212> TYPE: PRT
<213> ORGANISM: Artificial Sequence
<220> FEATURE:
<223> OTHER INFORMATION: Group I_Ab LCDR3 amino acid sequence (combined
      overlap)
<220> FEATURE:
<221> NAME/KEY: MISC_FEATURE
<222> LOCATION: (1)..(1)
<223> OTHER INFORMATION: Xaa = Gln or His
<220> FEATURE:
<221> NAME/KEY: MISC_FEATURE
<222> LOCATION: (2)..(2)
<223> OTHER INFORMATION: Xaa = Gln or Asn
<220> FEATURE:
<221> NAME/KEY: MISC_FEATURE
<222> LOCATION: (3)..(3)
<223> OTHER INFORMATION: Xaa = His, Tyr or Asp
<220> FEATURE:
<221> NAME/KEY: MISC_FEATURE
<222> LOCATION: (4)..(4)
<223> OTHER INFORMATION: Xaa = Tyr or His
<220> FEATURE:
<221> NAME/KEY: MISC_FEATURE
<222> LOCATION: (5)..(5)
<223> OTHER INFORMATION: Xaa = Ser or Arg
<220> FEATURE:
<221> NAME/KEY: MISC_FEATURE
<222> LOCATION: (6)..(6)
<223> OTHER INFORMATION: Xaa = Thr, Ser or Tyr

<400> SEQUENCE: 352

Xaa Xaa Xaa Xaa Xaa Xaa Pro Pro Thr
1               5

<210> SEQ ID NO 353
<211> LENGTH: 2
<212> TYPE: PRT
<213> ORGANISM: Artificial Sequence
<220> FEATURE:
<223> OTHER INFORMATION: Group I_Ab HCDR1 amino acid sequence (common
      sequence)

```
<400> SEQUENCE: 353

Asp Tyr
1

<210> SEQ ID NO 354
<211> LENGTH: 6
<212> TYPE: PRT
<213> ORGANISM: Artificial Sequence
<220> FEATURE:
<223> OTHER INFORMATION: Group I_Ab HCDR2 amino acid sequence (common
      sequence)
<220> FEATURE:
<221> NAME/KEY: MISC_FEATURE
<222> LOCATION: (4)..(4)
<223> OTHER INFORMATION: Xaa = Thr or Ser

<400> SEQUENCE: 354

Asp Pro Glu Xaa Gly Gly
1               5

<210> SEQ ID NO 355
<211> LENGTH: 1
<212> TYPE: PRT
<213> ORGANISM: Artificial Sequence
<220> FEATURE:
<223> OTHER INFORMATION: Group I_Ab HCDR3 amino acid sequence (common
      sequence)

<400> SEQUENCE: 355

Tyr
1

<210> SEQ ID NO 356
<211> LENGTH: 1
<212> TYPE: PRT
<213> ORGANISM: Artificial Sequence
<220> FEATURE:
<223> OTHER INFORMATION: Group I_Ab LCDR1 amino acid sequence (common
      sequence)

<400> SEQUENCE: 356

Ser
1

<210> SEQ ID NO 357
<211> LENGTH: 3
<212> TYPE: PRT
<213> ORGANISM: Artificial Sequence
<220> FEATURE:
<223> OTHER INFORMATION: Group I_Ab LCDR2 amino acid sequence (common
      sequence)
<220> FEATURE:
<221> NAME/KEY: MISC_FEATURE
<222> LOCATION: (1)..(1)
<223> OTHER INFORMATION: Xaa = Trp, Ser or Gly
<220> FEATURE:
<221> NAME/KEY: MISC_FEATURE
<222> LOCATION: (2)..(2)
<223> OTHER INFORMATION: Xaa = Ala or Thr

<400> SEQUENCE: 357

Xaa Xaa Ser
1

<210> SEQ ID NO 358
<211> LENGTH: 7
<212> TYPE: PRT
<213> ORGANISM: Artificial Sequence
<220> FEATURE:
```

```
<223> OTHER INFORMATION: Group I_Ab LCDR3 amino acid sequence (common
      sequence)
<220> FEATURE:
<221> NAME/KEY: MISC_FEATURE
<222> LOCATION: (1)..(1)
<223> OTHER INFORMATION: Xaa = His, Tyr, or Asp
<220> FEATURE:
<221> NAME/KEY: MISC_FEATURE
<222> LOCATION: (2)..(2)
<223> OTHER INFORMATION: Xaa = Tyr or His
<220> FEATURE:
<221> NAME/KEY: MISC_FEATURE
<222> LOCATION: (3)..(3)
<223> OTHER INFORMATION: Xaa = Ser or Arg
<220> FEATURE:
<221> NAME/KEY: MISC_FEATURE
<222> LOCATION: (4)..(4)
<223> OTHER INFORMATION: Xaa = Thr, Ser or Tyr

<400> SEQUENCE: 358

Xaa Xaa Xaa Xaa Pro Pro Thr
1               5

<210> SEQ ID NO 359
<211> LENGTH: 8
<212> TYPE: PRT
<213> ORGANISM: Artificial Sequence
<220> FEATURE:
<223> OTHER INFORMATION: Group II_Ab HCDR1 amino acid sequence (IMGT
      definition)

<400> SEQUENCE: 359

Gly Phe Thr Phe Ser Ser Tyr Gly
1               5

<210> SEQ ID NO 360
<211> LENGTH: 8
<212> TYPE: PRT
<213> ORGANISM: Artificial Sequence
<220> FEATURE:
<223> OTHER INFORMATION: Group II_Ab HCDR2 amino acid sequence (IMGT
      definition)
<220> FEATURE:
<221> NAME/KEY: MISC_FEATURE
<222> LOCATION: (4)..(4)
<223> OTHER INFORMATION: Xaa = Gly or Arg

<400> SEQUENCE: 360

Ile Ser Arg Xaa Ser Ile Tyr Thr
1               5

<210> SEQ ID NO 361
<211> LENGTH: 17
<212> TYPE: PRT
<213> ORGANISM: Artificial Sequence
<220> FEATURE:
<223> OTHER INFORMATION: Group II_Ab HCDR3 amino acid sequence (IMGT
      definition)

<400> SEQUENCE: 361

Ala Arg Leu Ser Leu Tyr Asp Tyr Asp Gly Ala Arg Tyr Thr Met Asp
1               5                   10                  15
Tyr

<210> SEQ ID NO 362
<211> LENGTH: 6
<212> TYPE: PRT
<213> ORGANISM: Artificial Sequence
<220> FEATURE:
<223> OTHER INFORMATION: Group II_Ab LCDR1 amino acid sequence (IMGT
``` definition)

<400> SEQUENCE: 362

Gln Asp Val Gly Thr Ala
1               5

<210> SEQ ID NO 363
<211> LENGTH: 3
<212> TYPE: PRT
<213> ORGANISM: Artificial Sequence
<220> FEATURE:
<223> OTHER INFORMATION: Group II_Ab LCDR2 amino acid sequence (IMGT
      definition)

<400> SEQUENCE: 363

Trp Ala Ser
1

<210> SEQ ID NO 364
<211> LENGTH: 8
<212> TYPE: PRT
<213> ORGANISM: Artificial Sequence
<220> FEATURE:
<223> OTHER INFORMATION: Group II_Ab LCDR3 amino acid sequence (IMGT
      definition)

<400> SEQUENCE: 364

Gln Gln Tyr Ser Ser Tyr His Thr
1               5

<210> SEQ ID NO 365
<211> LENGTH: 5
<212> TYPE: PRT
<213> ORGANISM: Artificial Sequence
<220> FEATURE:
<223> OTHER INFORMATION: Group II_Ab HCDR1 amino acid sequence (Kabat
      definition)

<400> SEQUENCE: 365

Ser Tyr Gly Met Ser
1               5

<210> SEQ ID NO 366
<211> LENGTH: 17
<212> TYPE: PRT
<213> ORGANISM: Artificial Sequence
<220> FEATURE:
<223> OTHER INFORMATION: Group II_Ab HCDR2 amino acid sequence (Kabat
      definition)
<220> FEATURE:
<221> NAME/KEY: MISC_FEATURE
<222> LOCATION: (5)..(5)
<223> OTHER INFORMATION: Xaa = Gly or Arg
<220> FEATURE:
<221> NAME/KEY: MISC_FEATURE
<222> LOCATION: (16)..(16)
<223> OTHER INFORMATION: Xaa = Lys or Gln

<400> SEQUENCE: 366

Thr Ile Ser Arg Xaa Ser Ile Tyr Thr Tyr Tyr Pro Asp Ser Val Xaa
1               5                   10                  15
Gly

<210> SEQ ID NO 367
<211> LENGTH: 15
<212> TYPE: PRT
<213> ORGANISM: Artificial Sequence
<220> FEATURE:

<223> OTHER INFORMATION: Group II_Ab HCDR3 amino acid sequence (Kabat
      definition)

<400> SEQUENCE: 367

Leu Ser Leu Tyr Asp Tyr Asp Gly Ala Arg Tyr Thr Met Asp Tyr
1               5                   10                  15

<210> SEQ ID NO 368
<211> LENGTH: 11
<212> TYPE: PRT
<213> ORGANISM: Artificial Sequence
<220> FEATURE:
<223> OTHER INFORMATION: Group II_Ab LCDR1 amino acid sequence (Kabat
      definition)

<400> SEQUENCE: 368

Lys Ala Ser Gln Asp Val Gly Thr Ala Val Ala
1               5                   10

<210> SEQ ID NO 369
<211> LENGTH: 7
<212> TYPE: PRT
<213> ORGANISM: Artificial Sequence
<220> FEATURE:
<223> OTHER INFORMATION: Group II_Ab LCDR2 amino acid sequence (Kabat
      definition)

<400> SEQUENCE: 369

Trp Ala Ser Thr Arg His Thr
1               5

<210> SEQ ID NO 370
<211> LENGTH: 8
<212> TYPE: PRT
<213> ORGANISM: Artificial Sequence
<220> FEATURE:
<223> OTHER INFORMATION: Group II_Ab LCDR3 amino acid sequence (Kabat
      definition)

<400> SEQUENCE: 370

Gln Gln Tyr Ser Ser Tyr His Thr
1               5

<210> SEQ ID NO 371
<211> LENGTH: 7
<212> TYPE: PRT
<213> ORGANISM: Artificial Sequence
<220> FEATURE:
<223> OTHER INFORMATION: Group II_Ab HCDR1 amino acid sequence (Chothia
      definition)

<400> SEQUENCE: 371

Gly Phe Thr Phe Ser Ser Tyr
1               5

<210> SEQ ID NO 372
<211> LENGTH: 6
<212> TYPE: PRT
<213> ORGANISM: Artificial Sequence
<220> FEATURE:
<223> OTHER INFORMATION: Group II_Ab HCDR2 amino acid sequence (Chothia
      definition)
<220> FEATURE:
<221> NAME/KEY: MISC_FEATURE
<222> LOCATION: (3)..(3)
<223> OTHER INFORMATION: Xaa = Gly or Arg

<400> SEQUENCE: 372

Ser Arg Xaa Ser Ile Tyr
1               5

<210> SEQ ID NO 373
<211> LENGTH: 15
<212> TYPE: PRT
<213> ORGANISM: Artificial Sequence
<220> FEATURE:
<223> OTHER INFORMATION: Group II_Ab HCDR3 amino acid sequence (Chothia
      definition)

<400> SEQUENCE: 373

Leu Ser Leu Tyr Asp Tyr Asp Gly Ala Arg Tyr Thr Met Asp Tyr
1               5                   10                  15

<210> SEQ ID NO 374
<211> LENGTH: 7
<212> TYPE: PRT
<213> ORGANISM: Artificial Sequence
<220> FEATURE:
<223> OTHER INFORMATION: Group II_Ab LCDR1 amino acid sequence (Chothia
      definition)

<400> SEQUENCE: 374

Ser Gln Asp Val Gly Thr Ala
1               5

<210> SEQ ID NO 375
<211> LENGTH: 3
<212> TYPE: PRT
<213> ORGANISM: Artificial Sequence
<220> FEATURE:
<223> OTHER INFORMATION: Group II_Ab LCDR2 amino acid sequence (Chothia
      definition)

<400> SEQUENCE: 375

Trp Ala Ser
1

<210> SEQ ID NO 376
<211> LENGTH: 6
<212> TYPE: PRT
<213> ORGANISM: Artificial Sequence
<220> FEATURE:
<223> OTHER INFORMATION: Group II_Ab LCDR3 amino acid sequence (Chothia
      definition)

<400> SEQUENCE: 376

Tyr Ser Ser Tyr His Thr
1               5

<210> SEQ ID NO 377
<211> LENGTH: 10
<212> TYPE: PRT
<213> ORGANISM: Artificial Sequence
<220> FEATURE:
<223> OTHER INFORMATION: Group II_Ab HCDR1 amino acid sequence (combined
      overlap)

<400> SEQUENCE: 377

Gly Phe Thr Phe Ser Ser Tyr Gly Met Ser
1               5                   10

<210> SEQ ID NO 378
<211> LENGTH: 17
<212> TYPE: PRT
<213> ORGANISM: Artificial Sequence
<220> FEATURE:

```
<223> OTHER INFORMATION: Group II_Ab HCDR2 amino acid sequence (combined
      overlap)
<220> FEATURE:
<221> NAME/KEY: MISC_FEATURE
<222> LOCATION: (5)..(5)
<223> OTHER INFORMATION: Xaa = Gly or Arg
<220> FEATURE:
<221> NAME/KEY: MISC_FEATURE
<222> LOCATION: (16)..(16)
<223> OTHER INFORMATION: Xaa = Lys or Gln

<400> SEQUENCE: 378

Thr Ile Ser Arg Xaa Ser Ile Tyr Thr Tyr Tyr Pro Asp Ser Val Xaa
1               5                   10                  15

Gly

<210> SEQ ID NO 379
<211> LENGTH: 17
<212> TYPE: PRT
<213> ORGANISM: Artificial Sequence
<220> FEATURE:
<223> OTHER INFORMATION: Group II_Ab HCDR3 amino acid sequence (combined
      overlap)

<400> SEQUENCE: 379

Ala Arg Leu Ser Leu Tyr Asp Tyr Asp Gly Ala Arg Tyr Thr Met Asp
1               5                   10                  15

Tyr

<210> SEQ ID NO 380
<211> LENGTH: 11
<212> TYPE: PRT
<213> ORGANISM: Artificial Sequence
<220> FEATURE:
<223> OTHER INFORMATION: Group II_Ab LCDR1 amino acid sequence (combined
      overlap)

<400> SEQUENCE: 380

Lys Ala Ser Gln Asp Val Gly Thr Ala Val Ala
1               5                   10

<210> SEQ ID NO 381
<211> LENGTH: 7
<212> TYPE: PRT
<213> ORGANISM: Artificial Sequence
<220> FEATURE:
<223> OTHER INFORMATION: Group II_Ab LCDR2 amino acid sequence (combined
      overlap)

<400> SEQUENCE: 381

Trp Ala Ser Thr Arg His Thr
1               5

<210> SEQ ID NO 382
<211> LENGTH: 8
<212> TYPE: PRT
<213> ORGANISM: Artificial Sequence
<220> FEATURE:
<223> OTHER INFORMATION: Group II_Ab LCDR3 amino acid sequence (combined
      overlap)

<400> SEQUENCE: 382

Gln Gln Tyr Ser Ser Tyr His Thr
1               5

<210> SEQ ID NO 383
<211> LENGTH: 2
```

```
<212> TYPE: PRT
<213> ORGANISM: Artificial Sequence
<220> FEATURE:
<223> OTHER INFORMATION: Group II_Ab HCDR1 amino acid sequence (common
      sequence)

<400> SEQUENCE: 383

Ser Tyr
1

<210> SEQ ID NO 384
<211> LENGTH: 6
<212> TYPE: PRT
<213> ORGANISM: Artificial Sequence
<220> FEATURE:
<223> OTHER INFORMATION: Group II_Ab HCDR2 amino acid sequence (common
      sequence)
<220> FEATURE:
<221> NAME/KEY: MISC_FEATURE
<222> LOCATION: (3)..(3)
<223> OTHER INFORMATION: Xaa = Gly or Arg

<400> SEQUENCE: 384

Ser Arg Xaa Ser Ile Tyr
1               5

<210> SEQ ID NO 385
<211> LENGTH: 15
<212> TYPE: PRT
<213> ORGANISM: Artificial Sequence
<220> FEATURE:
<223> OTHER INFORMATION: Group II_Ab HCDR3 amino acid sequence (common
      sequence)

<400> SEQUENCE: 385

Leu Ser Leu Tyr Asp Tyr Asp Gly Ala Arg Tyr Thr Met Asp Tyr
1               5                   10                  15

<210> SEQ ID NO 386
<211> LENGTH: 6
<212> TYPE: PRT
<213> ORGANISM: Artificial Sequence
<220> FEATURE:
<223> OTHER INFORMATION: Group II_Ab LCDR1 amino acid sequence (common
      sequence)

<400> SEQUENCE: 386

Gln Asp Val Gly Thr Ala
1               5

<210> SEQ ID NO 387
<211> LENGTH: 3
<212> TYPE: PRT
<213> ORGANISM: Artificial Sequence
<220> FEATURE:
<223> OTHER INFORMATION: Group II_Ab LCDR2 amino acid sequence (common
      sequence)

<400> SEQUENCE: 387

Trp Ala Ser
1

<210> SEQ ID NO 388
<211> LENGTH: 6
<212> TYPE: PRT
<213> ORGANISM: Artificial Sequence
<220> FEATURE:
<223> OTHER INFORMATION: Group II_Ab LCDR3 amino acid sequence (common
      sequence)
```

```
<400> SEQUENCE: 388

Tyr Ser Ser Tyr His Thr
1               5

<210> SEQ ID NO 389
<211> LENGTH: 8
<212> TYPE: PRT
<213> ORGANISM: Artificial Sequence
<220> FEATURE:
<223> OTHER INFORMATION: Group III_Ab HCDR1 amino acid sequence (IMGT
      definition)
<220> FEATURE:
<221> NAME/KEY: MISC_FEATURE
<222> LOCATION: (3)..(3)
<223> OTHER INFORMATION: Xaa = Asn or Thr
<220> FEATURE:
<221> NAME/KEY: MISC_FEATURE
<222> LOCATION: (5)..(5)
<223> OTHER INFORMATION: Xaa = Lys or Thr
<220> FEATURE:
<221> NAME/KEY: MISC_FEATURE
<222> LOCATION: (6)..(6)
<223> OTHER INFORMATION: Xaa = Ser or Asp
<220> FEATURE:
<221> NAME/KEY: MISC_FEATURE
<222> LOCATION: (8)..(8)
<223> OTHER INFORMATION: Xaa = Gly or Tyr

<400> SEQUENCE: 389

Gly Tyr Xaa Phe Xaa Xaa Tyr Xaa
1               5

<210> SEQ ID NO 390
<211> LENGTH: 8
<212> TYPE: PRT
<213> ORGANISM: Artificial Sequence
<220> FEATURE:
<223> OTHER INFORMATION: Group III_Ab HCDR2 amino acid sequence (IMGT
      definition)
<220> FEATURE:
<221> NAME/KEY: MISC_FEATURE
<222> LOCATION: (2)..(2)
<223> OTHER INFORMATION: Xaa = Tyr or Phe
<220> FEATURE:
<221> NAME/KEY: MISC_FEATURE
<222> LOCATION: (7)..(7)
<223> OTHER INFORMATION: Xaa = Asn or Ser

<400> SEQUENCE: 390

Ile Xaa Pro Gly Ser Gly Xaa Thr
1               5

<210> SEQ ID NO 391
<211> LENGTH: 2
<212> TYPE: PRT
<213> ORGANISM: Artificial Sequence
<220> FEATURE:
<223> OTHER INFORMATION: Group III_Ab HCDR3 amino acid sequence (IMGT
      definition)

<400> SEQUENCE: 391

Tyr Gly
1

<210> SEQ ID NO 392
<211> LENGTH: 1
<212> TYPE: PRT
<213> ORGANISM: Artificial Sequence
<220> FEATURE:
<223> OTHER INFORMATION: Group III_Ab LCDR1 amino acid sequence (IMGT
```

-continued definition)

<400> SEQUENCE: 392

Ser
1

<210> SEQ ID NO 393
<211> LENGTH: 3
<212> TYPE: PRT
<213> ORGANISM: Artificial Sequence
<220> FEATURE:
<223> OTHER INFORMATION: Group III_Ab LCDR2 amino acid sequence (IMGT
      definition)
<220> FEATURE:
<221> NAME/KEY: MISC_FEATURE
<222> LOCATION: (1)..(1)
<223> OTHER INFORMATION: Xaa = Arg or Ala
<220> FEATURE:
<221> NAME/KEY: MISC_FEATURE
<222> LOCATION: (2)..(2)
<223> OTHER INFORMATION: Xaa = Val or Thr

<400> SEQUENCE: 393

Xaa Xaa Ser
1

<210> SEQ ID NO 394
<211> LENGTH: 9
<212> TYPE: PRT
<213> ORGANISM: Artificial Sequence
<220> FEATURE:
<223> OTHER INFORMATION: Group III_Ab LCDR3 amino acid sequence (IMGT
      definition)
<220> FEATURE:
<221> NAME/KEY: MISC_FEATURE
<222> LOCATION: (1)..(1)
<223> OTHER INFORMATION: Xaa = Met or Gln
<220> FEATURE:
<221> NAME/KEY: MISC_FEATURE
<222> LOCATION: (3)..(3)
<223> OTHER INFORMATION: Xaa = His or Trp
<220> FEATURE:
<221> NAME/KEY: MISC_FEATURE
<222> LOCATION: (4)..(4)
<223> OTHER INFORMATION: Xaa = Leu or Ser
<220> FEATURE:
<221> NAME/KEY: MISC_FEATURE
<222> LOCATION: (5)..(5)
<223> OTHER INFORMATION: Xaa = Glu or Ser
<220> FEATURE:
<221> NAME/KEY: MISC_FEATURE
<222> LOCATION: (6)..(6)
<223> OTHER INFORMATION: Xaa = Tyr or Asn
<220> FEATURE:
<221> NAME/KEY: MISC_FEATURE
<222> LOCATION: (8)..(8)
<223> OTHER INFORMATION: Xaa = Phe or Leu

<400> SEQUENCE: 394

Xaa Gln Xaa Xaa Xaa Xaa Pro Xaa Thr
1               5

<210> SEQ ID NO 395
<211> LENGTH: 5
<212> TYPE: PRT
<213> ORGANISM: Artificial Sequence
<220> FEATURE:
<223> OTHER INFORMATION: Group III_Ab HCDR1 amino acid sequence (Kabat
      definition)
<220> FEATURE:
<221> NAME/KEY: MISC_FEATURE
<222> LOCATION: (1)..(1)
<223> OTHER INFORMATION: Xaa = Ser or Asp

```
<220> FEATURE:
<221> NAME/KEY: MISC_FEATURE
<222> LOCATION: (3)..(3)
<223> OTHER INFORMATION: Xaa = Gly or Tyr
<220> FEATURE:
<221> NAME/KEY: MISC_FEATURE
<222> LOCATION: (5)..(5)
<223> OTHER INFORMATION: Xaa = Ser or Asn

<400> SEQUENCE: 395

Xaa Tyr Xaa Ile Xaa
1               5

<210> SEQ ID NO 396
<211> LENGTH: 17
<212> TYPE: PRT
<213> ORGANISM: Artificial Sequence
<220> FEATURE:
<223> OTHER INFORMATION: Group III_Ab HCDR2 amino acid sequence (Kabat
      definition)
<220> FEATURE:
<221> NAME/KEY: MISC_FEATURE
<222> LOCATION: (1)..(1)
<223> OTHER INFORMATION: Xaa = Glu or Trp
<220> FEATURE:
<221> NAME/KEY: MISC_FEATURE
<222> LOCATION: (3)..(3)
<223> OTHER INFORMATION: Xaa = Tyr or Phe
<220> FEATURE:
<221> NAME/KEY: MISC_FEATURE
<222> LOCATION: (8)..(8)
<223> OTHER INFORMATION: Xaa = Asn or Ser
<220> FEATURE:
<221> NAME/KEY: MISC_FEATURE
<222> LOCATION: (15)..(15)
<223> OTHER INFORMATION: Xaa = Leu or Phe

<400> SEQUENCE: 396

Xaa Ile Xaa Pro Gly Ser Gly Xaa Thr Tyr Tyr Asn Glu Lys Xaa Lys
1               5                   10                  15
Gly

<210> SEQ ID NO 397
<211> LENGTH: 2
<212> TYPE: PRT
<213> ORGANISM: Artificial Sequence
<220> FEATURE:
<223> OTHER INFORMATION: Group III_Ab HCDR3 amino acid sequence (Kabat
      definition)

<400> SEQUENCE: 397

Tyr Gly
1

<210> SEQ ID NO 398
<211> LENGTH: 2
<212> TYPE: PRT
<213> ORGANISM: Artificial Sequence
<220> FEATURE:
<223> OTHER INFORMATION: Group III_Ab LCDR1 amino acid sequence (Kabat
      definition)

<400> SEQUENCE: 398

Ser Ser
1

<210> SEQ ID NO 399
<211> LENGTH: 7
<212> TYPE: PRT
<213> ORGANISM: Artificial Sequence
```

```
<220> FEATURE:
<223> OTHER INFORMATION: Group III_Ab LCDR2 amino acid sequence (Kabat
      definition)
<220> FEATURE:
<221> NAME/KEY: MISC_FEATURE
<222> LOCATION: (1)..(1)
<223> OTHER INFORMATION: Xaa = Arg or Ala
<220> FEATURE:
<221> NAME/KEY: MISC_FEATURE
<222> LOCATION: (2)..(2)
<223> OTHER INFORMATION: Xaa = Val or Thr
<220> FEATURE:
<221> NAME/KEY: MISC_FEATURE
<222> LOCATION: (4)..(4)
<223> OTHER INFORMATION: Xaa = Asn or Tyr

<400> SEQUENCE: 399

Xaa Xaa Ser Xaa Leu Ala Ser
1               5

<210> SEQ ID NO 400
<211> LENGTH: 9
<212> TYPE: PRT
<213> ORGANISM: Artificial Sequence
<220> FEATURE:
<223> OTHER INFORMATION: Group III_Ab LCDR3 amino acid sequence (Kabat
      definition)
<220> FEATURE:
<221> NAME/KEY: MISC_FEATURE
<222> LOCATION: (1)..(1)
<223> OTHER INFORMATION: Xaa = Met or Gln
<220> FEATURE:
<221> NAME/KEY: MISC_FEATURE
<222> LOCATION: (3)..(3)
<223> OTHER INFORMATION: Xaa = His or Trp
<220> FEATURE:
<221> NAME/KEY: MISC_FEATURE
<222> LOCATION: (4)..(4)
<223> OTHER INFORMATION: Xaa = Leu or Ser
<220> FEATURE:
<221> NAME/KEY: MISC_FEATURE
<222> LOCATION: (5)..(5)
<223> OTHER INFORMATION: Xaa = Glu or Ser
<220> FEATURE:
<221> NAME/KEY: MISC_FEATURE
<222> LOCATION: (6)..(6)
<223> OTHER INFORMATION: Xaa = Tyr or Asn
<220> FEATURE:
<221> NAME/KEY: MISC_FEATURE
<222> LOCATION: (8)..(8)
<223> OTHER INFORMATION: Xaa = Phe or Leu

<400> SEQUENCE: 400

Xaa Gln Xaa Xaa Xaa Xaa Pro Xaa Thr
1               5

<210> SEQ ID NO 401
<211> LENGTH: 7
<212> TYPE: PRT
<213> ORGANISM: Artificial Sequence
<220> FEATURE:
<223> OTHER INFORMATION: Group III_Ab HCDR1 amino acid sequence (Chothia
      definition)
<220> FEATURE:
<221> NAME/KEY: MISC_FEATURE
<222> LOCATION: (3)..(3)
<223> OTHER INFORMATION: Xaa = Asn or Thr
<220> FEATURE:
<221> NAME/KEY: MISC_FEATURE
<222> LOCATION: (5)..(5)
<223> OTHER INFORMATION: Xaa = Lys or Thr
<220> FEATURE:
<221> NAME/KEY: MISC_FEATURE
<222> LOCATION: (6)..(6)
<223> OTHER INFORMATION: Xaa = Ser or Asp
```

<400> SEQUENCE: 401

Gly Tyr Xaa Phe Xaa Xaa Tyr
1               5

<210> SEQ ID NO 402
<211> LENGTH: 6
<212> TYPE: PRT
<213> ORGANISM: Artificial Sequence
<220> FEATURE:
<223> OTHER INFORMATION: Group III_Ab HCDR2 amino acid sequence (Chothia
      definition)
<220> FEATURE:
<221> NAME/KEY: MISC_FEATURE
<222> LOCATION: (1)..(1)
<223> OTHER INFORMATION: Xaa = Tyr or Phe
<220> FEATURE:
<221> NAME/KEY: MISC_FEATURE
<222> LOCATION: (6)..(6)
<223> OTHER INFORMATION: Xaa = Asn or Ser

<400> SEQUENCE: 402

Xaa Pro Gly Ser Gly Xaa
1               5

<210> SEQ ID NO 403
<211> LENGTH: 2
<212> TYPE: PRT
<213> ORGANISM: Artificial Sequence
<220> FEATURE:
<223> OTHER INFORMATION: Group III_Ab HCDR3 amino acid sequence (Chothia
      definition)

<400> SEQUENCE: 403

Tyr Gly
1

<210> SEQ ID NO 404
<211> LENGTH: 1
<212> TYPE: PRT
<213> ORGANISM: Artificial Sequence
<220> FEATURE:
<223> OTHER INFORMATION: Group III_Ab LCDR1 amino acid sequence (Chothia
      definition)

<400> SEQUENCE: 404

Ser
1

<210> SEQ ID NO 405
<211> LENGTH: 3
<212> TYPE: PRT
<213> ORGANISM: Artificial Sequence
<220> FEATURE:
<223> OTHER INFORMATION: Group III_Ab LCDR2 amino acid sequence (Chothia
      definition)
<220> FEATURE:
<221> NAME/KEY: MISC_FEATURE
<222> LOCATION: (1)..(1)
<223> OTHER INFORMATION: Xaa = Arg or Ala
<220> FEATURE:
<221> NAME/KEY: MISC_FEATURE
<222> LOCATION: (2)..(2)
<223> OTHER INFORMATION: Xaa = Val or Thr

<400> SEQUENCE: 405

Xaa Xaa Ser
1

```
<210> SEQ ID NO 406
<211> LENGTH: 7
<212> TYPE: PRT
<213> ORGANISM: Artificial Sequence
<220> FEATURE:
<223> OTHER INFORMATION: Group III_Ab LCDR3 amino acid sequence (Chothia
      definition)
<220> FEATURE:
<221> NAME/KEY: MISC_FEATURE
<222> LOCATION: (1)..(1)
<223> OTHER INFORMATION: Xaa = His or Trp
<220> FEATURE:
<221> NAME/KEY: MISC_FEATURE
<222> LOCATION: (2)..(2)
<223> OTHER INFORMATION: Xaa = Leu or Ser
<220> FEATURE:
<221> NAME/KEY: MISC_FEATURE
<222> LOCATION: (3)..(3)
<223> OTHER INFORMATION: Xaa = Glu or Ser
<220> FEATURE:
<221> NAME/KEY: MISC_FEATURE
<222> LOCATION: (4)..(4)
<223> OTHER INFORMATION: Xaa = Tyr or Asn
<220> FEATURE:
<221> NAME/KEY: MISC_FEATURE
<222> LOCATION: (6)..(6)
<223> OTHER INFORMATION: Xaa = Phe or Leu

<400> SEQUENCE: 406

Xaa Xaa Xaa Xaa Pro Xaa Thr
1               5

<210> SEQ ID NO 407
<211> LENGTH: 10
<212> TYPE: PRT
<213> ORGANISM: Artificial Sequence
<220> FEATURE:
<223> OTHER INFORMATION: Group III_Ab HCDR1 amino acid sequence
      (combined overlap)
<220> FEATURE:
<221> NAME/KEY: MISC_FEATURE
<222> LOCATION: (3)..(3)
<223> OTHER INFORMATION: Xaa = Asn or Thr
<220> FEATURE:
<221> NAME/KEY: MISC_FEATURE
<222> LOCATION: (5)..(5)
<223> OTHER INFORMATION: Xaa = Lys or Thr
<220> FEATURE:
<221> NAME/KEY: MISC_FEATURE
<222> LOCATION: (6)..(6)
<223> OTHER INFORMATION: Xaa = Ser or Asp
<220> FEATURE:
<221> NAME/KEY: MISC_FEATURE
<222> LOCATION: (8)..(8)
<223> OTHER INFORMATION: Xaa = Gly or Tyr
<220> FEATURE:
<221> NAME/KEY: MISC_FEATURE
<222> LOCATION: (10)..(10)
<223> OTHER INFORMATION: Xaa = Ser or Asn

<400> SEQUENCE: 407

Gly Tyr Xaa Phe Xaa Xaa Tyr Xaa Ile Xaa
1               5                   10

<210> SEQ ID NO 408
<211> LENGTH: 17
<212> TYPE: PRT
<213> ORGANISM: Artificial Sequence
<220> FEATURE:
<223> OTHER INFORMATION: Group III_Ab HCDR2 amino acid sequence
      (combined overlap)
<220> FEATURE:
<221> NAME/KEY: MISC_FEATURE
<222> LOCATION: (1)..(1)
<223> OTHER INFORMATION: Xaa = Glu or Trp
```

```
<220> FEATURE:
<221> NAME/KEY: MISC_FEATURE
<222> LOCATION: (3)..(3)
<223> OTHER INFORMATION: Xaa = Tyr or Phe
<220> FEATURE:
<221> NAME/KEY: MISC_FEATURE
<222> LOCATION: (8)..(8)
<223> OTHER INFORMATION: Xaa = Asn or Ser
<220> FEATURE:
<221> NAME/KEY: MISC_FEATURE
<222> LOCATION: (15)..(15)
<223> OTHER INFORMATION: Xaa = Leu or Phe

<400> SEQUENCE: 408

Xaa Ile Xaa Pro Gly Ser Gly Xaa Thr Tyr Tyr Asn Glu Lys Xaa Lys
1               5                   10                  15

Gly

<210> SEQ ID NO 409
<211> LENGTH: 2
<212> TYPE: PRT
<213> ORGANISM: Artificial Sequence
<220> FEATURE:
<223> OTHER INFORMATION: Group III_Ab HCDR3 amino acid sequence
      (combined overlap)

<400> SEQUENCE: 409

Tyr Gly
1

<210> SEQ ID NO 410
<211> LENGTH: 2
<212> TYPE: PRT
<213> ORGANISM: Artificial Sequence
<220> FEATURE:
<223> OTHER INFORMATION: Group III_Ab LCDR1 amino acid sequence
      (combined overlap)

<400> SEQUENCE: 410

Ser Ser
1

<210> SEQ ID NO 411
<211> LENGTH: 7
<212> TYPE: PRT
<213> ORGANISM: Artificial Sequence
<220> FEATURE:
<223> OTHER INFORMATION: Group III_Ab LCDR2 amino acid sequence
      (combined overlap)
<220> FEATURE:
<221> NAME/KEY: MISC_FEATURE
<222> LOCATION: (1)..(1)
<223> OTHER INFORMATION: Xaa = Arg or Ala
<220> FEATURE:
<221> NAME/KEY: MISC_FEATURE
<222> LOCATION: (2)..(2)
<223> OTHER INFORMATION: Xaa = Val or Thr
<220> FEATURE:
<221> NAME/KEY: MISC_FEATURE
<222> LOCATION: (4)..(4)
<223> OTHER INFORMATION: Xaa = Asn or Tyr

<400> SEQUENCE: 411

Xaa Xaa Ser Xaa Leu Ala Ser
1               5

<210> SEQ ID NO 412
<211> LENGTH: 9
<212> TYPE: PRT
<213> ORGANISM: Artificial Sequence
```

```
<220> FEATURE:
<223> OTHER INFORMATION: Group III_Ab LCDR3 amino acid sequence
      (combined overlap)
<220> FEATURE:
<221> NAME/KEY: MISC_FEATURE
<222> LOCATION: (1)..(1)
<223> OTHER INFORMATION: Xaa = Met or Gln
<220> FEATURE:
<221> NAME/KEY: MISC_FEATURE
<222> LOCATION: (3)..(3)
<223> OTHER INFORMATION: Xaa = His or Trp
<220> FEATURE:
<221> NAME/KEY: MISC_FEATURE
<222> LOCATION: (4)..(4)
<223> OTHER INFORMATION: Xaa = Leu or Ser
<220> FEATURE:
<221> NAME/KEY: MISC_FEATURE
<222> LOCATION: (5)..(5)
<223> OTHER INFORMATION: Xaa = Glu or Ser
<220> FEATURE:
<221> NAME/KEY: MISC_FEATURE
<222> LOCATION: (6)..(6)
<223> OTHER INFORMATION: Xaa = Tyr or Asn
<220> FEATURE:
<221> NAME/KEY: MISC_FEATURE
<222> LOCATION: (8)..(8)
<223> OTHER INFORMATION: Xaa = Phe or Leu

<400> SEQUENCE: 412

Xaa Gln Xaa Xaa Xaa Xaa Pro Xaa Thr
1               5

<210> SEQ ID NO 413
<211> LENGTH: 2
<212> TYPE: PRT
<213> ORGANISM: Artificial Sequence
<220> FEATURE:
<223> OTHER INFORMATION: Group III_Ab HCDR1 amino acid sequence (common
      sequence)
<220> FEATURE:
<221> NAME/KEY: MISC_FEATURE
<222> LOCATION: (1)..(1)
<223> OTHER INFORMATION: Xaa = Ser or Asp

<400> SEQUENCE: 413

Xaa Tyr
1

<210> SEQ ID NO 414
<211> LENGTH: 6
<212> TYPE: PRT
<213> ORGANISM: Artificial Sequence
<220> FEATURE:
<223> OTHER INFORMATION: Group III_Ab HCDR2 amino acid sequence (common
      sequence)
<220> FEATURE:
<221> NAME/KEY: MISC_FEATURE
<222> LOCATION: (1)..(1)
<223> OTHER INFORMATION: Xaa = Tyr or Phe
<220> FEATURE:
<221> NAME/KEY: MISC_FEATURE
<222> LOCATION: (6)..(6)
<223> OTHER INFORMATION: Xaa = Asn or Ser

<400> SEQUENCE: 414

Xaa Pro Gly Ser Gly Xaa
1               5

<210> SEQ ID NO 415
<211> LENGTH: 2
<212> TYPE: PRT
<213> ORGANISM: Artificial Sequence
<220> FEATURE:
```

```
<223> OTHER INFORMATION: Group III_Ab HCDR3 amino acid sequence (common
      sequence)

<400> SEQUENCE: 415

Tyr Gly
1

<210> SEQ ID NO 416
<211> LENGTH: 1
<212> TYPE: PRT
<213> ORGANISM: Artificial Sequence
<220> FEATURE:
<223> OTHER INFORMATION: Group III_Ab LCDR1 amino acid sequence (common
      sequence)

<400> SEQUENCE: 416

Ser
1

<210> SEQ ID NO 417
<211> LENGTH: 3
<212> TYPE: PRT
<213> ORGANISM: Artificial Sequence
<220> FEATURE:
<223> OTHER INFORMATION: Group III_Ab LCDR2 amino acid sequence (common
      sequence)
<220> FEATURE:
<221> NAME/KEY: MISC_FEATURE
<222> LOCATION: (1)..(1)
<223> OTHER INFORMATION: Xaa = Trp or Ala
<220> FEATURE:
<221> NAME/KEY: MISC_FEATURE
<222> LOCATION: (2)..(2)
<223> OTHER INFORMATION: Xaa = Ala or Thr

<400> SEQUENCE: 417

Xaa Xaa Ser
1

<210> SEQ ID NO 418
<211> LENGTH: 7
<212> TYPE: PRT
<213> ORGANISM: Artificial Sequence
<220> FEATURE:
<223> OTHER INFORMATION: Group III_Ab LCDR3 amino acid sequence (common
      sequence)
<220> FEATURE:
<221> NAME/KEY: MISC_FEATURE
<222> LOCATION: (1)..(1)
<223> OTHER INFORMATION: Xaa = His or Trp
<220> FEATURE:
<221> NAME/KEY: MISC_FEATURE
<222> LOCATION: (2)..(2)
<223> OTHER INFORMATION: Xaa = Leu or Ser
<220> FEATURE:
<221> NAME/KEY: MISC_FEATURE
<222> LOCATION: (3)..(3)
<223> OTHER INFORMATION: Xaa = Glu or Ser
<220> FEATURE:
<221> NAME/KEY: MISC_FEATURE
<222> LOCATION: (4)..(4)
<223> OTHER INFORMATION: Xaa = Tyr or Asn
<220> FEATURE:
<221> NAME/KEY: MISC_FEATURE
<222> LOCATION: (6)..(6)
<223> OTHER INFORMATION: Xaa = Phe or Leu

<400> SEQUENCE: 418

Xaa Xaa Xaa Xaa Pro Xaa Thr
1               5
```

```
<210> SEQ ID NO 419
<211> LENGTH: 8
<212> TYPE: PRT
<213> ORGANISM: Artificial Sequence
<220> FEATURE:
<223> OTHER INFORMATION: Group IV_Ab HCDR1 amino acid sequence (IMGT
      definition)
<220> FEATURE:
<221> NAME/KEY: MISC_FEATURE
<222> LOCATION: (3)..(3)
<223> OTHER INFORMATION: Xaa = Thr or Ala
<220> FEATURE:
<221> NAME/KEY: MISC_FEATURE
<222> LOCATION: (6)..(6)
<223> OTHER INFORMATION: Xaa = Ser or Asn
<220> FEATURE:
<221> NAME/KEY: MISC_FEATURE
<222> LOCATION: (8)..(8)
<223> OTHER INFORMATION: Xaa = Trp or Leu

<400> SEQUENCE: 419

Gly Tyr Xaa Phe Thr Xaa Tyr Xaa
1               5

<210> SEQ ID NO 420
<211> LENGTH: 8
<212> TYPE: PRT
<213> ORGANISM: Artificial Sequence
<220> FEATURE:
<223> OTHER INFORMATION: Group IV_Ab HCDR2 amino acid sequence (IMGT
      definition)
<220> FEATURE:
<221> NAME/KEY: MISC_FEATURE
<222> LOCATION: (4)..(4)
<223> OTHER INFORMATION: Xaa = Ser or Gly
<220> FEATURE:
<221> NAME/KEY: MISC_FEATURE
<222> LOCATION: (5)..(5)
<223> OTHER INFORMATION: Xaa = Asn or Ser

<400> SEQUENCE: 420

Ile Asn Pro Xaa Xaa Gly Gly Thr
1               5

<210> SEQ ID NO 421
<211> LENGTH: 7
<212> TYPE: PRT
<213> ORGANISM: Artificial Sequence
<220> FEATURE:
<223> OTHER INFORMATION: Group IV_Ab HCDR3 amino acid sequence (IMGT
      definition)
<220> FEATURE:
<221> NAME/KEY: MISC_FEATURE
<222> LOCATION: (3)..(3)
<223> OTHER INFORMATION: Xaa = Gly or Trp
<220> FEATURE:
<221> NAME/KEY: MISC_FEATURE
<222> LOCATION: (5)..(5)
<223> OTHER INFORMATION: Xaa = Ile or Phe

<400> SEQUENCE: 421

Ala Arg Xaa Gly Xaa Tyr Tyr
1               5

<210> SEQ ID NO 422
<211> LENGTH: 1
<212> TYPE: PRT
<213> ORGANISM: Artificial Sequence
<220> FEATURE:
<223> OTHER INFORMATION: Group IV_Ab LCDR1 amino acid sequence (IMGT
      definition)

<400> SEQUENCE: 422
```

```
Ser
1

<210> SEQ ID NO 423
<211> LENGTH: 3
<212> TYPE: PRT
<213> ORGANISM: Artificial Sequence
<220> FEATURE:
<223> OTHER INFORMATION: Group IV_Ab LCDR2 amino acid sequence (IMGT
      definition)
<220> FEATURE:
<221> NAME/KEY: MISC_FEATURE
<222> LOCATION: (1)..(1)
<223> OTHER INFORMATION: Xaa = Arg or Ala
<220> FEATURE:
<221> NAME/KEY: MISC_FEATURE
<222> LOCATION: (2)..(2)
<223> OTHER INFORMATION: Xaa = Val or Ala

<400> SEQUENCE: 423

Xaa Xaa Ser
1

<210> SEQ ID NO 424
<211> LENGTH: 9
<212> TYPE: PRT
<213> ORGANISM: Artificial Sequence
<220> FEATURE:
<223> OTHER INFORMATION: Group IV_Ab LCDR3 amino acid sequence (IMGT
      definition)
<220> FEATURE:
<221> NAME/KEY: MISC_FEATURE
<222> LOCATION: (1)..(1)
<223> OTHER INFORMATION: Xaa = Met or Leu
<220> FEATURE:
<221> NAME/KEY: MISC_FEATURE
<222> LOCATION: (3)..(3)
<223> OTHER INFORMATION: Xaa = His or Tyr
<220> FEATURE:
<221> NAME/KEY: MISC_FEATURE
<222> LOCATION: (4)..(4)
<223> OTHER INFORMATION: Xaa = Leu or Ala
<220> FEATURE:
<221> NAME/KEY: MISC_FEATURE
<222> LOCATION: (5)..(5)
<223> OTHER INFORMATION: Xaa = Glu or Ser
<220> FEATURE:
<221> NAME/KEY: MISC_FEATURE
<222> LOCATION: (8)..(8)
<223> OTHER INFORMATION: Xaa = Phe or Leu

<400> SEQUENCE: 424

Xaa Gln Xaa Xaa Xaa Tyr Pro Xaa Thr
1               5

<210> SEQ ID NO 425
<211> LENGTH: 5
<212> TYPE: PRT
<213> ORGANISM: Artificial Sequence
<220> FEATURE:
<223> OTHER INFORMATION: Group IV_Ab HCDR1 amino acid sequence (Kabat
      definition)
<220> FEATURE:
<221> NAME/KEY: MISC_FEATURE
<222> LOCATION: (1)..(1)
<223> OTHER INFORMATION: Xaa = Ser or Asn
<220> FEATURE:
<221> NAME/KEY: MISC_FEATURE
<222> LOCATION: (3)..(3)
<223> OTHER INFORMATION: Xaa = Trp or Leu
<220> FEATURE:
<221> NAME/KEY: MISC_FEATURE
<222> LOCATION: (4)..(4)
```

```
<223> OTHER INFORMATION: Xaa = Met or Ile
<220> FEATURE:
<221> NAME/KEY: MISC_FEATURE
<222> LOCATION: (5)..(5)
<223> OTHER INFORMATION: Xaa = His or Glu

<400> SEQUENCE: 425

Xaa Tyr Xaa Xaa Xaa
1               5

<210> SEQ ID NO 426
<211> LENGTH: 17
<212> TYPE: PRT
<213> ORGANISM: Artificial Sequence
<220> FEATURE:
<223> OTHER INFORMATION: Group IV_Ab HCDR2 amino acid sequence (Kabat
      definition)
<220> FEATURE:
<221> NAME/KEY: MISC_FEATURE
<222> LOCATION: (1)..(1)
<223> OTHER INFORMATION: Xaa = Asn or Val
<220> FEATURE:
<221> NAME/KEY: MISC_FEATURE
<222> LOCATION: (5)..(5)
<223> OTHER INFORMATION: Xaa = Ser or Gly
<220> FEATURE:
<221> NAME/KEY: MISC_FEATURE
<222> LOCATION: (6)..(6)
<223> OTHER INFORMATION: Xaa = Asn or Ser
<220> FEATURE:
<221> NAME/KEY: MISC_FEATURE
<222> LOCATION: (17)..(17)
<223> OTHER INFORMATION: Xaa = Ser or Gly

<400> SEQUENCE: 426

Xaa Ile Asn Pro Xaa Xaa Gly Gly Thr Asn Tyr Asn Glu Lys Phe Lys
1               5                   10                  15

Xaa

<210> SEQ ID NO 427
<211> LENGTH: 4
<212> TYPE: PRT
<213> ORGANISM: Artificial Sequence
<220> FEATURE:
<223> OTHER INFORMATION: Group IV_Ab HCDR3 amino acid sequence (Kabat
      definition)
<220> FEATURE:
<221> NAME/KEY: MISC_FEATURE
<222> LOCATION: (2)..(2)
<223> OTHER INFORMATION: Xaa = Ile or Phe

<400> SEQUENCE: 427

Gly Xaa Tyr Tyr
1

<210> SEQ ID NO 428
<211> LENGTH: 3
<212> TYPE: PRT
<213> ORGANISM: Artificial Sequence
<220> FEATURE:
<223> OTHER INFORMATION: Group IV_Ab LCDR1 amino acid sequence (Kabat
      definition)
<220> FEATURE:
<221> NAME/KEY: MISC_FEATURE
<222> LOCATION: (2)..(2)
<223> OTHER INFORMATION: Xaa = Ser or Ala

<400> SEQUENCE: 428

Arg Xaa Ser
1
```

```
<210> SEQ ID NO 429
<211> LENGTH: 7
<212> TYPE: PRT
<213> ORGANISM: Artificial Sequence
<220> FEATURE:
<223> OTHER INFORMATION: Group IV_Ab LCDR2 amino acid sequence (Kabat
      definition)
<220> FEATURE:
<221> NAME/KEY: MISC_FEATURE
<222> LOCATION: (1)..(1)
<223> OTHER INFORMATION: Xaa = Arg or Ala
<220> FEATURE:
<221> NAME/KEY: MISC_FEATURE
<222> LOCATION: (2)..(2)
<223> OTHER INFORMATION: Xaa = Val or Ala
<220> FEATURE:
<221> NAME/KEY: MISC_FEATURE
<222> LOCATION: (4)..(4)
<223> OTHER INFORMATION: Xaa = Asn or Thr
<220> FEATURE:
<221> NAME/KEY: MISC_FEATURE
<222> LOCATION: (6)..(6)
<223> OTHER INFORMATION: Xaa = Ala or Asp

<400> SEQUENCE: 429

Xaa Xaa Ser Xaa Leu Xaa Ser
1               5

<210> SEQ ID NO 430
<211> LENGTH: 9
<212> TYPE: PRT
<213> ORGANISM: Artificial Sequence
<220> FEATURE:
<223> OTHER INFORMATION: Group IV_Ab LCDR3 amino acid sequence (Kabat
      definition)
<220> FEATURE:
<221> NAME/KEY: MISC_FEATURE
<222> LOCATION: (1)..(1)
<223> OTHER INFORMATION: Xaa = Met or Leu
<220> FEATURE:
<221> NAME/KEY: MISC_FEATURE
<222> LOCATION: (3)..(3)
<223> OTHER INFORMATION: Xaa = His or Tyr
<220> FEATURE:
<221> NAME/KEY: MISC_FEATURE
<222> LOCATION: (4)..(4)
<223> OTHER INFORMATION: Xaa = Leu or Ala
<220> FEATURE:
<221> NAME/KEY: MISC_FEATURE
<222> LOCATION: (5)..(5)
<223> OTHER INFORMATION: Xaa = Glu or Ser
<220> FEATURE:
<221> NAME/KEY: MISC_FEATURE
<222> LOCATION: (8)..(8)
<223> OTHER INFORMATION: Xaa = Phe or Leu

<400> SEQUENCE: 430

Xaa Gln Xaa Xaa Xaa Tyr Pro Xaa Thr
1               5

<210> SEQ ID NO 431
<211> LENGTH: 7
<212> TYPE: PRT
<213> ORGANISM: Artificial Sequence
<220> FEATURE:
<223> OTHER INFORMATION: Group IV_Ab HCDR1 amino acid sequence (Chothia
      definition)
<220> FEATURE:
<221> NAME/KEY: MISC_FEATURE
<222> LOCATION: (3)..(3)
<223> OTHER INFORMATION: Xaa = Thr or Ala
<220> FEATURE:
<221> NAME/KEY: MISC_FEATURE
<222> LOCATION: (6)..(6)
```

```
<223> OTHER INFORMATION: Xaa = Ser or Asn

<400> SEQUENCE: 431

Gly Tyr Xaa Phe Thr Xaa Tyr
1               5

<210> SEQ ID NO 432
<211> LENGTH: 6
<212> TYPE: PRT
<213> ORGANISM: Artificial Sequence
<220> FEATURE:
<223> OTHER INFORMATION: Group IV_Ab HCDR2 amino acid sequence (Chothia
      definition)
<220> FEATURE:
<221> NAME/KEY: MISC_FEATURE
<222> LOCATION: (3)..(3)
<223> OTHER INFORMATION: Xaa = Ser or Gly
<220> FEATURE:
<221> NAME/KEY: MISC_FEATURE
<222> LOCATION: (4)..(4)
<223> OTHER INFORMATION: Xaa = Asn or Ser

<400> SEQUENCE: 432

Asn Pro Xaa Xaa Gly Gly
1               5

<210> SEQ ID NO 433
<211> LENGTH: 4
<212> TYPE: PRT
<213> ORGANISM: Artificial Sequence
<220> FEATURE:
<223> OTHER INFORMATION: Group IV_Ab HCDR3 amino acid sequence (Chothia
      definition)
<220> FEATURE:
<221> NAME/KEY: MISC_FEATURE
<222> LOCATION: (2)..(2)
<223> OTHER INFORMATION: Xaa = Ile or Phe

<400> SEQUENCE: 433

Gly Xaa Tyr Tyr
1

<210> SEQ ID NO 434
<211> LENGTH: 1
<212> TYPE: PRT
<213> ORGANISM: Artificial Sequence
<220> FEATURE:
<223> OTHER INFORMATION: Group IV_Ab LCDR1 amino acid sequence (Chothia
      definition)

<400> SEQUENCE: 434

Ser
1

<210> SEQ ID NO 435
<211> LENGTH: 3
<212> TYPE: PRT
<213> ORGANISM: Artificial Sequence
<220> FEATURE:
<223> OTHER INFORMATION: Group IV_Ab LCDR2 amino acid sequence (Chothia
      definition)
<220> FEATURE:
<221> NAME/KEY: MISC_FEATURE
<222> LOCATION: (1)..(1)
<223> OTHER INFORMATION: Xaa = Arg or Ala
<220> FEATURE:
<221> NAME/KEY: MISC_FEATURE
<222> LOCATION: (2)..(2)
<223> OTHER INFORMATION: Xaa = Val or Ala

<400> SEQUENCE: 435
```

```
Xaa Xaa Ser
1

<210> SEQ ID NO 436
<211> LENGTH: 7
<212> TYPE: PRT
<213> ORGANISM: Artificial Sequence
<220> FEATURE:
<223> OTHER INFORMATION: Group IV_Ab LCDR3 amino acid sequence (Chothia
      definition)
<220> FEATURE:
<221> NAME/KEY: MISC_FEATURE
<222> LOCATION: (1)..(1)
<223> OTHER INFORMATION: Xaa = His or Tyr
<220> FEATURE:
<221> NAME/KEY: MISC_FEATURE
<222> LOCATION: (2)..(2)
<223> OTHER INFORMATION: Xaa = Leu or Ala
<220> FEATURE:
<221> NAME/KEY: MISC_FEATURE
<222> LOCATION: (3)..(3)
<223> OTHER INFORMATION: Xaa = Glu or Ser
<220> FEATURE:
<221> NAME/KEY: MISC_FEATURE
<222> LOCATION: (6)..(6)
<223> OTHER INFORMATION: Xaa = Phe or Leu

<400> SEQUENCE: 436

Xaa Xaa Xaa Tyr Pro Xaa Thr
1               5

<210> SEQ ID NO 437
<211> LENGTH: 10
<212> TYPE: PRT
<213> ORGANISM: Artificial Sequence
<220> FEATURE:
<223> OTHER INFORMATION: Group IV_Ab HCDR1 amino acid sequence (combined
      overlap)
<220> FEATURE:
<221> NAME/KEY: MISC_FEATURE
<222> LOCATION: (3)..(3)
<223> OTHER INFORMATION: Xaa = Thr or Ala
<220> FEATURE:
<221> NAME/KEY: MISC_FEATURE
<222> LOCATION: (6)..(6)
<223> OTHER INFORMATION: Xaa = Ser or Asn
<220> FEATURE:
<221> NAME/KEY: MISC_FEATURE
<222> LOCATION: (8)..(8)
<223> OTHER INFORMATION: Xaa = Trp or Leu
<220> FEATURE:
<221> NAME/KEY: MISC_FEATURE
<222> LOCATION: (9)..(9)
<223> OTHER INFORMATION: Xaa = Met or Ile
<220> FEATURE:
<221> NAME/KEY: MISC_FEATURE
<222> LOCATION: (10)..(10)
<223> OTHER INFORMATION: Xaa = His or Glu

<400> SEQUENCE: 437

Gly Tyr Xaa Phe Thr Xaa Tyr Xaa Xaa Xaa
1               5                   10

<210> SEQ ID NO 438
<211> LENGTH: 17
<212> TYPE: PRT
<213> ORGANISM: Artificial Sequence
<220> FEATURE:
<223> OTHER INFORMATION: Group IV_Ab HCDR2 amino acid sequence (combined
      overlap)
<220> FEATURE:
<221> NAME/KEY: MISC_FEATURE
<222> LOCATION: (1)..(1)
```

```
<223> OTHER INFORMATION: Xaa = Asn or Val
<220> FEATURE:
<221> NAME/KEY: MISC_FEATURE
<222> LOCATION: (5)..(5)
<223> OTHER INFORMATION: Xaa = Ser or Gly
<220> FEATURE:
<221> NAME/KEY: MISC_FEATURE
<222> LOCATION: (6)..(6)
<223> OTHER INFORMATION: Xaa = Asn or Ser
<220> FEATURE:
<221> NAME/KEY: MISC_FEATURE
<222> LOCATION: (17)..(17)
<223> OTHER INFORMATION: Xaa = Ser or Gly

<400> SEQUENCE: 438

Xaa Ile Asn Pro Xaa Xaa Gly Gly Thr Asn Tyr Asn Glu Lys Phe Lys
1               5                   10                  15

Xaa

<210> SEQ ID NO 439
<211> LENGTH: 7
<212> TYPE: PRT
<213> ORGANISM: Artificial Sequence
<220> FEATURE:
<223> OTHER INFORMATION: Group IV_Ab HCDR3 amino acid sequence (combined
      overlap)
<220> FEATURE:
<221> NAME/KEY: MISC_FEATURE
<222> LOCATION: (3)..(3)
<223> OTHER INFORMATION: Xaa = Gly or Trp
<220> FEATURE:
<221> NAME/KEY: MISC_FEATURE
<222> LOCATION: (5)..(5)
<223> OTHER INFORMATION: Xaa = Ile or Phe

<400> SEQUENCE: 439

Ala Arg Xaa Gly Xaa Tyr Tyr
1               5

<210> SEQ ID NO 440
<211> LENGTH: 3
<212> TYPE: PRT
<213> ORGANISM: Artificial Sequence
<220> FEATURE:
<223> OTHER INFORMATION: Group IV_Ab LCDR1 amino acid sequence (combined
      overlap)
<220> FEATURE:
<221> NAME/KEY: MISC_FEATURE
<222> LOCATION: (2)..(2)
<223> OTHER INFORMATION: Xaa = Ser or Ala

<400> SEQUENCE: 440

Arg Xaa Ser
1

<210> SEQ ID NO 441
<211> LENGTH: 7
<212> TYPE: PRT
<213> ORGANISM: Artificial Sequence
<220> FEATURE:
<223> OTHER INFORMATION: Group IV_Ab LCDR2 amino acid sequence (combined
      overlap)
<220> FEATURE:
<221> NAME/KEY: MISC_FEATURE
<222> LOCATION: (1)..(1)
<223> OTHER INFORMATION: Xaa = Arg or Ala
<220> FEATURE:
<221> NAME/KEY: MISC_FEATURE
<222> LOCATION: (2)..(2)
<223> OTHER INFORMATION: Xaa = Val or Ala
<220> FEATURE:
<221> NAME/KEY: MISC_FEATURE
```

```
<222> LOCATION: (4)..(4)
<223> OTHER INFORMATION: Xaa = Asn or Thr
<220> FEATURE:
<221> NAME/KEY: MISC_FEATURE
<222> LOCATION: (6)..(6)
<223> OTHER INFORMATION: Xaa = Ala or Asp

<400> SEQUENCE: 441

Xaa Xaa Ser Xaa Leu Xaa Ser
1               5

<210> SEQ ID NO 442
<211> LENGTH: 9
<212> TYPE: PRT
<213> ORGANISM: Artificial Sequence
<220> FEATURE:
<223> OTHER INFORMATION: Group IV_Ab LCDR3 amino acid sequence (combined
      overlap)
<220> FEATURE:
<221> NAME/KEY: MISC_FEATURE
<222> LOCATION: (1)..(1)
<223> OTHER INFORMATION: Xaa = Met or Leu
<220> FEATURE:
<221> NAME/KEY: MISC_FEATURE
<222> LOCATION: (3)..(3)
<223> OTHER INFORMATION: Xaa = His or Tyr
<220> FEATURE:
<221> NAME/KEY: MISC_FEATURE
<222> LOCATION: (4)..(4)
<223> OTHER INFORMATION: Xaa = Leu or Ala
<220> FEATURE:
<221> NAME/KEY: MISC_FEATURE
<222> LOCATION: (5)..(5)
<223> OTHER INFORMATION: Xaa = Glu or Ser
<220> FEATURE:
<221> NAME/KEY: MISC_FEATURE
<222> LOCATION: (8)..(8)
<223> OTHER INFORMATION: Xaa = Phe or Leu

<400> SEQUENCE: 442

Xaa Gln Xaa Xaa Xaa Tyr Pro Xaa Thr
1               5

<210> SEQ ID NO 443
<211> LENGTH: 2
<212> TYPE: PRT
<213> ORGANISM: Artificial Sequence
<220> FEATURE:
<223> OTHER INFORMATION: Group IV_Ab HCDR1 amino acid sequence (common
      sequence)
<220> FEATURE:
<221> NAME/KEY: MISC_FEATURE
<222> LOCATION: (1)..(1)
<223> OTHER INFORMATION: Xaa = Ser or Asn

<400> SEQUENCE: 443

Xaa Tyr
1

<210> SEQ ID NO 444
<211> LENGTH: 6
<212> TYPE: PRT
<213> ORGANISM: Artificial Sequence
<220> FEATURE:
<223> OTHER INFORMATION: Group IV_Ab HCDR2 amino acid sequence (common
      sequence)
<220> FEATURE:
<221> NAME/KEY: MISC_FEATURE
<222> LOCATION: (3)..(3)
<223> OTHER INFORMATION: Xaa = Ser or Gly
<220> FEATURE:
<221> NAME/KEY: MISC_FEATURE
<222> LOCATION: (4)..(4)
```

```
<223> OTHER INFORMATION: Xaa = Asn or Ser

<400> SEQUENCE: 444

Asn Pro Xaa Xaa Gly Gly
1               5

<210> SEQ ID NO 445
<211> LENGTH: 4
<212> TYPE: PRT
<213> ORGANISM: Artificial Sequence
<220> FEATURE:
<223> OTHER INFORMATION: Group IV_Ab HCDR3 amino acid sequence (common
      sequence)
<220> FEATURE:
<221> NAME/KEY: MISC_FEATURE
<222> LOCATION: (2)..(2)
<223> OTHER INFORMATION: Xaa = Ile or Phe

<400> SEQUENCE: 445

Gly Xaa Tyr Tyr
1

<210> SEQ ID NO 446
<211> LENGTH: 1
<212> TYPE: PRT
<213> ORGANISM: Artificial Sequence
<220> FEATURE:
<223> OTHER INFORMATION: Group IV_Ab LCDR1 amino acid sequence (common
      sequence)

<400> SEQUENCE: 446

Ser
1

<210> SEQ ID NO 447
<211> LENGTH: 3
<212> TYPE: PRT
<213> ORGANISM: Artificial Sequence
<220> FEATURE:
<223> OTHER INFORMATION: Group IV_Ab LCDR2 amino acid sequence (common
      sequence)
<220> FEATURE:
<221> NAME/KEY: MISC_FEATURE
<222> LOCATION: (1)..(1)
<223> OTHER INFORMATION: Xaa = Arg or Ala
<220> FEATURE:
<221> NAME/KEY: MISC_FEATURE
<222> LOCATION: (2)..(2)
<223> OTHER INFORMATION: Xaa = Val or Ala

<400> SEQUENCE: 447

Xaa Xaa Ser
1

<210> SEQ ID NO 448
<211> LENGTH: 7
<212> TYPE: PRT
<213> ORGANISM: Artificial Sequence
<220> FEATURE:
<223> OTHER INFORMATION: Group IV_Ab LCDR3 amino acid sequence (common
      sequence)
<220> FEATURE:
<221> NAME/KEY: MISC_FEATURE
<222> LOCATION: (1)..(1)
<223> OTHER INFORMATION: Xaa = His or Tyr
<220> FEATURE:
<221> NAME/KEY: MISC_FEATURE
<222> LOCATION: (2)..(2)
<223> OTHER INFORMATION: Xaa = Leu or Ala
<220> FEATURE:
<221> NAME/KEY: MISC_FEATURE
```

```
<222> LOCATION: (3)..(3)
<223> OTHER INFORMATION: Xaa = Glu or Ser
<220> FEATURE:
<221> NAME/KEY: MISC_FEATURE
<222> LOCATION: (6)..(6)
<223> OTHER INFORMATION: Xaa = Phe or Leu

<400> SEQUENCE: 448

Xaa Xaa Xaa Tyr Pro Xaa Thr
1               5

<210> SEQ ID NO 449
<211> LENGTH: 449
<212> TYPE: PRT
<213> ORGANISM: Artificial Sequence
<220> FEATURE:
<223> OTHER INFORMATION: Antibody A HC

<400> SEQUENCE: 449

Gln Val Gln Leu Gln Gln Pro Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Val Lys Gln Thr Pro Val His Gly Leu Glu Trp Ile
        35                  40                  45

Gly Gly Val Asp Pro Glu Thr Gly Thr Gly Tyr Asn Gln Lys Phe
    50                  55                  60

Arg Gly Lys Ala Ile Leu Thr Ala Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg His Gly Gly Ser Phe Tyr Ala Met Asp Tyr Trp Gly Gln Gly
            100                 105                 110

Thr Ser Val Thr Val Ser Ser Ala Lys Thr Thr Ala Pro Ser Val Tyr
        115                 120                 125

Pro Leu Ala Pro Val Cys Gly Asp Thr Thr Gly Ser Ser Val Thr Leu
    130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
        195                 200                 205

Ser Thr Lys Val Asp Lys Lys Ile Glu Pro Arg Gly Pro Thr Ile Lys
    210                 215                 220

Pro Cys Pro Pro Cys Lys Cys Pro Ala Pro Asn Leu Leu Gly Gly Pro
225                 230                 235                 240

Ser Val Phe Ile Phe Pro Pro Lys Ile Lys Asp Val Leu Met Ile Ser
                245                 250                 255

Leu Ser Pro Ile Val Thr Cys Val Val Val Asp Val Ser Glu Asp Asp
            260                 265                 270

Pro Asp Val Gln Ile Ser Trp Phe Val Asn Asn Val Glu Val His Thr
        275                 280                 285

Ala Gln Thr Gln Thr His Arg Glu Asp Tyr Asn Ser Thr Leu Arg Val
    290                 295                 300
```

Val Ser Ala Leu Pro Ile Gln His Gln Asp Trp Met Ser Gly Lys Glu
305                 310                 315                 320

Phe Lys Cys Lys Val Asn Asn Lys Asp Leu Pro Ala Pro Ile Glu Arg
            325                 330                 335

Thr Ile Ser Lys Pro Lys Gly Ser Val Arg Ala Pro Gln Val Tyr Val
            340                 345                 350

Leu Pro Pro Pro Glu Glu Met Thr Lys Lys Gln Val Thr Leu Thr
        355                 360                 365

Cys Met Val Thr Asp Phe Met Pro Glu Asp Ile Tyr Val Glu Trp Thr
        370                 375                 380

Asn Asn Gly Lys Thr Glu Leu Asn Tyr Lys Asn Thr Glu Pro Val Leu
385                 390                 395                 400

Asp Ser Asp Gly Ser Tyr Phe Met Tyr Ser Lys Leu Arg Val Glu Lys
            405                 410                 415

Lys Asn Trp Val Glu Arg Asn Ser Tyr Ser Cys Ser Val Val His Glu
            420                 425                 430

Gly Leu His Asn His His Thr Thr Lys Ser Phe Ser Arg Thr Pro Gly
            435                 440                 445

Lys

<210> SEQ ID NO 450
<211> LENGTH: 214
<212> TYPE: PRT
<213> ORGANISM: Artificial Sequence
<220> FEATURE:
<223> OTHER INFORMATION: Antibody A LC

<400> SEQUENCE: 450

Asp Ile Val Met Thr Gln Ser Pro Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Ser Thr Pro Pro
                85                  90                  95

Thr Phe Gly Gly Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
            165                 170                 175

Ser Thr Leu Thr Leu Thr Lys Asp Glu Tyr Glu Arg His Asn Ser Tyr
        180                 185                 190

Thr Cys Glu Ala Thr His Lys Thr Ser Thr Ser Pro Ile Val Lys Ser
    195                 200                 205

Phe Asn Arg Asn Glu Cys

```
            210

<210> SEQ ID NO 451
<211> LENGTH: 454
<212> TYPE: PRT
<213> ORGANISM: Artificial Sequence
<220> FEATURE:
<223> OTHER INFORMATION: Antibody B HC

<400> SEQUENCE: 451

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
        35                  40                  45

Ala Thr Ile Ser Arg Gly Ser Ile Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Leu Ser Leu Tyr Asp Tyr Asp Gly Ala Arg Tyr Thr Met Asp
            100                 105                 110

Tyr Trp Gly Gln Gly Thr Ser Val Thr Val Ser Ser Ala Lys Thr Thr
        115                 120                 125

Ala Pro Ser Val Tyr Pro Leu Ala Pro Val Cys Gly Asp Thr Thr Gly
    130                 135                 140

Ser Ser Val Thr Leu Gly Cys Leu Val Lys Gly Tyr Phe Pro Glu Pro
145                 150                 155                 160

Val Thr Leu Thr Trp Asn Ser Gly Ser Leu Ser Ser Gly Val His Thr
                165                 170                 175

Phe Pro Ala Val Leu Gln Ser Asp Leu Tyr Thr Leu Ser Ser Ser Val
            180                 185                 190

Thr Val Thr Ser Ser Thr Trp Pro Ser Gln Ser Ile Thr Cys Asn Val
        195                 200                 205

Ala His Pro Ala Ser Ser Thr Lys Val Asp Lys Lys Ile Glu Pro Arg
    210                 215                 220

Gly Pro Thr Ile Lys Pro Cys Pro Pro Cys Lys Cys Pro Ala Pro Asn
225                 230                 235                 240

Leu Leu Gly Gly Pro Ser Val Phe Ile Phe Pro Pro Lys Ile Lys Asp
                245                 250                 255

Val Leu Met Ile Ser Leu Ser Pro Ile Val Thr Cys Val Val Val Asp
            260                 265                 270

Val Ser Glu Asp Asp Pro Asp Val Gln Ile Ser Trp Phe Val Asn Asn
        275                 280                 285

Val Glu Val His Thr Ala Gln Thr Gln Thr His Arg Glu Asp Tyr Asn
    290                 295                 300

Ser Thr Leu Arg Val Val Ser Ala Leu Pro Ile Gln His Gln Asp Trp
305                 310                 315                 320

Met Ser Gly Lys Glu Phe Lys Cys Lys Val Asn Asn Lys Asp Leu Pro
                325                 330                 335

Ala Pro Ile Glu Arg Thr Ile Ser Lys Pro Lys Gly Ser Val Arg Ala
            340                 345                 350

Pro Gln Val Tyr Val Leu Pro Pro Pro Glu Glu Glu Met Thr Lys Lys
```

-continued

```
                355                 360                 365
Gln Val Thr Leu Thr Cys Met Val Thr Asp Phe Met Pro Glu Asp Ile
370                 375                 380
Tyr Val Glu Trp Thr Asn Asn Gly Lys Thr Glu Leu Asn Tyr Lys Asn
385                 390                 395                 400
Thr Glu Pro Val Leu Asp Ser Asp Gly Ser Tyr Phe Met Tyr Ser Lys
                405                 410                 415
Leu Arg Val Glu Lys Lys Asn Trp Val Glu Arg Asn Ser Tyr Ser Cys
                420                 425                 430
Ser Val Val His Glu Gly Leu His Asn His Thr Thr Lys Ser Phe
                435                 440                 445
Ser Arg Thr Pro Gly Lys
        450

<210> SEQ ID NO 452
<211> LENGTH: 213
<212> TYPE: PRT
<213> ORGANISM: Artificial Sequence
<220> FEATURE:
<223> OTHER INFORMATION: Antibody B LC

<400> SEQUENCE: 452

Asp Ile Val Met Thr Gln Ser Pro Lys Phe Met Ser Thr Ser Val Gly
1               5                   10                  15
Asp Arg Val Ser Ile Thr Cys Lys Ala Ser Gln Asp Val Gly Thr Ala
                20                  25                  30
Val Ala Trp Tyr Gln Gln Lys Pro Gly Gln Ser Pro Lys Leu Leu Ile
            35                  40                  45
Tyr Trp Ala Ser Thr Arg His Thr Gly Val Pro Asp Arg Phe Thr Gly
    50                  55                  60
Ser Gly Ser Gly Thr Asp Phe Thr Leu Thr Ile Ser Asn Val Gln Ser
65                  70                  75                  80
Glu Asp Leu Ala Asp Tyr Phe Cys Gln Gln Tyr Ser Ser Tyr His Thr
                85                  90                  95
Phe Gly Ala Gly Thr Lys Leu Glu Leu Lys Arg Ala Asp Ala Ala Pro
            100                 105                 110
Thr Val Ser Ile Phe Pro Pro Ser Glu Gln Leu Thr Ser Gly Gly
            115                 120                 125
Ala Ser Val Val Cys Phe Leu Asn Asn Phe Tyr Pro Lys Asp Ile Asn
            130                 135                 140
Val Lys Trp Lys Ile Asp Gly Ser Glu Arg Gln Asn Gly Val Leu Asn
145                 150                 155                 160
Ser Trp Thr Asp Gln Asp Ser Lys Asp Ser Thr Tyr Ser Met Ser Ser
                165                 170                 175
Thr Leu Thr Leu Thr Lys Asp Glu Tyr Glu Arg His Asn Ser Tyr Thr
            180                 185                 190
Cys Glu Ala Thr His Lys Thr Ser Thr Ser Pro Ile Val Lys Ser Phe
            195                 200                 205
Asn Arg Asn Glu Cys
    210

<210> SEQ ID NO 453
<211> LENGTH: 451
<212> TYPE: PRT
<213> ORGANISM: Artificial Sequence
<220> FEATURE:
<223> OTHER INFORMATION: Antibody C HC
```

<400> SEQUENCE: 453

Gln Val Gln Leu Lys Gln Ser Gly Ala Glu Leu Ala Arg Pro Gly Ala
1               5                   10                  15

Ser Val Lys Leu Ser Cys Lys Ala Ser Gly Tyr Asn Phe Lys Ser Tyr
            20                  25                  30

Gly Ile Ser Trp Val Lys Gln Arg Thr Gly Gln Gly Leu Glu Trp Ile
        35                  40                  45

Gly Glu Ile Tyr Pro Gly Ser Gly Asn Thr Tyr Tyr Asn Glu Lys Leu
    50                  55                  60

Lys Gly Lys Ala Thr Leu Thr Ala Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Thr Tyr Gly Tyr Asp Ser Phe Pro Trp Phe Ala Tyr Trp Gly
            100                 105                 110

Gln Gly Thr Leu Val Thr Val Ser Ala Lys Thr Thr Ala Pro Ser
        115                 120                 125

Val Tyr Pro Leu Ala Pro Val Cys Gly Asp Thr Thr Gly Ser Ser Val
    130                 135                 140

Thr Leu Gly Cys Leu Val Lys Gly Tyr Phe Pro Glu Pro Val Thr Leu
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Thr
            180                 185                 190

Ser Ser Thr Trp Pro Ser Gln Ser Ile Thr Cys Asn Val Ala His Pro
        195                 200                 205

Ala Ser Ser Thr Lys Val Asp Lys Lys Ile Glu Pro Arg Gly Pro Thr
    210                 215                 220

Ile Lys Pro Cys Pro Pro Cys Lys Cys Pro Ala Pro Asn Leu Leu Gly
225                 230                 235                 240

Gly Pro Ser Val Phe Ile Phe Pro Pro Lys Ile Lys Asp Val Leu Met
                245                 250                 255

Ile Ser Leu Ser Pro Ile Val Thr Cys Val Val Asp Val Ser Glu
            260                 265                 270

Asp Asp Pro Asp Val Gln Ile Ser Trp Phe Val Asn Asn Val Glu Val
        275                 280                 285

His Thr Ala Gln Thr Gln Thr His Arg Glu Asp Tyr Asn Ser Thr Leu
    290                 295                 300

Arg Val Val Ser Ala Leu Pro Ile Gln His Gln Asp Trp Met Ser Gly
305                 310                 315                 320

Lys Glu Phe Lys Cys Lys Val Asn Asn Lys Asp Leu Pro Ala Pro Ile
                325                 330                 335

Glu Arg Thr Ile Ser Lys Pro Lys Gly Ser Val Arg Ala Pro Gln Val
            340                 345                 350

Tyr Val Leu Pro Pro Glu Glu Glu Met Thr Lys Lys Gln Val Thr
        355                 360                 365

Leu Thr Cys Met Val Thr Asp Phe Met Pro Glu Asp Ile Tyr Val Glu
    370                 375                 380

Trp Thr Asn Asn Gly Lys Thr Glu Leu Asn Tyr Lys Asn Thr Glu Pro
385                 390                 395                 400

Val Leu Asp Ser Asp Gly Ser Tyr Phe Met Tyr Ser Lys Leu Arg Val 405                 410                 415
Glu Lys Lys Asn Trp Val Glu Arg Asn Ser Tyr Ser Cys Ser Val Val
            420                 425                 430

His Glu Gly Leu His Asn His Thr Thr Lys Ser Phe Ser Arg Thr
        435                 440                 445

Pro Gly Lys
    450

<210> SEQ ID NO 454
<211> LENGTH: 219
<212> TYPE: PRT
<213> ORGANISM: Artificial Sequence
<220> FEATURE:
<223> OTHER INFORMATION: Antibody C LC

<400> SEQUENCE: 454

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Val Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Glu Gly Val Tyr Tyr Cys Met Gln His
                85                  90                  95

Leu Glu Tyr Pro Phe Thr Phe Gly Ala Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 455
<211> LENGTH: 447
<212> TYPE: PRT
<213> ORGANISM: Artificial Sequence
<220> FEATURE:
<223> OTHER INFORMATION: Antibody D HC

<400> SEQUENCE: 455

Glu Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

-continued

```
Glu Met His Trp Val Gln Gln Thr Pro Val His Gly Leu Glu Trp Ile
         35                  40                  45

Gly Gly Ile Asp Pro Glu Thr Gly Gly Thr Gly Tyr Asn Gln Lys Phe
 50                  55                  60

Lys Gly Lys Ala Ile Leu Thr Ala Asp Lys Ser Ser Ser Thr Ala Tyr
 65                  70                  75                  80

Met Glu Leu Arg Ser Leu Thr Ser Glu Asp Ser Ala Val Tyr Phe Cys
             85                  90                  95

Thr Arg His Gly Ser Tyr Ala Met Asp Tyr Trp Gly Gln Gly Thr Ser
             100                 105                 110

Val Thr Val Ser Ser Ala Lys Thr Thr Ala Pro Ser Val Tyr Pro Leu
         115                 120                 125

Ala Pro Val Cys Gly Asp Thr Thr Gly Ser Ser Val Thr Leu Gly Cys
 130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
             165                 170                 175

Asp Leu Tyr Thr Leu Ser Ser Ser Val Thr Val Thr Ser Ser Thr Trp
             180                 185                 190

Pro Ser Gln Ser Ile Thr Cys Asn Val Ala His Pro Ala Ser Ser Thr
         195                 200                 205

Lys Val Asp Lys Lys Ile Glu Pro Arg Gly Pro Thr Ile Lys Pro Cys
         210                 215                 220

Pro Pro Cys Lys Cys Pro Ala Pro Asn Leu Leu Gly Gly Pro Ser Val
225                 230                 235                 240

Phe Ile Phe Pro Pro Lys Ile Lys Asp Val Leu Met Ile Ser Leu Ser
             245                 250                 255

Pro Ile Val Thr Cys Val Val Asp Val Ser Glu Asp Asp Pro Asp
             260                 265                 270

Val Gln Ile Ser Trp Phe Val Asn Asn Val Glu Val His Thr Ala Gln
         275                 280                 285

Thr Gln Thr His Arg Glu Asp Tyr Asn Ser Thr Leu Arg Val Val Ser
290                 295                 300

Ala Leu Pro Ile Gln His Gln Asp Trp Met Ser Gly Lys Glu Phe Lys
305                 310                 315                 320

Cys Lys Val Asn Asn Lys Asp Leu Pro Ala Pro Ile Glu Arg Thr Ile
             325                 330                 335

Ser Lys Pro Lys Gly Ser Val Arg Ala Pro Gln Val Tyr Val Leu Pro
             340                 345                 350

Pro Pro Glu Glu Glu Met Thr Lys Lys Gln Val Thr Leu Thr Cys Met
             355                 360                 365

Val Thr Asp Phe Met Pro Glu Asp Ile Tyr Val Glu Trp Thr Asn Asn
370                 375                 380

Gly Lys Thr Glu Leu Asn Tyr Lys Asn Thr Glu Pro Val Leu Asp Ser
385                 390                 395                 400

Asp Gly Ser Tyr Phe Met Tyr Ser Lys Leu Arg Val Glu Lys Lys Asn
             405                 410                 415

Trp Val Glu Arg Asn Ser Tyr Ser Cys Ser Val Val His Glu Gly Leu
             420                 425                 430

His Asn His His Thr Thr Lys Ser Phe Ser Arg Thr Pro Gly Lys
             435                 440                 445
```

```
<210> SEQ ID NO 456
<211> LENGTH: 214
<212> TYPE: PRT
<213> ORGANISM: Artificial Sequence
<220> FEATURE:
<223> OTHER INFORMATION: Antibody D LC

<400> SEQUENCE: 456
```

| Asp | Ile | Val | Met | Thr | Gln | Ser | Pro | Lys | Phe | Met | Ser | Thr | Ser | Val | Gly |
|---|---|---|---|---|---|---|---|---|---|---|---|---|---|---|---|
| 1 | | | | 5 | | | | | 10 | | | | | 15 | |

| Asp | Arg | Val | Ser | Ile | Thr | Cys | Lys | Ala | Ser | Gln | Asp | Val | Ser | Thr | Ala |
|---|---|---|---|---|---|---|---|---|---|---|---|---|---|---|---|
| | | | 20 | | | | | 25 | | | | | 30 | | |

| Val | Ala | Trp | Tyr | Gln | Gln | Lys | Pro | Gly | Gln | Ser | Pro | Lys | Leu | Leu | Ile |
|---|---|---|---|---|---|---|---|---|---|---|---|---|---|---|---|
| | | | 35 | | | | | 40 | | | | | 45 | | |

| Tyr | Trp | Ala | Ser | Thr | Arg | His | Thr | Gly | Val | Pro | Asp | Arg | Phe | Thr | Gly |
|---|---|---|---|---|---|---|---|---|---|---|---|---|---|---|---|
| | 50 | | | | | 55 | | | | | 60 | | | | |

| Ser | Gly | Ser | Gly | Thr | Asp | Tyr | Thr | Leu | Thr | Ile | Ser | Ser | Val | Gln | Ala |
|---|---|---|---|---|---|---|---|---|---|---|---|---|---|---|---|
| 65 | | | | | 70 | | | | | 75 | | | | | 80 |

| Glu | Asp | Leu | Ala | Leu | Tyr | Tyr | Cys | Gln | Gln | His | Tyr | Ser | Thr | Pro | Pro |
|---|---|---|---|---|---|---|---|---|---|---|---|---|---|---|---|
| | | | | 85 | | | | | 90 | | | | | 95 | |

| Thr | Phe | Gly | Gly | Gly | Thr | Arg | Leu | Glu | Ile | Lys | Arg | Ala | Asp | Ala | Ala |
|---|---|---|---|---|---|---|---|---|---|---|---|---|---|---|---|
| | | | 100 | | | | | 105 | | | | | 110 | | |

| Pro | Thr | Val | Ser | Ile | Phe | Pro | Pro | Ser | Ser | Glu | Gln | Leu | Thr | Ser | Gly |
|---|---|---|---|---|---|---|---|---|---|---|---|---|---|---|---|
| | | | 115 | | | | | 120 | | | | | 125 | | |

| Gly | Ala | Ser | Val | Val | Cys | Phe | Leu | Asn | Asn | Phe | Tyr | Pro | Lys | Asp | Ile |
|---|---|---|---|---|---|---|---|---|---|---|---|---|---|---|---|
| | 130 | | | | | 135 | | | | | 140 | | | | |

| Asn | Val | Lys | Trp | Lys | Ile | Asp | Gly | Ser | Glu | Arg | Gln | Asn | Gly | Val | Leu |
|---|---|---|---|---|---|---|---|---|---|---|---|---|---|---|---|
| 145 | | | | | 150 | | | | | 155 | | | | | 160 |

| Asn | Ser | Trp | Thr | Asp | Gln | Asp | Ser | Lys | Asp | Ser | Thr | Tyr | Ser | Met | Ser |
|---|---|---|---|---|---|---|---|---|---|---|---|---|---|---|---|
| | | | | 165 | | | | | 170 | | | | | 175 | |

| Ser | Thr | Leu | Thr | Leu | Thr | Lys | Asp | Glu | Tyr | Glu | Arg | His | Asn | Ser | Tyr |
|---|---|---|---|---|---|---|---|---|---|---|---|---|---|---|---|
| | | | 180 | | | | | 185 | | | | | 190 | | |

| Thr | Cys | Glu | Ala | Thr | His | Lys | Thr | Ser | Thr | Ser | Pro | Ile | Val | Lys | Ser |
|---|---|---|---|---|---|---|---|---|---|---|---|---|---|---|---|
| | | | 195 | | | | | 200 | | | | | 205 | | |

| Phe | Asn | Arg | Asn | Glu | Cys |
|---|---|---|---|---|---|
| | | 210 | | | |

```
<210> SEQ ID NO 457
<211> LENGTH: 450
<212> TYPE: PRT
<213> ORGANISM: Artificial Sequence
<220> FEATURE:
<223> OTHER INFORMATION: Antibody E HC

<400> SEQUENCE: 457
```

| Glu | Val | Lys | Leu | Leu | Glu | Ser | Gly | Ala | Glu | Leu | Val | Arg | Pro | Gly | Ala |
|---|---|---|---|---|---|---|---|---|---|---|---|---|---|---|---|
| 1 | | | | 5 | | | | | 10 | | | | | 15 | |

| Ser | Val | Thr | Leu | Ser | Cys | Lys | Ala | Ser | Gly | Tyr | Thr | Phe | Thr | Asp | Tyr |
|---|---|---|---|---|---|---|---|---|---|---|---|---|---|---|---|
| | | | 20 | | | | | 25 | | | | | 30 | | |

| Glu | Met | His | Trp | Val | Lys | Gln | Thr | Pro | Val | His | Gly | Leu | Glu | Trp | Ile |
|---|---|---|---|---|---|---|---|---|---|---|---|---|---|---|---|
| | | | 35 | | | | | 40 | | | | | 45 | | |

| Gly | Gly | Ile | Asp | Pro | Glu | Ser | Gly | Gly | Thr | Gly | Tyr | Asn | Gln | Lys | Phe |
|---|---|---|---|---|---|---|---|---|---|---|---|---|---|---|---|
| | 50 | | | | | 55 | | | | | 60 | | | | |

| Lys | Gly | Lys | Ala | Ile | Leu | Thr | Ala | Asp | Lys | Ser | Ser | Thr | Ala | Tyr |
|---|---|---|---|---|---|---|---|---|---|---|---|---|---|---|
| 65 | | | | | 70 | | | | | 75 | | | | | 80 |

| Met | Glu | Leu | Arg | Ser | Leu | Thr | Ser | Glu | Asp | Ser | Ala | Val | Tyr | Phe | Cys |
|---|---|---|---|---|---|---|---|---|---|---|---|---|---|---|---|
| | | | | 85 | | | | | 90 | | | | | 95 | |

```
Thr Arg Ser Gly Tyr Tyr Gly Ser Pro Leu Leu Asp Tyr Trp Gly Gln
                100                 105                 110

Gly Thr Thr Leu Thr Val Ser Ser Ala Lys Thr Thr Ala Pro Ser Val
            115                 120                 125

Tyr Pro Leu Ala Pro Val Cys Gly Asp Thr Thr Gly Ser Ser Val Thr
        130                 135                 140

Leu Gly Cys Leu Val Lys Gly Tyr Phe Pro Glu Pro Val Thr Leu Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Thr Ser
            180                 185                 190

Ser Thr Trp Pro Ser Gln Ser Ile Thr Cys Asn Val Ala His Pro Ala
        195                 200                 205

Ser Ser Thr Lys Val Asp Lys Lys Ile Glu Pro Arg Gly Pro Thr Ile
210                 215                 220

Lys Pro Cys Pro Pro Cys Lys Cys Pro Ala Pro Asn Leu Leu Gly Gly
225                 230                 235                 240

Pro Ser Val Phe Ile Phe Pro Pro Lys Ile Lys Asp Val Leu Met Ile
                245                 250                 255

Ser Leu Ser Pro Ile Val Thr Cys Val Val Val Asp Val Ser Glu Asp
            260                 265                 270

Asp Pro Asp Val Gln Ile Ser Trp Phe Val Asn Asn Val Glu Val His
        275                 280                 285

Thr Ala Gln Thr Gln Thr His Arg Glu Asp Tyr Asn Ser Thr Leu Arg
290                 295                 300

Val Val Ser Ala Leu Pro Ile Gln His Gln Asp Trp Met Ser Gly Lys
305                 310                 315                 320

Glu Phe Lys Cys Lys Val Asn Asn Lys Asp Leu Pro Ala Pro Ile Glu
                325                 330                 335

Arg Thr Ile Ser Lys Pro Lys Gly Ser Val Arg Ala Pro Gln Val Tyr
            340                 345                 350

Val Leu Pro Pro Pro Glu Glu Glu Met Thr Lys Lys Gln Val Thr Leu
        355                 360                 365

Thr Cys Met Val Thr Asp Phe Met Pro Glu Asp Ile Tyr Val Glu Trp
370                 375                 380

Thr Asn Asn Gly Lys Thr Glu Leu Asn Tyr Lys Asn Thr Glu Pro Val
385                 390                 395                 400

Leu Asp Ser Asp Gly Ser Tyr Phe Met Tyr Ser Lys Leu Arg Val Glu
                405                 410                 415

Lys Lys Asn Trp Val Glu Arg Asn Ser Tyr Ser Cys Ser Val Val His
            420                 425                 430

Glu Gly Leu His Asn His His Thr Thr Lys Ser Phe Ser Arg Thr Pro
        435                 440                 445

Gly Lys
    450

<210> SEQ ID NO 458
<211> LENGTH: 215
<212> TYPE: PRT
<213> ORGANISM: Artificial Sequence
<220> FEATURE:
<223> OTHER INFORMATION: Antibody E LC

<400> SEQUENCE: 458
```

Gln Ile Val Leu Ser Gln Ser Pro Ala Ile Met Ser Ala Ser Leu Gly
1               5                   10                  15

Glu Arg Val Thr Met Thr Cys Thr Ala Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95

Pro Thr Phe Gly Ala Gly Thr Lys Leu Glu Ile Lys Arg Ala Asp Ala
            100                 105                 110

Ala Pro Thr Val Ser Ile Phe Pro Pro Ser Ser Glu Gln Leu Thr Ser
            115                 120                 125

Gly Gly Ala Ser Val Val Cys Phe Leu Asn Asn Phe Tyr Pro Lys Asp
        130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
        195                 200                 205

Ser Phe Asn Arg Asn Glu Cys
    210                 215

<210> SEQ ID NO 459
<211> LENGTH: 449
<212> TYPE: PRT
<213> ORGANISM: Artificial Sequence
<220> FEATURE:
<223> OTHER INFORMATION: Antibody F HC

<400> SEQUENCE: 459

Gln Val Gln Leu Lys Glu Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Asn Trp Val Lys Gln Arg Pro Gly Gln Gly Leu Glu Trp Ile
        35                  40                  45

Gly Trp Ile Phe Pro Gly Ser Gly Ser Thr Tyr Tyr Asn Glu Lys Phe
50                  55                  60

Lys Gly Lys Ala Thr Leu Thr Val Asp Lys Ser Ser Thr Ala Tyr
65                  70                  75                  80

Met Leu Leu Ser Ser Leu Thr Ser Glu Asp Ser Ala Val Tyr Phe Cys
                85                  90                  95

Ala Asp Tyr Gly Ser Ser Tyr Arg Tyr Phe Asp Val Trp Gly Ala Gly
            100                 105                 110

Thr Thr Val Thr Val Ser Ser Ala Lys Thr Thr Ala Pro Ser Val Tyr
        115                 120                 125

Pro Leu Ala Pro Val Cys Gly Asp Thr Thr Gly Ser Ser Val Thr Leu
    130                 135                 140

-continued

```
Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Val Thr Val Thr Ser Ser
            180                 185                 190

Thr Trp Pro Ser Gln Ser Ile Thr Cys Asn Val Ala His Pro Ala Ser
        195                 200                 205

Ser Thr Lys Val Asp Lys Lys Ile Glu Pro Arg Gly Pro Thr Ile Lys
    210                 215                 220

Pro Cys Pro Pro Cys Lys Cys Pro Ala Pro Asn Leu Leu Gly Gly Pro
225                 230                 235                 240

Ser Val Phe Ile Phe Pro Pro Lys Ile Lys Asp Val Leu Met Ile Ser
                245                 250                 255

Leu Ser Pro Ile Val Thr Cys Val Val Val Asp Val Ser Glu Asp Asp
                260                 265                 270

Pro Asp Val Gln Ile Ser Trp Phe Val Asn Asn Val Glu Val His Thr
        275                 280                 285

Ala Gln Thr Gln Thr His Arg Glu Asp Tyr Asn Ser Thr Leu Arg Val
    290                 295                 300

Val Ser Ala Leu Pro Ile Gln His Gln Asp Trp Met Ser Gly Lys Glu
305                 310                 315                 320

Phe Lys Cys Lys Val Asn Asn Lys Asp Leu Pro Ala Pro Ile Glu Arg
                325                 330                 335

Thr Ile Ser Lys Pro Lys Gly Ser Val Arg Ala Pro Gln Val Tyr Val
                340                 345                 350

Leu Pro Pro Pro Glu Glu Glu Met Thr Lys Lys Gln Val Thr Leu Thr
        355                 360                 365

Cys Met Val Thr Asp Phe Met Pro Glu Asp Ile Tyr Val Glu Trp Thr
370                 375                 380

Asn Asn Gly Lys Thr Glu Leu Asn Tyr Lys Asn Thr Glu Pro Val Leu
385                 390                 395                 400

Asp Ser Asp Gly Ser Tyr Phe Met Tyr Ser Lys Leu Arg Val Glu Lys
                405                 410                 415

Lys Asn Trp Val Glu Arg Asn Ser Tyr Ser Cys Ser Val Val His Glu
                420                 425                 430

Gly Leu His Asn His His Thr Thr Lys Ser Phe Ser Arg Thr Pro Gly
            435                 440                 445

Lys

<210> SEQ ID NO 460
<211> LENGTH: 213
<212> TYPE: PRT
<213> ORGANISM: Artificial Sequence
<220> FEATURE:
<223> OTHER INFORMATION: Antibody F LC

<400> SEQUENCE: 460

Asp Ile Val Met Thr Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
                20                  25                  30

His Trp Tyr Gln Gln Lys Pro Gly Ser Ser Pro Lys Pro Trp Ile Tyr
            35                  40                  45

Ala Thr Ser Tyr Leu Ala Ser Gly Val Pro Ala Arg Phe Ser Gly Ser
```

```
                    50                  55                  60
Gly Ser Gly Thr Ser Tyr Ser Leu Thr Ile Gly Arg Val Glu Ala Glu
 65                  70                  75                  80

Asp Ala Ala Thr Tyr Tyr Cys Gln Gln Trp Ser Ser Asn Pro Leu Thr
                 85                  90                  95

Phe Gly Ala Gly Thr Lys Leu Glu Leu Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 461
<211> LENGTH: 454
<212> TYPE: PRT
<213> ORGANISM: Artificial Sequence
<220> FEATURE:
<223> OTHER INFORMATION: Antibody G HC

<400> SEQUENCE: 461

Gln Val Gln Leu Lys Gln Ser Gly Ala Glu Leu Val Arg Pro Gly Ala
  1               5                  10                  15

Ser Val Thr Leu Ser Cys Lys Ala Ser Gly Tyr Thr Phe Thr Asp Tyr
             20                  25                  30

Glu Met His Trp Val Lys Gln Thr Pro Val His Gly Leu Glu Trp Ile
         35                  40                  45

Gly Gly Ile Asp Pro Glu Thr Gly Gly Thr Ala Tyr Asn Gln Lys Phe
     50                  55                  60

Lys Gly Lys Ala Ile Leu Thr Ala Asp Lys Ser Ser Ser Thr Ala Tyr
 65                  70                  75                  80

Met Glu Leu Arg Ser Leu Thr Ser Glu Asp Ser Ala Val Tyr Tyr Cys
                 85                  90                  95

Thr Arg Trp Gly Ala Ile Thr Ser Phe Val Ala Leu Arg Gly Phe Ala
            100                 105                 110

Tyr Trp Gly Gln Gly Thr Leu Val Thr Val Ser Ser Ala Lys Thr Thr
        115                 120                 125

Ala Pro Ser Val Tyr Pro Leu Ala Pro Val Cys Gly Asp Thr Thr Gly
130                 135                 140

Ser Ser Val Thr Leu Gly Cys Leu Val Lys Gly Tyr Phe Pro Glu Pro
145                 150                 155                 160

Val Thr Leu Thr Trp Asn Ser Gly Ser Leu Ser Ser Gly Val His Thr
                165                 170                 175

Phe Pro Ala Val Leu Gln Ser Asp Leu Tyr Thr Leu Ser Ser Ser Val
            180                 185                 190

Thr Val Thr Ser Ser Thr Trp Pro Ser Gln Ser Ile Thr Cys Asn Val
```

```
                195                 200                 205
Ala His Pro Ala Ser Ser Thr Lys Val Asp Lys Lys Ile Glu Pro Arg
    210                 215                 220

Gly Pro Thr Ile Lys Pro Cys Pro Pro Cys Lys Cys Pro Ala Pro Asn
225                 230                 235                 240

Leu Leu Gly Gly Pro Ser Val Phe Ile Phe Pro Pro Lys Ile Lys Asp
                245                 250                 255

Val Leu Met Ile Ser Leu Ser Pro Ile Val Thr Cys Val Val Val Asp
            260                 265                 270

Val Ser Glu Asp Asp Pro Asp Val Gln Ile Ser Trp Phe Val Asn Asn
        275                 280                 285

Val Glu Val His Thr Ala Gln Thr Gln Thr His Arg Glu Asp Tyr Asn
    290                 295                 300

Ser Thr Leu Arg Val Val Ser Ala Leu Pro Ile Gln His Gln Asp Trp
305                 310                 315                 320

Met Ser Gly Lys Glu Phe Lys Cys Lys Val Asn Asn Lys Asp Leu Pro
                325                 330                 335

Ala Pro Ile Glu Arg Thr Ile Ser Lys Pro Lys Gly Ser Val Arg Ala
            340                 345                 350

Pro Gln Val Tyr Val Leu Pro Pro Pro Glu Glu Glu Met Thr Lys Lys
        355                 360                 365

Gln Val Thr Leu Thr Cys Met Val Thr Asp Phe Met Pro Glu Asp Ile
    370                 375                 380

Tyr Val Glu Trp Thr Asn Asn Gly Lys Thr Glu Leu Asn Tyr Lys Asn
385                 390                 395                 400

Thr Glu Pro Val Leu Asp Ser Asp Gly Ser Tyr Phe Met Tyr Ser Lys
                405                 410                 415

Leu Arg Val Glu Lys Lys Asn Trp Val Glu Arg Asn Ser Tyr Ser Cys
            420                 425                 430

Ser Val Val His Glu Gly Leu His Asn His His Thr Thr Lys Ser Phe
        435                 440                 445

Ser Arg Thr Pro Gly Lys
    450

<210> SEQ ID NO 462
<211> LENGTH: 220
<212> TYPE: PRT
<213> ORGANISM: Artificial Sequence
<220> FEATURE:
<223> OTHER INFORMATION: Antibody G LC

<400> SEQUENCE: 462

Asp Ile Gln Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Ala Trp Tyr Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp His Ser Tyr Pro Pro Thr Phe Gly Ala Gly Thr Lys Leu Glu Leu
```

```
              100                 105                 110
Lys Arg Ala Asp Ala Ala Pro Thr Val Ser Ile Phe Pro Pro Ser Ser
            115                 120                 125

Glu Gln Leu Thr Ser Gly Gly Ala Ser Val Val Cys Phe Leu Asn Asn
        130                 135                 140

Phe Tyr Pro Lys Asp Ile Asn Val Lys Trp Lys Ile Asp Gly Ser Glu
145                 150                 155                 160

Arg Gln Asn Gly Val Leu Asn Ser Trp Thr Asp Gln Asp Ser Lys Asp
                165                 170                 175

Ser Thr Tyr Ser Met Ser Ser Thr Leu Thr Leu Thr Lys Asp Glu Tyr
            180                 185                 190

Glu Arg His Asn Ser Tyr Thr Cys Glu Ala Thr His Lys Thr Ser Thr
        195                 200                 205

Ser Pro Ile Val Lys Ser Phe Asn Arg Asn Glu Cys
    210                 215                 220

<210> SEQ ID NO 463
<211> LENGTH: 454
<212> TYPE: PRT
<213> ORGANISM: Artificial Sequence
<220> FEATURE:
<223> OTHER INFORMATION: Antibody H HC

<400> SEQUENCE: 463

Glu Val Lys Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
        35                  40                  45

Ala Thr Ile Ser Arg Arg Ser Ile Tyr Thr Tyr Tyr Pro Asp Ser Val
    50                  55                  60

Gln Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Leu Ser Leu Tyr Asp Tyr Asp Gly Ala Arg Tyr Thr Met Asp
            100                 105                 110

Tyr Trp Gly Gln Gly Thr Ser Val Thr Val Ser Ser Ala Lys Thr Thr
        115                 120                 125

Ala Pro Ser Val Tyr Pro Leu Ala Pro Val Cys Gly Asp Thr Thr Gly
    130                 135                 140

Ser Ser Val Thr Leu Gly Cys Leu Val Lys Gly Tyr Phe Pro Glu Pro
145                 150                 155                 160

Val Thr Leu Thr Trp Asn Ser Gly Ser Leu Ser Ser Gly Val His Thr
                165                 170                 175

Phe Pro Ala Val Leu Gln Ser Asp Leu Tyr Thr Leu Ser Ser Ser Val
            180                 185                 190

Thr Val Thr Ser Ser Thr Trp Pro Ser Gln Ser Ile Thr Cys Asn Val
        195                 200                 205

Ala His Pro Ala Ser Ser Thr Lys Val Asp Lys Lys Ile Glu Pro Arg
    210                 215                 220

Gly Pro Thr Ile Lys Pro Cys Pro Pro Cys Lys Cys Pro Ala Pro Asn
225                 230                 235                 240

Leu Leu Gly Gly Pro Ser Val Phe Ile Phe Pro Pro Lys Ile Lys Asp
```

```
                        245                 250                 255
Val Leu Met Ile Ser Leu Ser Pro Ile Val Thr Cys Val Val Asp
                260                 265                 270

Val Ser Glu Asp Asp Pro Asp Val Gln Ile Ser Trp Phe Val Asn Asn
                275                 280                 285

Val Glu Val His Thr Ala Gln Thr Gln Thr His Arg Glu Asp Tyr Asn
                290                 295                 300

Ser Thr Leu Arg Val Val Ser Ala Leu Pro Ile Gln His Gln Asp Trp
305                 310                 315                 320

Met Ser Gly Lys Glu Phe Lys Cys Lys Val Asn Asn Lys Asp Leu Pro
                325                 330                 335

Ala Pro Ile Glu Arg Thr Ile Ser Lys Pro Lys Gly Ser Val Arg Ala
                340                 345                 350

Pro Gln Val Tyr Val Leu Pro Pro Glu Glu Glu Met Thr Lys Lys
                355                 360                 365

Gln Val Thr Leu Thr Cys Met Val Thr Asp Phe Met Pro Glu Asp Ile
                370                 375                 380

Tyr Val Glu Trp Thr Asn Asn Gly Lys Thr Glu Leu Asn Tyr Lys Asn
385                 390                 395                 400

Thr Glu Pro Val Leu Asp Ser Asp Gly Ser Tyr Phe Met Tyr Ser Lys
                405                 410                 415

Leu Arg Val Glu Lys Lys Asn Trp Val Glu Arg Asn Ser Tyr Ser Cys
                420                 425                 430

Ser Val Val His Glu Gly Leu His Asn His Thr Thr Lys Ser Phe
                435                 440                 445

Ser Arg Thr Pro Gly Lys
                450

<210> SEQ ID NO 464
<211> LENGTH: 213
<212> TYPE: PRT
<213> ORGANISM: Artificial Sequence
<220> FEATURE:
<223> OTHER INFORMATION: Antibody H LC

<400> SEQUENCE: 464

Asp Ile Lys Met Thr Gln Ser Pro Lys Phe Met Ser Thr Ser Val Gly
1               5                   10                  15

Asp Arg Val Ser Ile Thr Cys Lys Ala Ser Gln Asp Val Gly Thr Ala
                20                  25                  30

Val Ala Trp Tyr Gln Gln Lys Pro Gly Gln Ser Pro Lys Leu Leu Ile
                35                  40                  45

Tyr Trp Ala Ser Thr Arg His Thr Gly Val Pro Asp Arg Phe Thr Gly
                50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr His Thr
                85                  90                  95

Phe Gly Ala Gly Thr Lys Leu Glu Ile Lys Arg Ala Asp Ala Ala Pro
                100                 105                 110

Thr Val Ser Ile Phe Pro Pro Ser Glu Gln Leu Thr Ser Gly Gly
                115                 120                 125

Ala Ser Val Val Cys Phe Leu Asn Asn Phe Tyr Pro Lys Asp Ile Asn
                130                 135                 140

Val Lys Trp Lys Ile Asp Gly Ser Glu Arg Gln Asn Gly Val Leu Asn
```

-continued

```
            145                 150                 155                 160
Ser Trp Thr Asp Gln Asp Ser Lys Asp Ser Thr Tyr Ser Met Ser Ser
                    165                 170                 175

Thr Leu Thr Leu Thr Lys Asp Glu Tyr Glu Arg His Asn Ser Tyr Thr
                    180                 185                 190

Cys Glu Ala Thr His Lys Thr Ser Thr Ser Pro Ile Val Lys Ser Phe
                    195                 200                 205

Asn Arg Asn Glu Cys
        210

<210> SEQ ID NO 465
<211> LENGTH: 454
<212> TYPE: PRT
<213> ORGANISM: Artificial Sequence
<220> FEATURE:
<223> OTHER INFORMATION: Antibody J HC

<400> SEQUENCE: 465

Gln Val His Leu Gln Gln Ser Gly Thr Glu Leu Val Lys Pro Gly Ala
1               5                   10                  15

Ser Val Lys Leu Ser Cys Glu Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Asn Ile Asn Pro Ser Asn Gly Gly Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Gly Ile Tyr Tyr Gly Asn Tyr Asp Tyr Tyr Ala Met Asp
            100                 105                 110

Tyr Trp Gly Gln Gly Thr Ser Val Thr Val Ser Ser Ala Lys Thr Thr
        115                 120                 125

Ala Pro Ser Val Tyr Pro Leu Ala Pro Val Cys Gly Asp Thr Thr Gly
    130                 135                 140

Ser Ser Val Thr Leu Gly Cys Leu Val Lys Gly Tyr Phe Pro Glu Pro
145                 150                 155                 160

Val Thr Leu Thr Trp Asn Ser Gly Ser Leu Ser Ser Gly Val His Thr
                165                 170                 175

Phe Pro Ala Val Leu Gln Ser Asp Leu Tyr Thr Leu Ser Ser Ser Val
            180                 185                 190

Thr Val Thr Ser Ser Thr Trp Pro Ser Gln Ser Ile Thr Cys Asn Val
        195                 200                 205

Ala His Pro Ala Ser Ser Thr Lys Val Asp Lys Lys Ile Glu Pro Arg
    210                 215                 220

Gly Pro Thr Ile Lys Pro Cys Pro Pro Cys Lys Cys Pro Ala Pro Asn
225                 230                 235                 240

Leu Leu Gly Gly Pro Ser Val Phe Ile Phe Pro Pro Lys Ile Lys Asp
                245                 250                 255

Val Leu Met Ile Ser Leu Ser Pro Ile Val Thr Cys Val Val Val Asp
            260                 265                 270

Val Ser Glu Asp Asp Pro Asp Val Gln Ile Ser Trp Phe Val Asn Asn
        275                 280                 285

Val Glu Val His Thr Ala Gln Thr Gln Thr His Arg Glu Asp Tyr Asn
```

```
            290                 295                 300
Ser Thr Leu Arg Val Val Ser Ala Leu Pro Ile Gln His Gln Asp Trp
305                 310                 315                 320

Met Ser Gly Lys Glu Phe Lys Cys Lys Val Asn Asn Lys Asp Leu Pro
                325                 330                 335

Ala Pro Ile Glu Arg Thr Ile Ser Lys Pro Lys Gly Ser Val Arg Ala
            340                 345                 350

Pro Gln Val Tyr Val Leu Pro Pro Glu Glu Met Thr Lys Lys
        355                 360                 365

Gln Val Thr Leu Thr Cys Met Val Thr Asp Phe Met Pro Glu Asp Ile
    370                 375                 380

Tyr Val Glu Trp Thr Asn Asn Gly Lys Thr Glu Leu Asn Tyr Lys Asn
385                 390                 395                 400

Thr Glu Pro Val Leu Asp Ser Asp Gly Ser Tyr Phe Met Tyr Ser Lys
                405                 410                 415

Leu Arg Val Glu Lys Lys Asn Trp Val Glu Arg Asn Ser Tyr Ser Cys
            420                 425                 430

Ser Val Val His Glu Gly Leu His Asn His His Thr Thr Lys Ser Phe
        435                 440                 445

Ser Arg Thr Pro Gly Lys
    450

<210> SEQ ID NO 466
<211> LENGTH: 219
<212> TYPE: PRT
<213> ORGANISM: Artificial Sequence
<220> FEATURE:
<223> OTHER INFORMATION: Antibody J LC

<400> SEQUENCE: 466

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Val Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
```

-continued

```
                195                 200                 205
Pro Ile Val Lys Ser Phe Asn Arg Asn Glu Cys
    210                 215
```

<210> SEQ ID NO 467
<211> LENGTH: 448
<212> TYPE: PRT
<213> ORGANISM: Artificial Sequence
<220> FEATURE:
<223> OTHER INFORMATION: Antibody K HC

<400> SEQUENCE: 467

```
Gln Val Gln Leu Lys Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
            20                  25                  30

Leu Ile Glu Trp Val Lys Gln Arg Pro Gly Gln Gly Leu Glu Trp Ile
        35                  40                  45

Gly Val Ile Asn Pro Gly Ser Gly Gly Thr Asn Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Trp Gly Phe Tyr Tyr Ala Met Asp Tyr Trp Gly Gln Gly Thr
            100                 105                 110

Ser Val Thr Val Ser Ser Ala Lys Thr Thr Ala Pro Ser Val Tyr Pro
        115                 120                 125

Leu Ala Pro Val Cys Gly Asp Thr Thr Gly Ser Ser Val Thr Leu Gly
    130                 135                 140

Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Thr Ser Ser Thr
            180                 185                 190

Trp Pro Ser Gln Ser Ile Thr Cys Asn Val Ala His Pro Ala Ser Ser
        195                 200                 205

Thr Lys Val Asp Lys Lys Ile Glu Pro Arg Gly Pro Thr Ile Lys Pro
    210                 215                 220

Cys Pro Pro Cys Lys Cys Pro Ala Pro Asn Leu Leu Gly Gly Pro Ser
225                 230                 235                 240

Val Phe Ile Phe Pro Pro Lys Ile Lys Asp Val Leu Met Ile Ser Leu
                245                 250                 255

Ser Pro Ile Val Thr Cys Val Val Asp Val Ser Glu Asp Asp Pro
            260                 265                 270

Asp Val Gln Ile Ser Trp Phe Val Asn Asn Val Glu Val His Thr Ala
        275                 280                 285

Gln Thr Gln Thr His Arg Glu Asp Tyr Asn Ser Thr Leu Arg Val Val
    290                 295                 300

Ser Ala Leu Pro Ile Gln His Gln Asp Trp Met Ser Gly Lys Glu Phe
305                 310                 315                 320

Lys Cys Lys Val Asn Asn Lys Asp Leu Pro Ala Pro Ile Glu Arg Thr
                325                 330                 335

Ile Ser Lys Pro Lys Gly Ser Val Arg Ala Pro Gln Val Tyr Val Leu
```

```
            340                 345                 350
Pro Pro Pro Glu Glu Glu Met Thr Lys Lys Gln Val Thr Leu Thr Cys
        355                 360                 365

Met Val Thr Asp Phe Met Pro Glu Asp Ile Tyr Val Glu Trp Thr Asn
    370                 375                 380

Asn Gly Lys Thr Glu Leu Asn Tyr Lys Asn Thr Glu Pro Val Leu Asp
385                 390                 395                 400

Ser Asp Gly Ser Tyr Phe Met Tyr Ser Lys Leu Arg Val Glu Lys Lys
                405                 410                 415

Asn Trp Val Glu Arg Asn Ser Tyr Ser Cys Ser Val Val His Glu Gly
            420                 425                 430

Leu His Asn His His Thr Thr Lys Ser Phe Ser Arg Thr Pro Gly Lys
        435                 440                 445
```

<210> SEQ ID NO 468
<211> LENGTH: 214
<212> TYPE: PRT
<213> ORGANISM: Artificial Sequence
<220> FEATURE:
<223> OTHER INFORMATION: Antibody K LC

<400> SEQUENCE: 468

```
Asp Ile Val Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Tyr Pro Leu
                85                  90                  95

Thr Phe Gly Ala Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 469
<211> LENGTH: 7
<212> TYPE: PRT
<213> ORGANISM: Artificial Sequence
<220> FEATURE:
<223> OTHER INFORMATION: mAb_C LCDR3 amino acid sequence (IMGT, Kabat, and Chothia common sequences)

<400> SEQUENCE: 469

His Leu Glu Tyr Pro Phe Thr
1               5